United States Patent
Macdonald et al.

(10) Patent No.: US 11,261,248 B2
(45) Date of Patent: Mar. 1, 2022

(54) RESTRICTED IMMUNOGLOBULIN HEAVY CHAIN MICE

(71) Applicant: Regeneron Pharmaceuticals, Inc., Tarrytown, NY (US)

(72) Inventors: Lynn Macdonald, Harrison, NY (US); John McWhirter, Hastings-on-Hudson, NY (US); Andrew J. Murphy, Croton-on-Hudson, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 226 days.

(21) Appl. No.: 16/265,825

(22) Filed: Feb. 1, 2019

(65) Prior Publication Data
US 2019/0261612 A1 Aug. 29, 2019

Related U.S. Application Data

(62) Division of application No. 13/653,456, filed on Oct. 17, 2012, now Pat. No. 10,246,509.

(60) Provisional application No. 61/658,459, filed on Jun. 12, 2012, provisional application No. 61/597,969, filed on Feb. 13, 2012, provisional application No. 61/547,974, filed on Oct. 17, 2011.

(51) Int. Cl.
| | |
|---|---|
| *A01K 67/027* | (2006.01) |
| *C12N 5/10* | (2006.01) |
| *C12N 5/20* | (2006.01) |
| *C07K 16/28* | (2006.01) |
| *C12N 15/85* | (2006.01) |
| *C07K 16/00* | (2006.01) |
| *C07K 16/46* | (2006.01) |

(52) U.S. Cl.
CPC .......... *C07K 16/28* (2013.01); *A01K 67/0278* (2013.01); *C07K 16/00* (2013.01); *C07K 16/461* (2013.01); *C12N 15/8509* (2013.01); *A01K 2217/072* (2013.01); *A01K 2217/15* (2013.01); *A01K 2227/105* (2013.01); *A01K 2267/01* (2013.01); *C07K 2317/10* (2013.01); *C07K 2317/20* (2013.01); *C07K 2317/21* (2013.01); *C07K 2317/24* (2013.01); *C07K 2317/515* (2013.01); *C07K 2317/52* (2013.01); *C07K 2317/56* (2013.01); *C07K 2317/565* (2013.01); *C07K 2317/567* (2013.01); *C12N 2800/204* (2013.01)

(58) Field of Classification Search
CPC ................ C07K 16/00; A01K 67/0278; A01K 2227/105; A01K 2267/01
See application file for complete search history.

(56) References Cited

U.S. PATENT DOCUMENTS

| | | | |
|---|---|---|---|
| 5,545,807 | A | 8/1996 | Surani et al. |
| 5,633,425 | A | 5/1997 | Lonberg et al. |
| 5,770,429 | A | 6/1998 | Lonberg et al. |
| 5,939,598 | A | 8/1999 | Kucherlapati et al. |
| 6,075,181 | A | 6/2000 | Kucherlapati et al. |
| 6,150,584 | A | 11/2000 | Kucherlapati et al. |
| 6,162,963 | A | 12/2000 | Kucherlapati et al. |
| 6,586,251 | B2 | 7/2003 | Economides et al. |
| 6,596,541 | B2 | 7/2003 | Murphy et al. |
| 6,657,103 | B1 | 12/2003 | Kucherlapati et al. |
| 6,673,986 | B1 | 1/2004 | Kucherlapati et al. |
| 7,105,348 | B2 | 9/2006 | Murphy et al. |
| 7,183,076 | B2 | 2/2007 | Arathoon et al. |
| 7,501,552 | B2 | 3/2009 | Lonberg et al. |
| 7,582,298 | B2 | 9/2009 | Stevens et al. |
| 7,585,668 | B2 | 9/2009 | Buelow et al. |
| 7,910,798 | B2 | 3/2011 | Tanamachi et al. |
| 8,158,419 | B2 | 4/2012 | Lonberg et al. |
| 8,502,018 | B2 | 8/2013 | Murphy et al. |
| 8,642,835 | B2 | 2/2014 | Macdonald et al. |
| 8,697,940 | B2 | 4/2014 | Macdonald et al. |

(Continued)

FOREIGN PATENT DOCUMENTS

| | | |
|---|---|---|
| CN | 1203922 A | 1/1999 |
| EP | 2003960 B1 | 6/2015 |

(Continued)

OTHER PUBLICATIONS

Adderson et al. (1991) "Restricted Ig H Chain V Gene Usage in the Human Antibody Response to Haemophilus influenzae TYPE b CAPSULAR POLYSACCHARIDE," The Journal of Immunology, 147:1667-1674.

Adderson et al. (1993) "Restricted Immunoglobulin VH Usage and VDJ Combinations in the Human Response to Haemophilus influenzae Type b Capsular Polysaccharide," J. Clin. Invest., 91:2734-2743.

Adkins et al. (2004) "Neonatal Adaptive Immunity Comes of Age," Nature Reviews Immunol., 4:553-564.

Amit and Itskovitz-Eldor (2009) "Embryonic Stem Cells: Isolation, Characterization and Culture," Adv. Biochem. Eng. Biotechnol., 114:173-184.

(Continued)

*Primary Examiner* — Valarie E Bertoglio
(74) *Attorney, Agent, or Firm* — FisherBroyles, LLP; Rita S. Wu; Elysa Goldberg

(57) ABSTRACT

Mice having a restricted immunoglobulin heavy chain locus are provided, wherein the locus is characterized by a single polymorphic human $V_H$ gene segment, a plurality of human $D_H$ gene segments and a plurality of $J_H$ gene segments. Methods for making antibody sequences that bind an antigen (e.g., a viral antigen) are provided, comprising immunizing a mouse with an antigen of interest, wherein the mouse comprises a single human $V_H$ gene segment, a plurality of human $D_H$ gene segments and a plurality of $J_H$ gene segments, at the endogenous immunoglobulin heavy chain locus.

7 Claims, 24 Drawing Sheets
Specification includes a Sequence Listing.

(56) References Cited

U.S. PATENT DOCUMENTS

| | | | |
|---|---|---|---|
| 8,754,287 | B2 | 6/2014 | Macdonald et al. |
| 9,204,624 | B2 | 12/2015 | McWhirter et al. |
| 9,932,408 | B2 | 4/2018 | Macdonald et al. |
| 2002/0106628 | A1 | 8/2002 | Economides et al. |
| 2002/0106629 | A1 | 8/2002 | Murphy et al. |
| 2003/0108925 | A1 | 6/2003 | Dix et al. |
| 2003/0109021 | A1 | 6/2003 | Wu et al. |
| 2004/0018626 | A1 | 1/2004 | Murphy et al. |
| 2006/0015957 | A1 | 1/2006 | Lonberg et al. |
| 2006/0015958 | A1 | 1/2006 | Kuroiwa et al. |
| 2006/0199204 | A1 | 9/2006 | Dix et al. |
| 2008/0267982 | A1 | 10/2008 | Kiselev et al. |
| 2009/0258392 | A1 | 10/2009 | Gallo et al. |
| 2010/0146647 | A1 | 6/2010 | Logtenberg et al. |
| 2011/0111406 | A1 | 5/2011 | Igawa et al. |
| 2011/0145937 | A1 | 6/2011 | Macdonald et al. |
| 2011/0195454 | A1 | 8/2011 | McWhirter et al. |
| 2011/0236378 | A1 | 9/2011 | Green et al. |
| 2011/0314563 | A1 | 12/2011 | Craig et al. |
| 2012/0021409 | A1 | 1/2012 | McWhirter et al. |
| 2012/0047585 | A1 | 2/2012 | Rohrer et al. |
| 2012/0096572 | A1 | 4/2012 | Macdonald et al. |
| 2012/0167237 | A1 | 6/2012 | Bradley et al. |
| 2012/0204278 | A1 | 8/2012 | Bradley et al. |
| 2012/0272344 | A1 | 10/2012 | Tanamachi et al. |
| 2012/0322108 | A1 | 12/2012 | Macdonald et al. |
| 2013/0096287 | A1 | 4/2013 | Macdonald et al. |
| 2013/0185821 | A1 | 7/2013 | Babb et al. |
| 2013/0198879 | A1 | 8/2013 | McWhirter et al. |
| 2013/0198880 | A1 | 8/2013 | Babb et al. |
| 2013/0243759 | A1 | 9/2013 | Friedrich et al. |
| 2013/0243773 | A1 | 9/2013 | Van Berkel et al. |
| 2013/0263292 | A1 | 10/2013 | Liang et al. |
| 2013/0323235 | A1 | 12/2013 | Craig et al. |
| 2013/0323791 | A1 | 12/2013 | Macdonald et al. |
| 2013/0333057 | A1 | 12/2013 | Macdonald et al. |
| 2014/0245468 | A1 | 8/2014 | McWhirter et al. |
| 2015/0020224 | A1 | 1/2015 | McWhirter et al. |
| 2015/0201589 | A1 | 7/2015 | Macdonald et al. |
| 2015/0210776 | A1 | 7/2015 | Macdonald et al. |
| 2015/0250152 | A1 | 9/2015 | Jakobovits et al. |
| 2016/0100561 | A1 | 4/2016 | McWhirter et al. |
| 2019/0261612 | A1 | 8/2019 | Macdonald et al. |

FOREIGN PATENT DOCUMENTS

| | | |
|---|---|---|
| KR | 1020050042792 A | 5/2005 |
| RU | 2425880 C2 | 10/2011 |
| WO | WO 1990/004036 A1 | 4/1990 |
| WO | WO 1991/000906 A1 | 1/1991 |
| WO | WO 1994/025585 A1 | 11/1994 |
| WO | WO 1998/024893 A2 | 6/1998 |
| WO | WO 2000/073323 A2 | 12/2000 |
| WO | WO 2002/012437 A2 | 2/2002 |
| WO | WO 2002/046237 A2 | 6/2002 |
| WO | WO 2002/066630 A1 | 8/2002 |
| WO | WO 2002/085944 A2 | 10/2002 |
| WO | WO 2004/049794 A2 | 6/2004 |
| WO | WO 2004/103404 A1 | 12/2004 |
| WO | WO 2004/106375 A1 | 12/2004 |
| WO | WO 2005/019463 A1 | 3/2005 |
| WO | WO 2005/028510 A2 | 3/2005 |
| WO | WO 2005/038001 A2 | 4/2005 |
| WO | WO 2005/042743 A2 | 5/2005 |
| WO | WO 2006/029459 A1 | 3/2006 |
| WO | WO 2006/117699 A2 | 11/2006 |
| WO | WO 2007/096779 A2 | 8/2007 |
| WO | WO 2007/117410 A2 | 10/2007 |
| WO | WO 2008/151081 A1 | 12/2008 |
| WO | WO 2009/013620 A2 | 1/2009 |
| WO | WO 2009/042589 A1 | 4/2009 |
| WO | WO 2009/076464 A2 | 6/2009 |
| WO | WO 2009/097006 A2 | 8/2009 |
| WO | WO 2009/143472 A2 | 11/2009 |
| WO | WO 2010/039900 A2 | 4/2010 |
| WO | WO 2011/004192 A1 | 1/2011 |
| WO | WO 2011/072204 A1 | 6/2011 |
| WO | WO 2011/158009 A1 | 12/2011 |
| WO | WO 2012/063048 A1 | 5/2012 |
| WO | WO 2012/141798 A1 | 10/2012 |
| WO | WO 2012/148873 A2 | 11/2012 |
| WO | WO 2013/022782 A1 | 2/2013 |
| WO | WO 2013/041844 A2 | 3/2013 |
| WO | WO 2013/041845 A2 | 3/2013 |
| WO | WO 2013/041846 A2 | 3/2013 |
| WO | WO 2013/045916 A1 | 4/2013 |
| WO | WO 2013/059230 A1 | 4/2013 |
| WO | WO 2013/061078 A1 | 5/2013 |
| WO | WO 2013/061098 A2 | 5/2013 |
| WO | WO 2013/079953 A1 | 6/2013 |
| WO | WO 2013/138680 A1 | 9/2013 |
| WO | WO 2013/144566 A2 | 10/2013 |
| WO | WO 2013/144567 A1 | 10/2013 |
| WO | WO 2013/171505 A2 | 11/2013 |
| WO | WO 2013/187953 A1 | 12/2013 |
| WO | WO 2014/130690 A1 | 8/2014 |
| WO | WO 2014/160202 A1 | 10/2014 |

OTHER PUBLICATIONS

Astellas Negotiates $295M License Extension to Regeneron's VelocImmune mAb Platform, Genetic Engineering & Biotechnology News, Jul. 28, 2010, 2 pages.

Austin et al. (2004) "The Knockout Mouse Project," Nature Genetics, 36(9):921-924.

Bando et al. (2004) "Characterization of VH gene expressed in PBL from children with atopic diseases: detection of homologous VH1-69 derived transcripts from three unrelated patients," Immunology Letters, 94:99-106.

Baseggio et al. (2010) "CD5 expression identifies a subset of splenic marginal zone lymphomas with higher lymphocytosis: a clinicopathological, cytogenetic and molecular study of 24 cases," Haematologica, 95(4):604-612.

Bendig (1995) "Humanization of Rodent Monoclonal Antibodies by CDR Grafting," Methods, 8:83-93.

Berberian et al. (1991) "A VH Clonal Deficit in Human Immunodeficiency Virus Positive Individuals Reflects a B-Cell Maturational Arrest," Blood, 78(1):175-179.

Biao et al. (2013) "Human antibody expression in transgenic rats: Comparison of chimeric IgH loci with human VH, D and JH but bearing different rat C-gene regions," Journal of Immunological Methods, 400:78-86.

Brezinschek et al. (1995) "Analysis of the Heavy Chain Repertoire of Human Peripheral B Cells Using Single-Cell Polymerase Chain Reaction," Journal of Immunology, 155:190-202.

Briney et al. (2012) "Human Peripheral Blood Antibodies with Long HCDR3s Are Established Primarily at Original Recombination Using a Limited Subset of Germline Genes," PLoS ONE, 7(5):1-13.

Brouwers et al. (2015) "Unexpected Phenotypes in Mouse Models Carrying the Human Growth Hormone Minigene to Enhance Transgene Expression," Journal of Steroids & Hormonal Science, 6(2):1-2.

Brüggemann et al. (1989) "A repertoire of monoclonal antibodies with human heavy chains from transgenic mice," PNAS, 86:6709-6713.

Brüggemann and Neuberger (1996) "Strategies for expressing human antibody repertoires in transgenic mice," Review Immunology Today, 192(17):391-397.

Brüggeman (2001) "Human Antibody Expression in Transgenic Mice," Archivum Immunologiae et Therapiae Experimentalis, 49:203-208.

Brüggemann (2004) "Human Monoclonal Antibodies from Translocus Mice," Molecular Biology of B Cells, Eds. Honjo, T. and Neuberger, M.S., New York, NY: Academic Press, pp. 547-561.

Butler, (1998) "Immunoglobulin diversity, B-cell and antibody repertoire development in large farm animals," Rev. Sci. Tech. Off. Int. Epiz., 17(1):43-70.

Carbonari et al. (2005) "Hepatitis C Virus Drives the Unconstrained Monoclonal Expansion of VH1-69-Expressing Memory B Cells in

(56) References Cited

OTHER PUBLICATIONS

Type II Cryoglobulinemia: A Model of Infection-Driven Lymphomagenesis," The Journal of Immunology, 174:6532-6539.
Chan et al. (2001) "VH1-69 gene is preferentially used by hepatitis C virus associated B cell lymphomas and by normal B cells responding to the E2 viral antigen," Blood, 97(4):1023-1026.
Charles et al. (2011) "A flow cytometry-based strategy to identify and express IgM from VH1-69+ clonal peripheral B cells," Journal of Immunological Methods, 363:210-220.
Cheval et al. (2012) Of Mice and Men: Divergence of Gene Expression Patterns in Kidney, PLoS One, 7(10):e46876 (12 pages).
Choi et al. (2004) "Characterization and comparative genomic analysis of intronless Adams with testicular gene expression," Genomics, 83(4):636-46.
Choi et al. (2011) "Expression of the metabotropic glutamate receptor 5 (mGluR5) induces melanoma in transgenic mice," PNAS, 108(37):15219-15224.
Chothia et al. (1992) "Structural Repertoire of the Human $V_H$ Segments," J. Mol. Biol., 227:799-817.
Clark et al. (2003) "A future for transgenic livestock," Nature Reviews Genetics, 4:825-833.
Davidkova et al. (1997) "Selective Usage of VH Genes in Adult Human B Lymphocyte Repertoires," Scand. J. Immunol., 45:62-73.
Defrancesco (1999) "Transgenic Mice that Produce Fully Humanized Antibodies—Abgenix Granted Patent," Bioprocess Online, 2 pages, Aug. 23, 1999.
Dennis (2002) "Welfare issues of genetically modified animals," ILAR Journal, 43(2):100-109.
De Wildt et al. (1999) "Analysis of heavy and light chain pairings indicates that receptor editing shapes the human antibody repertoire", J. Mol. Biol., 285(3):895-901.
Echelard, (2009) "Year of the ox," Nat. Biotechnol., 27(2):146-147.
Edwards et al. (2008) "The ADAM metalloproteinases," Molecular Aspects of Medicine, 29(5):258-89.
Fan "The Potential Role of VH Replacement in Editing and Generating Autoreactive Antibodies, A Dissertation," The University of Alabama (2009) 24-26 (http://www.mhsl.uab.edu/dt/2010r/fan.pdf).
Featherstone et al. (2010) "The Mouse Immunoglobulin Heavy Chain V—D Intergenic Sequence Contains Insulators That May Regulate Ordered V(D))J Recombination," Journal of Biological Chemistry, 58(13):9327-38.
Forconi et al. (2010) "The normal IGHV1-69-derived B-cell repertoire contains stereotypic patterns characteristic of unmutated CLL," Blood, 115(l):71-77.
Gallo et al. (2000) "The human immunoglobulin loci introduced into mice: V (D) and J gene segment usage similar to that of adult humans," Eur. J. Immunol., 30(2):534-540.
Gay et al. (1993) "Receptor Editing: An Approach by Autoreactive B Cells to Escape Tolerance," J. Exp. Med., 177:999-1008.
GENBANK Accession AAA53514.1; GI:553403, 1 page, first referenced Jul. 30, 1993, updated Nov. 23, 1994.
Giallourakis et al. (2010) "Elements between the IgH variable (V) and diversity (D) clusters influence antisense transcription and lineage-specific V(D)J recombination," Proceedings of the National Academy of Sciences of the USA, 107(51):22207-22212.
Glick and Pasternak (2002) Molekulyarnaya biotekhnologiya. Printsipy i primeneniye, Moscow Mir., 45-47, including English translation.
Gorman et al. (1996) "The IGK 3' Enhancer Influences the Ratio of IGK Versus IGL B Lymphocytes," Immunity, 5(3):241-252.
Han et al. (2009) "Comprehensive Analysis of Reproductive ADAMs: Relationship of ADAM4 and ADAM6 with an ADAM Complex Required for Fertilization in Mice," Biology of Reproduction, 80:1001-1008.
Harding and Lonberg (1995) "Class switching in human immunoglobulin transgenic Mice," Ann. N Y Acad. Sci., 764:536-546.
Hendricks et al. (2010) "Organization of the variable region of the immunoglobulin heavy-chain gene locus of the rat," Immunogenetics, 62(7):479-86.
Hoiruchi and Blobel (2005) Studies from Adam Knockout Mice, in Hooper and Lendeckel, The ADAM Family of proteases, Netherlands 2005, Springer (37 pages).
Huang et al. (1993) "A Majority of Ig H Chain cDNA of Normal Human Adult Blood Lymphocytes Resembles cDNA for Fegal Ig and Natural Autoantibodies," The Journal of Immunology, 151(10):5290-5300.
Johnson et al. (1997) "Ig VH1 Genes Expressed in B Cell Chronic Lymphocytic Leukemia Exhibit Distinctive Molecular Features," The Journal of Immunology, 158:235-246.
Ju et al. (2020) "Potent human neutralizing antibodies elicited by SARS-CoV-2 infection", bioRxiv preprint doi: https://doi.org/10.1101/2020.03.21.990770, pp. 1-42.
Kantor et al. (1997) "An Unbiased Analysis of VH-D-JH Sequences from B-1a, B-1b, and Conventional B Cells," The Journal of Immunology, 158:1175-1186.
Kenny, et al. (2000) Positive and negative selection of antigen-specific B cells in transgenic mice expressing variant forms of the VH1 (T15) heavy chain, International Immunology, 12(6):873-885.
Kim et al. (2006) "Expression and relationship of male reproductive ADAMs in mouse," Biology of Reproduction, 74(4):744-750.
Kong et al. (2009) "Transgene expression is associated with copy number and cytomegalovirus promoter methylation in transgenic pigs," PLoS One 4(8):1-10.
Kunert et al. (2004) "Characterization of Molecular Features, Antigen-Binding, and in Vitro Properties of IgG and IgM Variants of 4E10, an Anti-HIV Type 1 Neutralizing Monoclonal Antibody," Aids Research and Human Retroviruses, 20(7):755-762.
Kuroiwa et al. (2002) "Cloned transchromosomic calves producing human immunoglobulin," Nat. Biotechnol., 20(9):889-894.
Kuroiwa et al. (2004) "Sequential targeting of the genes encoding immunoglobulin-µ and prion protein in cattle," Nature Genetics, 36:775-780.
Lee et al. (2014) "Complete humanization of the mouse immunoglobulin loci enables efficient therapeutic antibody discovery," Nature Biotechnology, 32(4):356.
Lefranc et al. (2000) "Nomenclature of the Human Immunoglobulin Genes," Current Protocols in Immunology, A.1P.1-A.1P.37.
Lin et al. (1990) "Research of Immune Globulin in Mice," Guangzhou Medical Journal, 1:49-50, including English Translation.
Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).
Lonberg (2005) "Human antibodies from transgenic animals," Nature Biotechnology, 23:(9)1117-1125.
Lovell-Badge (2007) "Many ways to pluripotency," Nature Biotechnology, 25:1114-1116.
MacDonald et al. (2006) "Velocigene Technology Extended to Humanization of Several Megabases of complex Gene Loci," First International MUGEN Conference on Animal Models for Human Immunological Disease, Sep. 10-13, 2006—Athens, Greece, Abstract 21 and Poster, 2 pages original (pp. 3-11 are p. 2 of the original, enlarged).
MacDonald et al. (2014) "Precise and in situ genetic humanization of 6 Mb of mouse immunoglobulin genes," Proceedings of the National Academy of Sciences, 111(14):5147-5152.
Mageed et al. (2001) "Rearrangement of the human heavy chain variable region gene V3-23 in transgenic mice generates antibodies reactive with a range of antigens on the basis of $V_H$CDR3 and residues intrinsic to the heavy chain variable region," Clin Exp Immunol, 123:1-8.
Mahmoud et al. (2011) "Limiting CDR-H3 Diversity Abrogates the Antibody Response to the Bacterial Polysaccharide α 1 →3 Dextran," The Journal of Immunology, 187: 879-886.
Mahmoudi et al. "V region gene analysis of human IgM hybridoma monoclonal anti-Sm antibodies," Lupus, 6:578-589, 1997.
Manis et al. (2002) "Mechanism and control of class-switch recombination," TRENDS in Immunology, 23(1):31-39.
Marasca et al. (2001) "Immunoglobulin Gene Mutations and Frequent Use of VH1-69 and VH4-34 Segments in Hepatitis C Virus

(56) References Cited

OTHER PUBLICATIONS

Positive and Hepatitis C Virus Negative Nodal Marginal Zone B-Cell Lymphoma," American Journal of Pathology, 159(1): 253-261.
Matsuda et al. (1998) "The Complete Nucleotide Sequence of the Human Immunoglobulin Heavy Chain Variable Region Locus," J. Exp. Med., 188(11):2151-2162.
McGoldrick et al. (2013) "Rodent models of amyotrophic lateral sclerosis," Biochimica et Biophysica Acta, 1832:1421-1436.
Melton (2002) Chapter 8: Gene-Targeting Strategies, Methods in Molecular Biology, Transgenesis Techniques, 2nd Edition, Principles and Protocols, 180:19 pages.
Mendez et al. (1997) "Functional Transplant of Megabase Human Immunoglobulin Loci Recapitulates Human Antibody Response in Mice," Nature 15:146-156.
Miklos et al. (2000) "Salivary gland mucosa-associated lymphoid tissue lymphoma immunoglobulin VH genes show frequent use of V1-69 with distinctive CDR3 features," Blood, 95:3878-3884.
Moran (2013) "Mouse platforms jostle for slice of humanized antibody market," Nature Biotechnology, 31(4):267-268.
Mortari et al. (1993) "Human Cord Blood Antibody Repertoire," The Journal of Immunology, 150(4):1348-1357.
Muller et al. (1993) "B-Cell Abnormalities in AIDS: Stable and Clonally-Restricted Antibody Response in HIV-1 Infection," Scand. J. Immunol., 38:327-334.
Munoz et al. (2009) "Constraints to Progress in Embryonic Stem Cells from Domestic Species," Stem Cell Rev. and Rep, 5:6-9.
Murphy and Silha (2000) "Unexpected and unexplained phenotypes in transgenic models," Growth Hormone & IGF Research, 10:233-235.
Murphy PowerPoint (2009) BAC-based Modifications of the Mouse Genome: The Big and the Backward, Welcome Trust Advanced Course: Genetic Manipulation of ES Cells, 58 pages.
Murphy (2014) Declaration Under 37 C.F.R. §1.132, 4 pages.
Murphy et al. (2014) "Mice with megabase humanization of their immunoglobulin genes generate antibodies as efficiently as normal mice," Proceedings of the National Academy of Sciences, 111(14):5153-5158.
Nagle, Regeneron helps make Sanofi VelocImmune to its "weak pipeline". <http://www.outsourcing-pharma.com> Published Dec. 3, 2007.
Niemann et al. (2005) "Transgenic farm animals: present and future," Rev. sci tech Off. Int. Epiz., 24 (1):285-298.
Osborn et al. (2013) "High-Affinity IgG Antibodies Develop Naturally in Ig-Knockout Rats Carrying Germline Human IgH/IgK/Igλ Loci Bearing the Rat CH Region," J. Immunol., 190:1481-1490.
Pasqualini and Arap (2004) "Hybridoma-free generation of monoclonal antibodies," Proceedings of the National Academy of Sciences USA, 101(1):257-259.
Paul (1993) "Fv Structure and Diversity in Three Dimensions," Fundamental Immunology, Third Edition, pp. 292-295.
Perez et al. (2010) "Primary cutaneous B-cell lymphoma is associated with somatically hypermutated immunoglobulin variable genes and frequent use of VH1-69 and VH4-59 segments," British Journal of Dermatology, 162:611-618.
Popov et al. (1999) "A Human Immunoglobulin lambda locus is Similarly Well Expressed in Mice and Humans," J. Exp. Med., 189(10):1611-1619.
Pos et al. (2008) "VH1-69 germline encoded antibodies directed towards ADAMTSI3 in patients with acquired thrombotic thrombocytopenic purpura," Journal of Thrombosis & Haemostasis, 7:421-428.
Poueymirou et al (2007) "F0 generation mice fully derived from gene-targeted embryonic stem cells allowing immediate phenotypic analyses," Nat Biotechnol 25, 91-99.
Prelle et al. (2002) "Pluripotent Stem Cells—Model of Embryonic Development, Tool for Gene Targeting, and Basis of Cell Therapy," Anat. Histol. Embryol., 31:169-186.
Ramsden et al. (1994) "Conservation of sequence in recombination signal sequence spacers," Nucleic Acids Res., 22(10):1785-1796.

Ray (1991) "Ectopic expression of a c-kitW42 minigene in transgenic mice: recapitulation of W phenotypes and evidence for c-kit function in melanoblast progenitors," Genes Dev., 5(12A):2265-73.
Rodriguez et al. (2000) "High-efficiency deleter mice show that FLPe is an alternative to Cre-IoxP," Nature Genetics, 25:139-140.
Roebroek et al. (2003) "Chapter 10: Knockin Approaches," Methods in Molecular Biology, Transgenic Mouse Methods and Protocols, 209:16 pages.
Romo-González and Vargas-Madrazo (2005) "Structural analysis of substitution patterns in alleles of human immunoglobulin VH genes," Molecular Immunology, 42:1085-1097.
Rudikoff et al. (1982) "Single amino acid substitution altering antigen-binding specificity," PNAS 79:1979-1983.
Sasso et al. (1993) "A Fetally Expressed Immunoglobulin $V_H1$ Gene Belongs to a Complex Set of Alleles," Journal of Clinical Investigation, 91:2358-2367.
Sasso et al. (1996) "Expression of the Immunoglobulin VH Gene 51p1 Is Proportional to Its Germline Gene Copy Number" Journal of Clinical Investigation, 97(9):2074-2080.
Sasso et al., (1990) "Prevalence and Polymorphism of Human $V_h3$ Genes," Journal of Immunology, 145(8):2751-2757.
Schelonka et al. (2005) "A Single $D_H$ Gene Segment Creates Its Own Unique CDR-H3 Repertoire and Is Sufficient for B cell Development and Immune Function," Journal of Immunology, 175:6624-6632.
Schulze et al. (2006) "Derivation, Maintenance, and Characterization of Rat Embryonic Stem Cells in Vitro," Methods in Molecular Biology, 329:45-58.
Schwartz and Cantor (1984) "Separation of Yeast Chromosome-Sized DNAs by Pulsed Field Gradient Gel Electrophoresis," Cell, 37:67-75.
Seals et al. (2003) "The ADAMs family of metalloproteases: multidomain: proteins with multiple functions," Genes and Development, 17(1):7-30.
Shmerling et al. (2005) "Strong and ubiquitous expression of transgenes targeted into the β-actin locus by Cre/lox cassette replacement," Genesis, 42(5):229-235.
Sibilia et al. (1997) "Structural Analysis of Human Antibodies to Proteinase 3 from Patients with Wegener Granulomatosis," Journal of Immunology, 159:712-719.
Sigmund (2000) "Viewpoint: Are Studies in Genetically Altered Mice Out of Control?" Arteriscler. Thomb. Vasc. Biol., 20(6):1425-1429.
Sorrell and Kolb (2004) "Chapter XI: Targeted Modification of Mammalian Genomes," Focus on Genome Research, Nova Biomedical Books, New York, pp. 365-396.
Souroujon et al. (1989) "Polymorphisms In Human H Chain V Region Genes From The VHIII Gene Family," Journal of Immunology, 143(2):706-711.
Stevens et al. (2006) "Velocimmune: Humanization of Immunoglobulin Loc Using Velocigene Technology," First International MUGEN Conference on Animal Models for Human Immunological Disease, Sep. 10-13, 2016—Athens, Greece, Abstract 4 and Poster, 2 pages original (pp. 3-11 are p. 2 of the original, enlarged).
Storb et al. (1986) "Transgenic Mice with μ and κ Genes Encoding Antiphosphorycholine Antibodies," J. Exp. Med., 164:627-664.
Suarez et al. (2006) "Rearrangement of only one human IGHV gene is sufficient to generate a wide repertoire of antigen specific antibody responses in transgenic mice," Molecular Immunology, 43:1827-1835.
Sui et al. (2009) "Structural and functional bases for broad-spectrum neutralization of avian and human influenza A viruses," Nature Structural & Molecular Biology, 16(3):265-273.
Suzuki et al. (1995) "Representation of Rearranged $V_H$ Gene Segments in the Human Adult Antibody Repertoire," Journal of Immunology, 154:3902-3911.
Taki et al. (1993) "Targeted Insertion of a Variable Region Gene into the Immunoglobulin Heavy Chain Locus," Science, 262:1268-1271.
Taylor et al. (1992) "A transgenic mouse that expresses a diversity of human sequence heavy and light chain immunoglobulins," Nucleic Acids Research, 20(23):6287-6295.

(56) References Cited

OTHER PUBLICATIONS

Tiller et al. (2013) "A fully synthetic human Fab antibody library based on fixed VH/VL framework pairings with favorable biophysical properties," mAbs, 5(3):445-470 (http://www.tandfonline.com/loi/kmab20).

Timetable for Mouse ES Cells course at Wellcome Trust Sanger Institute Oct. 26, 2009-Nov. 8, 2009 (black and white), 5 pages original (pp. 6-13 are pp. 1-5 of the original, enlarged).

Timetable for Mouse ES Cells course at Wellcome Trust Sanger Institute Oct. 26, 2009-Nov. 8, 2009 (greyscale), 5 pages original (pp. 6-13 are pp. 1-5 of the original, enlarged).

Tobin et al. (2004) "Subsets with restricted immunoglobulin gene rearrangement features indicate a role for antigen selection in the development of chronic lymphocytic leukemia," Blood, 104:2879-2885.

Tong et al. (2010) "Production of p53 gene knockout rats by homologous recombination in embryonic stem cells," Nature Letters, 467:211-213.

Tuaillon (2000) "Repertoire analysis in human immunoglobulin heavy chain minilocus transgenic, [mu]MT/ [mu]MT mice," Molecular Immunology, 37(5):221-231.

Tuaillon et al. (1993) "Human immunoglobulin heavy-chain minilocus recombination in transgenic mice: Gene-segment use in μ and γ transcripts," PNAS, 90:3720-3724.

UniProtKB/Swiss-Prot Accession No. P23083, HV103_Human, 7 pages, integrated into UniProtKB/Swiss-Prot Nov. 1, 1991, last modified Nov. 11, 2015, last accessed Dec. 9, 2015 <http://www.uniprot.org/P23083>.

Vakil et al. (1991) "Antigen-Independent Selection of T15 Idiotype During B-Cell Ontogeny In Mice," Developmental Immunology, 1:203-212.

Valenzuela et al (2003) "High-throughput engineering of the mouse genome coupled with high-resolution expression analysis," Nat. Biotechnol. 21:652-659.

Wagner et al. (1994) "Antibodies generated from human immunoglobulin miniloci in transgenic mice," Nucleic Acids Research, 22(8):1389-1393.

Wagner et al. (1996) "Antibody Expression from the Core Region of the Human IgH Locus Reconstructed in Transgenic Mice Using Bacteriophage P1 Clones," Genomics, 35:405-414.

Wagner et al. (1994) "The diversity of antigen-specific monoclonal antibodies from transgenic mice bearing human immunoglobulin gene miniloci," European Journal of Immunology, 24:2672-2681.

Wang and Palese (2009) "Universal epitopes of influenza virus hemagglutinins?," Nature Structural & Molecular Biology, 16(3):233-234.

Wheeler, et al., (2001) "Transgenic Technology and Applications in Swine," Theriogenology, 56:1345-1369.

Widhopf et al. (2004) "Chronic lymphocytic leukemia B cells of more than 1% of patients express virtually identical immunoglobulins," Blood, 104:2499-2504.

Xu and Davis (2000) "Diversity in the CDR3 Region of VH Is Sufficient for Most Antibody Specificities," Immunity, 13(1):37-45.

Yamada et al. (1991) "Preferential Utilization of Specific Immunoglobulin Heavy Chain Diversity and Joining Segments in Adult Human Peripheral Blood B Lymphocytes," Journal of Experimental Medicine, 173:395-407.

Yantha et al. (2010) "Unexpected Acceleration of Type 1 Diabetes by Transgenic Expression of B7-H1 in NOD Mouse Peri-Islet Glia," Diabetes, 59:2588-2596.

Zhang et al. (1998) "A new logic for DNA engineering using recombination in *Escherichia coli*," Nature Genetics, 20:123-128.

Zhou et al., (2009) "Developing tTA transgenic rats for inducible and reversible gene expression," International Journal of Biological Sciences, 5:171-181.

Zou et al. (1994) Cre-IoxP-mediated gene replacement: a mouse strain producing humanized antibodies, Current Biology, 4:1099-1103.

International Search Report & Written Opinion with respect to PCT/US2012/026416, dated Jun. 25, 2012.

International Search Report & Written Opinion with respect to PCT/US2013/029624, dated Aug. 2, 2013.

International Search Report & Written Opinion with respect to PCT/US2014/017427 dated Aug. 1, 2014.

International Search Report & Written Opinion with respect to PCT/US2012/060487 dated Feb. 1, 2013.

PCT/US2013/029624 Invitation to Pay Additional Fees and Where Applicable, Protest Fee dated May 17, 2013, 9 pages.

EP1360287 Appeal Decision Mar. 10, 2016.

Extended European Search Report with respect to EP 14754019.9 dated Aug. 28, 2015.

Extended European Search Report with respect to EP 18158956.5 dated Jun. 8, 2018.

Final Office Action dated Dec. 1, 2017 with respect to U.S. Appl. No. 14/185,679.

Non-Final Office Action dated Oct. 30, 2015 with Respect to U.S. Appl. No. 14/137,902.

*Regeneron v. Merus B.V.* Opinion and Order Nov. 2, 2015 (114 pages).

UK Decision EP1360287 and EP2264163 Feb. 1, 2016.

Third Party Observations for European Patent Application No. 12783456.2 submitted on Mar. 12, 2014.

Third Party Observations with Respect to European Patent Application No. EP12783456.2, EPO Communication submitted on Feb. 25, 2015.

Third Party Observations with Respect to European Patent Application No. EP12783456.2, EPO Communication submitted on Jun. 22, 2016.

Canadian Office Action for Application No. 2,820,824, 3 pages, dated Aug. 5, 2014.

Statement of Relatedness under MPEP 2001.06 with Respect to U.S. Appl. No. 16/265,825 dated Feb. 1, 2021.

```
             10        20        30        40        50        60        70
VH1-69*01 CAGGTgCAGCTGGTGCAGTCTGGGGCTGAGGTGAAGAAGCCTGGGTCCTCGGTGAAGGTCTCCTGCAAGGCTTCT
VH1-69*02 CAGGTCCAGCTGGTGCAaTCTGGGGCTGAGGTGAAGAAGCCTGGGTCCTCGGTGAAGGTCTCCTGCAAGGCTTCT
VH1-69*03 CAGGTgCAGCTGGTGCAGTCTGGGGCTGAGGTGAAGAAGCCTGGGTCCTCGGTGAAGGTCTCCTGCAAGGCTTCT
VH1-69*04 CAGGTCCAGCTGGTGCAGTCTGGGGCTGAGGTGAAGAAGCCTGGGTCCTCGGTGAAGGTCTCCTGCAAGGCTTCT
VH1-69*05 CAGGTCCAGCTGGTGCAGTCTGGGGCTGAGGTGAAGAAGCCTGGGTCCTCGGTGAAGGTCTCCTGCAAGGCTTCT
VH1-69*06 CAGGTgCAGCTGGTGCAGTCTGGGGCTGAGGTGAAGAAGCCTGGGTCCTCGGTGAAGGTCTCCTGCAAGGCTTCT
VH1-69*07 -----------------------------------AGAAGCCTGGGTCCTCGGTGAAGGTCTCCTGCAAGGCTTCT
VH1-69*08 CAGGTCCAGCTGGTGCAaTCTGGGGCTGAGGTGAAGAAGCCTGGGTCCTCGGTGAAGGTCTCCTGCAAGGCTTCT
VH1-69*09 CAGGTgCAGCTGGTGCAGTCTGGGGCTGAGGTGAAGAAGCCTGGGTCCTCGGTGAAGGTCTCCTGCAAGGCTTCT
VH1-69*10 CAGGTCCAGCTGGTGCAGTCTGGGGCTGAGGTGAAGAAGCCTGGGTCCTCaGTGAAGGTCTCCTGCAAGGCTTCT
VH1-69*11 CAGGTCCAGCTGGTGCAGTCTGGGGCTGAGGTGAAGAAGCCTGGGTCCTCGGTGAAGGTCTCCTGCAAGGCTTCT
VH1-69*12 CAGGTCCAGCTGGTGCAGTCTGGGGCTGAGGTGAAGAAGCCTGGGTCCTCGGTGAAGGTCTCCTGCAAGGCTTCT
VH1-69*13 CAGGTCCAGCTGGTGCAGTCTGGGGCTGAGGTGAAGAAGCCTGGGTCCTCaGTGAAGGTCTCCTGCAAGGCTTCT
          CAGGTCCAGCTGGTGCAGTCTGGGGCTGAGGTGAAGAAGCCTGGGTCCTCGGTGAAGGTCTCCTGCAAGGCTTCT 80        90       100       110       120       130       140       150
VH1-69*01 GGAGGCACCTTCAGCAGCTATGCTATCAGCTGGGTGCGACAGGCCCCTGGACAAGGGCTTGAGTGGATGGGAGGG
VH1-69*02 GGAGGCACCTTCAGCAGCTATaCTATCAGCTGGGTGCGACAGGCCCCTGGACAAGGGCTTGAGTGGATGGGAaGG
VH1-69*03 GGAGGCACCTTCAGCAGCTATGCTATCAGCTGGGTGCGACAGGCCCCTGGACAAGGGCTTGAGTGGATGGGAGGG
VH1-69*04 GGAGGCACCTTCAGCAGCTATGCTATCAGCTGGGTGCGACAGGCCCCTGGACAAGGGCTTGAGTGGATGGGAaGG
VH1-69*05 GGAGGCACCTTCAGCAGCTATGCTATCAGCTGGGTGCGACAGGCCCCTGGACAAGGGCTTGAGTGGATGGGAGGG
VH1-69*06 GGAGGCACCTTCAGCAGCTATGCTATCAGCTGGGTGCGACAGGCCCCTGGACAAGGGCTTGAGTGGATGGGAGGG
VH1-69*07 GGAGGCACCTTCAGCAGCTATGCTATCAGCTGGGTGCGACAGGCCCCTGGACAAGGGCTTGAGTGGATGGGAaGG
VH1-69*08 GGAGGCACCTTCAGCAGCTATaCTATCAGCTGGGTGCGACAGGCCCCTGGACAAGGGCTTGAGTGGATGGGAaGG
VH1-69*09 GGAGGCACCTTCAGCAGCTATGCTATCAGCTGGGTGCGACAGGCCCCTGGACAAGGGCTTGAGTGGATGGGAaGG
VH1-69*10 GGAGGCACCTTCAGCAGCTATGCTATCAGCTGGGTGCGACAGGCCCCTGGACAAGGGCTTGAGTGGATGGGAGGG
VH1-69*11 GGAGGCACCTTCAGCAGCTATGCTATCAGCTGGGTGCGACAGGCCCCTGGACAAGGGCTTGAGTGGATGGGAaGG
VH1-69*12 GGAGGCACCTTCAGCAGCTATGCTATCAGCTGGGTGCGACAGGCCCCTGGACAAGGGCTTGAGTGGATGGGAGGG
VH1-69*13 GGAGGCACCTTCAGCAGCTATGCTATCAGCTGGGTGCGACAGGCCCCTGGACAAGGGCTTGAGTGGATGGGAGGG
          GGAGGCACCTTCAGCAGCTATGCTATCAGCTGGGTGCGACAGGCCCCTGGACAAGGGCTTGAGTGGATGGGAGGG 160       170       180       190       200       210       220
VH1-69*01 ATCATCCCTATCTTTGGTACAGCAAACTACGCACAGAAGTTCCAGGGCAGAGTCACGATTACCGCGGACGAATCC
VH1-69*02 ATCATCCCTATCcTTGGTAtAGCAAACTACGCACAGAAGTTCCAGGGCAGAGTCACGATTACCGCGGACaAATCC
VH1-69*03 ATCATCCCTATCTTTGGTACAGCAAACTACGCACAGAAGTTCCAGGGCAGAGTCACGATTACCGCGGACGAATCC
VH1-69*04 ATCATCCCTATCcTTGGTAtAGCAAACTACGCACAGAAGTTCCAGGGCAGAGTCACGATTACCGCGGACaAATCC
VH1-69*05 ATCATCCCTATCTTTGGTACAGCAAACTACGCACAGAAGTTCCAGGGCAGAGTCACGATTACCaCGGACGAATCC
VH1-69*06 ATCATCCCTATCTTTGGTACAGCAAACTACGCACAGAAGTTCCAGGGCAGAGTCACGATTACCGCGGACaAATCC
VH1-69*07 ATCATCCCTATCTTTGGTACAGCAAACTACGCACAGAAGTTCCAGGGCAGAGTCACGATTACCGCGGACGAATCC
VH1-69*08 ATCATCCCTATCcTTGGTACAGCAAACTACGCACAGAAGTTCCAGGGCAGAGTCACGATTACCGCGGACaAATCC
VH1-69*09 ATCATCCCTATCcTTGGTAtAGCAAACTACGCACAGAAGTTCCAGGGCAGAGTCACGATTACCGCGGACaAATCC
VH1-69*10 ATCATCCCTATCcTTGGTAtAGCAAACTACGCACAGAAGTTCCAGGGCAGAGTCACGATTACCGCGGACaAATCC
VH1-69*11 ATCATCCCTATCcTTGGTACAGCAAACTACGCACAGAAGTTCCAGGGCAGAGTCACGATTACCGCGGACGAATCC
VH1-69*12 ATCATCCCTATCTTTGGTACAGCAAACTACGCACAGAAGTTCCAGGGCAGAGTCACGATTACCGCGGACGAATCC
VH1-69*13 ATCATCCCTATCTTTGGTACAGCAAACTACGCACAGAAGTTCCAGGGCAGAGTCACGATTACCGCGGACGAATCC
          ATCATCCCTATCTTTGGTACAGCAAACTACGCACAGAAGTTCCAGGGCAGAGTCACGATTACCGCGGACGAATCC 230       240       250       260       270       280       290
VH1-69*01 ACGAGCACAGCCTACATGGAGCTGAGCAGCCTGAGATCTGAGGACACGGCCGTGTATTACTGTGCGAGAGAA
VH1-69*02 ACGAGCACAGCCTACATGGAGCTGAGCAGCCTGAGATCTGAGGACACGGCCGTGTATTACTGTGCGAGA---
VH1-69*03 ACGAGCACAGCCTACATGGAGCTGAGCAGCCTGAGATCTGAtGACACGGC-----------------------
VH1-69*04 ACGAGCACAGCCTACATGGAGCTGAGCAGCCTGAGATCTGAGGACACGGCCGTGTATTACTGTGCGAGAGAA
VH1-69*05 ACGAGCACAGCCTACATGGAGCTGAGCAGCCTGAGATCTGAGGACACGGCCGTGTATTACTGTGCGAGA---
VH1-69*06 ACGAGCACAGCCTACATGGAGCTGAGCAGCCTGAGATCTGAGGACACGGCCGTGTATTACTGTGCGAGAGAA
VH1-69*07 ACGAGCACAGCCTACATGGAGCTGAGCAGCCTGAGATCTGAG-----------------------
VH1-69*08 ACGAGCACAGCCTACATGGAGCTGAGCAGCCTGAGATCTGAGGACACGGCCGTGTATTACTGTGCGAGAGAA
VH1-69*09 ACGAGCACAGCCTACATGGAGCTGAGCAGCCTGAGATCTGAGGACACGGCCGTGTATTACTGTGCGAGAGAA
VH1-69*10 ACGAGCACAGCCTACATGGAGCTGAGCAGCCTGAGATCTGAGGACACGGCCGTGTATTACTGTGCGAGAGAA
VH1-69*11 ACGAGCACAGCCTACATGGAGCTGAGCAGCCTGAGATCTGAGGACACGGCCGTGTATTACTGTGCGAGAGAA
VH1-69*12 ACGAGCACAGCCTACATGGAGCTGAGCAGCCTGAGATCTGAGGACACGGCCGTGTATTACTGTGCGAGAGAA
VH1-69*13 ACGAGCACAGCCTACATGGAGCTGAGCAGCCTGAGATCTGAGGACACGGCCGTGTATTACTGTGCGAGAGAA
          ACGAGCACAGCCTACATGGAGCTGAGCAGCCTGAGATCTGAGGACACGGCCGTGTATTACTGTGCGAGAGA
```

FIG. 13

| | | 10 | 20 | 30 | 40 | 50 | 60 |
|---|---|---|---|---|---|---|---|
| VH1-69*01 | | QVQLVQSGAEVKKPGSSVKVSCKASGGTFSSYAISWVRQAPGQGLEWMGGIIPIFGTANY |
| VH1-69*02 | | QVQLVQSGAEVKKPGSSVKVSCKASGGTFSSYAISWVRQAPGQGLEWMGrIIPIlGiANY |
| VH1-69*03 | | QVQLVQSGAEVKKPGSSVKVSCKASGGTFSSYtISWVRQAPGQGLEWMGrIIPIFGiANY |
| VH1-69*04 | | QVQLVQSGAEVKKPGSSVKVSCKASGGTFSSYAISWVRQAPGQGLEWMGGIIPIFGTANY |
| VH1-69*05 | | QVQLVQSGAEVKKPGSSVKVSCKASGGTFSSYAISWVRQAPGQGLEWMGrIIPIlGiANY |
| VH1-69*06 | | QVQLVQSGAEVKKPGSSVKVSCKASGGTFSSYAISWVRQAPGQGLEWMGGIIPIFGTANY |
| VH1-69*07 | | -------KPGSSVKVSCKASGGTFSSYAISWVRQAPGQGLEWMGrIIPIlGiANY |
| VH1-69*08 | | QVQLVQSGAEVKKPGSSVKVSCKASGGTFSSYtISWVRQAPGQGLEWMGrIIPIlGiANY |
| VH1-69*09 | | QVQLVQSGAEVKKPGSSVKVSCKASGGTFSSYAISWVRQAPGQGLEWMGrIIPIlGiANY |
| VH1-69*10 | | QVQLVQSGAEVKKPGSSVKVSCKASGGTFSSYAISWVRQAPGQGLEWMGGIIPIlGiANY |
| VH1-69*11 | | QVQLVQSGAEVKKPGSSVKVSCKASGGTFSSYAISWVRQAPGQGLEWMGGIIPIFGTANY |
| VH1-69*12 | | QVQLVQSGAEVKKPGSSVKVSCKASGGTFSSYAISWVRQAPGQGLEWMGGIIPIFGTANY |
| VH1-69*13 | | QVQLVQSGAEVKKPGSSVKVSCKASGGTFSSYAISWVRQAPGQGLEWMGGIIPIFGTANY |

| | | 70 | 80 | 90 | 100 |
|---|---|---|---|---|---|
| VH1-69*01 | | AQKFQGRVTITADESTSTAYMELSSLRSEDTAVYYCARR |
| VH1-69*02 | | AQKFQGRVTITADESTSTAYMELSSLRSEDTAVYYCARR |
| VH1-69*03 | | AQKFQGRVTITADkSTSTAYMELSSLRSEDTAVYYCARR |
| VH1-69*04 | | AQKFQGRVTITADkSTSTAYMELSSLRSEDTAVYYCARR |
| VH1-69*05 | | AQKFQGRVTITADkSTSTAYMELSSLRSEDTAVYYCARR |
| VH1-69*06 | | AQKFQGRVTITADtSTSTAYMELSSLRSEDTAVYYCARR |
| VH1-69*07 | | AQKFQGRVTITADkSTSTAYMELSSLRSEDTAVYYCARR |
| VH1-69*08 | | AQKFQGRVTITADESTSTAYMELSSLRSDDT------ |
| VH1-69*09 | | AQKFQGRVTITADESTSTAYMELSSLRSE------ |
| VH1-69*10 | | AQKFQGRVTITADESTSTAYMELSSLRSEDTAVYYCARR |
| VH1-69*11 | | AQKFQGRVTITADESTSTAYMELSSLRSEDTAVYYCARR |
| VH1-69*12 | | AQKFQGRVTITADESTSTAYMELSSLRSEDTAVYYCARR |
| VH1-69*13 | | AQKFQGRVTITADESTSTAYMELSSLRSEDTAVYYCAR |

FIG. 14

| $V_H$1-69 Allele | 01 | 02 | 03 | 04 | 05 | 06 | 07 | 08 | 09 | 10 | 11 | 12 | 13 |
|---|---|---|---|---|---|---|---|---|---|---|---|---|---|
| 01 | 100 | 94.9 | 91.8 | 95.9 | 99 | 99 | 77.6 | 95.9 | 95.9 | 96.9 | 98 | 100 | 100 |
| 02 | 95.9 | 100 | 86.7 | 99 | 93.9 | 95.9 | 74.5 | 99 | 99 | 98 | 96.9 | 100 | 94.9 |
| 03 | 92.9 | 88.8 | 100 | 87.8 | 90.8 | 90.8 | 82.4 | 87.8 | 87.8 | 88.8 | 89.8 | 91.8 | 91.8 |
| 04 | 95.9 | 100 | 88.8 | 100 | 94.9 | 96.9 | 75.5 | 98 | 100 | 99 | 98 | 95.9 | 95.9 |
| 05 | 100 | 95.9 | 92.9 | 95.9 | 100 | 98 | 76.5 | 94.9 | 94.9 | 95.9 | 96.9 | 95.9 | 95.9 |
| 06 | 99.0 | 96.9 | 91.8 | 96.9 | 99 | 100 | 76.5 | 96.9 | 96.9 | 98 | 96.9 | 99 | 99 |
| 07 | 77.6 | 75.5 | 83.5 | 75.5 | 77.6 | 76.5 | 100 | 75.5 | 75.5 | 74.5 | 77.6 | 77.6 | 77.6 |
| 08 | 96.9 | 99 | 89.8 | 99 | 96.9 | 98 | 76.5 | 100 | 98 | 96.9 | 98 | 95.9 | 95.9 |
| 09 | 95.9 | 99 | 88.8 | 100 | 95.9 | 96.9 | 75.5 | 99 | 100 | 99 | 98 | 95.9 | 95.9 |
| 10 | 96.9 | 98 | 89.8 | 98 | 96.9 | 98 | 74.5 | 98 | 99 | 100 | 96.9 | 96.9 | 96.9 |
| 11 | 98 | 96.9 | 90.8 | 95.9 | 98 | 96.9 | 77.6 | 99 | 98 | 96.9 | 100 | 98 | 98 |
| 12 | 100 | 95.9 | 92.9 | 95.9 | 100 | 99 | 77.6 | 96.9 | 95.9 | 96.9 | 98 | 100 | 100 |
| 13 | 100 | 95.9 | 92.9 | 95.9 | 100 | 99 | 77.6 | 96.9 | 95.9 | 96.9 | 98 | 100 | 100 |

% Identity / % Similarity

```
         10        20         30        40        50
VH1-2*01 QVQLVQSGAEVKKPGASVKVSCKAS GYTFTGYYM HWVRQAPGQGLEWMGr
VH1-2*02 QVQLVQSGAEVKKPGASVKVSCKAS GYTFTGYYM HWVRQAPGQGLEWMGW
VH1-2*03 QVQLVQSGAEVKKPGASVKVSCKAS GYTFTGYYM HWVRQAPGQGLEWMGW
VH1-2*04 QVQLVQSGAEVKKlGASVKVSCKAS GYTFTGYYM HWVxQAPGQGLEWMGW
VH1-2*05 QVQLVQSGAEVKKPGASVKVSCKAS GYTFTGYYM HWVRQAPGQGLEWMGr
VH1-2*06 QVQLVQSGAEVKKPGASVKVSCKAS GYTFTGYYM HWVRQAPGQGLEWMGW 60        70        80        90
VH1-2*01 INPNSGGT NYAQKFQGRVTsTRDTSISTAYMELSRLRSDDTVVYYCAR
VH1-2*02 INPNSGGT NYAQKFQGRVTMTRDTSISTAYMELSRLRSDDTAVYYCAR
VH1-2*03 INPNSGGT NYAQKFQGRVTMTRDTSISTAYMELSRLRSDDTAVYYCAR
VH1-2*04 INPNSGGT NYAQKFQGwVTMTRDTSISTAYMELSRLRSDDTAVYYCAR
VH1-2*05 INPNSGGT NYAQKFQGRVTMTRDTSISTAYMELSRLRSDDTVVYYCAR
VH1-2*06 INPNSGGT NYAQKFQGRVTMTRDTSISTAYMELSRLRSDDTAVYYCAR
```

FIG. 17

| $V_H$1-2 Allele | 01 | 02 | 03 | 04 | 05 |
|---|---|---|---|---|---|
| 01 | 100 | 96.9 | 94.9 | 95.9 | 99.0 |
| 02 | 96.9 | 100 | 98.0 | 99.0 | 98.0 |
| 03 | 94.9 | 98.0 | 100 | 96.9 | 95.9 |
| 04 | 95.9 | 99.0 | 96.9 | 100 | 96.9 |
| 05 | 99.0 | 98.0 | 95.9 | 96.9 | 100 |

% Identity / % Similarity — $V_H$1-2 Allele

FIG. 18

SEQUENCE LISTING

<160> NUMBER OF SEQ ID NOS: 81

<210> SEQ ID NO 1
<211> LENGTH: 872
<212> TYPE: DNA
<213> ORGANISM: Homo sapiens
<220> FEATURE:
<223> OTHER INFORMATION: synthetic

<400> SEQUENCE: 1

```
gcaggattta gggcttggtc tctcagcatc ccacacttgt acagctgatg tggcatctgt    60 gtttctttc tcatcgtaga tcaggctttg agctgtgaaa taccctgcct catgcatatg     120
caaataacct gaggtcttct gagataaata tagatatatt ggtgccctga gagcatcaca    180
taacaaccac attcctcctc taaagaagcc cctgggagca cagctcatca ccatggactg    240
```

```
gacctggagg ttcctctttg tggtggcagc agctacaggt aagggcttc ctagtcctaa      300 ggctgaggaa gggatcctgg tttagttaaa gaggatttta ttcaccctg tgtcctctcc      360 acaggtgtcc agtcccaggt gcagctggtg cagtctgggg ctgaggtgaa gaagcctggg    420
tcctcggtga aggtctcctg caaggcttct ggaggcacct tcagcagcta tgctatcagc    480
tgggtgcgac aggcccctgg acaagggctt gagtggatgg gagggatcat ccctatcttt    540
ggtacagcaa actacgcaca gaagttccag ggcagagtca cgattaccgc ggacgaatcc    600
acgagcacag cctacatgga gctgagcagc ctgagatctg aggacacggc cgtgtattac    660
tgtgcgagag acacagtgtg aaaacccaca tcctgagagt gtcagaaacc ctgagggaga    720
aggcagctgt gccgggctga ggagatgaca gggtttatta ggtttaaggc tgtttacaaa    780
atgggttata tatttgagaa aaaaagaaca gtagaaacaa gtacatactc ctctaatttt    840
aagataatta ttccattcaa gagtcgtaat at                                   872
```

<210> SEQ ID NO 2
<211> LENGTH: 118
<212> TYPE: PRT
<213> ORGANISM: Homo sapiens
<220> FEATURE:
<223> OTHER INFORMATION: synthetic

<400> SEQUENCE: 2

```
Met Asp Trp Thr Trp Arg Phe Leu Phe Val Val Ala Ala Ala Thr Gly
1               5                   10                  15

Gly Val Gln Ser Gln Val Gln Leu Val Gln Ser Gly Ala Glu Val Lys
            20                  25                  30

Lys Pro Gly Ser Ser Val Lys Val Ser Cys Lys Ala Ser Gly Gly Thr
        35                  40                  45

Phe Ser Ser Tyr Ala Ile Ser Trp Val Arg Gln Ala Pro Gly Gln Gly
    50                  55                  60

Leu Glu Trp Met Gly Gly Ile Ile Pro Ile Phe Gly Thr Ala Asn Tyr
65                  70                  75                  80

Ala Gln Lys Phe Gln Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg
        115
```

<210> SEQ ID NO 3
<211> LENGTH: 99294
<212> TYPE: DNA
<213> ORGANISM: Artificial Sequence
<220> FEATURE:
<223> OTHER INFORMATION: synthetic

<400> SEQUENCE: 3

```
aagcttatct ctctgttgct cagactcatc taggaatttc agaaatttct gttctagcat     60
ctcttccagc ttttgtctcc aaccctcatt ctcttctttc tttttttttt taaattatat    120
gttctctgtc ttttaaaaa acttttaaa attaggtatt tatgtcattt acatttccaa      180
tgctatccca aaagtcccac ccacgctccc caacccacta tcccacccac ccactcccac    240
ttcttggccc tggcattcac agtgtactga gacatataaa gtttgcacaa ccaatgggcc    300 tctcttttcca ctgatggccg actaggccat cttctgatac atatgcagct agagacacga   360
```

```
gattctgggg gtactggtta gttcatattg ttgttccacc tatagggttg cagatccttt     420
tagctccttg ggtactttct ctagctcctc cattggggc cctgtgatcc atccaatagc      480
tgactgtgag catccacttc tgtgtttgct aggccccaga tagtctcaca agagacagct    540
atatctgggt cctttcagca aaatcttgct agtgtatgca acggtgtcag agtttggaag    600
ctgattatgg gatggatccc cggatatggc attctctagt tggttcatcc ttttgtctca    660
gctccaaact ttgtctctgt aactccttcc atgggtgttt tgttcccagt tctaaggagg    720
ggcaaagtat ccacactttg gtcttcattc ttcttgagtt tcatgtgttt tgcaaattgt    780
atcttatatc ttgggtattc taagtttctg ggctaatatc cacttatcag tgagtacaca    840
ttgtgtgagt tcttttgtga ttgggttacc tcactcagta tgatgccctc caggtccatc    900
catttgccta ggaatttcat aaattcattc tttttaatag ctcagtagta ctccattgtg    960
tagatgtacc acattttctg tattcattcc tctgttgagg ggcatctggg ttctttccag   1020
cttctggcta ttataaataa ggctgctatg aacatagtgg agcatgtgac cttcttaccg   1080
gttgggacat cttctggata tatgcccagg agaggtattg ctggatcttc cggtagtact   1140
atgtccaatt ttctgaggaa ctgacaaact gatttccaga gtggttagta ccagcttgca   1200
atcccaccaa caatgagagg agtgttcgtc tttctccaca tcctcaccag catgctgctg   1260
tcacctgaat ttttgatgct tagccattct gactggtgtg aggtggaatc tcagggttgt   1320
tttgatttgt atttccctga tgattaagga tgctgaacat tttctcaggt gcttctcagc   1380
cattcagtat tctttaggtg agaattcttt gtttagctct aagccccatt tttttaatgg   1440
ggttatttga ttttctggag tccaccttct tgagttttttt tttccatttt ttattacata   1500
atttcctcaa ttacatttcc aatgctatcc caaaagtccc ccatacccctc ccccccccaa   1560
ttccctaccc accccttccc attttttggg ccctggcgtt ccctgtact ggggcatata     1620
aagtttgtgt gtccaatggg cttctctttc cagtgatggc tgactaggcc atcttttgat   1680
acatatgcag ctagagtcaa gagctcccgg gtactggtta gttcataatg ttgttccacc   1740
tatagggttg cagatcccctt tagcttcttg ggtactttct ctagctcctc cattgggagc   1800
cctgtgatcc atccaatagc tgactgtgag catccacttc tgtgtttgct aggccccggc   1860
atagtctcac aagagacagc tacatctggg tccttttgat aaaatcttgc tagtgtatgc   1920
aagggtgtca gcatttggaa gctgattatg gggtggatcc ctggatatgg cagtctctac   1980
atggtccatc cttttgtctc agctccaaac tttgtctctg taacttcttc catgagtgtt   2040
ttgttcccaa ttctaaggag gggcatagtg tccacacttc attcttcatt cttcttgagt   2100
ttcatgtgtt tagcaaattg tatcttatat cttgggtatc ctaggttttg ggctaatatc   2160
cacttatcag tgagtacata ttgtgtgagt tcctttgtaa atgtgttacc tcactcagga   2220
tgacgccctc caggtccatc catttggcta ggaatttcat aaattcattc tttttaatag   2280
ctgagtagta ctccattgtg taaatgtacc acattttctg tactcattcc tctgttgagg   2340
ggcatctggg ttctttatag gttctggcta ttataaataa ggttgctatg aacatagtgg   2400
agcatgtgtc cttcttaccg gttgagacat cttctggata tatgcccagg cgaggtattg   2460
ctggatcctc cggtagtact atgtccaatt ttctgaggaa ctgccagact gatttccaga   2520
gtggttgtac aagcctgcac tctcaccaac aatggaggag tgttcctctt tctccacatc   2580
cacgccagca tctgctgtca cctgaatttt tgatcttagc cattctgact ggtgtgaggt   2640
ggaatctcag ggttgttttg atttgcattt ccctgatgat taaggatgtt gaacattttt   2700
ttcaggtgct tctctgccat tcggtattcc tcaggtgaga attctttgtt cagttctgag   2760
```

```
ccccattttt taatggggtt atttgatttt ctgaagtcca ccttcttgag ttctttatat    2820
atgttggata ttagtcccct atctgattta cgataggtaa agatcctttc ccaatctgtt    2880
ggtggtcttt ttctcttatt gacggtgtct tttgccttgc agaaactttg gagtgagttc    2940
tttatatata ttggatatta gtccccctatc tgatttagga taggtaaaga tccttccca    3000 atctgttggt gaccttttg tcttattgac ggtgtctttt gccttgcaga atctttgcaa    3060
ttttatgagg tcgcatttgt caattctcga tcttacagca caagtcattg ctgttctgtt    3120
caggaatttt tcctctgtgc ccatatcttc gaggctttta cctgctttct cctctatatg    3180
tttgagtgtc tctggtttaa tgtggagttc cttaatccac ttagatttga ccttagtaca    3240
aggagatagg aatggatcaa ttcgcattct tctacatgat aaccgctagt tgtgccagca    3300
ccatttgttg ataatgctgt cttttttcca ctggatggtt tttgctccct tgtctaagat    3360
caagtgacca taggtgtgtg ggttcatttc tgggtcttca attctatttc attggtctac    3420
ttgtctgttg ttataccagt accatgcaga ttttatcaca attgctctgt agtagagttt    3480
taggtcaggc atggtgatta caccagaggt tttttttatc cttgagcaga gttttgcta    3540 tcctaggttt tgtgttattt cagatgaatt tgcagattgc cctttccagt tcgttgaaga    3600
attgagttgg aattttgatg gggattgcat tgaatctgta gattgctttg gcaatatagc    3660 cattttact atattgatcc tgccaatcca tgagcatggg agatctttcc atcttctcaa    3720
atcttcttta atttctttct tcagagactt gaagttcttg tcatacagat ctttcacttc    3780
cttagttaga gtcacgctaa ggtatttat attattgtg actattgaga agggtgttgt    3840
ttccctaatt tctttctcag cctgtttatc ctttgtgtac agaaaagcca ttgacttgtg    3900
ttagttaatc tcatatccag ctacttcact gaagcggttt atcaggttta ggagttctct    3960
ggtgtaattt ttagggtcac tcatatatac tatcatatca tctgcaaaaa gtgacatttt    4020
gacttcttcc tttccaattt gtatcccctt gatctccttt tgttgtcgaa ttgctctggc    4080
aaggacatca agtactatat tgaataggta gggagaaaat cggcaccctt gtctagtccc    4140 tgatttagt aggattgctt caagtttctc accatttact ttgatgttgg ctactggttt    4200
gctgttgaat gcttttatc atgtttaggt atgggccttg aattcctgat cttttccaaga    4260 ctttatcat gaaagggtgt tggattttgt caaatgcttt ctccagcctt tcattctgag    4320
gttgtgtctg tcttttttccc tgagatgggt ttcctgtaag cagcaaaatg ttgggtcctg    4380
tttgtgtagc ccgtctgtta ttctatgtct ttttattggg gagttgagtc cattgatatt    4440
aagatatatt aaggaaaagt aattgttgct tcctattatt tttgttttta aagttggcat    4500
tctgttcttg tggctgtctt cttttaggtt tgttgaagga ttcctttctt gcttttccta    4560
ggtcgtggtt tccatccttg tattcatttt ttttctgtta ttatcctttg aaggactgga    4620
ttcatggata gataatgtgt gaatttggtt ttgtcttgga atacttttgt ttctccatct    4680
acggtaattg agagtttggc tgggtatagt agcctgggct ggcaattgtg ttgtcttagt    4740
gtctatataa tgtctgtcca ggatcttctg gctttcatag tctgtggtga aaaatctggt    4800
gtaattctga taggcttgcc tttatatgtt acttgaattt ttcacttact gcttttaata    4860
ttctttcttt atttagtgca tttgttgttc tgattattat gtgtcgggag gaatttcttt    4920
tctggtccag tctatttgga gttctgtagg cttcttgtat gttcacgggc atctctttct    4980
ttaggtttgg gaagttttct tctataattt tgttgaagat atttgctggc ccttcaagtt    5040
gaaaatgttc attctcatct actcctatta ttcgtatggt tggtcttctc attgtgtcct    5100
```

```
ggatttcctg gatgttttga gttaggatct ttttgcattt tccattttct ttgattgttg    5160
tgcagatgtt ctctatggaa tcttctgcac ctgatattct ctcttccatc tcttgtagtc    5220
tgttgctgat gctcgcatct atggttccag atttctttcc tagggtttct atctccagtg    5280
ttgccccact ttgggttttc tgtatagtgt ctacttccct ttttagatct agtatggttt    5340
tgttcatttc catcacctgt ttgggtgtgt tttcctgttt ttctttaaag acttgcaact    5400
ctttagcaga gttctcctgt atttaagtga gttattaaag tccttcttga tgtccagtac    5460
cataattgtg agatatgcct ttaaatccaa gtctaggttt ttgggtgtgt tggggtgccc    5520
tggactggct gagttgggag tgctgcattc tgatgatggt gagtggtctt ggtttctgct    5580
agtaagattc ttacatctgc ctttcgccat ctggtaatct ctggagtcag ttgttaaagt    5640
tgtctctggt taaagcttgt tcctctcgtg attctgttat tctcttccag cagacctggg    5700
agactagctc tttcctgagt ttcagtggtc agagcactct ctgcaggcag gatttcctct    5760
ttcagggaag gtgcacagat atctggtgtt cagatttgcc tcctggcaga agatgatggc    5820
ctgaaacagg acctgtccca gaagctgtta gcttctgtag tcaacactgt cacctgtgca    5880
gactagtctc ggtggagtcc gggaaccaag atgtctcctg cagatgctct ggcattccct    5940
tctgggccgg gtgatcacct ctcctctggc agggaaggtg ccctggtgtc tggaacccga    6000 aaaggggggct gcctcagaag ctctgtggct actgcctgtc ccagaagctg ttagcttctg    6060
tagtccacac tctcacctgt gcagactagt cttggtggag tctgggaacc aagatgtctc    6120
ccgcagatgc tccagccatt ctcctctttc tgttgcttat tttgacctat gaaatcctgg    6180
acatatagtt ctagtgttgc ttgtaatctc ttttctaagc caaggaattt ttttttatcta    6240 gggcacaatc ttttgagaag acatattaaa tcaagagaat aaatattgca agaccaataa    6300
atgataaggt atctattttc tttaaatcca tcgctgtcaa accattcaaa atatcctcac    6360
ataaagccaa aaagatattt attgtgtttc ccatcttagt tgagttcaag tcaatatttt    6420
ggtgccattt tgttgcagta aatctctaac acaaatatgc ctgggcaatg aaaacacaac    6480
tcagttaata tgaatacaga ttgttcagat ctaccactac actaccatct tcttcatcta    6540 agagaccct tagaacttgc agtttctcca ggccttgtgc ttctgcgctg ctttttcttct    6600 tcttcctctt ctacattgct tctctcataa acctacttct ttttttcccct ccttctgttc    6660 catcttccct tttatctgcc caatcattag ctctcccttta ttttacaaat taaggtgtga    6720
agccggtttc taggaaatca cctgagtgct gacttgttcc ttgttcagag ccacgcacag    6780
gagaacagaa ttaacatcaa atataattat ccccagggct atccacaaca cgtgcatcct    6840
ataagatcac cacggactaa tgctggtctt caattacaac ataaacaaca aaacccac      6900 atatatgtgg aaacaaatcg aactatacaa agaatcaatg aaaccaggag cttgttcttt    6960
gagaaaaatc aacaagatag ataaacccctt agccagacta accagagggc acagagacag    7020
tatccaaatt aataaagtca gaaatgaaag gaagacataa caatgaaata tatcttaaaa    7080
taattaatct gtttgtagac tattagcagt tgaaaatatt aaaatcatgt tctacaaacg    7140
tggaattatt attgataatt ttctcactgt gcttgaaatt agcattttct taatgtttaa    7200
cttcaaagag tttttgctat tttgaaatat taaacatata cttactgata aaataatttc    7260
cctcctaaca acactgataa tctttttta agtaaactga ttattagaca atgtacacag    7320
atatataatg tgttttaaat actctcccac tgtcaggtgg tatcatatag ggcctttgaa    7380 tatatttta aatgtattat ttgtaatatt ttatggtctc tcctatgctt atttctgaaa    7440
gaatattttg tatgttttga aacaatttag tatttaacat tagatatagg atcctcagtt    7500
```

```
atggatagta ttaaatattc attaatgata tttttaaggt ataaaaggat atgaatataa    7560
aagtttaaca aattttatgt attatttgat tctaaaaata ctcaatatta ttaatatgtt    7620
tgatgtttaa aatgcattta aataataaaa acatttaaaa aaataaaatc aagaaatgag    7680
gttctaagca gaggtcaagg aaaatgagga atagaaaat agtaaaaatc aatatgtcca     7740
tttattcaag gaaagctcct acatagacat tgcaccagat tagcaaatat tatggtcctc    7800
atattagttt aagttaggag actatgctta tgttatctat ttacattcta aggagcctag    7860
acatttgtga atggattaca ttataagagg aggatgtcta cttaagtagg catgaacgcc    7920
tgtgcattgc accctatgag ttccatcagc attccatgat tggagtatga agaacagcat    7980
tatagacatt acccagaacc ttagtggttc tagaatgcca agataaaaca atctaacctt    8040
ctggatagta gggataaatg ttcctatatc atcagaattc actggtgccc tgaggatgtt    8100
accctgctaa ctgacaattc acaggacatc acatggattc tgataagttg cagaaaagag    8160
gagatgcatt caattggtcc tcctccttct aagctgcaat attaggtgca tccaatttgt    8220
gaacttcaat ttagattaca atagacatga ataatctgaa ttcatgtagt acatattttt    8280
gttttaatat gagttaccat tgttcagaaa attaaataca catgatcaca tattcctaca    8340
tagtgctgtt agttttttcac atctctggga caatattcca aatatctcct tcattagtga    8400
aaatatcaac tactgtaaag cttagctaac atgcctttgc aggaataaga acatcctgga    8460
ttgaaagcta cacagggaga tgtaaaactt tctaagcaca cacattctcc atccattagg    8520
atcatggtcc atgagatttt tctctctctc ttcttcccat taaatgcatg tacatgcagg    8580
ttgggaaaca gattgtgttg cagaatacat ttgcttgatt tccacttcct tctcaatgca    8640 aatattttg aagtgttaat tttgctgtga gtaccacagt ggttcttgct ctttctgttg     8700
actcctgtct gtgaatgttc caggaattca cacatggaca cacgtggggc tgcatctgag    8760
ctccagactc actgttgtcc ttctgtcctc agctgctctg gcccaggcac agcctcgtga    8820
attcaacaaa gaccctgatc tctcttgttt acacctcatt acaaatggga actgttagag    8880
gtggacccaa ctgcatttcc atgaggaaag cacatgagtt tgagagggtc gttgatgata    8940
aggtagaaac aactttaatt cataggctga gatatcagtc atcacctcca gataaacaag    9000
agccatttct tcctgcatct gagccctgta agcacactag ctttaggaat atgttactgc    9060
tgaagtcaga ttgggcaact tcatagtata caatagaaaa tctacctgca gatgagttca    9120
gaaccagcag ggggcacaat ggggccaaga atccctagca gagagatgtg gtgtgtgtgc    9180
aggggactct gcatcctctg tggtttcctt tcttaactta catgtacctg tagtgattga    9240
catgtaacgt ttccacgctc aaacactgtg aagatacttt gctaaacact tcaaagattt    9300
atgttttctt gatgtgtgca tgtgtgtatt cttttttgtt tttagacaca gggtttctct    9360
gtgtagtcct ggctgccctg gaactcactc tgtagaccag gctggcctcg aactcagaaa    9420
tctgcctgct tctgcctccc aagtgctgaa gttaaagaca tgtgccacca ttgcctggcc    9480
atgtgtgtat tcttgatgca ctcttctgtt gacagataca cagtttattt ccataattta    9540
tttattgtga tggtgctgca ataatcactt atgtacaaat gtttctgaag tatatttagt    9600
tttggtcatt tgggtgatta ttttttttctt tctagtatat agcatttggg aaaggtagat    9660
attaattgta tgtatgggaa ggaggctgta aattctaata acttagctgc ttttgaaatt    9720
tgtcctcaat tctatcatcc ttgtaaccac cttaaatcca tctattagcc ttgtcacaag    9780
tgagccactg tctcaggctg caaatctttt tatagattag gtcgtgatgt tacatccaca    9840
```

```
gcctctgcac aatgctcagg ggtgggatat gggatgaatt ccctcagaca gcattaggac      9900
ttggatctca gcagactgat tcttgaccca aatgtctctt cttctctagc aggagtaagt      9960
ccttatctaa gatgtactct gctcatgaat atgcaaatca attgagtcta tggtggtaaa     10020
tatagggatg tctacacccc tcaaaaactt aagatcactg tcgtcttcac agtcacagga     10080
gtacacagga catcaccatg tgttggagct gtatcatcct cttcctgtta gcaacagctg     10140
cacgtaaggg gcttcagta gcaggcttga ggtctggcca tacactcatg tgacaatgac      10200
atccactctg tccttcccctt cacaggtgtg cactcccagg tccagctgca gcagtctggg    10260
gctgagctgg tgaggcctgg ggcctcagtg aagatttcct gcaaggcttt tggctacacc    10320
ttcacaaacc atcatataaa ctgggtgaag cagaggcctg acagggcct ggactggatt      10380 ggatatatta atccttataa tgattatact agctacagaa ccagaagttc aagggcaagg    10440
ccacattgac tgtagacaaa tcctccagca cagcctatat ggagcttagc agcctgacat    10500
ctgaggactc tgcagtctat tactgtgcaa gacacagtgc tacaaacaca tcctgagtgt     10560
gtcagaaacc ctggaggaga agcaagcaga gctggaatgg agatgacaga aagattatca    10620
tttagacttg ctcagaaaga gaaattttga atgcccattt attgcctctt ccttacagta    10680
ctatagtgcc tgtttttgtt gacattttca aactaatttc caaagtcact accacaattt    10740
acaatcacat aaaaagcaag caaggataac attattttct gtgcttactt gccatttata    10800
ttcttgctta ttctcatctc actgaggtca tattgggaca ttaaatttct ggggttactt    10860
tttattaaaa atttttcatt attcattcac tttacatcct tctagtcttc ctctcacaca    10920
tgccctatcc ctttctcctc tgagaggatg gagcccctccc tacccctcgta tcccttacc   10980 caggcacatc aagtgtctgc agtactagga atattctctg tcaatgctgc cagacaaggc    11040
agacaagtta ggggatcagg attcacagga aggcaacagc ttgagggaca gcccccactg    11100
aagttattgg tggattcaca tgaagactga gttgcacatc tgctacatat attcaggggt    11160
cctatttaca gctcaagtag actcttgttg gtggtttagt ctcttagaac cccaagtgtc    11220
caggttagtt gactctgtgg gtcttccttt ggagttccta tcccctccag atccctcagt    11280
tcttctccca actcttccat aagacacccg taggtccatc caatgttttgg ttttgggttt    11340 ttctgcatct gcttcagtca gctgctgggt ggagcatctc tgaggataat tatgagaagc    11400
tcttatgtgc aagcataaca ggatatcatt attagtgtca gggactggtg cttggccatg    11460
ggatgggtct caagtttggt cagttatttg gccattccca cagtctctga taatctttgt    11520
ccctgcattt cttgtagaca ggaaaaatat tgggttgaaa gttttgtggg tgggttggcg    11580
tctctattgc tccactgggc ttctttctgg atataggagt ttgcctcttc aggttccata    11640
ttcccaaagt agtgtgtcac actaaggtca ctcccataca gagggacact cattctcttg    11700
ccacgtctct gtccacctttc attggacctg aggttcctga atcatacaga actgcatgtg    11760
tgcaaccaca cagaacaagg ctatctatca gaggcctacc ataccaggac catcaaggtt    11820
caccttactc ccaatactga ctacaaaaag aacatcaagg accaatgcag tctatatgga    11880
taaacacact tgaaagaaca caaacaagat tgagggcaac atgacacctc caaagcatac    11940
ctaaccgagt acagcatgcc ctggatatcc taacacaatc aaaacacaag aaagttacct    12000
taaatccagt cttataaagg tgatgaaggc ctttaaatag gaaatgaatt aatccttagg    12060 ataatcagg acaatacatt cgaacagata gaggtctttta ggaggaaaga aataaatccc    12120
tcaaagacat acatgaaaat acaattaaac aggtgaaagt aataactaca atggtgtaag    12180
acctaaaaat ggaaatagaa gcaataaagt aacacaaact tagaatcttg aaggtggaaa    12240
```

```
acctagagaa caggaatact agatgcaagg atgatatctt ctaggtccat ccatttgctt   12300
gcacaattta tcatgtcctt gcttttaata gttgaacagt atttcattgt ttaaatgaac   12360
cacatgttct gtctccattc tctggatgag ggggtgagca agttttttcca cattctggct   12420 attacaaata gagctgctat gaacctagta gaaaacatat cctgtgtatg gtggagagtt   12480
ttggagtata tcaccaagag tgttatagct gggtcttcat gtagaactat tcctaatttt   12540
ctgagaaatc ccaagtcaga tttctagaat ggttgttcaa gtgttcactc caaccatcaa   12600
tggaggactg ttttccttgc cagcatgtgc tgtattttga gttttttgatc ctagccagtt   12660 ttatcctgca tttcacactt agatatggac tatggtacag gacagagaga aaccaacctt   12720
ctactcacca ggatattcta cctgctacca atttatttat ttatttattt atttatttat   12780
ttatttattt atttatttat attagagaac aacaccatgc agtttagaag aagtactaag   12840
acgtcagtga tgttatactg tgcctaacct tgcattgtac aatctcagct ttcaggtaag   12900
acagtgcatg actcttatgc agtgccaact gttttctgat tgtatttatg gtctattgcc   12960
taggaatgac ctcctctcaa ataaacatgg tcaaaagccc atggcctgag atgacagagc   13020
ccctagtaga ccctagttgt atttctgaag tttagatatc ataatgactt ataaatactt   13080
atgtttatac aatagattag agctgctctc agccatgacc aaggagcttc tgtgttcaat   13140
gaataatgat tgatgcagac attcgtgagt ggtcaaagtg gtgagaatga ttagagagtc   13200
ctcagccaca caagcgttaa tgatatgaac tttccaatat attaactgta ttaatgaata   13260
aatgcagaca tcatatgaga tctcattagt agttcttagg tattgcattt ttatatacaa   13320
ttatgcatat cagtacatta tagtgtataa aggaaattgt ctagcataat agagaaaaat   13380
aggacagtca agaaacaaaa gagtagaaat tatgggtgaa atatgcagtg tgaaatattt   13440
acatgaaaat tttaaccata tgtaaaattg ttattttttgt ttttcagaat gagtttgctc   13500
attctttgac attttttattc ctgtgtgaaa tatatcagga tcatatgtat cccattctga   13560
tggtctgact tccactggga atttccaata tatctcttcc aactaactga ccagtttctt   13620
tttttcttat tttctctctt tctcgttttg ttttgctttg ttttgttttt caagacaggg   13680
tttctctgtg tagctctggc tgtcctggaa ctcactttgt agatcaggct ggcttcgagc   13740
tcataaatcc acttgcctct gcctcctgag tgctgggatt aaaggagtgg ctaccacgcc   13800
cggctagttt ttttttttct tataagaaca acatttactg gatggtcact tacatattca   13860
gaggttcagt caattattat caaggcagaa gcatggcagt ggtccagtag tcatggcact   13920
ggggaaggag ctgagagatc tacatcttgc tccaaaggga agaggaata gtctgacttc   13980 catgtgtttc agaggagggt ttcatttccc accccccacag tgacacactt cctccaacac   14040
ggccacacct cctaatattg ccactcttgg atcaagcata ttcacaccac aaaggaaagt   14100
ttagagataa acattaagaa aattaatgaa gtcattttat cttatatgct caacatgact   14160
agtacttaaa accataattt tacatgtaca atatttcatg gcataacata tttttttatat   14220 ttttattaga tattttcttt atttatattt caaatgtgat acctttccc aattcccctc   14280 caaaaatccc ctatgccttc ccctcatagc cagctcccaa acccaccac tcctgctttc   14340 tggtcctggc attcccctat actggggcat aaaaccttca caggaccaag tgcctcttct   14400
ccattgatgg ccaattaggc catcctctgc tacatatgca gctagagcca tgagttccac   14460
catgtgtttt ctttgattgg tggtttagtt ccagggagct ctgggggtat tggttagttc   14520
atattgttcc tcctatgggg ctgcaaaccc tttcagcccc ttgggtattt tttctagctc   14580
```

```
cttcattggg gaccctgtgc tccatccaat ggatgagtga gcctccactt ttgtatttgt  14640
caggaactgg cagagtctct caggagacaa ttatatcagg ctcctgtcag caaaatctcg  14700
ttggcatctg caatagtgtc tgggtttggt ggttgtttat gggatggatt tctgggtggg  14760
gcagtctctg gattgtcatt cctttagtct ctgcttccac ctttgtcttt gtaactccat  14820
ccatgggtat tttgttcccc cttcaaagaa ggatcaaaat atccacactt tagtcttcct  14880
tcttcttgag tctcatgtgt ttttcaaatt gtatcttggg tattctgagc ttctaggcta  14940
atatccactt atcagtgagt gattatcatg tctgttcttt tgtgattgag ttacctcact  15000
tagcatgata tcctccaggt ctatccattt gtctaagaat ttcataaagt cattgtcttt  15060
aatagctgca tcgtactcaa ttgtgtaaat gcaccacatt ttctttatcc attcctctgt  15120
tgagggacac ttggttttc ccagcttctg gttattataa ataaggctgc tatgaacata  15180
gtggaacatg tgtccttagt acatgttgga acatcttctg ggtatatgcc caggagtggt  15240
attgctggat cttctggtgg tactatgtcc aaatttttgg ggaaccatca aactgatttc  15300
ctgagtggtt gtacaagctt gcaatcccac accagcaata gtggaatgtt catctttgtc  15360
caagtccttg ccagcatctg ctgtcacctg agtttttgat cttagccatt cttactggtg  15420
tgaggtggaa tcttggggtt gttttgattt gcatttccct gatgtttaag ggttttgaac  15480
atttttaggt gcttattaga catttggtat tcctcagttt agaaatcttt gtttagctct  15540
gtaccacatt tttgaatagg gttatttggt tttctggagt ctaacttctt gagttctttg  15600
tacatattgg atattagccc tctatcagat ttagaattag taaggatctt tccccaaact  15660
gttggtggtt cttttgtctt attgacagtg tactttgcct tagagaagct ttgcaatttt  15720
atgaggtccc atttgtcaat tcttgatctt atagtacaag ccattggtct tttgttcagg  15780
aattttcccc atgtgtccat atgttcaagg catttcccca ctttctccac tacaagtttt  15840
agtgtctctg gttttatgtg gaggtccttg atccacttag atttgagctt tgtacaagga  15900
gataagaatg gatagattca cattcttcta catgctctct gccagttgag ctagcaccat  15960
ttgttgaaaa tgctgtcttt ttttttccccc actggatggt ttttagctct tttggccaag  16020
atcaagtgac cattggtgtg tgggttcatt tcttggtctt caattctagt tcactgactt  16080
acctgtttgt cactgtacaa ggaccatgca gcttttttca caattgctct gtagtacagc  16140
ttgaggtctg ggatggtgat tctaccagag agattctttt actgttgtga ataattttg  16200 ctatcatagg atattttttt atttcagatg aatttacaaa ttgctctttc taactctgtg  16260
aacaattgag ttggaatttt gattgtgatt gctttgaata tcaagatat aatttacaaa  16320 acacatgaaa cttaacaagg actactaaag tgcagatact tcgatccttc ttagaagggg  16380
gaacaaaata cccatagatg gagttacaga gacaaagttc ggagcagaga ctataggaac  16440
gaccatccag aggtccacct ggggatccat catgtaaaca accacccaaa acagacacta  16500
ttgtggatgc caagaagaac ttgctgacag gagtctgata tagctgtctc ttgagaggct  16560
ctgccagggc ctcagaaagt ggaggctcac agccatccat tggatggagc acagggtccc  16620
caatgaagga gctagagaaa gtactcaagg agctgaaggg gtttgcagcc ccataggagg  16680
aacaacaata tgaactaacc agtacccca gagctccctg ggactaaacc accaatcaaa  16740
gaaaacacat ggagggactt gaagctcttg ctgcatttat agcagaggat ggcctagatg  16800
gtcatcaatg ggaggagagg tcaatggtcc tgggaaggtt ccatgcccca gtataggga  16860 atgccagggc caggaagcag gagtgggtgg gctgggatc agggagggg agatgatagg  16920 gcatttttcag tggggaaact aggaaagagg ataacattta aaatataaat aaagaaaata  16980
```

```
tctaattaaa aaggattacc tatgtgcatg ggagctcatg agcagcaggg gtcactctaa    17040
ggccaataat ccacatagag cgatgagctg tgtgtgaaca ggactctgta tcctctgtgg    17100
tttcctttct taagtgtatt aactgatctg tccagctgtg attgacatgt gatgtctcca    17160
tgctcaagcc cagtaaagat tctctgttaa ataccttaca gacttatgtt tacttgtttt    17220
tatttgcttt tcatatttt ttaaaaagtc atacaatgta ttctaataac tcattctccc    17280
atctccaatt tattctaagt tttcttaac tcatccaacc acacacttt taattctgat    17340 aaagcacccc ccccccaaa aaaaaccca accaaccaaa aaaaaaaaa gccaaggaat    17400 ttaaaagggg attgaaagca aataaaaact aaacaaaaaa gtaaaaacta cacacacaca    17460
cacacacaca cacacacaca cacacacaca cacacactca cacacacaca cacacaccac    17520
acacacacac acccatgcac gaacacacac acacacacac acacacacac acacacacac    17580
acacacacac acacatggaa tccagtaaaa ccacaactct ttacccatga tacacaggaa    17640
aatataagtc aaacaaacag aatggaagaa ggtggtatta taaaaatgtc tgcacaaata    17700
ccattaagtt cattttcttg ttggctacca actgctaagc ctgtctccct tgattaattg    17760
tgcttatcat ccctatgaa ctccattgga ggacactaat ttttccttct gtctccagga    17820
attgaagtgt tgcagaactc tcagtagctt tatttacctg cacaatacag cctctaatcc    17880
aaccagtgaa aattaccaca tgagagactt ccaaatgaaa gaacaggtaa agttgtctac    17940
tggcaagctt agtaatatca tgtaaatgcc ttagaattta atgacatatg tcatcctctg    18000
aggttaataa atccattttg gtgcatatat accctgaact caccactaac ataatacaac    18060
aattaaaaaa ttccaacatg gatgcagagg aatccctgag ggacatttgt tgatttgtga    18120
gcacaatata attattttt gggggggaaa tgtctgaatg ttaactcttt accagtgata    18180
atctattcta ttaatgtgta cataggtagc actaattaaa atcactgtgt tatcaggtaa    18240
tgaaacagag gaagtaggat gctgggaaac agacttttgg aaggtcccaa gggaaaccac    18300
agggacctag tggtgataga ttatggtgag agtcctgaga gtggtcatag attatagcat    18360
atttcatatg caattgaaaa tttcaaagaa tgaaaatcct tatgaaatat agaaataaca    18420
actttactta tgtacatata cttcatagta caatttttac actgtgcata tttctcctgt    18480
aacatctggt tcctcctatt ttcctttatt ctcctagaca atttcactga tacaatctca    18540
tgtttttgta taaatagttg tatataacta ttaaatacat aagctgttaa tgagtcttca    18600
ttaatgtctg tgatttttt attgtcttaa ttaatactat tatctctaat tgcatccaca    18660
ttttcaaaag caatgtaaat ttcttactca tttctgttca aaaacttctg ttgttgtatc    18720
attaccatgc cttagtgata aaatcctttc ttgacacatc tatagctatt gctataattt    18780
agttattgat gatcctcctg caataatcat tgataggtaa atattttaag cacttttact    18840
tttagtcatt ttagtgagat ttgaagtagt atataacctg ttggaaaggc aaatattaat    18900
tccatatatg tgaaagaaga cgctaaaact aaaaacatta gccactttta gatatcttct    18960
ccttcttctt cttcttcttc ttcttcttct tcttcttctt cttcttcttc ttcttcttct    19020
tcttcttctt cttcttttct tcttcttctt ctccttctcc ttcctcttct ccttctcctt    19080
ctcctcttcc tcctccttcc ttccttcctt ccttccttcc ttccttcctt ccttccttcc    19140
ttccttcctt ccttccttcc ttccttcctt ccttccttcc ttccttcctt ccttccttcc    19200
ttcctttctt tctttctttc tttctttctt tctttctttc tttctttctt tctttctttc    19260
tttctttctt tctttctttc tttctttctt ctcctcctcc ttctttttcc ttctccttcc    19320
```

```
ccttcacctt ccccttcctt cctctttccc ttccccttct ccttctcctc aatctacaat    19380
ctgttaacat attaacatgt cccagagtag agcaacagac tcaggtcaaa catctactga    19440
gaaatttgcc catgtagtta acatctacag catctgtcta ggggttacaa aaagtctatg    19500
ggatacaatt cctcagaaag gaataggatt tggacctgag catactgctg cctaacacat    19560
gaaatggcag ttcttctcca gctggactag gtccttaact aagaaatgca ctgctcatga    19620
atatgcaaat tacccaagtc tatggcagta aatacagaga tgtccacacc ctgaagacaa    19680
cctatgaaca atgttctctc cacagtccct gaagacactg attctaggac cgaagttcct    19740
attccgaagt tcctattctc tagaaagtat aggaacttct cgcgcgtctg cctccgagg    19800 cctccgcgcc gggttttggc gcctcccgcg ggcgccccc cctcacggc gagcgctgcc    19860 acgtcagacg aagggcgcag cgagcgtcct gatccttccg cccggacgct caggacagcg    19920
gcccgctgct cataagactc ggccttagaa ccccagtatc agcagaagga cattttagga    19980
cgggacttgg gtgactctag ggcactggtt ttctttccag agagcggaac aggcgaggaa    20040
aagtagtccc ttctcggcga ttctgcggag ggatctccgt ggggcggtga acgccgatga    20100
ttatataagg acgcgccggg tgtggcacag ctagttccgt cgcagccggg atttgggtcg    20160
cggttcttgt ttgtggatcg ctgtgatcgt cacttggtga gtagcgggct gctgggctgg    20220
ccggggcttt cgtggccgcc gggccgctcg gtgggacgga agcgtgtgga gagaccgcca    20280
agggctgtag tctgggtccg cgagcaaggt tgccctgaac tgggggttgg ggggagcgca    20340
gcaaaatggc ggctgttccc gagtcttgaa tggaagacgc ttgtgaggcg ggctgtgagg    20400
tcgttgaaac aaggtggggg gcatggtggg cggcaagaac ccaaggtctt gaggccttcg    20460
ctaatgcggg aaagctctta ttcgggtgag atgggctggg gcaccatctg ggaccctga    20520 cgtgaagttt gtcactgact ggagaactcg gtttgtcgtc tgttgcgggg gcggcagtta    20580
tggcggtgcc gttgggcagt gcacccgtac ctttgggagc gcgcgccctc gtcgtgtcgt    20640
gacgtcaccc gttctgttgg cttataatgc agggtggggc cacctgccgg taggtgtgcg    20700
gtaggctttt ctccgtcgca ggacgcaggg ttcgggccta gggtaggctc tcctgaatcg    20760
acaggcgccg gacctctggt gaggggaggg ataagtgagg cgtcagtttc tttggtcggt    20820
tttatgtacc tatcttctta agtagctgaa gctccggttt tgaactatgc gctcggggtt    20880
ggcgagtgtg ttttgtgaag ttttttaggc accttttgaa atgtaatcat ttgggtcaat    20940
atgtaatttt cagtgttaga ctagtaaatt gtccgctaaa ttctggccgt ttttggcttt    21000
tttgttagac gtgttgacaa ttaatcatcg gcatagtata tcggcatagt ataatacgac    21060
aaggtgagga actaaaccat gggatcggcc attgaacaag atggattgca cgcaggttct    21120
ccggccgctt gggtggagag gctattcggc tatgactggg cacaacagac aatcggctgc    21180
tctgatgccg ccgtgttccg gctgtcagcg caggggcgcc cggttctttt tgtcaagacc    21240
gacctgtccg gtgccctgaa tgaactgcag gacgaggcag cgcggctatc gtggctggcc    21300
acgacgggcg ttccttgcgc agctgtgctc gacgttgtca ctgaagcggg aagggactgg    21360
ctgctattgg gcgaagtgcc ggggcaggat ctcctgtcat ctcaccttgc tcctgccgag    21420
aaagtatcca tcatggctga tgcaatgcgg cggctgcata cgcttgatcc ggctacctgc    21480
ccattcgacc accaagcgaa acatcgcatc gagcgagcac gtactcggat ggaagccggt    21540
cttgtcgatc aggatgatct ggacgaagag catcaggggc tcgcgccagc cgaactgttc    21600
gccaggctca aggcgcgcat gcccgacggc gatgatctcg tcgtgaccca tggcgatgcc    21660
tgcttgccga atatcatggt ggaaaatggc cgcttttctg gattcatcga ctgtggccgg    21720
```

```
ctgggtgtgg cggaccgcta tcaggacata gcgttggcta cccgtgatat tgctgaagag   21780
cttggcggcg aatgggctga ccgcttcctc gtgctttacg gtatcgccgc tcccgattcg   21840
cagcgcatcg ccttctatcg ccttcttgac gagttcttct gaggggatcc gctgtaagtc   21900
tgcagaaatt gatgatctat taaacaataa agatgtccac taaaatggaa gttttcctg    21960
tcatactttg ttaagaaggg tgagaacaga gtacctacat tttgaatgga aggattggag   22020
ctacggggt ggggtgggg tgggattaga taaatgcctg ctctttactg aaggctcttt     22080
actattgctt tatgataatg tttcatagtt ggatatcata atttaaacaa gcaaaaccaa   22140
attaagggcc agctcattcc tcccactcat gatctataga tctatagatc tctcgtggga   22200
tcattgtttt tctcttgatt cccactttgt ggttctaagt actgtggttt ccaaatgtgt   22260
cagtttcata gcctgaagaa cgagatcagc agcctctgtt ccacatacac ttcattctca   22320
gtattgtttt gccaagttct aattccatca gacctcgacc tgcagcccct agagaagttc   22380
ctattccgaa gttcctattc tctagaaagt ataggaactt cctagggttt caccggttaa   22440
atggcatgtc ccctgttagt ggttcatgca agcagaagct gtatcctgtt tgacaaagat   22500
tcagcatgaa aggtcctgct acctaaaaaa aaatagacag atgagattta attaacctaa   22560
ataattttt tcacaacaac agagtgaata cgcaatttac agaatgacag aaaacttttg   22620
cacactttgc ctgtgacagg gaactaatat gaagaatttg caaggaactc aaacaactct   22680
acaacaacaa cagcaacaag aaccaaataa ctccgttaaa atgagcaaag gacatgagta   22740
gacattttca aaagaacaca tagaaatgga taataaatat ataaacaata ctcaacatca   22800
ctaaccatca gggaaatgca aattaaaacc acaataagat atcatcttcc accagtcaca   22860
atgactatta ctaaaaactc aaataatatc agatgttgct gaggatggga aatgaaggca   22920
actcttagac attgttgatg aggatgtaga tgagtacaac ctctgtggaa aatggtatgg   22980
agatttccca gaaaactaga aatagaactg tcatttggtc cagcaatccc actactgggt   23040
aactacccaa aggaaaataa actattattt caaaaagata cccaccttct atgcttacca   23100
taaaactact ctcaatagca catatgtcaa actgagtgtc tgccaaccga tgattttata   23160
aaagaatata gcatgtatgc acaattcaat actagtcagc cacaataagg aatgaaactg   23220
tgtcttttgc agcaagatgc atagaagtgg gggacaatat aattagtgaa ctaactcaca   23280
aacagaatgt cacatgtcac acattattac ttgtaagtgg gaggtaaaca gcgtgtacac   23340
aaggatttgt agagagaaat tacacacatt ggagacttac aaggatgggc gggcagaagg   23400
tgggagcatg atgagtcatt acataacagg cacaatataa aataattaag aattgaccaa   23460
tgatcttaaa attaaaatgt agaatatgat caataaatga acttgatatt agttgacctc   23520
attaaattta aaaactttt ctactcaaat gactgtaaga aaatgaatgc ccggttacag    23580
atgagaaact gtttgcgagt caaataacca ccaatgtaac tataataaga aacttcagaa   23640
ctcaactgtg aataaaaaag aaacaactga tggataaatt aggcaagggt ttctacagac   23700
atttcgtcaa agaagatgtg cagatgacac tgaagcatat aaacaggatc tcaacaggat   23760
tttccgttag agaaattcaa atcaagcccg caaagagaca ccactgtaca ctttttaaaa   23820
tggctgaaat taagaagaaa tacagataac atcaatgctg gtgagcatac caggttgcta   23880
gaggctaaaa cattgctaac aggaatgcaa aatgaaacag atactcagga aaataatttt   23940
tagttttctc taaaatcaaa catacccctta acacctgaat atttgcatca gagaaaaaca   24000
atcttacatt cacgcataac ttctattcaa atattcaaga tatcgtgtgt atgtgtgtta   24060
```

```
gaaagtaaaa ataacataaa tgtctcaaaa tttgaatagg tgaagaacta ggaagcatct   24120
ataaattgaa taccaccagc aataaaaaaa taacaagtga ccgatacata aactattaca   24180
ggtgaactcc agacattgtg ctaagtgaga aagccagtc tcaaagatca aagggacaca    24240
gctgtaagca ccacggtcat cctcaggtgt cagtggtttg ggctggactt tctgtgtctc   24300
tttcctgacc agacccagat attgagctcc accacttgca gatggaaaat cctattttca   24360
accatgcagt gaggtttgaa ctgcttcaca gactgaacga aacaaacacg ggctcctttg   24420
aacagcgtcc ggcatttgtt ccaaccacaa gagaacgtcc ctcagctctc ccacctcctc   24480
ggttctctcc tgcaagccag cagccctgca gtttagcctg catctcccgt gcatccaccc   24540
atctccctcc aagcaccttc ccccacaccc tccactgttt ctgagagcac aggcaggctt   24600
tgaacttttc cgcattctgt tgttattgaa gttaggatgt ttaggaccaa cttaaggatc   24660
atattttatg actgaattcc agtgcccctt ctctcctggg acagagtgca taaccaagtt   24720
tctgcaggtg gagacgaagt tgagcttttt tcttcctcag cctaggagat gagcgctaat   24780
tggagggttg gcagaagctt cccaccatcc cagcactttg gttctggtgg ggcggaatcg   24840
gtgccatagg gcagagctag aaaccgcgga ctgaatgttc ccagtggcac tggacccagg   24900
gcagagcctc catccacgag tggggctcta tggaagaagt gagtctctgg ctctcagtag   24960
ctctcgtcca gcactgaacc tcagcatcat gtgctgtgtg cagggtcaga gggccaacgt   25020
actggcccct gggaaagcgt ttcctctggt gggagttggt agaaggtgtc ctgtcttctt   25080
ggctgcatct gtccgcagtg gagtttacat catgctgagc tgggatgtgg aaggaaggaa   25140
gagcatctta gatcaaatat gatgactggc cttactgagt tttctagatt ttcctgaata   25200
aatgtttctt cactcactgt gtgctgttag agtcttttcca aacctgtaat ttcccaaaat   25260
aattttcact ggtctcatga gggcatggat tcattgagcc cctcatgctg tcaaagagaa   25320
atagaactgt tttttttttt cacttcatag cgaacatcca tgggttatca ataatgggc    25380 tggcttttct tccaacactt tacagacacc atcaattttc ttcttgctta taaggtttta   25440
accagaagaa tgctgtcatg gtcttttctg ttcttttgga aggaatgccc cctctactca   25500
cctccacttg tctgcctgta tttctatttg tctttggttt tcaacaattt taataagatt   25560
tacctaaatg tgtgtggggg gagcatgggg tgttattctg ctgttctgtg ttctctgaga   25620
tgcatggatt caccatttac tctgtctcca tttttgtgaa aacaattaga aaaaagtca    25680 gtatgagccc agaaacaagc ctccctgaag tgggcacagg accacctggg ggcgctcagg   25740
acccactgaa cacaagagcc agccccaggg caggtgcaga tgcgggttaa gttctggttt   25800
cctgtcaacc ctgtggcttc ctctccataa aacagtttcc tttgtggcat atctctggat   25860
tccttatcct gttcttcctg tgaagtctct gaagaagaaa catttgtcgt aacaagagaa   25920
aaactttctc acatgcacca aaggcagagt cacctacagt cacttactcc tgtttctcaa   25980
tgtcaataag ttaccaatgc ttctgaagtt aatcagctaa atctataaaa ggtgcggtgt   26040
ttaactcagc attacagccc agctcaacag aactccaaag gtcagccagc agcagccagg   26100
aaaaagtgca tgctgggcat tggggcagag ggagttacca tccagtgcaa gagaagaaag   26160
cccccgtggt ggtcattgtc aggactccaa tcccacagtt ccaattgtag gtgatgccag   26220
gcaaaggaag agagacccca ccaatggtta gtgtggatgt cgagtttgat gtttccacac   26280
tcacactcca ggtgaatatg aaaagattta ttagctctat ttctgaggtg tctgctgaga   26340
gcagcacagt cctctcaaga aattacagat tggaatttcc tcagtagagc aggaaaggag   26400
gctggctcag ggctttataa tgatttggtg gtggggtcgg cggggggggg gggcgtttc    26460
```

```
tactcaggag aaggagcttg tgtgatttaa acctcacact gacatcacat gagggagctt    26520
ccatgatttc ttactagatt tcccatgtgt gggggacaag gatgagggag aataaacctt    26580
aattcatcag catcaaggca ccaaaaatag gacctgacac tttattctcc ctagcagctt    26640
aagaaaatga gtgaaaaaga gagataagag tccacccatg tgctgaaaag catagctctt    26700
ggtaaagacg agaaaaaggc actcctacga agaaggggtt gggcagaagc tttatgctga    26760
agggtttggc taaagagaca taatcaacag gttacaggag gggctactga tgttcatgga    26820
ggtggtcctc acacatgcat actgaacaaa catgtctgta acgtatgacc cctgttcact    26880
taccagtgga gacttagcat ttaaattcat tccagtcagg ccctatgtgc aaacagcaga    26940
agcagagaca caaaggtact cagggtgcag cctctgtgaa cggccagagc caggccatgg    27000
tcagcggtct cggattagga gaaagttcct gatatcactg tagtgttcaa tcaaagctgg    27060
ggttatggtt tgtggaacag gggtcagttc atcagggggt gggctgcaat tgtcttcata    27120
gtgcttgtct cagtgccggt gcttactgag ccactagaga aaaaggttta attgagcttc    27180
tttaaaatca acattttgaa ttatttatca gacgtttcaa atatgtcatg ttgtttagat    27240
tctattgctg gagagttaag gtgatatttg gggttttgta actctgtttt ttcatacttc    27300
ctgaattgct tatctgtttg cttttcatta gctaaactat cgcttcttct tattttttaa    27360
ttcattctga ttttgatgaa tatttaattc cctttagaat gtgaatataa tgtacattgt    27420
gtgggtattt tgattttggt tcttggttta cttagtggca aagactctgt aagagttcct    27480
tgtctataga tagccattat ttagtggctt tctgaaatgg tggttttagt accaaagtac    27540
tggacttgtg agtaggctca ctgcccctg caggtcctag atagtggagg cctcaggaac    27600
tgtttctcat ttggaatgcc tttgtttcag cagattttgt gttgggttgt taagttcacc    27660
ctccacatta gtagatgtcc ttacagatta gagctgactc tggtagaagc agttgagtgc    27720
atgcttgata tctgtgcaca gggagaagct ctctgttgcc tcaggcgatg gactggtcta    27780
tgaaatgcac agtgacctga gttccctgct cagcccctga gaggtggacc aagctggaca    27840
cacatgagcc accgagcctg gcaagcaaaa gcgccagcct tgatggaaat ggcgagctga    27900
gcggcatcta ctcagtgtgg tttcttttgt tattaagagc tttagtgtgg tggctgtttc    27960
aaattcccgt tgtagtagta atatactggg tatgtgagca ggcccgtggt cttttgcggg    28020
gttggaatca ccgaagtaat gagaagctaa tctcattttc aactgctgta cactggtggt    28080
attgagtttg tatgaggtca tgcagtttga acgtcaggcc agtaggtggt gctcgcaggt    28140
aagagccggc tatggtggca gcagaagggt ttatgcttta ctggtgatta agtgggaaa    28200
cttggcgtgt tccagatctt agagaaaaga tttttagtta tttctcattc aacctgatac    28260
tacctgaaag tctctcgaat gtaacttta ttttgtcgag atgggttctt tctatacca    28320
ttttttatgt ttttttttgtg aaaggatgtt gtttcatcaa atgcgttttc agcatcaatt    28380
gaaaaaagtt atatgtggat taaagatcaa aatgtaaaac ctaacactat aaaacctctg    28440
gataataaca taggaaacag aatttaggag gtaagaactg acaaaggttt tataatgaaa    28500
atgctagaag tagttgcaac aaaattgaaa attgacaaat gggacctaag taaattaaag    28560
aacttctgta cagcaaaaga cactatcgac agagtaaaca ggcaacctac agaatgggaa    28620
ataaaatatt tgcagcctat acatctgaca aaggtccgac acttagtata tacatggaaa    28680
tttaacaaac atacaagaaa taaaaagtga ccaaaggaca tgaaaagaca cttcaaaaaa    28740
gacctacatg tggccaacaa gcataggaaa aaatgctgaa tatcactatc attagagaaa    28800
```

```
tacatatcaa aacctcaatg aggtaccgtc tcacatcagt caggatggct aatcttaaaa    28860
aaaaaataac agattttaa  ggttacagaa aaaaggggaa atttatacac ttttggcggg    28920
aatataaatg agttcaacca ttgtggaaag cagtgtggtg atccctccaa taacctaaaa    28980
cagaagtttc atttgaccca acaatcctac aactggacat atacctaaag gaatataaac    29040
atgtaggttc actgcagcac tatccacaat agcatagaca tggaatttac ctaaatcccc    29100
atcactggca gaatgataga gaaaaatgtg gtacatacaa ccatggaata ctatgcagct    29160
aaggaaagaa tgaaactatg tcctttgtag gaacatgatg gaactggcag tcaatactct    29220
tagaaaacta attcaggaac agaaaaccag atattatata ttctcccttta tttgttggag    29280 ataaataaaa gcaaatattc ttccagggcc tgagtcttcc ttattcaaca agtcattcta    29340
aattaagtgt tcagcaagtt gctgatactc atctaaatat tctatttcat ctgggccact    29400
tacatcactc aaaaagcaat gagagctata tttctaaggg gggttctagg ataataaata    29460
cctgaatagt gagaatatga aggatatgga aactgggcca cttatatcac tcaaaaagga    29520
atgagagcta tatttataag gggggttcta ggataataaa tacctgaata gtgagaatat    29580
gaaggatatg gaaactgggc cacttatatc actcaaaaag caatgaaagc tatatttaca    29640
aggggggttc taggataata aatatctgaa tagtgagaat atgaaggata tggatggttt    29700
ttttttaact caatgggcac ataactgtgg gagatactat attcctatga agaaggtatt    29760
cagacttcag agataagtaa tgtttcctac attgtgcttg tgacttggaa gcagtggatt    29820
gaagagtgtg ataagtgccc agaccaagca gaacagaaat cagcatgtaa agatgatgat    29880
ctatggatat gatctaaaac catgtaaata cttcaaataa ttctatttaa tgcagtttga    29940
aataaaacac aaacttattc aaaatacaaa ttacttggta attattttgg gagctatgag    30000
ttcaccaaga aactcaaatt cctatttcta tttcaacccc tgattcctac tgtcaatggg    30060
agggaagtct cagaaccaat cacacatcag acggcaaatc tgtcaaccaa gagtctttcc    30120
actgaaggac ctgggaggtc aggaccctca ggaaagtgct ggggaccctg tcttgggagt    30180
gcccagcaga tctcagaact ctccatgggt cctgctggac actcatgtag ggtaacgagt    30240
ggccaccttt tcagtgttac cagtgagctc tgagtgttcc taatgggacc aggatgggtc    30300
taggtgcctg ctcaatgtca gagacagcaa tggtcccaca aaaacccag gtaatcttta    30360 ggccaataaa atgtgggttc acagtgagga gtgcatcctg gggttggggt tgttctgca    30420 gcgggaagag cgctgtgcac agaaagctta gaaatggggc aagagatgct tttcctcagg    30480
caggatttag ggcttggtct ctcagcatcc cacacttgta cagctgatgt ggcatctgtg    30540
ttttctttct catcctagat caggctttga gctgtgaaat accctgcctc atgcatatgc    30600
aaataacctg aggtcttctg agataaatat agatatattg gtgccctgag agcatcacat    30660
aacaaccaca ttcctcctct gaagaagccc ctgggagcac agctcatcac catggactgg    30720
acctggaggt tcctctttgt ggtggcagca gctacaggta aggggcttcc tagtcctaag    30780
gctgaggaag ggatcctggt ttagttaaag aggattttat tcaccctgt gtcctctcca    30840 caggtgtcca gtcccaggtg cagctggtgc agtctggggc tgaggtgaag aagcctgggt    30900
cctcggtgaa ggtctcctgc aaggcttctg gaggcacctt cagcagctat gctatcagct    30960
gggtgcgaca ggcccctgga caagggcttg agtggatggg agggatcatc cctatctttg    31020
gtacagcaaa ctacgcacag aagttccagg gcagagtcac gattaccgcg gacaaatcca    31080
cgagcacagc ctacatggag ctgagcagcc tgagatctga ggacacggcc gtgtattact    31140
gtgcgagaga cacagtgtga aaacccacat cctgagagtg acaaaaaccc tgagggagaa    31200
```

```
ggcagctgtg ccgggctgag gagatgacag gggttattag gtttaaggct gtttacaaaa   31260
tgggttatat atttgagaaa aaagaacag tagaaacaag tacatactct aattttaaga    31320
taaatattcc attcaagagt cgtaatataa gccaaattca cagagtggaa aaggcgcgat   31380
cgcggagcag gggatcctta gatattggtt ggggttatct caccttaggt ctgaatatgg   31440
ggttgtctta gactgttttg tgctgttaga atagaatacc caagactggg aaatttatac   31500
tgaacggaaa tttatttctc acagttctag aggctgtgaa gtccaagagc acaggtgcca   31560
gagcaagtcc aagagcaagg gaaagtccaa agcaagtcca ggagcatctg gcgaggacct   31620
tcttgctgtg tcatcacatg gcggaaggca agaaagagag caagaggggg ccgaactcac   31680 cctttataa cagcaccaat cccacccatg aggtggggac cttatgacct aatcactctt    31740
catactgtta caatggcaat gaaatttcaa catgagtttt ggaggagaga agcattcaaa   31800
ccacagcaag ggtgctccta cctcctctct cagggcatct gcagaaagag ctgcaactgc   31860
acgtccttcc tccgtccatc ctccatccct tcccaatgtc cgtgcatatc ctgtgaccca   31920
ggaggtctgg catagggggt gctcctgcct taggtctgag gccctgtctg aagaggggta   31980
ggtgaggagg ccatctgatg gtctgggcca agacagtcac aggacgcatc atttatcatc   32040
aaggaggctg agggttgagt ctccaggtcc agggaactcc ccacaaagtg ggaaccctgc   32100
ccagctccac acagcctctg ctgggggacc ctgctctggt gcagagcctg gggacaggtc   32160
ttgagctcag ccagagtctg cctccctgtc atttaggaac taaaccaagc ggcaggatgc   32220
tggagcccag cccccatctg accttacagg gccaaggctg gggccctggg ttcccctcaa   32280
ggcgcagcag gactggagcc ccaggcagtg caggagtggc caaagctggg gcttcctcca   32340
gagcccccaa gcatcacggc accaagaagg gtaggaccct ggcctgagga attggcacca   32400
aagcccagaa actaccctg gacaccatgg agagaggcct ggagggaag caccaggcac     32460 tgcctcccct tctgatccca cctgaggtgg ctgccaagcc cagagagccg ctctgatgtc   32520
ccccagccct gcagcccagg gatacctgta ctgtgcccct gggggacccc tggccagtct   32580
gtgcaaagaa gtcaccaccc tacactcaga gacagtgggg gtcctcgtcc cacatcctca   32640
gagcatggcc cggctgctgc agggatggtc tcctggtcct cagagcatgg cccggctgct   32700
gcagggatgg tctcctggtc ctcagagcat ggcccagctg ctgcagggat ggtctcctgg   32760
aggcccccca gtgctctatt gtcagggctc cctccacccc ccgcaccaa gagagagcca    32820 gaccccagca aggcttccag tggcttcagg tcacacccct aggctgaccc cagccccatt   32880
aacacctgcc tgagaaagct ccacgcacca gaactgaccg tctgctccaa ctcttgacct   32940
cccgttctca gggcgtctgc tgaaaaggct gcaactgcac atccttcctc cgtccgttcc   33000
cgatgtccgt gtgtctcctg tggccaggaa ggtctttctc gggacctgag agccgctccc   33060
tgaagtgtcc ccattgggaa ggatggggcc tgtgtctcca ggctctggga ggacagaatc   33120
ctgacctcaa cagtggccgg cacgacaca actggcccca tcccggggac gctgaccagc    33180
gctgggcaac ttttcccttc cccgacgact gagccccgag caccctccct gctcccctac   33240 cacctcccctt tacaaggctg tggcctctgc acagatgata atggagcttg gctcattccc   33300
ctagagtcgg tagggagtta aggacaaaac tcagtttcct ccacctgaac tcaagtctgc   33360
ctatgtttac ctaatcacac ctggtggaca gtttggacaa acttgcacac tcagagacac   33420
agacacttct agaaatcatt atctccctgc cccggggacc ccactccagc agaagtctgc   33480
taggcactgg cctgggccct cctgctgtcc taggaggctg ctgacctcct gcctggctcc   33540
```

```
tgtcccagg tccagagtca gagcagactc cagggacgct gcaggctagg aagccgcccc    33600
ctccaggcca gggtctagtg caggtgccca ggacaagaaa gattgtgaat gcaggaatga    33660
ctgggccaca cccctcccgt gcacgccccc tcttgccctg caccccacag cccagccccc    33720
cgtgctggat gccccccccac agcagaggtg ctgttctgtg atccctgggg aaagacgccc   33780
tcaacctcca ccctgtccca cggcccaagg aagacaagac acaggccctc tcctcacagt    33840
ctccccacct ggctcctgct gggaccctca aggtgtgaac agggaggatg gttgtctggg    33900
tggcccctag gagcccagat cttcactcta cagaccccaa cccaagcacc cccttctgca    33960
gggcccagct catcccctc ctcctccctc tgctctcctc tcgtcgcctc tacgggaaat     34020
ccgggactca gcagtaaccc tcaggaagca gggcccaggc gccgtttaat aggaggcttc    34080
ctcacaatga aacttttaga aagccttgac tacaatgatg accttggtgt ggctgtgaac    34140
actgtcagct cccacagctg ctgcagcaaa aaatgtccat agacagggtg ggggcccggg    34200
gtcgtctgct gtcctgctca gcccacagca cgcatggagg atctgaggtg ccacacctga    34260
cgcccaggcc agaacatgcc tccctccagg gtgacctgcc atgtcctgca ttgctggagg    34320
gacaggggca gcctatgagg atctggggcc aggagatgaa tcctattaac ccagaggaaa    34380
actaacagga cccaagcacc ctccccgttg aagctgacct gcccagaggg gcctgggccc    34440
accccacaca ccggggcgga atgtgtacag gccccggtct ctgtgggtgt tccgctaact    34500
ggggctccca gtgctcaccc cacaactaaa gcgagcccca gcctccagag ccccgaagg    34560 agatgccgcc cacaagccca gcccccatcc aggaggcccc agagctcagg gcgccggggc    34620
agattctgaa cagccccgag tcacggtggg tacaactgga acgaccaccg tgagaaaaac    34680
tgtgtccaaa actgtctcct ggccctgct ggaggccgcg ccagagaggg gagcagccgc     34740
cccgaaccta ggtcctgctc agctcacacg accccagca cccagagcac aacgagtcc      34800 ccattgaatg gtgaggacgg ggaccagggc tccagggggt catggaaggg gctggacccc    34860
atcctactgc tatggtccca gtgctcctgg ccagaactga ccctaccacc gacaagagtc    34920
cctcagggaa acgggggtca ctggcacctc ccagcatcaa cccaggcag cacaggcata     34980 aaccccacat ccagagccga ctccaggagc agagacaccc cagtaccctg ggggacaccg    35040
accctgatga ctccccactg gaatccaccc cagagtccac caggaccaaa gaccccgccc    35100
ctgtctctgt ccctcactca ggacctgctg cgggggcggc catgagacca gactcgggct    35160
tagggaacac cactgtggcc ccaacctcga ccaggccaca ggcccttcct tcctgccctg    35220
cggcagcaca gactttgggg tctgtgcaga gaggaatcac agaggcccca ggctgaggtg    35280
gtgggggtgg aagaccccca ggaggtggcc cacttccctt cctcccagct ggaacccacc    35340
atgaccttct taagataggg gtgtcatccg aggcaggtcc tccatggagc tcccttcagg    35400
ctcctccccg gtcctcacta ggcctcagtc ccggctgcgg gaatgcagcc accacaggca    35460
caccaggcag cccagaccca gccagcctgc agtgccaag cccacattct ggagcagagc     35520
aggctgtgtc tgggagagtc tgggctcccc accgcccccc cgcacacccc acccacccct    35580
gtccaggccc tatgcaggag ggtcagagcc cccatggggg tatggactta gggtctcact    35640
cacgtggctc ccctcctggg tgaaggggtc tcatgcccag atccccacag cagagctggt    35700
caaaggtgga ggcagtggcc ccagggccac cctgacctgg accctcaggc tcctctagcc    35760
ctggctgccc tgctgtccct gggaggcctg gactccacca gaccacaggt ccagggcacc    35820
gcccataggt gctgcccaca ctcagttcac aggaagaaga taagctccag acccccaaga    35880
ctgggacctg ccttcctgcc accgcttgta gctccagacc tccgtgcctc ccccgaccac    35940
```

```
ttacacacgg gccagggagc tgttccacaa agatcaaccc caaaccggga ccgcctggca    36000
ctcgggccgc tgccacttcc ctctccattt gttcccagca cctctgtgct ccctccctcc    36060
tccctccttc aggggaacag cctgtgcagc ccctccctgc accccacacc ctggggaggc    36120
ccaaccctgc ctccagccct ttctccccg ctgctcttcc tgcccatcca gacaaccctg    36180
gggtcccatc cctgcagcct acaccctggt ctccacccag acccctgtct ctccctccag    36240 acaccctcc caggccaacc ctgcacatgc aggccctccc cttttctgct gccagagcct    36300
cagtttctac cctctgtgcc taccccctgc ctcctcctgc ccacaactcg agctcttcct    36360
ctcctggggc cctgagcca tggcactgac cgtgcactcc cacccccaca ctgcccatgc    36420
cctcaccttc ctcctggaca ctctgacccc gctcccctct tggacccagc cctggtattt    36480
ccaggacaaa ggctcaccca agtcttcccc atgcaggccc ttgccctcac tgcccggtta    36540
cacggcagcc tcctgtgcac agaagcaggg agctcagccc ttccacaggc agaaggcact    36600
gaaagaaatc ggcctccagc accctgatgc acgtccgcct gtgtctctca ctgcccgcac    36660
ctgcagggag gctcggcact ccctgtaaag acgagggatc caggcagcaa catcatggga    36720
gaatgcaggc ctcccagaca gcccagccct ctcgcaggcc tctcctggga agagacctgc    36780
agccaccact gaacagccac ggagcccgct ggatagtaac tgagtcagtg accgacctgg    36840
agggcagggg agcagtgaac cggagcccag accatagggga cagagaccag ccgctgacat    36900
cccgagcccc tcactggcgg ccccagaaca ccgcgtggaa acagaacaga cccacattcc    36960
cacctggaac agggcagaca ctgctgagcc cccagcacca gccctgagaa acaccaggca    37020
acggcatcag agggggctcc tgagaaagaa aggaggggag gtctccttca ccagcaagta    37080
cttcccttga ccaaaaacag ggtccacgca actcccccag acaaaggag gagcccctg    37140 tacagcactg ggctcagagt cctctcccac acaccctgag tttcagacaa aaacccctg    37200 gaaatcatag tatcagcagg agaactagcc agagacagca agaggggact cagtgactcc    37260
cgcggggaca ggaggatttt gtggggctc gtgtcactgt gaggatattg tagtagtacc    37320
agctgctata cccacagtga cacagcccca ttcccaaagc cctgctgtaa acgcttccac    37380
ttctggagct gaggggctgg ggggagcgtc tgggaagtag ggcctagggg tggccatcaa    37440
tgcccaaaac gcaccagact ccccccaga catcaccca ctggccagtg agcagagtaa    37500
acagaaaatg agaagcagct gggaagcttg cacaggcccc aaggaaagag ctttggcggg    37560
tgtgcaagag gggatgcggg cagagcctga gcagggcctt ttgctgtttc tgctttcctg    37620
tgcagatagt tccataaact ggtgttcaag atcgatggct gggagtgagc ccaggaggac    37680
agtgtgggaa gggcacaggg aaggagaagc agccgctatc ctacactgtc atctttcaag    37740
agtttgccct gtgcccacaa tgctgcatca tgggatgctt aacagctgat gtagacacag    37800
ctaaagagag aatcagtgaa atggatttgc agcacagatc tgaataaatt ctccagaatg    37860
tggagccaca cagaagcaag cacaaggaaa gtgcctgatg caagggcaaa gtacagtgtg    37920
taccttcagg ctgggcacag acactctgaa aagccttggc aggaactccc tgcaacaaag    37980
cagagccctg caggcaatgc cagctccaga gccctccctg agagcctcat gggcaaagat    38040
gtgcacaaca ggtgtttctc atagccccaa actgagaatg aagcaaacag ccatctgaag    38100
gaaaacaggc aaataaacga tggcaggttc atgaaatgca aacccagaca gccagaagga    38160
caacagtgag ggttacaggt gactctgtgg ttgagttcat gacaatgctg agtaattgga    38220
gtaacaaagg aaagtccaaa aaatactttc aatgtgattt cttctaaata aaatttacag    38280
```

```
ccggcaaaat gaactatctt cttaagggat aaactttcca ctaggaaaac tataaggaaa   38340
atcaagaaaa ggatgatcac ataaacacag tggtcgttac ttctactggg gaaggaagag   38400
ggtatgaact gagacacaca gggttggcaa gtctcctaac aagaacagaa caaatacatt   38460
acagtacctt gaaaacagca gttaaaattc taaattgcaa gaagaggaaa atgcacacag   38520
ctgtgtttag aaaattctca gtccagcact gttcataata gcaaagacat taacccaggt   38580
tggataaata aacgatgaca caggcaattg cacaatgata cagacataca ttcagtatat   38640
gagacattga tgatgtatcc ccaaagaaat gactttaaag agaaaaggcc tgatatgtgg   38700
tggcactcac ctccctgggc atccccggac aggctgcagg cacactgtgt ggcagggcag   38760
gctggtacct gctggcagct cctggggcct gatgtggagc aggcacagag ccgtatcccc   38820
ccgaggacat atacccccaa ggacggcaca gttggtacat tccggagaca agcaactcag   38880
ccacactccc aggccagagc ccgagaggga cgcccatgca cagggaggca gagcccagct   38940
cctccacagc cagcagcacc cgtgcagggg ccgccatctg gcaggcacag agcatgggct   39000
gggaggaggg gcagggacac caggcagggt tggcaccaac tgaaaattac agaagtctca   39060
tacatctacc tcagccttgc ctgacctggg cctcacctga cctggacctc acctggcctg   39120
gacctcacct ggcctagacc tcacctctgg gcttcacctg agctcggcct cacctgactt   39180
ggaccttgcc tgtcctgagc tcacatgatc tgggcctcac ctgacctggg tttcacctga   39240
cctgggcttc acctgacctg ggcctcatct gacctgggcc tcactggcct ggacctcacc   39300
tggcctgggc ttcacctggc tcaggcctc atctgcacct gctccaggtc ttgctggaac   39360
ctcagtagca ctgaggctgc aggggctcat ccagggttgc agaatgactc tagaacctcc   39420
cacatctcag ctttctgggt ggaggcacct ggtggcccag ggaatataaa aagcctgaat   39480
gatgcctgcg tgatttgggg gcaatttata aacccaaaag acatggcca tgcagcgggt   39540 agggacaata cagacagata tcagcctgaa atggagcctc agggcacagg tgggcacgga   39600
cactgtccac ctaagccagg ggcagacccg agtgtcccg cagtagacct gagagcgctg   39660
ggcccacagc ctccctcgg tgccctgcta cctcctcagg tcagccctgg acatcccggg   39720
tttccccagg cctggcggta ggtttggggt gaggtctgtg tcactgtggt attacgattt   39780
ttggagtggt tattataccc acagtgtcac agagtccatc aaaaacccat ccctgggaac   39840
cttctgccac agccctccct gtggggcacc gccgcgtgcc atgttaggat tttgactgag   39900
gacacagcac catgggtatg gtggctaccg cagcagtgca gcccgtgacc caaacacaca   39960
gggcagcagc cacaacagac aagcccacaa gtgaccaccc tgagctcctg cctgccagcc   40020
ctggagacca tgaaacagat ggccaggatt atcccatagg tcagccagac ctcagtccaa   40080
caggtctgca tcgctgctgc cctccaatac cagtccggat ggggacaggg ctggcccaca   40140
ttaccatttg ctgccatccg gccaacagtc ccagaagccc ctccctcaag gctgggccac   40200
atgtgtggac cctgagagcc cccatgtctt gagtaggggc accaggaagg tggggctggc   40260
cctgtgcact gtccctgccc ctgtggtccc tggcctgcct ggccctgaca cctgggcctc   40320
tcctgggtca tttccaagac agaagacatt cccaggacag ctggagctgg gagtccatca   40380
tcctgcctgg ccgtcctgag tcctgcgcct ttccaaacct cacccgggaa gccaacagag   40440
gaatcacctc ccacaggcag agacaaagac cttccagaaa tctctgtctc tctccccagt   40500 gggcacctc ttccagggca gtcctcagtg atatcacagt gggaaccac atctggatcg   40560 ggactgcccc cagaacacaa gatggcccac agggacagcc ccacagccca gcccttccca   40620 gaccctaaa aggcgtccca ccccctgcat ctgccccagg gctcaaactc caggaggact   40680
```

```
gactcctgca cacccctcctg ccagacatca cctcagcccc tcctggaagg gacaggagcg   40740
cgcaagggtg agtcagaccc tcctgccctc gatggcaggc ggagaagatt cagaaaggtc   40800
tgagatcccc aggacgcagc accactgtca atgggggccc cagacgcctg gaccagggcc   40860
tgcgtgggaa aggcctctgg gcacactcag gggcttttttg tgaagggtcc tcctactgtg   40920
tgactacagt aactaccaca gtgatgaacc cagcagcaaa aactgaccgg actcccaagg   40980
tttatgcaca cttctccgct cagagctctc caggatcaga gagccgggc ccaagggttt   41040 ctgcccagac cctcggcctc tagggacatc ttggccatga cagcccatgg gctggtgccc   41100
cacacatcgt ctgccttcaa acaagggctt cagagggctc tgaggtgacc tcactgatga   41160
ccacaggtgc cctggcccct tccccaccag ctgcaccaga ccccgtcatg acagatgccc   41220
cgattccaac agccaattcc tggggccagg aatcgctgta gacaccagcc tccttccaac   41280
acctcctgcc aattgcctgg attcccatcc cggttggaat caagaggaca gcatccccca   41340
ggctcccaac aggcaggact cccacaccct cctctgagag gccgctgtgt tccgtagggc   41400
caggctgcag acagtccccc tcacctgcca ctagacaaat gcctgctgta gatgtcccca   41460
cctggaaaat accactcatg gagccccag ccccaggtac agctgtagag agtctctg   41520 aggcccctaa gaagtagcca tgcccagttc tgccgggacc ctcggccagg ctgacaggag   41580
tggacgctgg agctgggccc atactgggcc ataggagc tcaccagtga gggcaggaga   41640
gcacatgccg gggagcaccc agcctcctgc tgaccagagg cccgtcccag agcccaggag   41700
gctgcagagg cctctccagg gggacactgt gcatgtctgg tccctgagca gcccccacg   41760 tccccagtcc tgggggcccc tggcacagct gtctggaccc tctctattcc ctgggaagct   41820
cctcctgaca gccccgcctc cagttccagg tgtggttatt gtcagggggt gtcagactgt   41880
ggtggataca gctatggtta ccacagtggt gctgcccata gcagcaacca ggccaagtag   41940
acaggcccct gctgtgcagc cccaggcctc cagctcacct gcttctcctg gggctctcaa   42000
ggctgctgtt ttctgcactc tcccctctgt ggggagggtt ccctcagtgg gagatctgtt   42060
ctcaacatcc cacggcctca ttcctgcaag gaaggccaat ggatgggcaa cctcacatgc   42120
cgcggctaag atagggtggg cagcctggcg gggacaggac atcctgctgg ggtatctgtc   42180
actgtgccta gtggggcact ggctcccaaa caacgcagtc cttgccaaaa tccccacggc   42240 ctccccgct aggggctggc ctgatctcct gcagtcctag gaggctgctg acctccagaa   42300
tggctccgtc cccagttcca gggcgagagc agatcccagg ccggctgcag actgggaggc   42360 cacccctcc ttcccagggt tcactgcagg tgaccagggc aggaaatggc ctgaacacag   42420
ggataaccgg gccatccccc aacagagtcc acccctcct gctctgtacc ccgcaccccc   42480
caggccagcc catgacatcc gacaaccccca caccagagtc actgcccggt gctgccctag   42540
ggaggacccc tcagccccca ccctgtctag aggactgggg aggacaggac acgccctctc   42600
cttatggttc ccccacctgg ctctggctgg gaccctgggg gtgtggacag aaaggacgct   42660
tgcctgattg gcccccagga gcccagaact tctctccagg gaccccagcc cgagcacccc   42720
cttacccagg acccagccct gccctcctc ccctctgctc tcctctcatc acccccatggg   42780 aatccagaat ccccaggaag ccatcaggaa gggctgaggg aggaagtggg gccactgcac   42840
caccaggcag gaggctctgt ctttgtgaac ccagggaggt gccagcctcc tagagggtat   42900
ggtccaccct gcctatggct cccacagtgg caggctgcag ggaaggacca gggacggtgt   42960
gggggagggc tcagggcccc gcgggtgctc catcttggat gagcctatct ctctcaccca   43020
```

| | |
|---|---|
| cggactcgcc cacctcctct tcaccctggc cacacgtcgt ccacaccatc ctaagtccca | 43080 |
| cctacaccag agccggcaca gccagtgcag acagaggctg gggtgcaggg gggccgactg | 43140 |
| ggcagcttcg gggagggagg aatggaggaa ggggagttca gtgaagaggc cccctcccc | 43200 |
| tgggtccagg atcctcctct ggaccccccg gatcccatcc cctccaggct ctgggaggag | 43260 |
| aagcaggatg ggagaatctg tgcgggaccc tctcacagtg gaatacctcc acagcggctc | 43320 |
| aggccagata caaaagcccc tcagtgagcc ctccactgca gtgctgggcc tgggggcagc | 43380 |
| cgctcccaca caggatgaac ccagcacccc gaggatgtcc tgccaggggg agctcagagc | 43440 |
| catgaaggag caggatatgg gaccccccgat acaggcacag acctcagctc cattcaggac | 43500 |
| tgccacgtcc tgccctggga ggaaccccctt tctctagtcc ctgcaggcca ggaggcagct | 43560 |
| gactcctgac ttggacgcct attccagaca ccagacagag gggcaggccc ccagaaacca | 43620 |
| gggatgagga cgccccgtca aggccagaaa agaccaagtt gcgctgagcc cagcaaggga | 43680 |
| aggtccccaa acaaaccagg aagtttctga aggtgtctgt gtcacagtgg agtatagcag | 43740 |
| ctcgtcccac agtgacactc gccaggccag aaacccatcc ccaagtcagc ggaatgcaga | 43800 |
| gagagcaggg aggacatgtt taggatctga ggccgcacct gacacccagg ccagcagacg | 43860 |
| tctcctgtcc acggcaccct gccatgtcct gcatttctgg aagaacaagg gcaggctgaa | 43920 |
| gggggtccag gaccaggaga tgggtccgct ctacccagag aaggagccag gcaggacaca | 43980 |
| agccccctcc ccattgaggc tgacctgccc agagggtcct gggcccaccc aacacaccgg | 44040 |
| ggcggaatgt gtgcaggcct cggtctctgt gggtgttccg ctagctgggg ctcacagtgc | 44100 |
| tcaccccaca cctaaaacga gccacagcct ccggagcccc tgaaggagac cccgcccaca | 44160 |
| agcccagccc ccacccagga ggccccagag cacagggcgc cccgtcggat tctgaacagc | 44220 |
| cccgagtcac agtgggtata actggaacta ccactgtgag aaaagcttcg tccaaaacgg | 44280 |
| tctcctggcc acagtcggag gccccgccag agagggagc agccaccca aacccatgtt | 44340 |
| ctgccggctc ccatgacccc gtgcacctgg agccccacgg tgtccccact ggatgggagg | 44400 |
| acaagggccg ggggctccgg cgggtcgggg caggggcttg atggcttcct tctgccgtgg | 44460 |
| ccccattgcc cctggctgga gttgaccctt ctgacaagtg tcctcagaga gtcagggatc | 44520 |
| agtggcacct cccaacatca accccacgca gcccaggcac aaaccccaca tccagggcca | 44580 |
| actccaggaa cagagacacc ccaatacccct ggggaccccc gaccctgatg actcccgtcc | 44640 |
| catctctgtc cctcacttgg ggcctgctgc ggggcgagca cttgggagca aactcaggct | 44700 |
| taggggacac cactgtgggc ctgacctcga gcaggccaca gacccttccc tcctgccctg | 44760 |
| gtgcagcaca gactttgggg tctgggcagg gaggaacttc tggcaggtca ccaagcacag | 44820 |
| agccccagg ctgaggtggc ccaggggga accccagcag gtggcccact acccttcctc | 44880 |
| ccagctggac cccatgtctt ccccaagata ggggtgccat ccaaggcagg tcctccatgg | 44940 |
| agccccttc aggctcctct ccagacccca ctgggcctca gtccccactc taggaatgca | 45000 |
| gccaccacgg gcacaccagg cagcccaggc ccagccaccc tgcagtgccc aagcccacac | 45060 |
| cctggaggag agcagggtgc gtctgggagg ggctgggctc ccacccccca cccccacctg | 45120 |
| cacaccccac ccaccccttgc ccgggccccc tgcaggaggg tcagagcccc catgggtatt | 45180 |
| ggacttaggg tctcactcac gcacctcccc tcctgggaga aggggtctca tgcccagatc | 45240 |
| ccccccagcag cgctggtcac aggtagaggc agtggcccca gggccaccct gacctggccc | 45300 |
| ctcaggctcc tctagccctg gctgccctgc tgtccctggg aggcctgggc tccaccgac | 45360 |
| cacaggtcta gggcaccgcc cacactgggg ccgcccacac acagctcaca ggaagaagat | 45420 |

```
aagctccaga cccccaggcc cgggacctgc cttgctgcta cgacttcctg ccccagacct   45480
cgttgccctc cccgtccac ttacacacag gccaggaagc tgttcccaca cagaccaacc    45540
ccagacgggg accacctggc actcaggtca ctgccatttc cttctccatt cacttccaat   45600
gcctctgtgc ttcctccctc ctccttcctt cgggggagca ccctgtgcag ctcctccctg   45660
cagtccacac cctggggaga cccgaccctg cagcccacac cctggggaga cctgaccctc   45720
ctccagccct ttctcccccg ctgctcttgc caccaccaa dacagccctg gggtcctgtc     45780
cctacagccc ccacccagtt ctctacctag acccgtcttc ctccctctaa acacctctcc   45840
caggccaacc ctacacctgc aggccctccc ctccactgcc aaagaccctc agtttctcct   45900
gcctgtgccc accccgtgc tcctcctgcc cacagctcga gctcttcctc tcctagggcc     45960
cctgagggat ggcattgacc gtgccctcgc acccacacac tgcccatgcc ctcacattcc   46020
tcctggccac tccagcccca ctcccctctc aggcctggct ctggtatttc tgggacaaag   46080
ccttacccaa gtcttccca tgcaggcctg ggcccttacc ctcactgccc ggttacaggg    46140
cagcctcctg tgcacagaag cagggagctc agcccttcca caggcagaag gcactgaaag   46200
aaatcggcct ccagcgcctt dacacacgtc tgcctgtgtc tctcactgcc cgcacctgca   46260
gggaggctcg gcactccctc taaagacgag ggatccaggc agcagcatca caggagaatg   46320
cagggctacc agacatccca gtcctctcac aggcctctcc tgggaagaga cctgaagacg   46380
cccagtcaac ggagtctaac accaaacctc cctggaggcc gatgggtagt aacggagtca   46440
ttgccagacc tggaggcagg ggagcagtga gcccgagccc acaccatagg gccagaggac   46500
agccactgac atcccaagcc actcactggt ggtcccacaa caccccatgg aaagaggaca   46560
gacccacagt cccacctgga ccagggcaga gactgctgag acccagcacc agaaccaacc   46620
aagaaacacc aggcaacagc atcagagggg gctctggcag aacagaggag gggaggtctc   46680
cttcaccagc aggcgcttcc cttgaccgaa gacaggatcc atgcaactcc cccaggacaa   46740
aggaggagcc ccttgttcag cactgggctc agagtcctct ccaagacacc cagagtttca   46800
gacaaaaacc ccctggaatg cacagtctca gcaggagagc cagccagagc cagcaagatg   46860
gggctcagtg acacccgcag ggacaggagg atttgtggg ggctcgtgtc actgtgagga    46920
tattgtacta atggtgtatg ctatacccac agtgacacag ccccattccc aaagccctac   46980
tgcaaacgca ttccacttct ggggctgagg ggctggggga gcgtctggga aatagggctc   47040
aggggtgtcc atcaatgccc aaaacgcacc agactcccct ccatacatca cacccaccag   47100
ccagcgagca gagtaaacag aaaatgagaa gcaagctggg gaagcttgca caggcccaa    47160 ggaaagagct ttggcgggtg tgtaagaggg gatgcgggca gagcctgagc agggccttt    47220 gctgtttctg ctttcctgtg cagagagttc cataaactgg tgttcgagat caatggctgg   47280
gagtgagccc aggaggacag cgtgggaaga gcacagggaa ggaggagcag ccgctatcct   47340
acactgtcat ctttcgaaag tttgccttgt gcccacactg ctgcatcatg ggatgcttaa   47400
cagctgatgt agacacagct aaagagagaa tcagtgagat ggatttgcag cacagatctg   47460
aataaattct ccagaatgtg gagcagcaca gaagcaagca cacagaaagt gcctgatgca   47520
aggacaaagt tcagtgggca ccttcaggca ttgctgctgg gcagagacac tctgaaaagc   47580
cctggcagga actccctgtg acaaagcaga accctcaggc aatgccagcc ccagagccct   47640
ccctgagagc ctcatgggca aagatgtgca caacaggtgt ttctcatagc cccaaactga   47700
gagcaaagca aacgtccatc tgaaggagaa caggcaaata aacgatggca ggttcatgaa   47760
```

```
atgcaaaccc agacagccac aagcacaaaa gtacaggggtt ataagcgact ctggttgagt    47820
```
*(correcting)*
```
atgcaaaccc agacagccac aagcacaaaa gtacagggtt ataagcgact ctggttgagt    47820
tcatgacaat gctgagtaat tggagtaaca aagtaaactc caaaaaatac tttcaatgtg    47880
atttcttcta aataaaattt acaccctgca aaatgaactg tcttcttaag ggatacattt    47940
cccagttaga aaaccataaa gaaaccaag aaaaggatga tcacataaac acagtggtgg    48000
ttacttctgc tggggaagga agagggtatg aactgagata cacagggtgg gcaagtctcc    48060
taacaagaac agaacgaata cattacagta ccttgaaaac agcagttaaa cttctaaatt    48120
gcaagaagag gaaaatgcac acagttgtgt ttagaaaatt ctcagtccag cactgttcat    48180
aatagcaaag acattaaccc aggtcggata aataagcgat gacacaggca attgcacaat    48240
gatacagaca tatatttagt atatgagaca tcgatgatgt atccccaaat aaacgacttt    48300
aaagagataa agggctgatg tgtggtggca ttcacctccc tgggatcccc ggacaggttg    48360
caggctcact gtgcagcagg gcaggcgggt acctgctggc agttcctggg gcctgatgtg    48420
gagcaagcgc agggccatat atcccggagg acggcacagt cagtgaattc cagagagaag    48480
caactcagcc acactcccca ggcagagccc gagagggacg cccacgcaca gggaggcaga    48540
gcccagcacc tccgcagcca gcaccacctg cgcacgggcc accaccttgc aggcacagag    48600
tgggtgctga gaggagggc agggacacca ggcagggtga gcacccagag aaaactgcag    48660
acgcctcaca catccacctc agcctcccct gacctggacc tcactggcct gggcctcact    48720
taacctgggc ttcacctgac cttggcctca cctgacttgg acctgcctg tcccaagctt    48780
tacctgacct gggcctcaac tcacctgaac gtctcctgac ctgggtttaa cctgtcctgg    48840
aactcacctg gccttggctt ccctgacct ggacctcatc tggcctgggc ttcacctggc    48900
ctgggcctca cctgacctgg acctcatctg gcctggacct cacctggcct ggacttcacc    48960
tggcctgggc ttcacctgac ctggacctca cctggcctcg gcctcacct gcacctgctc    49020
caggtcttgc tggagcctga gtagcactga gggtgcagaa gctcatccag ggttggggaa    49080
tgactctaga agtctcccac atctgacctt tctgggtgga ggcagctggt ggccctggga    49140
atataaaaat ctccagaatg atgactctgt gatttgtggg caacttatga acccgaaagg    49200
acatggccat ggggtgggta gggacatagg gacagatgcc agcctgaggt ggagcctcag    49260
gacacaggtg ggcacggaca ctatccacat aagcgaggga tagacccgag tgtccccaca    49320
gcagacctga gagcgctggg cccacagcct cccctcagag ccctgctgcc tcctccggtc    49380
agccctggac atcccaggtt tccccaggcc tggcggtagg tttagaatga ggtctgtgtc    49440
actgtggtat tacgatattt tgactggtta ttataaccac agtgtcacag agtccatcaa    49500
aaacccatgc ctggaagctt cccgccacag ccctccccat ggggccctgc tgcctcctca    49560
ggtcagcccc ggacatcccg ggtttcccca ggctgggcgg taggtttggg gtgaggtctg    49620
tgtcactgtg gtattactat ggttcgggga gttattataa ccacagtgtc acagagtcca    49680
tcaaaaaccc atccctggga gcctcccgcc acagccctcc ctgcagggga ccggtacgtg    49740
ccatgttagg attttgatcg aggagacagc accatgggta tggtggctac acagcagtg    49800
cagcctgtga cccaaacccg cagggcagca ggcacgatgg acaggcccgt gactgaccac    49860
gctgggctcc agcctgccag ccctggagat catgaaacag atggcaagg tcaccctaca    49920
ggtcatccag atctggctcc gagggggtctg catcgctgct gccctcccaa cgccagtcca    49980
aatgggacag ggacgcctc acagcaccat ctgctgccat caggccagcg atcccagaag    50040
ccctccctc aaggctgggc acatgtgtgg acactgagag ccctcatatc tgagtagggg    50100
caccaggagg gaggggctgg ccctgtgcac tgtccctgcc cctgtggtcc ctggcctgcc    50160
```

```
tggccctgac acctgagcct ctcctgggtc atttccaaga cagaagacat tcctggggac   50220
agccggagct gggcgtcgct catcctgccc ggccgtcctg agtcctgctc atttccagac   50280
ctcaccgggg aagccaacag aggactcgcc tcccacattc agagacaaag aaccttccag   50340
aaatccctgc ctctctcccc agtggacacc ctcttccagg acagtcctca gtggcatcac   50400
agcggcctga gatccccagg acgcagcacc gctgtcaata ggggcccaa atgcctggac    50460
cagggcctgc gtgggaaagg cctctggcca cactcgggct ttttgtgaag ggccctcctg   50520
ctgtgtgact acagtaacta ccatagtgat gaacccagtg gcaaaaactg gctggaaacc   50580
cagggctgt gtgcacgcct cagcttggag ctctccagga gcacaagagc cgggcccaag    50640
gatttgtgcc cagaccctca gcctctaggg acacctgggt catctcagcc tgggctggtg   50700
ccctgcacac catcttcctc caaatagggg cttcagaggg ctctgaggtg acctcactca   50760
tgaccacagg tgacctggcc cttccctgcc agctatacca gaccctgtct tgacagatgc   50820
cccgattcca acagccaatt cctgggaccc tgaatagctg tagacaccag cctcattcca   50880
gtacctcctg ccaattgcct ggattcccat cctggctgga atcaagaagg cagcatccgc   50940
caggctccca acaggcagga ctcccgcaca ccctcctctg agaggccgct gtgttccgca   51000
gggccaggcc ctggacagtt cccctcacct gccactagag aaacacctgc cattgtcgtc   51060
cccacctgga aaagaccact cgtggagccc ccagccccag gtacagctgt agagacagtc   51120
ctcgaggccc ctaagaagga gccatgccca gttctgccgg gaccctcggc caggccgaca   51180
ggagtggacg ctggagctgg gcccacactg ggccacatag gagctcacca gtgagggcag   51240
gagagcacat gccggggagc acccagcctc ctgctgacca gaggcccgtc ccagagccca   51300
ggaggctgca gaggcctctc cagggagaca ctgtgcatgt ctggtaccta agcagccccc   51360
cacgtcccca gtcctggggg cccctggctc agctgtctgg gccctccctg ctccctggga   51420
agctcctcct gacagccccg cctccagttc caggtgtggt tattgtcagg cgatgtcaga   51480
ctgtggtgga tatagtggct acgattacca cagtggtgcc gcccatagca gcaaccaggc   51540
caagtagaca ggcccctgct cgcagcccc aggcatccac ttcacctgct tctcctgggg    51600
ctctcaaggc tgctgtctgt cctctggccc tctgtgggga gggttccctc agtgggaggt   51660
ctgtgctcca gggcagggat gattgagata gaaatcaaag gctggcaggg aaaggcagct   51720
tcccgccctg agaggtgcag gcagcaccac ggagccacgg agtcacagag ccacggagcc   51780
cccattgtgg gcatttgaga gtgctgtgcc cccggcaggc ccagccctga tggggaagcc   51840
tgtcccatcc cacagcccgg gtcccacggg cagcgggcac agaagctgcc aggttgtcct   51900
ctatgatcct catccctcca gcagcatccc ctccacagtg gggaaactga ggcttggagc   51960
accaccggg ccctggaaa tgaggctgtg agcccagaca gtgggccag agcactgtga     52020
gtaccccggc agtacctggc tgcagggatc agccagagat gccaaaccct gagtgaccag   52080
cctacaggag gatccggccc cacccaggcc actcgattaa tgctcaaccc cctgccctgg   52140
agacctcttc cagtaccacc agcagctcag cttctcaggg cctcatccct gcaaggaagg   52200
tcaagggctg ggcctgccag aaacacagca ccctccctag ccctggctaa dacagggtgg   52260
gcagacggct gtggacggga catattgctg gggcatttct cactgtcact tctggtggt   52320
agctctgaca aaaacgcaga ccctgccaaa atccccactg cctcccgcta ggggctggcc   52380
tggaatcctg ctgtcctagg aggctgctga cctccaggat ggctccgtcc ccagttccag   52440
ggcgagagca gatcccaggc aggctgtagg ctgggaggcc acccctgccc ttgccggggt   52500
```

```
tgaatgcagg tgcccaaggc aggaaatggc atgagcacag ggatgaccgg gacatgcccc    52560
accagagtgc gccccttcct gctctgcacc ctgcaccccc caggccagcc cacgacgtcc    52620
aacaactggg cctgggtggc agccccaccc agacaggaca gacccagcac cctgaggagg    52680
tcctgccagg gggagctaag agccatgaag gagcaagata tggggccccc gatacaggca    52740
cagatgtcag ctccatccag gaccacccag cccacaccct gagaggaacg tctgtctcca    52800
gcctctgcag gtcgggaggc agctgacccc tgacttggac ccctattcca gacaccagac    52860
agaggcgcag gccccccaga accagggttg agggacgccc cgtcaaagcc agacaaaacc    52920 aagggggtgtt gagcccagca agggaaggcc cccaaacaga ccaggaggtt tctgaaggtg    52980
tctgtgtcac agtggggtat agcagcagct ggtaccacag tgacactcac ccagccagaa    53040
accccattcc aagtcagcgg aagcagagag agcaggagg acacgtttag gatctgagac    53100
tgcacctgac acccaggcca gcagacgtct cccctccagg gcaccccacc ctgtcctgca    53160
tttctgcaag atcaggggcg gcctgagggg gggtctaggg tgaggagatg ggtcccctgt    53220
acaccaagga ggagttaggc aggtcccgag cactctcccc attgaggctg acctgcccag    53280
agagtcctgg gcccacccca cacaccgggg cggaatgtgt gcaggcctcg gtctctgtgg    53340
gtgttccgct agctggggct cacagtgctc accccacacc taaaatgagc cacagcctcc    53400
ggagcccccg caggagaccc cgcccacaag cccagccccc acccaggagg ccccagagct    53460
cagggcgccc cgtcggattc cgaacagccc cgagtcacag cgggtataac cggaaccacc    53520
actgtcagaa tagctacgtc aaaaactgtc cagtggccac tgccggaggc cccgccagag    53580
agggcagcag ccactctgat cccatgtcct gccggctccc atgaccccca gcacgcggag    53640
ccccacagtg tccccactgg atgggaggac aagagctggg gattccggcg ggtcggggca    53700
ggggcttgat cgcatccttc tgccgtggct ccagtgcccc tggctggagt tgacccttct    53760
gacaagtgtc ctcagagaga caggcatcac cggcgcctcc caacatcaac cccaggcagc    53820
acaggcacaa accccacatc cagagccaac tccaggagca gagacacccc aatccctgg     53880 gggaccccga ccctgatgac ttcccactgg aattcgccgt agagtccacc aggaccaaag    53940
accctgcctc tgcctctgtc cctcactcag gacctgctgc cgggcgaggc cttgggagca    54000
gacttgggct taggggacac cagtgtgacc ccgaccttga ccaggacgca gacctttcct    54060
tcctttcctg gggcagcaca gactttgggg tctgggccag gaggaacttc tggcaggtcg    54120
ccaagcacag aggccacagg ctgaggtggc cctggaaaga cctccaggag gtggccactc    54180
cccttcctcc cagctggacc ccatgtcctc cccaagataa gggtgccatc caaggcaggt    54240
gctccttgga gccccattca gactcctccc tggacccccac tgggcctcag tcccagctct    54300
ggggatgaag ccaccacaag cacaccaggc agcccaggcc cagccaccct gcagtgccca    54360
agcacacact ctggagcaga gcagggtgcc tctgggaggg gctgagctcc ccaccccacc    54420
cccacctgca caccccaccc acccctgccc agcggctctg caggagggtc agagcccac     54480 atggggtatg gacttagggt ctcactcacg tggctcccat catgagtgaa ggggcctcaa    54540
gcccaggttc ccacagcagc gcctgtcgca agtggaggca gaggcccgag ggccaccctg    54600
acctggtccc tgaggttcct gcagcccagg ctgccctgct gtccctggga ggcctgggct    54660
ccaccagacc acaggtccag ggcaccgggt gcaggagcca cccacacaca gctcacagga    54720
agaagataag ctccagaccc ccagggccag aacctgcctt cctgctactg cttcctgccc    54780
cagacctggg cgccctcccc cgtccactta cacacaggcc aggaagctgt cccacacag    54840 aacaacccca aaccaggacc gcctggcact caggtggctg ccatttcctt ctccatttgc    54900
```

```
tcccagcgcc tctgtcctcc ctggttcctc cttcggggga acagcctgtg cagccagtcc   54960
ctgcagccca caccctgggg agacccaacc ctgcctgggg cccttccaac cctgctgctc   55020
ttactgccca cccagaaaac tctggggtcc tgtccctgca gtccctaccc tggtctccac   55080
ccagacccct gtgtatcact ccagacaccc ctcccaggca aaccctgcac ctgcaggccc   55140
tgtcctcttc tgtcgctaga gcctcagttt ctcccccctg tgcccacacc ctacctcctc   55200
ctgcccacaa ctctaactct tcttctcctg gagcccctga gccatggcat tgaccctgcc   55260
ctcccaccac ccacagccca tgccctcacc ttcctcctgg ccactccgac cccgcccct   55320 ctcaggccaa gccctggtat ttccaggaca aggctcacc caagtctttc ccaggcaggc   55380
ctgggctctt gccctcactt cccggttaca cgggagcctc ctgtgcacag aagcagggag   55440
ctcagccctt ccacaggcag aaggcactga agaaatcgg cctccagcac cttgacacac   55500
gtccgcccgt gtctctcact gcccgcacct gcagggaggc tccgcactcc ctctaaagac   55560
aagggatcca ggcagcagca tcacgggaga atgcagggct cccagacatc ccagtcctct   55620
cacaggcctc tcctgggaag agacctgcag ccaccaccaa acagccacag aggctgctgg   55680
atagtaactg agtcaatgac cgacctggag ggcaggggag cagtgagccg agcccatac   55740 catagggaca gagaccagcc gctgacatcc cgagctcctc aatggtggcc ccataacaca   55800
cctaggaaac ataacacacc cacagcccca cctggaacag ggcagagact gctgagcccc   55860
cagcaccagc cccaagaaac accaggcaac agtatcagag ggggctcccg agaaagagag   55920
gaggggagat ctccttcacc atcaaatgct tcccttgacc aaaaacaggg tccacgcaac   55980
tcccccagga caaaggagga gcccctata cagcactggg ctcagagtcc tctctgagac   56040
accctgagtt tcagacaaca acccgctgga atgcacagtc tcagcaggag aacagaccaa   56100
agccagcaaa agggacctcg gtgacaccag tagggacagg aggattttgt gggggctcgt   56160
gtcactgtga ggatattgta gtggtggtag ctgctactcc cacagtgaca cagacccatt   56220
cccaaagccc tactgcaaac acacccactc ctggggctga ggggctgggg gagcgtctgg   56280
gaagtagggt ccaggggtgt ctatcaatgt ccaaaatgca ccagactccc cgccaaacac   56340 cacccccacca gccagcgagc agggtaaaca gaaaatgaga ggctctggga agcttgcaca   56400 ggcccccaagg aaagagcttt ggcgggtgtg caagagggga tgcaggcaga gcctgagcag   56460 ggcctttgc tgtttctgct ttcctgtgca gagagttcca taaactggtg ttcaagatca   56520
gtggctggga atgagcccag gagggcagtc tgtgggaaga gcacagggaa ggaggagcag   56580
ccgctatcct acactgtcat cttcaaaag tttgccttgt gaccacacta ttgcatcatg   56640
ggatgcttaa gagctgatgt agacacagct aaagagagaa tcagtgagat gaatttgcag   56700
catagatctg aataaactct ccagaatgtg gagcagtaca gaagcaaaca cacagaaagt   56760
gcctgatgca aggacaaagt tcagtgggca ccttcaggca ttgctgctgg gcacagacac   56820
tctgaaaagc cttggcagga tctccctgcg acaaagcaga accctcaggc aatgccagcc   56880
ccagagccct ccctgagagc gtcatgggga agatgtgca gaacagctga ttatcataga   56940
ctcaaactga gaacagagca aacgtccatc tgaagaacag tcaaataagc aatggtaggt   57000
tcatgcaatg caaacccaga cagccagggg acaacagtag agggctacag gcggctttgc   57060
ggttgagttc atgacaatgc tgagtaattg gagtaacaga ggaaagccca aaaatactt   57120 ttaatgtgat ttcttctaaa taaaatttac accaggcaaa atgaactgtc ttcttaaggg   57180
ataaactttc ccctggaaaa actacaagga aaattaagaa aacgatgatc acataaacac   57240
```

| | |
|---|---|
| agttgtggtt acttctactg gggaaggaag agggtatgag ctgagacaca cagagtcggc | 57300 |
| aagtctccaa gcaagcacag aacgaataca ttacagtacc ttgaatacag cagttaaact | 57360 |
| tctaaatcgc aagaacagga aaatgcacac agctgtgttt agaaaattct cagtccagca | 57420 |
| ctattcataa tagcaaagac attaacccag gttggataaa taaatgatga cacaggcaat | 57480 |
| tgcacaatga tacagacata catttagtac atgagacatc gatgatgtat ccccaaagaa | 57540 |
| atgactttaa agagaaaagg cctgatgtgt ggtggcactc acctccctgg gatcccggga | 57600 |
| caggttgcag gcacactgtg tggcagggca ggctggtaca tgctggcagc tcctggggcc | 57660 |
| tgatgtggag caagcgcagg gctgtatacc cccaaggatg gcacagtcag tgaattccag | 57720 |
| agagaagcag ctcagccaca ctgcccaggc agagcccgag agggacgccc acgtacaggg | 57780 |
| aggcagagcc cagctcctcc acagccacca ccacctgtgc acgggccacc accttgcagg | 57840 |
| cacagagtgg gtgctgagag gagggcagg acaccaggca agggtgagca cccagagaaa | 57900 |
| actgcagaag cctcacacat ccacctcagc ctcccctgac ctggacctca cctggtctgg | 57960 |
| acctcacctg gcctgggcct cacctgacct ggacctcacc tggcctgggc ttcacctgac | 58020 |
| ctggacctca cctggcctcc ggcctcacct gcacctgctc caggtcttgc tggaacctga | 58080 |
| gtagcactga ggctgcagaa gctcatccag ggttggggaa tgactctgga actctcccac | 58140 |
| atctgacctt tctgggtgga ggcatctggt ggccctggga atataaaaag ccccagaatg | 58200 |
| gtgcctgcgt gatttggggg caatttatga acccgaaagg acatggccat ggggtgggta | 58260 |
| gggacatagg gacagatgcc agcctgaggt ggagcctcag gacacagttg gacgcggaca | 58320 |
| ctatccacat aagcgaggga cagacccgag tgttcctgca gtagacctga gagcgctggg | 58380 |
| cccacagcct cccctcggtg ccctgctgcc tcctcaggtc agccctggac atcccgggtt | 58440 |
| tccccaggcc agatggtagg tttgaagtga ggtctgtgtc actgtggtat tatgattacg | 58500 |
| tttgggggag ttatcgttat acccacagca tcacacggtc catcagaaac ccatgccaca | 58560 |
| gccctccccg caggggaccg ccgcgtgcca tgttacgatt ttgatcgagg acacagcgcc | 58620 |
| atgggtatgg tggctaccac agcagtgcag cccatgaccc aaacacacag gcagcaggc | 58680 |
| acaatggaca ggcctgtgag tgaccatgct gggctccagc ccgccagccc cggagaccat | 58740 |
| gaaacagatg gccaaggtca ccccacagtt cagccagaca tggctccgtg gggtctgcat | 58800 |
| cgctgctgcc ctctaacacc agcccagatg gggacaaggc caaccccaca ttaccatctc | 58860 |
| ctgctgtcca cccagtggtc ccagaagccc ctccctcatg gctgagccac atgtgtgaac | 58920 |
| cctgagagca cccccatgtca gagtaggggc agcagaaggg cggggctggc cctgtgcact | 58980 |
| gtccctgcac ccatggtccc tcgcctgcct ggccctgaca cctgagcctc ttctgagtca | 59040 |
| tttctaagat agaagacatt cccgggggaca gccggagctg ggcgtcgctc atcccgcccg | 59100 |
| gccgtcctga gtcctgcttg tttccagacc tcaccaggga agccaacaga ggactcacct | 59160 |
| cacacagtca gagacaaaga accttccaga aatccctgtc tcactcccca gtgggcacct | 59220 |
| tcttccagga cattcctcgg tcgcatcaca gcaggcaccc acatctggat caggacggcc | 59280 |
| cccagaacac aagatggccc atggggacag cccacaaacc caggccttcc cagacccta | 59340 |
| aaaggcgtcc cacccctgc acctgcccca gggctaaaaa tccaggaggc ttgactcccg | 59400 |
| cataccctcc agccagacat cacctcagcc ccctcctgga ggggacagga gcccgggagg | 59460 |
| gtgagtcaga cccacctgcc ctcgatggca ggcggggaag attcagaaag gcctgagatc | 59520 |
| cccaggacga agcaccactg tcaatggggg ccccagacgc ctggaccagg gcctgcgtgg | 59580 |
| gaaaggccgc tgggcacact caggggcttt ttgtgaaggc ccctcctact gtgtgactac | 59640 |

```
ggtgactacc acagtgatga aactagcagc aaaaactggc cggacaccca gggaccatgc   59700
acacttctca gcttggagct ctccaggacc agaagagtca ggtctgaggg tttgtagcca   59760
gaccctcggc tctagggac accctggcca tcacagcgga tgggctggtg ccccacatgc    59820
catctgctcc aaacagggc ttcagagggc tctgaggtga cttcactcat gaccacaggt    59880
gccctggccc cttccccgcc agctacaccg aaccctgtcc caacagctgc cccagttcca   59940
acagccaatt cctggggccc agaattgctg tagacaccag cctcgttcca gcacctcctg   60000
ccaattgcct ggattcacat cctggctgga atcaagaggg cagcatccgc caggctccca   60060
acaggcagga ctcccgcaca ccctcctctg agaggccgct gtgttccgca gggccaggc    60120 ctggacagtt cccctcacct gccactagag aaacacctgc cattgtcgtc cccacctgga   60180
aaagaccact cgtggagccc ccagcccag gtacagctgt agagagactc cccgagggat    60240
ctaagaagga gccatgcgca gttctgccgg gaccctcggc caggccgaca ggagtggaca   60300
ctggagctgg gccacactg ggccacatag gagctcacca gtgagggcag gagagcacat    60360
gccggggagc acccagcctc ctgctgacca gaggcccgtc ccagagccca ggaggctgca   60420
gaggcctctc caggggaca ctgtgcatgt ctggtccctg agcagccccc cacgtcccca    60480
gtcctggggg ccctggcac agctgtctgg accctccctg ttccctggga agctcctcct   60540
gacagccccg cctccagttc caggtgtggt tattgtcagg gggtgtcaga ctgtggtgga   60600
tacagctatg gttaccacag tggtgctgcc catagcagca accaggccaa gtagacaggc   60660
ccctgctgtg cagccccagg cctccacttc acctgcttct cctggggctc tcaaggtcac   60720
tgttgtctgt actctgccct ctgtggggag ggttccctca gtgggaggtc tgttctcaac   60780
atcccagggc ctcatgtctg cacggaaggc caatggatgg gcaacctcac atgccgcggc   60840
taagataggg tgggcagcct ggcggggac agtacatact gctgggtgt ctgtcactgt     60900 gcctagtggg gcactggctc ccaaacaacg cagtcctcgc caaaatcccc acagcctccc   60960
ctgctagggg ctggcctgat ctcctgcagt cctaggaggc tgctgacctc cagaatgtct   61020
ccgtccccag ttccagggcg agagcagatc ccaggccggc tgcagactgg gaggccaccc   61080
cctccttccc agggttcact ggaggtgacc aaggtaggaa atggccttaa cacagggatg   61140
actgcgccat cccccaacag agtcagcccc ctcctgctct gtaccccgca cccccaggc    61200 cagtccacga aaaccagggc cccacatcag agtcactgcc tggcccggcc ctggggcgga   61260
cccctcagcc ccccaccctgt ctagaggact tgggggaca ggacacaggc cctctcctta   61320
tggttccccc acctgcctcc ggccgggacc cttggggtgt ggacagaaag gacacctgcc   61380
taattggccc ccaggaaccc agaacttctc tccagggacc ccagcccgag cacccccctta  61440 cccaggaccc agccctgccc ctcctcccct ctgctctcct ctcatcaccc catgggaatc   61500
cggtatcccc aggaagccat caggaagggc tgaaggagga agcggggccg tgcaccaccg   61560
ggcaggaggc tccgtcttcg tgaacccagg gaagtgccag cctcctagag ggtatggtcc   61620
accctgcctg gggctcccac cgtggcaggc tgcgggaag gaccagggac ggtgtggggg    61680
agggctcagg gccctgcggg tgctcctcca tcttcggtga gcctccccct tcacccaccg   61740
tcccgcccac ctcctctcca ccctggctgc acgtcttcca caccatcctg agtcctacct   61800
acaccagagc cagcaaagcc agtgcagaca aaggctgggg tgcagggggg ctgccagggc   61860
agcttcgggg agggaaggat ggagggaggg gaggtcagtg aagaggcccc cttcccctgg   61920
gtccaggatc ctcctctggg accccggat cccatcccct cctggctctg ggaggagaag    61980
```

```
caggatggga gaatctgtgc gggaccctct cacagtggaa tatccccaca gcggctcagg    62040
ccagacccaa aagccctca gtgagccctc cactgcagtc ctgggcctgg gtagcagccc     62100
ctcccacaga ggacagaccc agcaccccga agaagtcctg ccaggggag ctcagagcca     62160
tgaaagagca ggatatgggg tccccgatac aggcacagac ctcagctcca tccaggccca    62220
ccgggaccca ccatgggagg aacacctgtc tccgggttgt gaggtagctg gcctctgtct    62280
cggaccccac tccagacacc agacagaggg gcaggccccc caaaaccagg gttgagggat    62340
gatccgtcaa ggcagacaag accaaggggc actgacccca gcaagggaag gctcccaaac    62400
agacgaggag gtttctgaag ctgtctgtat cacagtgggg tatagcagtg gctggtacca    62460
cagtgacact cgccaggcca gaaaccccgt cccaagtcag cggaagcaga gagagcaggg    62520
aggacacgtt taggatctga ggccgcacct gacacccagg gcagcagacg tctcccctcc    62580
agggcaccct ccaccgtcct gcgtttcttc aagaataggg gcggcctgag ggggtccagg    62640
gccaggcgat aggtccctc taccccaagg aggagccagg caggacccga gcaccgtccc    62700
cattgaggct gacctgccca gacgggcctg ggcccacccc acacaccggg gcggaatgtg    62760
tgcaggcccc agtctctgtg ggtgttccgc tagctggggc ccccagtgct caccccacac    62820
ctaaagcgag cccagcctc cagagcccc taagcattcc ccgcccagca gcccagcccc      62880
tgcccccacc caggaggccc cagagctcag ggcgcctggt cggattctga acagccccga    62940
gtcacagtgg gtataactgg aacgaccacc gtgagaaaaa ctgtgtccaa aactgactcc    63000
tggcagcagt cggaggcccc gccagagagg ggagcagccg gcctgaaccc atgtcctgcc    63060
ggttcccatg accccagca cccagagccc cacggtgtcc ccgttggata atgaggacaa      63120
gggctggggg ctccggtggt ttgcggcagg gacttgatca catccttctg ctgtggcccc    63180
attgcctctg gctggagttg acccttctga caagtgtcct cagaaagaca gggatcaccg    63240
gcacctccca atatcaaccc caggcagcac agacacaaac cccacatcca gagccaactc    63300
caggagcaga gacaccccaa cactctgggg accccaacc gtgataactc cccactggaa      63360
tccgccccag agtctaccag gaccaaaggc cctgccctgt ctctgtccct cactcagggc    63420
ctcctgcagg gcgagcgctt gggagcagac tcggtcttag gggacaccac tgtgggcccc    63480
aactttgatg aggccactga cccttccttc ctttcctggg gcagcacaga ctttggggtc    63540
tgggcaggga agaactactg gctggtggcc aatcacagag cccccaggcc gaggtggccc    63600
caagaaggcc ctcaggaggt ggccactcca cttcctccca gctggacccc aggtcctccc    63660
caagataggg gtgccatcca aggcaggtcc tccatggagc ccccttcaga ctcctcccgg    63720
gaccccactg gacctcagtc cctgctctgg gaatgcagcc accacaagca caccaggaag    63780
cccaggccca gccaccctgc agtgggcaag cccacactct ggagcagagc agggtgcgtc    63840
tgggaggggc taacctcccc accccccacc ccccatctgc acacagccac ctaccactgc    63900
ccagaccctc tgcaggaggg ccaagccacc atggggtatg gacttagggt ctcactcacg    63960
tgcctcccct cctgggagaa ggggcctcat gcccagatcc ctgcagcact agacacagct    64020
ggaggcagtg gccccagggc caccctgacc tggcatctaa ggctgctcca gcccagacag    64080
cactgccgtt cctgggaagc ctgggctcca ccagaccaca ggtccagggc acagcccaca    64140
ggagccaccc acacacagct cacaggaaga agataagctc cagaccccag ggcgggacct    64200
gccttcctgc caccacttac acacaggcca gggagctgtt cccacacaga tcaacccaa     64260
accgggactg cctggcacta gggtcactgc catttccctc tccattccct cccagtgcct    64320
ctgtgctccc tccttctggg gaacaccctg tgcagcccct ccctgcagcc cacacgctgg    64380
```

```
ggagacccca ccctgcctcg ggccttttct acctgctgca cttgccgccc acccaaacaa    64440
ccctgggtac gtgaccctgc agtcctcacc ctgatctgca accagacccc tgtccctccc    64500
tctaaacacc cctcccaggc caactctgca cctgcaggcc ctccgctctt ctgccacaag    64560
agcctcaggt tttcctacct gtgcccaccc cctaacccct cctgcccaca acttgagttc    64620
ttcctctcct ggagcccttg agccatggca ctgaccctac actcccaccc acacactgcc    64680
catgccatca ccttcctcct ggacactctg accccgctcc cctccctctc agacccggcc    64740
ctggtatttc caggacaaag gctcacccaa gtcttcccca tgcaggccct gccctcact    64800 gcctggttac acgggagcct cctgtgcgca gaagcaggga gctcagctct tccacaggca    64860
gaaggcactg aaagaaatca gcctccagtg ccttgacaca cgtccgcctg tgtctctcac    64920
tgcctgcacc tgcagggagg ctccgcactc cctctaaaga tgagggatcc aggcagcaac    64980
atcacgggag aatgcagggc tcccagacag cccagccctc tcgcaggcct ctcctgggaa    65040
gagacctgca gccaccactg aacagccacg gaggtcgctg gatagtaacc gagtcagtga    65100
ccgacctgga gggcagggga gcagtgaacc ggagcccata ccatagggac agagaccagc    65160
cgctaacatc ccgagcccct cactggcggc cccagaacac cccgtggaaa gagaacagac    65220
ccacagtccc acctggaaca gggcagacac tgctgagccc ccagcaccag ccccaagaaa    65280
cactaggcaa cagcatcaga gggggctcct gagaaagaga ggaggggagg tctccttcac    65340
catcaaatgc ttcccttgac caaaaacagg gtccacgcaa ctcccccagg acaaaggagg    65400 agcccctgt acagcactgg gctcagagtc ctctctgaga caggctcagt ttcagacaac    65460
aacccgctgg aatgcacagt ctcagcagga gagccaggcc agagccagca agaggagact    65520
cggtgacacc agtctcctgt agggacagga ggattttgtg ggggttcgtg tcactgtgag    65580
catattgtgg tggtgactgc tattcccaca gtgacacaac cccattccta aagccctact    65640
gcaaacgcac ccactcctgg gactgagggg ctggggagc gtctgggaag tatggcctag    65700
gggtgtccat caatgcccaa aatgcaccag actctcccca agacatcacc ccaccagcca    65760
gtgagcagag taaacagaaa atgagaagca gctgggaagc ttgcacaggc cccaaggaaa    65820
gagctttggc aggtgtgcaa gaggggatgt gggcagagcc tcagcagggc cttttgctgt    65880
ttctgctttc ctgtgcagag agttccataa actggtattc aagatcaatg gctgggagtg    65940
agcccaggag gacagtgtgg gaagagcaca gggaaggagg agcagccgct atcctacact    66000
gtcatctttt gaaagtttgc cctgtgccca caatgctgca tcatgggatg cttaacagct    66060
gatgtagaca cagctaaaga gagaatcagt gaaatgcatt tgcagcacag atctgaataa    66120
atcctccaga atgtggagca gcacagaagc aagcacacag aaagtgcctg atgccaaggc    66180
aaagttcagt gggcaccttc aggcattgct gctgggcaca gacactctga aaagcactgg    66240
caggaactgc ctgtgacaaa gcagaaccct caggcaatgc cagccctaga gcccttcctg    66300
agaacctcat gggcaaagat gtgcagaaca gctgtttgtc atagcccaa actatgggc    66360 tggacaaagc aaacgtccat ctgaaggaga acagacaaat aaacgatggc aggttcatga    66420
aatgcaaact aggacagcca gaggacaaca gtagagagct acaggcggct ttgcggttga    66480
gttcatgaca atgctgagta attggagtaa cagaggaaag cccaaaaaat acttttaatg    66540
tgatttcttc taaataaaat ttacacccgg caaaatgaac tatcttctta agggataaac    66600
tttcccctgg aaaaactata aggaaaatca agaaaacgat gatcacataa acacagtggt    66660
ggttacttct actggggaag gaagagggta tgagctgaga cacacagagt cggcaagtct    66720
```

```
cctaacaaga acagaacaaa tacattacag taccttgaaa acagcagtta aacttctaaa   66780
tcgcaagaag aggaaaatgc acacacctgt gtttagaaaa ttctcagtcc agcactgttc   66840
ataatagcaa agacattaac ccaggttgga taaataagcg atgacacagg caattgcaca   66900
atgatacaga catacattca gtatatgaga catcgatgat gtatccccaa agaaatgact   66960
ttaaagagaa aaggcctgat gtgtggtggc aatcacctcc ctgggcatcc ccggacaggc   67020
tgcaggctca ctgtgtggca gggcaggcag gcacctgctg gcagctcctg ggcctgatg    67080 tggagcaggc acagagctgt atatccccaa ggaaggtaca gtcagtgcat tccagagaga   67140
agcaactcag ccacactccc tggccagaac ccaagatgca cacccatgca cagggaggca   67200
gagcccagca cctccgcagc caccaccacc tgcgcacggg ccaccacctt gcaggcacag   67260
agtgggtgct gagaggaggg gcagggacac caggcagggt gagcacccag agaaaactgc   67320
agaagcctca cacatccacc tcagcctccc ctgacctgga cctcacctgg cctgggcctc   67380
acctgacctg gacctcacct ggcctgggct tcacctggcc tgggcttcac ctgacctgga   67440
cctcacctgg cctcgggcct cacctggcct gggcttcacc tggcctgggc ttacctgac   67500 ctggacctca cctggcctgg gcctcacctg acctggacct cacctggcct gggcttcacc   67560
tggcctgggc ttcacctggc ctgggcttca cctgacctgg acctcacctg gcctgggctt   67620
cacctgacct ggacctcacc tggcctcggg cctcacctgc acctgctcca ggtcttgctg   67680
gagcctgagt agcactgagg ctgtagggac tcatccaggg ttggggaatg actctgcaac   67740
tctcccacat ctgacctttc tgggtggagg cacctggtgg cccagggaat ataaaaagcc   67800
ccagaatgat gcctgtgtga tttgggggca atttatgaac ccgaaaggac atggccatgg   67860
ggtgggtagg gacagtaggg acagatgtca gcctgaggtg aagcctcagg acacaggtgg   67920
gcatggacag tgtccaccta gcgagggac agacccgagt gtccctgcag tagacctgag    67980
agcgctgggc ccacagcctc ccctcggggc cctgctgcct cctcaggtca gccctggaca   68040
tcccgggttt ccccaggcct ggcggtaggt ttgaagtgag gtctgtgtca ctgtggtatt   68100
actatgatag tagtggttat tactaccaca gtgtcacaga gtccatcaaa aactcatgcc   68160
tgggagcctc ccaccacagc cctccctgcg ggggaccgct gcatgccgtg ttaggatttt   68220
gatcgaggac acggcgccat gggtatggtg gctaccacag cagtgcagcc catgacccaa   68280
acacacgggg cagcagaaac aatggacagg cccacaagtg accatgatgg gctccagccc   68340
accagcccca gagaccatga aacagatggc caaggtcacc ctacaggtca tccagatctg   68400
gctccaaggg gtctgcatcg ctgctgccct cccaacgcca aaccagatgg agacagggcc   68460
ggccccatag caccatctgc tgccgtccac ccagcagtcc cggaagcccc tccctgaacg   68520
ctgggccacg tgtgtgaacc ctgcgagccc cccatgtcag agtagggca gcaggagggc    68580 ggggctggcc ctgtgcactg tcactgcccc tgtggtccct ggcctgcctg gccctgacac   68640
ctgagcctct cctgggtcat ttccaagaca ttcccaggga cagccggagc tgggagtcgc   68700
tcatcctgcc tggctgtcct gagtcctgct catttccaga cctcaccagg gaagccaaca   68760
gaggactcac ctcacacagt cagagacaac gaaccttcca gaaatccctg tttctctccc   68820
cagtgagaga aaccctcttc cagggtttct cttctctccc accctcttcc aggacagtcc   68880
tcagcagcat cacagcggga acgcacatct ggatcaggac ggccccccaga acacgcgatg   68940 gcccatgggg acagcccagc ccttcccaga cccctaaaag gtatcccac cttgcacctg    69000 ccccagggct caaactccag gaggcctgac tcctgcacac cctcctgcca gatatccacct  69060 cagccccctc ctgaggggga caggagcccg ggagggtgag tcagacccac ctgccctcaa   69120
```

```
tggcaggcgg ggaagattca gaaaggcctg agatccccag gacgcagcac cactgtcaat   69180
gggggcccca gacgcctgga ccagggcctg tgtgggaaag gcctctggcc acactcaggg   69240 gcttttgtg aagggccctc ctgctgtgtg actacggtgg taactcccac agtgatgaaa    69300
ccagcagcaa aaactgaccg gactcgcagg gtttatgcac acttctcggc tcggagctct   69360
ccaggagcac aagagccagg cccgagggtt tgtgcccaga ccctcggcct ctagggacac   69420
ccgggccatc ttagccgatg ggctgatgcc ctgcacaccg tgtgctgcca aacaggggct   69480
tcagagggct ctgaggtgac ttcactcatg accacaggtg ccctggtccc ttcactgcca   69540
gctgcaccag ccctgttcc gagagatgcc ccagttccaa aagccaattc ctggggccgg    69600
gaattactgt agacaccagc tcattccag tacctcctgc caattgcctg gattcccatc    69660
ctggctggaa tcaagagggc agcatccgcc aggctcccaa caggcaggac tcccacacac   69720
cctcctctga gaggccgctg tgttccgcag gccaggccg cagacagttc ccctcacctg    69780
cccatgtaga aacacctgcc attgtcgtcc ccacctggca aagaccactt gtggagcccc   69840
cagccccagg tacagctgta gagagagtcc tcgaggcccc taagaaggag ccatgcccag   69900
ttctgccggg accctcggcc aggccgacag gagtggacgc tggagctggg cccacactgg   69960
gccacatagg agctcaccag tgagggcagg agagcacatg ccggggagca cccagcctcc   70020
tgctgaccag agaccgtcc cagagcccag gaggctgcag aggcctctcc agggggacac    70080
agtgcatgtc tggtccctga gcagcccca ggctctctag cactgggggc ccctggcaca    70140
gctgtctgga ccctcctgt tccctgggaa gctcctcctg acagcccgc ctccagttcc     70200 aggtgtggtt attgtcaggg ggtgccaggc cgtggtagag atggctacaa ttaccacagt   70260
ggtgccgccc atagcagcaa ccaggccaag tagacagacc cctgccacgc agccccaggc   70320
ctccagctca cctgcttctc ctggggctct caaggctgct gtctgccctc tggccctctg   70380
tggggagggt tccctcagtg ggaggtctgt gctccagggc agggatgact gagatagaaa   70440
tcaaaggctg gcagggaaag gcagcttccc gccctgagag gtgcaggcag caccacagag   70500
ccatggagtc acagagccac ggagccccca gtgtgggcgt gtgagggtgc tgggctcccg   70560
gcaggcccag ccctgatggg gaagcctgcc ccgtcccaca gccaggtcc ccaggggcag    70620 caggcacaga agctgccaag ctgtgctcta cgatcctcat ccctccagca gcatccactc   70680
cacagtgggg aaactgagcc ttggagaacc acccagcccc ctggaaacaa ggcggggagc   70740
ccagacagtg ggcccagagc actgtgtgta tcctggcact aggtgcaggg accacccgga   70800
gatccccatc actgagtggc cagcctgcag aaggacccaa ccccaaccag gccgcttgat   70860
taagctccat cccctgtcc tgggaacctc ttcccagcgc caccaacagc tcggcttccc    70920
aggccctcat ccctccaagg aaggccaaag gctgggcctg ccaggggcac agtaccctcc   70980
cttgccctgg ctaagacagg gtgggcagac ggctgcagat aggacatatt gctggggcat   71040
cttgctctgt gactactggg tactggctct caacgcagac cctaccaaaa tccccactgc   71100
ctcccctgct aggggctggc ctggtctcct cctgctgtcc taggaggctg ctgacctcca   71160
ggatggcttc tgtcccagt tctagggcca gagcagatcc caggcaggct gtaggctggg    71220
aggccacccc tgtccttgcc gaggttcagt gcaggcaccc aggacaggaa atggcctgaa   71280
cacagggatg actgtgccat gccctaccta agtccgcccc tttctactct gcaacccca    71340 ctccccaggt cagcccatga cgaccaacaa cccaacacca gagtcactgc ctggcccctgc 71400 cctggggagg acccctcagc ccccaccctg tctagaggag ttgggggac aggacacagg    71460
```

```
ctctctccttt atggttcccc cacctggctc ctgccgggac ccttggggtg tggacagaaa    71520
ggacgcctgc ctaattggcc cccaggaacc cagaacttct ctccagggac cccagcccga    71580 gcacccccctt acccaggacc cagccctgcc cctcctcccc tctgctctcc tctcatcact   71640
ccatgggaat ccagaatccc caggaagcca tcaggaaggg ctgaaggagg aagcggggcc    71700
gctgcaccac cgggcaggag gctccgtctt cgtgaaccca gggaagtgcc agcctcctag    71760
agggtatggt ccaccctgcc tggggctccc accgtggcag gctgcgggga aggaccaggg    71820
acggtgtggg ggagggctca gggccctgca ggtgctccat cttggatgag cccatccctc    71880
tcacccaccg acccgcccac ctcctctcca ccctggccac acgtcgtcca caccatcctg    71940
agtcccacct acaccagagc cagcagagcc agtgcagaca gaggctgggg tgcaggggggg   72000 ccgccagggc agctttgggg agggaggaat ggaggaaggg gaggtcagtg aagaggcccc    72060
cctcccctgg gtctaggatc cacctttggg accccccggat cccatccccct ccaggctctg  72120 ggaggagaag caggatggga gattctgtgc aggaccctct cacagtggaa tacctccaca    72180
gcggctcagg ccagatacaa aagccccctca gtgagccctc cactgcagtg cagggcctgg   72240
gggcagcccc tcccacagag gacagaccca gcacccgaa gaagtcctgc caggggggagc    72300 tcagagccat gaaggagcaa gatatgggga ccccaatact ggcacagacc tcagctccat    72360
ccaggcccac caggacccac catgggtgga cacctgtct ccggcccctg ctggctgtga     72420
ggcagctggc ctctgtctcg gaccccccatt ccagacacca gacagaggga caggccccccc  72480 agaaccagtg ttgagggaca cccctgtcca gggcagccaa gtccaagagg cgcgctgagc    72540
ccagcaaggg aaggcccccca aacaaaccag gaggtttctg aagctgtctg tgtcacagtc   72600
gggtatagca gcggctacca caatgacact gggcaggaca gaaacccccat cccaagtcag   72660 ccgaaggcag agagagcagg caggacacat ttaggatctg aggccacacc tgacactcaa    72720
gccaacagat gtctccccctc cagggcgccc tgccctgttc agtgttcctg agaaaacagg   72780
ggcagcctga ggggatccag ggccaggaga tgggtcccct ctaccccgag gaggagccag    72840
gcgggaatcc cagccccctc cccattgagg ccatcctgcc cagaggggcc cggacccacc    72900
ccacacaccc aggcagaatg tgtgcaggcc tcaggctctg tgggtgccgc tagctgggggc   72960 tgccagtcct caccccacac ctaaggtgag ccacagccgc cagagcctcc acaggagacc    73020
ccacccagca gcccagcccc tacccaggag gccccagagc tcaggcgcc tgggtggatt     73080 ctgaacagcc ccgagtcacg gtgggtatag tgggagctac taccactgtg agaaaagcta    73140
tgtccaaaac tgtctcccgg ccactgctgg aggcccagcc agagaaggga ccagccgccc    73200
gaacatacga ccttcccaga cctcatgacc cccagcactt ggagctccac agtgtcccca    73260
ttggatggtg aggatggggg ccgggggccat ctgcacctcc caacatcacc cccaggcagc    73320
acaggcacaa accccaaatc cagagccgac accaggaaca cagacacccc aatacccctgg  73380 gggaccctgg ccctggtgac ttcccactgg gatccacccc cgtgtccacc tggatcaaag    73440
accccaccgc tgtctctgtc cctcactcag ggcctgctga ggggcgggtg ctttggagca    73500
gactcaggtt taggggccac cattgtgggg cccaacctcg accaggacac agattttttct  73560 ttcctgccct ggggcaacac agactttggg gtctgtgcag ggaggacctt ctggaaagtc   73620
accaagcaca gagccctgac tgaggtggtc tcaggaagac cccaggagg gggcttgtgc     73680 ccccttcctct catgtggacc ccatgccccc caagataggg gcatcatgca gggcaggtcc   73740
tccatgcagc caccactagg caactccctg gcgccggtcc ccactgcgcc tccatcccgg    73800 ctctgggggat gcagccacca tggccacacc aggcagcccg ggtccagcaa ccctgcagtg   73860
```

```
cccaagccct tggcaggatt cccagaggct ggagcccacc cctcctcatc ccccacacc    73920 tgcacacaca cacctacccc ctgcccagtc cccctccagg agggttggag ccgcccatag    73980
ggtgggggct ccaggtctca ctcactcgct tcccttcctg ggcaaaggag cctcgtgccc    74040
cggtcccccc tgacgcgct gggcacaggt gtgggtactg ggcccaggg ctcctccagc     74100 cccagctgcc ctgctctccc tgggaggcct gggcaccacc agaccaccag tccagggcac    74160
agccccaggg agccgcccac tgccagctca caggaagaag ataagcttca gaccctcagg    74220
gccgggagct gccttcctgc caccccttcc tgccccagac ctccatgccc tccccaacc    74280 acttacacac aagccaggga gctgtttcca cacagttcaa ccccaaacca ggacggcctg    74340
gcactcgggt cactgccatt tctgtctgca ttcgctccca gcgcccctgt gttccctccc    74400
tcctccctcc ttcctttctt cctgcattgg gttcatgccg cagagtgcca ggtgcaggtc    74460
agccctgagc ttggggtcac ctcctcactg aaggcagcct cagggtgccc aggggcaggc    74520
agggtggggg tgaggcttcc agctccaacc gctccactag ccgagactaa ggaagtgaga    74580
ggcagccaga aatccagacc attccatagc aaatggattt cattaaagtt accagacttc    74640
agtgtaagta acatgagccc catgcacaac aatcccttat gaaggggaag tcagtgtcgc    74700
ctcggatttc ttgaaaaaca caaaaactta tcaatgcctg taaaagtctg ttggaaagaa    74760
aatatgattc aagaatgtta tgcccaacaa agctggcata ttttctaccc ggacacactc    74820
agggaatgtg gtcccttgag tgcttctctc actgcgtaaa tcctacgtgg tgtttaagca    74880
tattcataaa tgtgtatgtc tatttttatg tgtaagatgg ttcattttta ttttatttat    74940
tcaatatgta caataaagaa tattgacaaa taggctggac atggtggctc ccacctgtaa    75000
tcccagccct ttgggaggcc gaggcgggca gatcacctga ggtctggagt tcgagaccag    75060
cctggccaac atgatgaaaa cccatctcta ctaaaaatac aaagattagc caggcatggt    75120
ggtgcatgcc tgtaatccca gccactcagg aggctgagac aggagaaatg cgtgaacccg    75180
gaaggcggag gttgcagtga ccgagatca caccactgca ctccagcctg gcgacagagc     75240
aagattccat ctcaaaaaaa aaaaaagaca aagaaatttg ttttttgaa taaagacaaa    75300 tttcatcaca cgaagataaa gatgcaaagc tccagacagg aaggcacgga cagcacagtg    75360
aagcccggag cgggcgctgg ggggccaggg gcatggcggg ggtgccagcg tctctcggtt    75420
cctaccatgg ccactccagc ctgtgttctc acgaggatgg ctgtgcaatg ctaggagcgt    75480
gttcgaagct ctagggcaac cactggaagt gaggctgagg agcagagccc agaggcccgt    75540
ggagctgatg aaaagaaagc tggagaaagt gtttgctgcc tcccaacatg gtaagaaaag    75600
atagaaagag agagcacacg gcaaagggag cttgctgagg gactctttac aatggcttgc    75660
acagagctca gggggtctgg gaggctaggg ccctgcgcag ggcagtcacc ccagcctgct    75720
gaccaaggtt tgctgcaggc agctctgggg gtggttgagg cgcggtccct ggagccaccc    75780
ctcaagggaa cgaggcagca gagtgggcca aggcccaggt cggctgcaag gctgcccagg    75840
acttggggtc cttacatcag cagccactga tgcagctggc ccagagagag gcgccgagca    75900
ggttgcctcc aggggacaaa ccaggtcgga gagggtgagg cagtggatgg agccacaaca    75960
accccgggca cgggtgacac gcacgttcat gcacatctga cccttcctcc ctcaccaaac    76020 aggtcccct gccttcccca tggttgcgaa aaagcaaaat gtagacgttt tttctttttt    76080
aattcatgtt ttaattgaca aatgaagccg tatatattta ttgtgtacaa catgatgctt    76140
taaaatatgt atacatcgtg gaacagcaac gttgagctaa tttaacacgc attacttcac    76200
```

```
atacttgtca tcttttgtgg cgagaatgct taaaatccac tctcttagta ttttttaaga    76260
atgcaataca ttgttgtcaa ctgtggtcac cgtcatgcat agccaagctc ccgacctcac    76320
cctcctgcca gctcaggctg tgcatccttt caccagcatc ccccaccccg gcccctggcc    76380
ctggtaacta ccactctata ctctacgtat gagttcagct ttttaagatt ccacagatga    76440
atgagatcat acagtatttg cttctatgc ctggcttatt ttagttaaca cactgtcctc     76500
cagatccatc cgttgttgca aatgacaggg tttcattctt tttaaagtct aaagagtatt    76560
ccattgtgtc aatggacctc atttgcttta tccatgcatc aactatggac atttaggttg    76620
attccatttc ttagctgttg tggatggtgc tgcagtaaac atggggctgc agatgtctct    76680
tcaacatact gacatcatgt cctttggata ataccagt agtgggatcg ctggatcaca     76740
atgtacagtt ttttttttaa tggaaacttt cattttttgg tgaaattagg aaaacagata    76800
aaacccacag aatccaaaat atatgtgaag atgccaaaaa cagttgacat tgggcagagg    76860
tcacatggaa ggaagtgaat acatgacggg gtgtgagggc ccagaggcag ctgaaatacg    76920 cttttctaaac acaaggacct cttctgagag ggcagaagtt ttatcctgca catgcaatga   76980
ccagcacagc taaaatacac tttctaaaca tgaggacctc ttctgagagg gcagctttat    77040
cctgcaaatg caatgaccag cacaggaccc agaataaaga gagttgccag cggacgcctg    77100
gtgtccatgt gtccaggtga gttcgagatg cggacggcgc tggccagcca gtcacaccct    77160
aagtcaatct gctgcatgca tttgtccttg ccacagcaga aaacgagaaa gcctttgggc    77220
tgcaaagctt cacaggctcc tcttctcccg actccatgga aacagctaca aagagcaggc    77280
ccagtagagc ttaattcatg aaaatgagta ataaacttga actggaacag tatcgactttt   77340 ttagaaacgg cagcaaagtg tataaaaaat attcaccaga acaatatttc caaacgatga    77400
gatgagaatt tcagccaagt aatcctccat ggatagaaaa taatgaaggg attggattta    77460
tgaaggaaaa tcatggagct caaatacaag aaaagagaat caaaatgaa caggaggaga     77520 taaaatatgt tttggccaaa gttacaaaat aaattttta aaaacccttc atcatggcaa     77580
gtagaaagag cgagaggaaa aacagatccc gtggaagaca caaataggac atggggagaa    77640
aaatgaatga gatgaaacag agcagaaata aaattttacg gaactaaaga caagtgatct    77700
gaacctgcct ggggcctggg ggacctcgcc accctgaagg gaagaacat gcctggctgg      77760 ctttgccacc tgctcattgc agagccccac agcttgcaac aaacataggc ggtagccagg    77820
gagtggttac agcaggcctt gagcaagacc cagtgttgtg ctgacttcag gtctgaccca    77880
gcactgtcat agtggtggtg tccatagtgg tagtgggggt gcttgtgtca ctccaccccc    77940
atctccagga ggctcagaac agacagagag agactccatt tgtttgggag aaagtaaggg    78000
atgagaacaa gagtctctgc ctggtaatcc agagaattat tctagatctt ggccaagatt    78060
atcaaagcag tacctctatg agtcttttgg gcttggagtc cccctaaagc agatatagct    78120
aagatcacaa cacccaagtc cttttgaata tgtgggaaga cttcccaagg acaggagcaa    78180
acaaacaagc ccagactgca aaaaacaag ccgagactgc aataaacacc tcactcttca     78240
atgcccaggc actgaagaac atctcctagc agcaacacca tccaggaaaa catggcctca    78300
accagtgaac taaataaggc caccgggacc agtctcggag aaatagaggt atgttatctt    78360
tcagagaatt caaagtagct ttgttgagga aactcaaaga aattcaagat aacacagtga    78420
aggaattcag aatcctatcc gataaattta acagagattg aagcaattaa aaagaattaa    78480
gcagaaatta tggagctgaa aaatgcaatt ggcactactga aaaatgcatc agagtatttt   78540
catagcctca tatatcaagt agaagaaaga attagtgagc ttgaaaacag gctatttgga    78600
```

```
aaagcacgat aaaaggagac aaaagagaaa agaataaata acaatgaagc atatctacag   78660
gatctagaaa atagcctcaa aaggccaaat ctaagaatta ttagccttaa agaggaggta   78720
gagaaagagg gatggagagt ttattcaaag ggataataac agaaaacttc ccaaacctag   78780
agaaagatat caatatccaa atgcaagaag gatgtagtac accaaggaga tttaatgcaa   78840
agaagactac ctcaaggcat tcaatactca aactcccata tgacaaggac tttaaaaga    78900 tcctaaaagc agcaaaagaa aagaaatgaa taaaatacta tggagctcca atatgtctgg   78960
cagcagactt ttcagtgaag actttatatg ccaggagaga gtgtcataat ggatttaaag   79020
tgctgaagga aaaaactttt accctcgaac agtatagctg gtgaaattat ccttcaaaca   79080
tgaaggagaa ataatttgtt tccagacaaa tgttgaggga tttcatgaac accagacctg   79140
tcttttaaga aatgctaaag ggagtacttc aatcagaaag aaacacgtta gtgaacaata   79200
agaaatcatc tgaaggcaca aaactcaccg gtaatagtaa gtacacagaa aaacacagaa   79260
tattataaca ctgtaactgt ggtgtgtaaa ctccttttgt ttgtttgttt gtttgtttgt   79320 ttgttttgt ttttagacgg agttttgctc cagcccaggc tggagtgcaa tggcacaatc    79380
tcagctcact gcaacttcca cctcccgggt tcaagcaatt ctcctgcctc agcctcccaa   79440
gtagctggga ttacaggcat gtgctaccat gtccagctaa ttttgtattt tagtagagac   79500
ggtgtttcac catgttggtc aggctagcct tatcttgagt agaaaaacta atgatgaag    79560 caatgaaaaa taataactac aacttttcaa gacatagtac aataagatat aaatcataac   79620
aaaaagttaa aaggtggagg gatgaagtta aggcatagag tctttattag ttttcttttt   79680
acttgtctgt ttatgcaaac agtgttaagt tgtcatcagt ttaaaataat gggtcataag   79740
atactatttg caagcctcat ggtaacgtca aaccaaaagc aatacaacag atacacaaaa   79800
aacaaaaagc aagaagctaa attacgtcat cagagaaaat caccttcact aaaaggaaga   79860
cggagaaaag aatgaagaga gagaagacca aaagcaaata gcaatatggc aggagtaagt   79920
ccttacttat caataatacc attgaatgta aatggactaa actctccaat caaaagacat   79980
agagtggctg aatcaattaa agaaaaaaca agacccattg atctgttgtc cacaagaaac   80040
acactttatc tataaagaca cacatagact gaaaacaaag ggatggaaaa agatactcca   80100
cgccaatgga aaccaaagaa agagcaggag tagctacact tatatcaggc aaaatagatt   80160
tcaagacaaa aactataaga agagacaagg tcactaatga taaacaggtc aattcagcaa   80220
gaggatataa caattgtaaa tatatatgca cccaatgctg gagcacccag atatataaag   80280
caagtattta ctagagctaa agagagaaat agactccaat gcaataatag ctggagattt   80340
caacatccca ctttcaacat tgaacagatc ctccagatag aaaatcaaca agaaatatt    80400 ggacttaatc tgcactatcg accaaatgga tctaacagat atttacgaa catttcatcc    80460 aacagctgca gaacacacat tcttttcctc agcacataga tcattctcaa ggatagacca   80520
tatgttgggt cacaaaacaa gttttaaaat attcaaatac attgaaataa tatcaagcat   80580
cttctgtgac cacaatggac taaaactaga aatcaataac aagaggaatt ttggaaacta   80640
tataaatata tggaaattaa tgaatgctga gtgggtcaat gaagcaatta agaaggaaac   80700 tgaaatttt cttggaacga atgatcatgg aaacagaaaa taccaaaacc tatgggtac     80760 agcaaaagca gtactaagag ggaagtttac agctacaaat gcttacatta aaaaagaaga   80820 aaacttcaa taaaaaaacc taacaatgca tcttaaagaa ctagaaaagc aagaggaaat    80880
caaatccaaa attagtagaa gaaaacagta aaggtcagag cagaaataag taaaattgaa   80940
```

```
atgaagaaaa caatacaaaa gatcaataaa acaacaggtt gttttcttga aaagttaaac    81000
aaaattgaca aacctttagc cagactaaga aaaaagaca gaagatccaa ataaataaaa    81060
tcagagatga aaaaggtgac attacaactt acaccacaga aattcaaagg atcattagtg    81120
gctactataa gcaactatat gccaataaat tggaaaatct agaagaaatg cagaaattcc    81180
tagacacata caacctccca agattaaacc aagaagaaat tcaaaacctg aacagactga    81240
taacaagtaa tgagatcaaa gccgtaataa aaagcctccc agtaaagaga agcccaggac    81300
ccgacggctt cactgctgaa ttctaccaaa catttaaagt agaactaata ccaatcctac    81360
tcaaactatt ccaaaaaata gaggtggaag gaatacttca aaactcatta tacgaggcca    81420
gtattaacct gacaccaaaa ctagacaaag acacatgaaa aaagaaaac tacaggccaa    81480 tatgtctgat gaatattgac acaaaaatcc tcaacaaaat actagcaaac caaattcaac    81540
tacacattag aaagttcact catcatgacc aagtggaatt tatctaactt gggatgcaaa    81600
gatggttcaa catatgcaaa tcaatcaatg tgatacatca tatcaacaga atgaacaaca    81660
aaaaccattt gatcatttaa ttgatactga aaaagcattt gataaaattc aacattcctt    81720
cataataaaa attctcttct atactaggta caaaagaaac ttacctcaac ataataaagc    81780
catatatgac agtcccacag tatgatacta aatgaggaaa aactgagagc ctttcctcta    81840
cgatctggaa catgacaaag atgcccactt tcatcactgt tattcaacat agtactggaa    81900
gtcctagctg gagcgatcag acaagagaaa gatataaaag acatccaaat tggaaaggaa    81960
taagtcaaat tatcctcatt tgcatatggt atgatcttct atttagagct aactaaagac    82020
tccaccaaaa aaagttatta gaactgacga acaaattcag taaagctgca ggatacaaaa    82080
tcaacataca aaaatcagta gcatttctat atgccaacaa tgaccaatgt gaaaagaaa    82140 ttaaaaagta accctattta caataaccac aaataaacac ctaggaatta ccaaagagg    82200 taaaagattt ctgtaatgaa aactataaaa cactgatgaa agaaattgaa gagtacacca    82260
aaaaatggaa agcaattgca tgttcatgga ttagaagaat cagtgttgtt ataatgtcca    82320
tactatccaa agcaatctac agattcaatg caatccttat caaaatacca atgacatcat    82380
tcacagaaat agaaaaaaaa aatcctaaaa tttacgtgga accacaaaga cccagaatag    82440
ccaaagctct cctaagcaaa aagaacgaaa ctgtaggaat gacattgcct gtcttcaaat    82500
tctactacag agctatagat agtaaccaaa acagcgtggt actggcataa aaacagacac    82560
agagacaaac agaacaaaat ttaaaaaccc agaaataaat ccacacacct acagcaaatt    82620 cattttttgac aaagttgcca agaacatact ctggggaata gataatgata tctcttcaat    82680
aaatagtgtg gggaaaactg gatatccata tacataacag tgaaactaga cccctctctc    82740
tctcactata tacaaaaatc aaatcaaaat tgtttaagga cttaaatcta agacctcata    82800
ctatgaaacc actgcaagac aaccttggcg gaaactctcc aagacatcag tccaggcaaa    82860
gatttcttga gtaatatccc acaagcacag acaaccaaag caaaaatgga caaatgggat    82920
cacatcaagt taaaaagctt ctgcacagta agggaaacaa ccaacaaaat gaagagacaa    82980
cccacagaat gggagaaaat atttgaaaaa tacccatctg gcaagggatt aaaaaccaga    83040
atatatgcag aatatataag gagctcaaac agtgctatag aaaaaaaaat ctaataatct    83100
gatttaaaaa tgggaaaaat gttagaatag acatttctta aaataagaca tacagatggc    83160
aaaccgacat ggaacggtgc tcaacatcat ggattatcac agaaacacaa tcaatcaaaa    83220
ctaaaactaa aatgtgctat catctcaccc cagttaaaat ggctgatatc cagaagacag    83280
gcaataacaa atgctggcaa ggatgtgggg aaagggagc ccccatacac tgttgctggg    83340
```

```
attgtaaatt agtacaacca ctgtggagag cagcatgaaa gttcctcaaa aaactgaaag    83400
aaagctacca taggatccag caatcccact gctgtgtata tactacaaaa gaaaggaagt    83460
cagtatatga agaggtatct gcactcccat gtttgttgca gccctgttca caacagccaa    83520
gatttggaag caacctaagt gtccatcagc agttgaatgt ataaagaaaa tgtggtgcat    83580
atacacaatg gagtattatt caataataaa aaggaatgag attgagtcat ttgcaacaac    83640
atggatggaa ctggagatca ttatgtgaag tgaaataagc caggcacaga aagacaaaca    83700
ttacaatgtt cttacttatt aatgagatct aaaaatcaaa acaattgcac ccatgttcat    83760
aaagagtaaa aggatggtta ccagatgctg agaacggtgg tgggggata gggaaaggtg     83820 gcagtggtta acgggtacaa aaaaatagaa gaatgaata agacttgcta cttgatagca     83880
cagcaaggtg gctatagtca gtaatttagt tgtatatttt taataatgaa aggtgtataa    83940
ttggattgtt tctaacacaa aggataatgc ttaagaggat ggatacccca ttttccatga    84000
tgtgattatt tcacattgca cgcctagatc aaaacatcca atgtacccca taaatatata    84060
catcttctat gtacccataa aaattctgta aaataaaata tataaaaaga ggtgacagat    84120
atggaagaca ggcaaagaag agacgacatc cacataatcc gagtacctaa gaaagaatgg    84180
agtccagtgc atctcaggag ccaccattct aagccaattt tctctggttc tctcagtcac    84240
cctaccaata cgtgggcaat cttgttttat ttcaggatag agtttttgaa attatagatt    84300
taagtatgct ttctgttcta ttacttttgg taattaattt tagaaagaac taatttgggc    84360
acaaatttga aaaaattcta aatccaaaaa aaaaagaaa aaaacacaca cacaatcatc     84420
tataaggggg atgatgacca gtcctagatt tctcaccagc cacattcaag atcagtaaat    84480
ggtaggacaa aacctgtagg gtccttaagg gggaaagaag tagtggatag tccagagtct    84540
atatacagcc aactgttctt gaagaaaaaa ggctgctgaa aaggagttcc aaacattcta    84600
taatccataa tctcatgatg aaactactag aggaagacca ccagccatca aaaggtgctt    84660 ggagaacccca gggccaagaa ccaaaagtaa atattaagtg tccttaactg cgagactaag    84720
atagaaatga ctgtggggga ccatgtggcc tcaacagagg tgaaatggtg tctgcctgac    84780
aaagtggaca ttttacaatg atcaaaacac agaatatgag atagagagca cttctgaatt    84840
actgcctcac tccaaataac tctcagccaa aggacttcag taaaaccaaa ttgggcatat    84900
tagacagtac aaacaaattc taagaaaata atattactga ttacaatcac atgatgctag    84960
agatggaggg gaaaggaag aggaaaccag gtaatttcat actcgtatat agtaaagaac     85020
taaagtacat tgtccaaaga agaacaaaga atattttgga aagttataaa ggtagccact    85080
acacatagaa gatagcaaag aacaagaaaa cttaagatgg aaaactttt ggaagcataa     85140 gaatagaaaa tataaactac taagataaga ttgaagccaa acagatctat gaaaacaaca    85200
aacatcaatg gccttaactt gcctattaaa aggaagagac tttcaaattg gaccacaaga    85260
taaaacccaa ctctatatag catatgagta ttacacacaa aatgggaaaa gctgaaaaaa    85320
cttgggcaaa attcaccccca agcaaattcc actgtttcct ttgggacaaa atgccaagct   85380
ccatgccagg gaagatgatt ctcctcagac cttctcctca ctctcccagt cctcttaggg    85440
aaggaattgg gtgttagagg agggagactc tgtcgattat cagctgaagc agtggtgtgc    85500
tcctgcgttg cttctgacct gggaaatgaa gcagcaagac tctttctgct gtgtctttgc    85560
ccagaagggc catccccca gagcagagta cccaggccgg caggagcagt ggtggaagcg     85620
tggaaaccac gtctcctaca gcagagacca tcagaagcgg agcctcgggt ataagggaaa    85680
```

```
caacgcgttc tccctaacct gggagtgaca gacagcgtca ttcctcacag tgatacccty    85740
tgttctagcc atctggccca tgacagagcc agcccagagc cagccagag  ccagcccctc    85800 accatcctgg agcctggcca gctcgccaag ctgcaccata ggcctggaag gcgtggagac    85860
ctgcggcagt gccctgtcct cccgtgaggc ctgccatccc tgccagggt  cgcctctggc    85920 ttctccttct ccaggaccgc acggtccaga ggctcagtgc ctggagtagg tgttgcctcc    85980
ctgcttctag gcccagaccc tcccttgttc ctgaccccgg gcctttccct ctggcttgga    86040
catccagggc cctgtctcag ctggggagct gctcctgctc aaggactgtc ttccgcggga    86100
tcgaaaggcc gcgtcctgaa caatgcgtgg gccacgtaag cggagcaggc tctaaaggcc    86160
gcgtcctaaa cagtgcgtgg gccacgtgag cggagcaggc tctaaaggcc gcgtcctaaa    86220
cagtgcgtgg gccacgtgag cggagcaggc tctaaaggcc gcgtcctaaa cagtgcgtgg    86280
gccacgtgag cggagcaggc tctaaaggcc gcgtcctaaa cagtgcgtgg gccacgtgag    86340
cggagcaggc tctaaaggcc gcgtcctaaa cagtgcgtgg gccacgtgag cggagcaggc    86400
tctaaaggcc gcgtcctaaa cagtgcgtgg gccacgtgag cggagcaggc tctaaaggcc    86460
gcgtcctaaa cagtgcgtgg gccacgtgag cggagcaggc tctaaaggcc gcgtcctaaa    86520
cagtgcgtgg gccacgtgag cggagcaggc tctaaaggcc gcgtcctaaa cagtgcgtgg    86580
gccacgggag cggagcagac tctaaaggcc gcgtcctaaa cagtgtgtgg gccacgtgag    86640
cggagcgccc tctccactgc cctcggggcc gcagctccca gctcagctcc cagccctgct    86700
cagggcagcc aggccaggag gtaccatcca ggctaagtga ccctcagggg ggacaggtgc    86760
cccaggagat gccagctgtt gggagaggct gggggaccaa ctcgacctgg cctgtgggcc    86820
ctgccctggc cacccattgt aggatccagc cgccacgcct gtgacactcg tgtgctttcc    86880
ctggtgtgtg cttgtggcag gtgggggcag agggtcctca ggccagagag ccactccccc    86940
agcgccagac caccctcttc ctcactcccc cacctcaccc cctcacaggt gcctcccagg    87000
ccatcagggc ccaaccaccc ctaaacaaat gggttctcgg cccctcgtgg ctggaggtgg    87060
gttctctcac cattcccagc ctaagactcc atccccatgc tggcagctgt caaccatgt    87120 ctagagagat ccactgtccc agacagcacc tcagggtccc ccgtcctgcc tggaaccctg    87180
taggaaactc cacaaaccgc cgccattctg tccacacccc tacaggagcc caaccctct    87240 ccccacatcc aggcttccct cccagacccc tcatccctgc ccgcacggtg cctgagggg    87300 ccttcttggg cagcgcctaa gcaagccccc agcacccttc ggcccttca  aggcacacag    87360 gcccccttc  cacccagcct caggaaacca cctgtgtcct ccaacgacag gtcccagcct    87420
cccagccttt gccttgcctg ttcctctccc tggaactctg ccccgacaca gaccctcccc    87480
agcaagcccg caggggcacc tccctgccc  cagacacccc tgtgccgtc  agttcatccc    87540 cagcagaggc cctcaccagg cacacccca  tgctcacacc tggccccagg cctcagcctc    87600
cctgagggcc ccaccagcc  cgcgtctggc cagtggtgcg tgcaaagccc ctcacccaga    87660
ctcggcggaa ggcagccagt gcaggcctgg ggagggctc  tccttagacc accttgcacc    87720
ttccctggca cccaccatgg gaagagctga gactcactga ggaccagctg aggctcagag    87780
aagggaccca gcactggtgg acacgcaggg agcccacgcc agggcgccgt ggtgagtgag    87840
gcccagtgcc acccactgag gcctcccgtt cagtgggacg acggtgaaca ggtggaacca    87900
accaggcaac cccgccgggg ccccacagac gggatcagag caggaaaggc ttcctgcccc    87960
tgcaggccag cgaggagccc tggcggggc  cgtggccctc caggcgagga ggctcccctg    88020
gccaccgcca cccgggcctc tctgctgctg ggaaaacaag tcagaaagca agtggatgag    88080
```

```
aggtggcgtg acagacccag cttcagatct gctctaattt acaaaagaaa aggaaaaaca   88140
cacttggcag ccttcagcac tctaatgatt cttaacagca gcaaattatt ggcacaagac   88200
tccagagtga ctggcagggt tgagggctgg ggtctcccac gtgttttggg gctaacagcg   88260
gaagggagag cactggcaaa ggtgctgggg gcccctggac ccgacccgcc ctggagaccg   88320
cagccacatc agcccccagc cccacaggcc cctaccagc cgcagggttt tggctgagct    88380
gagaaccact gtgctaactg gggacacagt gattggcagc tctacaaaaa ccatgctccc   88440
ccgggacccc gggctgtggg tttctgtagc ccctggctca gggctgactc accgtggctg   88500
aatacttcca gcactggggc cagggcaccc tggtcaccgt ctcctcaggt gagtctgctg   88560
tctggggata gcggggagcc aggtgtactg ggccaggcaa gggctttggc ttcagacttg   88620
gggacaggtg ctcagcaaag gaggtcggca ggagggcgga gggtgtgttt ttgtatggga   88680
gaagcaggag ggcagaggct gtgctactgg tacttcgatc tctggggccg tggcaccctg   88740
gtcactgtct cctcaggtga gtcccactgc agccccctcc cagtcttctc tgtccaggca   88800
ccaggccagg tatctggggt ctgcagccgg cctgggtctg gcctgaggcc acaccagctg   88860
ccatccctgg ggtctccgcc atgggctgca tgccagagcc ctgctgtcac ttagccctgg   88920
ggccagctgg agcccccaag gacaggcagg gaccccgctg ggcttcagcc ccgtcaggga   88980
ccctccacag gtagcaagca ggccgagggc agggacggga aggagaagtt gtgggcgagg   89040
cctgggctgg ggctgggcgc tggctgttca tgtgccgggg accaggcctg cgctttagtg   89100
tggctacaag tgcttggagc actggggcca gggcagcccg gccaccgtct ccctgggaac   89160
gtcacccctc cctgcctggg tctcagcccg gggtctgtg tggctgggga cagggacgcc    89220
ggctgcctct gctctgtgct tgggccatgt gacccattcg agtgtcctgc acgggcacag   89280
gtttgtgtct gggcaggaac agggactgtg tccctgtgtg atgcttttga tatctggggc   89340
caagggacaa tggtcaccgt ctcttcaggt aagatggctt tccttctgcc tcctttctct   89400
gggcccagcg tcctctgtcc tggagctggg agataatgtc cgggggctcc ttggtctgcg   89460
ctgggccatg tgggggcctc cggggctcct tctccggctg tttgggacca cgttcagcag   89520
aaggcctttc tttgggaact gggactctgc tgctgggca aagggtgggc agagtcatgc    89580
ttgtgctggg gacaaaatga ccttgggaca cggggctggc tgccacggcc ggcccgggac   89640
agtcggagag tcaggttttt gtgcaccct taatgggcc tcccacaatg tgactacttt      89700
gactactggg gccagggaac cctggtcacc gtctcctcag gtgagtcctc acaacctctc   89760
tcctgcttta actctgaagg gttttgctgc attttgggg ggaataagg gtgctgggtc      89820 tcctgccaag agagccccgg agcagcctgg ggggctcagg aggatgccct gaggcaacag   89880
cggccacaca gacgagggc aagggctcca gatgctcctt cctcctgagc ccagcagcac    89940
gggtctctct gtggccaggg ccaccctagg cctctggggt ccaatgccca acaaccccg    90000 ggccctcccc gggctcagtc tgagagggtc ccagggacgt agcggggcgc cagttcttgc   90060
ctggggtcct ggcattgttg tcacaatgtg acaactggtt cgacccctgg ggccagggaa   90120
ccctggtcac cgtctcctca ggtgagtcct caccaccccc tctctgagtc cacttaggga   90180
gactcagctt gccagggtct cagggtcaga gtcttggagg cattttggag gtcaggaaag   90240
aaagccgggg agagggaccc ttcgaatggg aacccagcct gtcctcccca agtccggcca   90300
cagatgtcgg cagctggggg gctccttcgg ctggtctggg gtgacctctc tccgcttcac   90360
ctggagcatt ctcaggggct gtcgtgatga ttgcgtggtg ggactctgtc ccgctccaag   90420
```

```
gcacccgctc tctgggacgg gtgcccccg gggttttgg actcctgggg gtgacttagc    90480
agccgtctgc ttgcagttgg acttcccagg ccgacagtgg tctggcttct gaggggtcag    90540
gccagaatgt ggggtacgtg ggaggccagc agagggttcc atgagaaggg caggacaggg    90600
ccacggacag tcagcttcca tgtgacgccc ggagacagaa ggtctctggg tggctgggtt    90660
tttgtggggt gaggatggac attctgccat tgtgattact actactacta cggtatggac    90720
gtctggggcc aagggaccac ggtcaccgtc tcctcaggta agaatggcca ctctagggcc    90780
tttgttttct gctactgcct gtggggtttc ctgagcattg caggttggtc ctcggggcat    90840
gttccgaggg gacctgggcg gactggccag gaggggacgg gcactggggt gccttgagga    90900
tctgggagcc tctgtggatt ttccgatgcc tttggaaaat gggactcagg ttgggtgcgt    90960
ctgatggagt aactgagcct ctagactgag cattgcagac taatcttgga tatttgtccc    91020
tgagggagcc ggctgagaga agttgggaaa taaactgtct agggatctca gagcctttag    91080
gacagattat ctccacatct ttgaaaaact aagaatctgt gtgatggtgt tggtggagtc    91140
cctgatgat gggataggga ctttggaggc tcatttgagg gagatgctaa aacaatccta    91200
tggctggagg gatagttggg gctgtagttg gagattttca gttttagaa taaaagtatt    91260
agctgcggaa tatacttcag gaccacctct gtgacagcat ttatacagta tccgatgcat    91320
agggacaaag agtggagtgg ggcactttct ttagatttgt gaggaatgtt ccacactaga    91380
ttgttaaaa cttcatttgt tggaaggaga gctgtcttag tgattgagtc aagggagaaa    91440
ggcatctagc ctcggtctca aaagggtagt tgctgtctag agaggtctgg tggagcctgc    91500
aaaagtccag ctttcaaagg aacacagaag tatgtgtatg gaatattaga agatgttgct    91560
tttactctta agttggttcc taggaaaaat agttaaatac tgtgactttta aaatgtgaga    91620
gggttttcaa gtactcattt ttttaaatgt ccaaaattct tgtcaatcag tttgaggtct    91680
tgtttgtgta gaactgatat tacttaaagt ttaaccgagg aatgggagtg aggctctctc    91740
ataacctatt cagaactgac ttttaacaat aataaattaa gtttcaaata ttttttaaatg    91800
aattgagcaa tgttgagttg gagtcaagat ggccgatcag aaccagaaca cctgcagcag    91860
ctggcaggaa gcaggtcatg tggcaaggct atttggggaa gggaaaataa aaccactagg    91920
taaacttgta gctgtggttt gaagaagtgg ttttgaaaca ctctgtccag ccccaccaaa    91980
ccgaaagtcc aggctgagca aaacaccacc tgggtaattt gcatttctaa aataagttga    92040
ggattcagcc gaaactggag aggtcctctt ttaacttatt gagttcaacc ttttaatttt    92100
agcttgagta gttctagttt ccccaaactt aagtttatcg acttctaaaa tgtatttaga    92160
attcattttc aaaattaggt tatgtaagaa attgaaggac tttagtgtct ttaatttcta    92220
atatatttag aaaacttctt aaaattactc tattattctt ccctctgatt attggtctcc    92280
attcaattct tttccaatac ccgaagcatt tacagtgact tgttcatga tcttttttag    92340
ttgttttgttt tgccttacta ttaagacttt gacattctgg tcaaaacggc ttcacaaatc    92400
ttttttcaaga ccactttctg agtattcatt ttaggagaaa acttttttt ttaaatgaat    92460
gcaattatct agacttattt cagttgaaca tgctggttgg tggttgagag acactcagt    92520
cagtcagtga cgtgaaggc ttctaagcca gtccacatgc tctgtgtgaa ctccctctgg    92580
ccctgcttat tgttgaatgg gccaaaggtc tgagaccagg ctgctgctgg gtaggcctgg    92640
actttgggtc tcccacccag acctgggaat gtatggttgt ggcttctgcc acccatccac    92700
ctggctgctc atgaccagc cagcctcggt ggctttgaag gaacaattcc acacaaagac    92760
tctggacctc tccgaaacca ggcaccgcaa atggtaagcc agaggcagcc acagctgtgg    92820
```

```
ctgctgctct taaagcttgt aaactgtttc tgcttaagag ggactgagtc ttcagtcatt   92880
gctttagggg gagaaagaga catttgtgtg tcttttgagt accgttgtct gggtcactca   92940
catttaactt tccttgaaaa actagtaaaa gaaaaatgtt gcctgttaac caataatcat   93000
agagctcatg gtactttgag gaaatcttag aaagcgtgta tacaattgtc tggaattatt   93060
tcagttaagt gtattagttg aggtactgat gctgtctcta cttcagttat acatgtgggt   93120
ttgaattttg aatctattct ggctcttctt aagcagaaaa tttagataaa atggatacct   93180
cagtggtttt taatggtggg tttaatatag aaggaattta aattggaagc taatttagaa   93240
tcagtaagga gggacccagg ctaagaaggc aatcctggga ttctggaaga aaagatgttt   93300
ttagttttta tagaaaacac tactacattc ttgatctaca actcaatgtg gtttaatgaa   93360
tttgaagttg ccagtaaatg tacttcctgg ttgttaaaga atggtatcaa aggacagtgc   93420
ttagatccga ggtgagtgtg agaggacagg ggctggggta tggatacgca gaaggaaggc   93480
cacagctgta cagaattgag aaagaataga gacctgcagt tgaggccagc aggtcggctg   93540
gactaactct ccagccacag taatgaccca gacagagaaa gccagactca taaagcttgc   93600
tgagcaaaat taagggaaca aggttgagag ccctagtaag cgaggctcta aaaagcacag   93660
ctgagctgag atgggtgggc ttctctgagt gcttctaaaa tgcgctaaac tgaggtgatt   93720
actctgaggt aagcaaagct gggcttgagc caaaatgaag tagactgtaa tgaactggaa   93780
tgagctgggc cgctaagcta aactaggctg gcttaaccga gatgagccaa actggaatga   93840
acttcattaa tctaggttga atagagctaa actctactgc ctacactgga ctgttctgag   93900
ctgagatgag ctggggtgag ctcagctatg ctacgctgtg ttggggtgag ctgatctgaa   93960
atgagatact ctggagtagc tgagatgggg tgagatgggg tgagctgagc tgggctgagc   94020
tagactgagc tgagctaggg tgagctgagc tgggtgagct gagctaagct ggggtgagct   94080
gagctgagct tggctgagct agggtgagct gggctgagct ggggtgagct gagctgagct   94140
ggggtaagct gggatgagct ggggtgagct gagctgagct ggagtgagct gagctgggct   94200
gagctggggt gagctgggct gagctgggct gagctgggct gagctggggt gagctgagct   94260
ggggtgagct gagctgagct ggggtgagct gagctgagct ggggtgagct ggggtgagct   94320
gagctggggt gagctgagct gagctggggt gagctgagct ggggtgagct gagctgagct   94380
ggggtgagct gagctgagct gagctgagct gagctggggt gagctgagct gagctgagct   94440
ggggtgagct ggggtgagct gagctgagct ggagtgagct gagctgggct gagctggggt   94500
gagctgggct gagctggggt gagctgagct gagctgagct gagctggggt gagctgagct   94560
gagctggggt gagctgagct ggggtgagct gggctgagct gagctgagct gagctgagct   94620
gagctgagct gagctgagct gagctgagct gagctgagct gagctgagct gagctgagct   94680
ggggtgagct gagctgagct ggggtgagct ggggtgagct gggctgagct gggctgagct   94740
gggctgagct ggggtgagct gagctggggt gagctgagct gagctgggct gagctgagct   94800
gagctggggt gagctgagct gagctggggt gagctgagct gagctgagct ggggtgagct   94860
gagctgagct gggctgagca gggctgagct ggggtgagct gagctgagct ggggtgagct   94920
gggctgagct gggctgagct gagctgagct gggctgagct gggctgagct gggctgagct   94980
gggctgagct gggctgagct gggctgagct gagctggggt gagctggggt gagctgagct   95040
ggggtgagct gagctggggt gagctgagct gagctggggt gagctgagct ggggtgagct   95100
gagctgagct ggggtgagct gagctgagct ggggtgagct gagctagggt gaactgggct   95160
```

```
gggtgagctg gagtgagctg agctgaggtg aactggggtg agccgggatg ttttgagttg   95220
agctggggta agatgagctg aactggggta aactgggatg agctgtggtg agcggagctg   95280
gattgaactg agctgtgtga gctgagctgg ggtcagctga gcaagagtga gtagagctgg   95340
ctggccagaa ccagaatcaa ttaggctaag tgagccagat tgtgctggga tcagctgtac   95400
tcagatgagc tgggatgagg taggctggga tgagctgggc tagctgacat ggattatgtg   95460
aggctgagct agcatgggct ggcctagctg atgagctaag cttgaatgag cggggctgag   95520
ctggactcag atgtgctaga ctgagctgta ctggatgatc tggtgtaggg tgatctggac   95580
tcaactgggc tggctgatgg gatgcgccag gttgaactag gctcagataa gttaggctga   95640
gtagggcctg gttgagatgg ttcgggatga gctgggaaaa gatggactcg gaccatgaac   95700
tgggctgagc tgggttggga gaccatgaat tgagctgaac tgagtgcagc tgggataaac   95760
tgggttgagc taagaataga ctacctgaat tgtgccaaac tcggctggga tcaattggaa   95820
attatcagga tttagatgag ccggactaaa ctatgctgag ctggactggt tggatgtgtt   95880
gaactggcct gctgctgggc tggcatagct gagttgaact taaatgagga aggctgagca   95940
aggctagcct gcttgcatag agctgaactt tagcctagcc tgagctggac cagcctgagc   96000
tgagtaggtc taaactgagt taaaaatcaa cagggataat ttaacagcta atttaacaag   96060
cctgaggtct gagattgaat gagcagagct gggatgaact gaatgagttt caccaggcct   96120
ggaccagtta ggctaggacc tcgttctata gaggcagact gtgtgctaca gtggagtttc   96180
aagatgattc catgagtcct ccccgccccc aacataaccc accttcctcc taccctacac   96240
gcctgtctgg tgtgtaaatc ccagctttgt gtgctgatac agaagcctga gcccctcccc   96300
cacctccacc tacctattac tttgggatga gaatagttct cccagccagt gtctcagagg   96360
gaagccaagc aggacaggcc caaggctact tgagaagcca ggatctaggc ctctccctga   96420
gaacgggtgt tcatgcccct agagttggct gaagggccag atccacctac tctagaggca   96480
tctctccctg tctgtgaagg cttccaaagt cacgttcctg tggctagaag gcagctccat   96540
agccctgctg cagtttcgtc ctgtatacca ggttcaccta ctaccatatc tagccctgcc   96600
tgccttaaga gtagcaacaa ggaaatagca gggtgtagag ggatctcctg tctgacagga   96660
ggcaagaaga cagattctta cccctccatt tctcttttat ccctctctgg tcctcagaga   96720
gtcagtcctt cccaaatgtc ttcccccctcg tctcctgcga gagcccctg tctgataaga   96780
atctggtggc catgggctgc ctggcccggg acttcctgcc cagcaccatt tccttcacct   96840
ggaactacca gaacaacact gaagtcatcc agggtatcag aaccttccca acactgagga   96900
caggggcaa gtacctagcc acctcgcagg tgttgctgtc tcccaagagc atccttgaag   96960
gttcagatga atacctggta tgcaaaatcc actacggagg caaaaacaaa gatctgcatg   97020
tgcccattcc aggtaagaac caaaccctcc cagcaggggt gcccaggccc aggcatggcc   97080
cagagggagc agcggggtgg ggcttaggcc aagctgagct cacaccttga cctttcattc   97140
cagctgtcgc agagatgaac cccaatgtaa atgtgttcgt cccaccacgg gatggcttct   97200
ctggccctgc accacgcaag tctaaactca tctgcgaggc cacgaacttc actccaaaac   97260
cgatcacagt atcctggcta aaggatggga agctcgtgga atctggcttc accacagatc   97320
cggtgaccat cgagaacaaa ggatccacac cccaaaccta caaggtcata agcacactta   97380
ccatctctga aatcgactgg ctgaacctga atgtgtacac ctgccgtgtg gatcacaggg   97440
gtctcacctt cttgaagaac gtgtcctcca catgtgctgc cagtgagtgg cctgggctaa   97500
gcccaatgcc tagccctccc agattaggga agtcctccta caattatggc caatgccacc   97560
```

```
cagacatggt catttgctcc ttgaactttg ctccccaga gtggccaagg acaagaatga  97620
gcaataggca gtagaggggt gagaatcagc tggaaggacc agcatcttcc cttaagtagg  97680
tttgggggat ggagactaag cttttttcca acttcacaac tagatatgtc ataacctgac  97740
acagtgttct cttgactgca ggtccctcca cagacatcct aaccttcacc atccccccct  97800
cctttgccga catcttcctc agcaagtccg ctaacctgac ctgtctggtc tcaaacctgg  97860
caacctatga aaccctgaat atctcctggg cttctcaaag tggtgaacca ctggaaacca  97920
aaattaaaat catggaaagc cctcccaatg gcaccttcag tgctaagggt gtggctagtg  97980
tttgtgtgga agactggaat aacaggaagg aatttgtgcg tactgtgact cacagggatc  98040
tgccttcacc acagaagaaa ttcatctcaa acccaatgg taggtatccc cccttccctt  98100
cccctccaat tgcaggaccc ttcctgtacc tcatagggag ggcaggtcct cttccaccct  98160
atcctcacta ctgtcttcat ttacagaggt gcacaaacat ccacctgctg tgtacctgct  98220
gccaccagct cgtgagcaac tgaacctgag ggagtcagcc acagtcacct gcctggtgaa  98280
gggcttctct cctgcagaca tcagtgtgca gtggcttcag agagggcaac tcttgcccca  98340
agagaagtat gtgaccagtg ccccgatgcc agagcctggg gccccaggct tctactttac  98400
ccacagcatc ctgactgtga cagaggagga atggaactcc ggagagacct ataccctgtgt  98460 tgtaggccac gaggccctgc cacacctggt gaccgagagg accgtggaca agtccactgg  98520
taaacccaca ctgtacaatg tctccctgat catgtctgac acaggcggca cctgctattg  98580
accatgctag cgctcaacca ggcaggccct gggtgtccag ttgctctgtg tatgcaaact  98640
aaccatgtca gagtgagatg ttgcatttta taaaattag aaataaaaaa aatccattca  98700
aacgtcactg gttttgatta tacaatgctc atgcctgctg agacagttgt gttttgcttg  98760
ctctgcacac accctgcata cttgcctcca ccctggccct tcctctacct tgccagtttc  98820
ctccttgtgt gtgaactcag tcaggcttac aacagacaga gtatgaacat gcgattcctc  98880
cagctacttc tagatatatg gctgaaagct tgcatgcctg caggtcgact ctagaggatc  98940
cccgggtacc gagctcgaat tcgccctata gtgagtcgta ttacaattca ctggccgtcg  99000
ttttacaacg tcgtgactgg gaaaaccctg gcgttaccca acttaatcgc cttgcagcac  99060 atccccctttt cgccagctgg cgtaatagcg aagaggcccg caccgatcgc ccttcccaac  99120
agttgcgcag cctgaatggc gaatggcgcc tgatgcggta ttttctcctt acgcatctgt  99180
gcggtatttc acaccgcata tggtgcactc tcagtacaat ctgctctgat gccgcatagt  99240
taagccagcc ccgacacccg ccaacacccg ctgacgcgaa ccccttgcgg ccgc         99294
```

<210> SEQ ID NO 4
<211> LENGTH: 17
<212> TYPE: DNA
<213> ORGANISM: Artificial Sequence
<220> FEATURE:
<223> OTHER INFORMATION: synthetic

<400> SEQUENCE: 4

```
tgcggccgat cttagcc                                                  17
```

<210> SEQ ID NO 5
<211> LENGTH: 18
<212> TYPE: DNA
<213> ORGANISM: Artificial Sequence
<220> FEATURE:
<223> OTHER INFORMATION: synthetic

```
<400> SEQUENCE: 5
ttgaccgatt ccttgcgg                                                    18

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
acgagcgggt tcggcccatt c                                                21

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
ggtggagagg ctattcggc                                                   19

<210> SEQ ID NO 8
<211> LENGTH: 17
<212> TYPE: DNA
<213> ORGANISM: Artificial Sequence
<220> FEATURE:
<223> OTHER INFORMATION: synthetic

<400> SEQUENCE: 8
gaacacggcg gcatcag                                                     17

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
tgggcacaac agacaatcgg ctg                                              23

<210> SEQ ID NO 10
<211> LENGTH: 19
<212> TYPE: DNA
<213> ORGANISM: Artificial Sequence
<220> FEATURE:
<223> OTHER INFORMATION: synthetic

<400> SEQUENCE: 10
tcctccaacg acaggtccc                                                   19

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gatgaactga cgggcacagg                                                  20

<210> SEQ ID NO 12
<211> LENGTH: 24
```

```
<212> TYPE: DNA
<213> ORGANISM: Artificial Sequence
<220> FEATURE:
<223> OTHER INFORMATION: synthetic

<400> SEQUENCE: 12
tccctggaac tctgccccga caca                                          24

<210> SEQ ID NO 13
<211> LENGTH: 25
<212> TYPE: DNA
<213> ORGANISM: Artificial Sequence
<220> FEATURE:
<223> OTHER INFORMATION: synthetic

<400> SEQUENCE: 13
ctctgtggaa aatggtatgg agatt                                         25

<210> SEQ ID NO 14
<211> LENGTH: 26
<212> TYPE: DNA
<213> ORGANISM: Artificial Sequence
<220> FEATURE:
<223> OTHER INFORMATION: synthetic

<400> SEQUENCE: 14
ggtaagcata gaaggtgggt atcttt                                        26

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
atagaactgt catttggtcc agcaatccca                                    30

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tggtcacctc caggagcctc                                               20

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
gctgcagggt gtatcaggtg c                                             21

<210> SEQ ID NO 18
<211> LENGTH: 30
<212> TYPE: DNA
<213> ORGANISM: Artificial Sequence
<220> FEATURE:
<223> OTHER INFORMATION: synthetic

<400> SEQUENCE: 18
```
agtctctgct tccccttgt ggctatgagc                          30

<210> SEQ ID NO 19
<211> LENGTH: 28
<212> TYPE: DNA
<213> ORGANISM: Artificial Sequence
<220> FEATURE:
<223> OTHER INFORMATION: synthetic

<400> SEQUENCE: 19
gatgggaaga gactggtaac atttgtac                           28

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
ttcctctatt tcactctttg aggctc                             26

<210> SEQ ID NO 21
<211> LENGTH: 27
<212> TYPE: DNA
<213> ORGANISM: Artificial Sequence
<220> FEATURE:
<223> OTHER INFORMATION: synthetic

<400> SEQUENCE: 21
cctccactgt gttaatggct gccacaa                            27

<210> SEQ ID NO 22
<211> LENGTH: 23
<212> TYPE: DNA
<213> ORGANISM: Artificial Sequence
<220> FEATURE:
<223> OTHER INFORMATION: synthetic

<400> SEQUENCE: 22
ggtgtgcgat gtaccctctg aac                                23

<210> SEQ ID NO 23
<211> LENGTH: 25
<212> TYPE: DNA
<213> ORGANISM: Artificial Sequence
<220> FEATURE:
<223> OTHER INFORMATION: synthetic

<400> SEQUENCE: 23
tgtggcagtt taatccagct ttatc                              25

<210> SEQ ID NO 24
<211> LENGTH: 32
<212> TYPE: DNA
<213> ORGANISM: Artificial Sequence
<220> FEATURE:
<223> OTHER INFORMATION: synthetic

<400> SEQUENCE: 24
ctaaaaatgc tacacctggg gcaaaacacc tg                      32

<210> SEQ ID NO 25
<211> LENGTH: 17
<212> TYPE: DNA
<213> ORGANISM: Artificial Sequence

```
<220> FEATURE:
<223> OTHER INFORMATION: synthetic

<400> SEQUENCE: 25
gccatgcaag gccaagc                                                      17

<210> SEQ ID NO 26
<211> LENGTH: 24
<212> TYPE: DNA
<213> ORGANISM: Artificial Sequence
<220> FEATURE:
<223> OTHER INFORMATION: synthetic

<400> SEQUENCE: 26
agttcttgag ccttagggtg ctag                                              24

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ccaggaaaat gctgccagag cctg                                              24

<210> SEQ ID NO 28
<211> LENGTH: 22
<212> TYPE: DNA
<213> ORGANISM: Artificial Sequence
<220> FEATURE:
<223> OTHER INFORMATION: synthetic

<400> SEQUENCE: 28
aactacgcac agaagttcca gg                                                22

<210> SEQ ID NO 29
<211> LENGTH: 18
<212> TYPE: DNA
<213> ORGANISM: Artificial Sequence
<220> FEATURE:
<223> OTHER INFORMATION: synthetic

<400> SEQUENCE: 29
gctcgtggat ttgtccgc                                                     18

<210> SEQ ID NO 30
<211> LENGTH: 16
<212> TYPE: DNA
<213> ORGANISM: Artificial Sequence
<220> FEATURE:
<223> OTHER INFORMATION: synthetic

<400> SEQUENCE: 30
cagagtcacg attacc                                                       16

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
tgagcagcac cctcacgtt                                                    19
```

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32
gtggcctcac aggtatagct gtt                                          23

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
accaaggacg agtatgaa                                                18

<210> SEQ ID NO 34
<211> LENGTH: 296
<212> TYPE: DNA
<213> ORGANISM: Homo sapiens
<220> FEATURE:
<223> OTHER INFORMATION: synthetic

<400> SEQUENCE: 34
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac    180
gcacagaagt tccagggcag agtcacgatt accgcggacg aatccacgag cacagcctac   240
atggagctga gcagcctgag atctgaggac acggccgtgt attactgtgc gagaga       296

<210> SEQ ID NO 35
<211> LENGTH: 98
<212> TYPE: PRT
<213> ORGANISM: Homo sapiens
<220> FEATURE:
<223> OTHER INFORMATION: synthetic

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 36
<211> LENGTH: 294
<212> TYPE: DNA
<213> ORGANISM: Homo sapiens
<220> FEATURE:
<223> OTHER INFORMATION: synthetic

<400> SEQUENCE: 36

```
caggtccagc tggtgcaatc tggggctgag gtgaagaagc ctgggtcctc ggtgaaggtc      60
tcctgcaagg cttctggagg caccttcagc agctatacta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240
atggagctga gcagcctgag atctgaggac acggccgtgt attactgtgc gaga            294
```

<210> SEQ ID NO 37
<211> LENGTH: 98
<212> TYPE: PRT
<213> ORGANISM: Homo sapiens
<220> FEATURE:
<223> OTHER INFORMATION: synthetic

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 38
<211> LENGTH: 275
<212> TYPE: DNA
<213> ORGANISM: Homo sapiens
<220> FEATURE:
<223> OTHER INFORMATION: synthetic

<400> SEQUENCE: 38

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac    240
atggagctga gcagcctgag atctgatgac acggc                                275
```

<210> SEQ ID NO 39
<211> LENGTH: 91
<212> TYPE: PRT
<213> ORGANISM: Homo sapiens
<220> FEATURE:
<223> OTHER INFORMATION: synthetic

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr
                85                  90
```

<210> SEQ ID NO 40
<211> LENGTH: 296
<212> TYPE: DNA
<213> ORGANISM: Homo sapiens
<220> FEATURE:
<223> OTHER INFORMATION: synthetic

<400> SEQUENCE: 40

```
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240 atggagctga gcagcctgag atctgaggac acggccgtgt attactgtgc gagaga        296
```

<210> SEQ ID NO 41
<211> LENGTH: 98
<212> TYPE: PRT
<213> ORGANISM: Homo sapiens
<220> FEATURE:
<223> OTHER INFORMATION: synthetic

<400> SEQUENCE: 41

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 42
<211> LENGTH: 294
<212> TYPE: DNA
<213> ORGANISM: Homo sapiens
<220> FEATURE:
<223> OTHER INFORMATION: synthetic

<400> SEQUENCE: 42

```
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
```

```
gcacagaagt tccagggcag agtcacgatt accacggacg aatccacgag cacagcctac    240
atggagctga gcagcctgag atctgaggac acggccgtgt attactgtgc gaga          294
```

<210> SEQ ID NO 43
<211> LENGTH: 98
<212> TYPE: PRT
<213> ORGANISM: Homo sapiens
<220> FEATURE:
<223> OTHER INFORMATION: synthetic

<400> SEQUENCE: 43

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 44
<211> LENGTH: 296
<212> TYPE: DNA
<213> ORGANISM: Homo sapiens
<220> FEATURE:
<223> OTHER INFORMATION: synthetic

<400> SEQUENCE: 44

```
caggtgcagc tggtgcagtc tggggctgag gtgaagaagc ctgggtcctc ggtgaaggtc     60
tcctgcaagg cttctggagg cacctt cagc agctatgcta tcagctgggt gcgacaggcc   120
cctggacaag gcttgagtg gatgggaggg atcatcccta tctttggtac agcaaactac    180
gcacagaagt tccagggcag agtcacgatt accgcggaca atccacgag cacagcctac    240 atggagctga gcagcctgag atctgaggac acggccgtgt attactgtgc gagaga       296
```

<210> SEQ ID NO 45
<211> LENGTH: 98
<212> TYPE: PRT
<213> ORGANISM: Homo sapiens
<220> FEATURE:
<223> OTHER INFORMATION: synthetic

<400> SEQUENCE: 45

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg

<210> SEQ ID NO 46
<211> LENGTH: 233
<212> TYPE: DNA
<213> ORGANISM: Homo sapiens
<220> FEATURE:
<223> OTHER INFORMATION: synthetic

<400> SEQUENCE: 46
agaagcctgg gtcctcggtg aaggtctcct gcaaggcttc tggaggcacc ttcagcagct    60
atgctatcag ctgggtgcga caggcccctg gacaagggct tgagtggatg ggaaggatca   120
tccctatctt tggtacagca aactacgcac agaagttcca gggcagagtc acgattaccg   180
cggacgaatc cacgagcaca gcctacatgg agctgagcag cctgagatct gag          233

<210> SEQ ID NO 47
<211> LENGTH: 77
<212> TYPE: PRT
<213> ORGANISM: Homo sapiens
<220> FEATURE:
<223> OTHER INFORMATION: synthetic

<400> SEQUENCE: 47

Lys Pro Gly Ser Ser Val Lys Val Ser Cys Lys Ala Ser Gly Gly Thr
1               5                   10                  15

Phe Ser Ser Tyr Ala Ile Ser Trp Val Arg Gln Ala Pro Gly Gln Gly
            20                  25                  30

Leu Glu Trp Met Gly Arg Ile Ile Pro Ile Phe Gly Thr Ala Asn Tyr
        35                  40                  45

Ala Gln Lys Phe Gln Gly Arg Val Thr Ile Thr Ala Asp Glu Ser Thr
    50                  55                  60

Ser Thr Ala Tyr Met Glu Leu Ser Ser Leu Arg Ser Glu
65                  70                  75

<210> SEQ ID NO 48
<211> LENGTH: 296
<212> TYPE: DNA
<213> ORGANISM: Homo sapiens
<220> FEATURE:
<223> OTHER INFORMATION: synthetic

<400> SEQUENCE: 48
caggtccagc tggtgcaatc tggggctgag gtgaagaagc ctgggtcctc ggtgaaggtc    60
tcctgcaagg cttctggagg caccttcagc agctatacta tcagctgggt gcgacaggcc   120
cctggacaag gcttgagtg gatgggaagg atcatcccta tccttggtac agcaaactac   180
gcacagaagt tccagggcag agtcacgatt accgcggaca atccacgag cacagcctac   240 atggagctga gcagcctgag atctgaggac acggccgtgt attactgtgc gagaga       296

<210> SEQ ID NO 49
<211> LENGTH: 98
<212> TYPE: PRT
<213> ORGANISM: Homo sapiens
<220> FEATURE:
<223> OTHER INFORMATION: synthetic

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 50
<211> LENGTH: 296
<212> TYPE: DNA
<213> ORGANISM: Homo sapiens
<220> FEATURE:
<223> OTHER INFORMATION: synthetic

<400> SEQUENCE: 50
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaagg atcatcccta tccttggtat agcaaactac    180
gcacagaagt tccagggcag agtcacgatt accgcggaca atccacgag cacagcctac     240 atggagctga gcagcctgag atctgaggac acggccgtgt attactgtgc gagaga        296

<210> SEQ ID NO 51
<211> LENGTH: 98
<212> TYPE: PRT
<213> ORGANISM: Homo sapiens
<220> FEATURE:
<223> OTHER INFORMATION: synthetic

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 52
<211> LENGTH: 296
<212> TYPE: DNA
<213> ORGANISM: Homo sapiens
<220> FEATURE:
<223> OTHER INFORMATION: synthetic

<400> SEQUENCE: 52

```
caggtccagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag gcttgagtg gatgggaggg atcatccta tccttggtat agcaaactac       180
gcacagaagt tccagggcag agtcacgatt accgcggaca atccacgag cacagcctac      240 atggagctga gcagcctgag atctgaggac acggccgtgt attactgtgc gagaga          296
```

<210> SEQ ID NO 53
<211> LENGTH: 98
<212> TYPE: PRT
<213> ORGANISM: Homo sapiens
<220> FEATURE:
<223> OTHER INFORMATION: synthetic

<400> SEQUENCE: 53

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 54
<211> LENGTH: 296
<212> TYPE: DNA
<213> ORGANISM: Homo sapiens
<220> FEATURE:
<223> OTHER INFORMATION: synthetic

<400> SEQUENCE: 54

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatccta tccttggtac agcaaactac       180
gcacagaagt tccagggcag agtcacgatt accgcggacg aatccacgag cacagcctac     240
atggagctga gcagcctgag atctgaggac acggccgtgt attactgtgc gagaga          296
```

<210> SEQ ID NO 55
<211> LENGTH: 98
<212> TYPE: PRT
<213> ORGANISM: Homo sapiens
<220> FEATURE:
<223> OTHER INFORMATION: synthetic

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Arg Ile Ile Pro Ile Leu Gly Thr Ala Asn Tyr Ala Gln Lys Phe
                50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg

<210> SEQ ID NO 56
<211> LENGTH: 296
<212> TYPE: DNA
<213> ORGANISM: Homo sapiens
<220> FEATURE:
<223> OTHER INFORMATION: synthetic

<400> SEQUENCE: 56
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 57
<211> LENGTH: 98
<212> TYPE: PRT
<213> ORGANISM: Homo sapiens
<220> FEATURE:
<223> OTHER INFORMATION: synthetic

<400> SEQUENCE: 57

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg

<210> SEQ ID NO 58
<211> LENGTH: 296
<212> TYPE: DNA
<213> ORGANISM: Homo sapiens
<220> FEATURE:
<223> OTHER INFORMATION: synthetic

<400> SEQUENCE: 58
caggtccagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240

```
atggagctga gcagcctgag atctgaggac acggccgtgt attactgtgc gagaga        296
```

<210> SEQ ID NO 59
<211> LENGTH: 98
<212> TYPE: PRT
<213> ORGANISM: Homo sapiens
<220> FEATURE:
<223> OTHER INFORMATION: synthetic

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 60
<211> LENGTH: 305
<212> TYPE: DNA
<213> ORGANISM: Homo sapiens
<220> FEATURE:
<223> OTHER INFORMATION: synthetic

<400> SEQUENCE: 60

```
gagcccactc ccaggtgcag ctggtgcagt ctggggctga ggtgaagaag cctggggcct    60
cagtgaaggt ctcctgcaag gcttctggat acaccttcac cggctactat atgcactggg   120
tgcgacaggc ccctggacaa gggcttgagt ggatgggacg gatcaaccct aacagtggtg   180
gcacaaacta tgcacagaag tttcagggca gggtcaccag taccagggac acgtccatca   240
gcacagccta catggagctg agcaggctga gatctgacga cacggtcgtg tattactgtg   300
cgaga                                                              305
```

<210> SEQ ID NO 61
<211> LENGTH: 98
<212> TYPE: PRT
<213> ORGANISM: Homo sapiens
<220> FEATURE:
<223> OTHER INFORMATION: synthetic

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg

<210> SEQ ID NO 62
<211> LENGTH: 307
<212> TYPE: DNA
<213> ORGANISM: Homo sapiens
<220> FEATURE:
<223> OTHER INFORMATION: synthetic

<400> SEQUENCE: 62
gagcccactc ccaggtgcag ctggtgcagt ctggggctga ggtgaagaag cctggggcct      60
cagtgaaggt ctcctgcaag gcttctggat acaccttcac cggctactat atgcactggg     120
tgcgacaggc ccctggacaa gggcttgagt ggatgggatg gatcaaccct aacagtggtg     180
gcacaaacta tgcacagaag tttcagggca gggtcaccat gaccagggac acgtccatca     240
gcacagccta catggagctg agcaggctga gatctgacga cacggccgtg tattactgtg     300
cgagaga                                                                307

<210> SEQ ID NO 63
<211> LENGTH: 98
<212> TYPE: PRT
<213> ORGANISM: Homo sapiens
<220> FEATURE:
<223> OTHER INFORMATION: synthetic

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg

<210> SEQ ID NO 64
<211> LENGTH: 307
<212> TYPE: DNA
<213> ORGANISM: Homo sapiens
<220> FEATURE:
<221> NAME/KEY: variation
<222> LOCATION: (124)...(124)
<223> OTHER INFORMATION: n=a, g, t, or c

<400> SEQUENCE: 64
gagcccactc ccaggtgcag ctggtgcagt ctggggctga ggtgaagaag cttggggcct      60
cagtgaaggt ctcctgcaag gcttctggat acaccttcac cggctactat atgcactggg     120
tgcnacaggc ccctggacaa gggcttgagt ggatgggatg gatcaaccct aacagtggtg     180
gcacaaacta tgcacagaag tttcagggca gggtcaccat gaccagggac acgtccatca     240
gcacagccta catggagctg agcaggctga gatctgacga cacggccgtg tattactgtg     300
cgagaga                                                              307

<210> SEQ ID NO 65
<211> LENGTH: 98
<212> TYPE: PRT
<213> ORGANISM: Homo sapiens
<220> FEATURE:
<221> NAME/KEY: VARIANT
<222> LOCATION: (38)...(38)
<223> OTHER INFORMATION: Xaa=any amino acid

<400> SEQUENCE: 65

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Thr Gly Tyr
            20                  25                  30

Tyr Met His Trp Val Xaa Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 66
<211> LENGTH: 294
<212> TYPE: DNA
<213> ORGANISM: Homo sapiens
<220> FEATURE:
<223> OTHER INFORMATION: synthetic

<400> SEQUENCE: 66
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acagtggtgg cacaaactat      180
gcacagaagt tcagggctg ggtcaccatg accaggaca cgtccatcag cacagcctac       240
atggagctga gcaggctgag atctgacgac acggccgtgt attactgtgc gaga            294

<210> SEQ ID NO 67
<211> LENGTH: 98
<212> TYPE: PRT
<213> ORGANISM: Homo sapiens
<220> FEATURE:
<223> OTHER INFORMATION: synthetic

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 68
<211> LENGTH: 346
<212> TYPE: DNA
<213> ORGANISM: Homo sapiens
<220> FEATURE:
<223> OTHER INFORMATION: synthetic

<400> SEQUENCE: 68
aggatgtggg ttttcacact gtgtctctcg cacagtaata cacgaccgtg tcgtcagatc    60
tcagcctgct cagctccatg taggctgtgc tgatggacgt gtccctggtc atggtgaccc   120
tgccctgaaa cttctgtgca tagtttgtgc caccactgtt agggttgatc cgtcccatcc   180
actcaagccc ttgtccaggg gcctgtcgca cccagtgcat atagtagccg gtgaaggtgt   240
atccagaagc cttgcaggag accttcactg aggcccagg cttcttcacc tcagcccag    300 actgcaccag ctgcacctgg gagtggacac ctgtggagac tcgcga                  346

<210> SEQ ID NO 69
<211> LENGTH: 98
<212> TYPE: PRT
<213> ORGANISM: Homo sapiens
<220> FEATURE:
<223> OTHER INFORMATION: synthetic

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 70
<211> LENGTH: 150288
<212> TYPE: DNA
<213> ORGANISM: Artificial Sequence
<220> FEATURE:
<223> OTHER INFORMATION: synthetic

<400> SEQUENCE: 70
gcgcgccctg gcatggagga aatgacaaag attattagat tgaagacttt ctcagaaaat    60
gatattaagt cattaaggaa aaggaacaat ataaacgtgt atttgagaaa ttttaattat   120
ttgagagatt tttcatacaa tatttattct gcaagcaaat ttcagggatt gaattaataa   180
aactgataca gaacttcctc tgtaggtatc tgtgtaaaca tcaatttctg aatcagtgtt   240
gtaaatattt tggaacacac acacaaatca cattttatct ctactttat ctctatttt    300 aaaaatgcca aaaaaactca ttttgtgcat gtagcatttt gaattcccac catcaatgca   360

```
tgatagttct tggttttcca cattcatatt gccatttatc attatgagaa ttgtgtgttt      420
taaccattct aataggtgag taatggtatc taatttttag ttaaatgcac atttccctaa      480
taaaaattca catttaacaa ttttcatata attttttgcca agatgcctct tctcatattt     540
ggttcatttt taactgcatt gttttctttt gattagttgt aagttacttt gcatattgat      600
tataaaatca tttaacaaat taaaagaatt catttaacaa atatgtgact tggaagtatt      660
ttctccaagt ctgcggctgt cttttactcc cttatcagta tgtattgcag aaaagtgtgt      720
gtgtgtgtgt gtgtgtgtgt ttatacaaat ttagatttaa aaaatgtaaa atgttattca      780
tccacagatc atgtctttgg tattatatct gaaatctcat tataaaatac agtaatagca      840 attactttt ccacgtctct aatctcaggc tacaatcaac tcatgagtgt ttaagcttca       900
cctacttgat tagaggacta tcaacctaac atatttggaa tacttctgta aaagatgtg       960 ttcctcttcc tattatttct ttatttgatc acttattaat atgtgtattg gtttatggat     1020
gtctatttca tactctgaag aagatccatg ctacattatt cattttattt ttcaaaccac     1080
cacggcttta ttatgtgctg ggagctcatt gagtttggat cctgcatcct tacagctcac     1140
ctcatgcttt tgttttgaa cacttccctg tttcctgcta ttataataaa ttctaaactc      1200
attttctata ttatctttt catacataga atcagccatt tttctaaaga ttgcttgctt      1260
ctgatgttaa agaatagtat ttaaaaaatt gtaatactgg gtatgtgcat tgttaatgtg     1320
gtataagtac ttgcaggacc tctcaaccaa ctggcctagt aaactatgta tctaaccttc     1380
tgtaatgtga ttcattaaa aatgagaaca cactggtctc tctacccaat tatgctacca      1440
catggatctt tctagccttc cttccttgac tgtctataac ctctcactgc aaaatgagga     1500 acccccatcca accatatgcc atttttattac ttagctgcac aatttcagga cacatgcata   1560
gcagtatcag aaatgtaaag ctgtacccctt gtaggaaaca tgtttatcta ctagaataga   1620
gtgcttatgt tcagtttctt tacactttaa acttacagag tttcctcatt ttcaaagttc     1680
cttaggtcag caacttcatt ttccactttc ttcagtgagg tcatttcaat gacactgtat     1740
aatttgattt atttgaaatt ctataaaagc caaaactgta gtcaagtgaa caacaacata     1800
tagaggatat tcgaggagtt tagagactgg tataaaataa gttaaaaaga cactgtttaa     1860
gaagattaaa attatttta gtgatatgca atggttcaga tatgacacaa ttaatttgtc      1920
taagcacata gttttgtgat ggaaaatata aacctaaata tatacaatta aaaaaaaatt    1980
tagcagttca ttaacccaag gatcaaatgc agattgtata aaattatctc attacttatt    2040
ttgtgagggt ggagatttca tgagatgtat gcaacaaaga atgaggtaat tttcctgatt    2100
tgcatataag atgttgccat tcactaaaga cctttaattt tttaaattgt ttttttttta    2160
aatcaatttt ctatgtgacc caggtttttt tctcttgaca agcaaataac ccacaggatt    2220
attttctttc cttggttgag aaatatttcc ccaaacttca gctcagttca ggcatacact    2280
gtccctgaat gggcatttac cctcagatgg gtacacacac ctgtcaacat gtggactctt   2340
ctgtcagaca aacgcacctt tactcacgtg gattcttctc tcagacaaac acacatgtcc    2400
ccacgtggac tctttcctca gactaccaca tatgttctta catttactct ttcctcagaa    2460
aacagacatt tcctcatgtg gactcttgtc tcagacaagc aaacatgtct ccatgtgaac    2520
tcttcactca cataagtaca catatgtcca cattgactgt ttccttacac aagtacatat    2580
atccaatgtc gaattgttct gtggcaaaat gatctcaaga taatgataat cataaacccc    2640
ctccctgaca aggcatagat ctgtattttt ttcattgcaa cctaactttg ccttattgtc    2700
```

```
aagaacagta gtttgcagct ctaaatatac caattagaga caggtgtcca tttttctctgg    2760 aaacgtattt ttatgttctt actggacata tttgttgata atgtttgcta ttatgaagat    2820
accccaacag tgtccacatt agagaataaa aaatagtaat gggcagatta actctgtgca    2880
tccagaccca gaaatccttt gaccttgact tccctgaaat gtagacacag aggatggatg    2940
agcaatgctg agcagtgcac ccatgaccac aaaaagaaag acgtggaaat gtgtcccctc    3000
cacttctcat gaaaggcagc tcatcccctg ttccctcagg ccctggcgag gagccacccc    3060
atgtctgtgc ccttcctcag tgtccacacc gtggggtctg cattgatctg gattctcttc    3120
tcatccccgt caatattagt gtccttcgta aatcaggtcc agctgtggct tctcctcacg    3180
gggctgttct cagtctgttt gctgtgttca cggaagtcct gtgtgaagtt tactgatgga    3240
gtcagagggg gaaaaaattt acagcccagt ggtgagactc tcctgcaaag cctctggttt    3300
cacctttact ggttacagca tgagcttggt ccagcacgct tcacaacagg ataggtgtg    3360 ggtgccaaca gtgagtgatc aagtatgaat tctcagggtt actttccatg agtacaaata    3420
aattaacaat ctcaagcaac ccctttttaa gtgcagtctg ccttacaatg accaatctga    3480
aagccaagga caaggtcatg tattactgtg agtgacacag tgagggaaac cctgtgtgag    3540
cccagacaca aagctcaccg cagggagaca ggaggggact atgtggtaga tgctgctcag    3600
aaccaccagg gggcatcagg accatcaggg agggtgcaca gaaccaccag gagggctca    3660 ggacaccagg gggcgctcag aaccaccagg gggccctcag gacaccagag ggtgctcaga    3720
accaccagga ggcgctcagg acaccagggg gcgctcagaa cactaggagg tgctatgaat    3780
cactaggggg cgctcaggac acaagggagc actcagaacc accagggata gctcaggata    3840
ccagggggca ctcggaaccg ccagggggcg ctcaggacac taggggcgc tcagaaccac    3900 caggggcac tcaggaccat cagggagggt gcacagaacc accaggaggg gctcaggaca    3960 ccaggggcg ctcaggacca aaggggcc ctcaggacac caggggcac tcggaaccac    4020 caggggcac tcagaaccat caggagggt gcacagaacc accaggaggg gctcaggacc    4080
accaggaggt gctcaggaca ccaggggcg ctcagaacac taggaggtgc tatgaatcac    4140
tagggggcgc tcaggacaca agggagcact cagaaccacc agggatagct caggacacca    4200 ggggcactc ggaaccgcca ggggcgctc aggacactag ggggcgctca gaaccaccag    4260
gaggcactca ggaccatcag ggagggtgca cagaaccacc aggaggtgct caggacacca    4320 gggcgctc agaacactag gaggtgctat gaatcactag ggggcgctca ggacacaagg    4380
gagcactcag aaccaccagg atagctcag gataccagg ggcactcgga accgccaggg    4440
ggcgctcagg acactagggg gcgctcagaa ccaccagggg gcactcagga ccatcaggga    4500
gggtgcacag aaccaccagg aggggctcag gacaccaggg ggcgctcagg accacaaggg    4560
ggccctcagg acaccagggg gcactcggaa ccaccagggg gcactcagaa ccatcaggga    4620
gggtgcacag aaccaccagg aggggctcag gaccaccagg aggtgctcag gacaccaggg    4680
ggcgctcaga cactaggag gtgctatgaa tcactagggg gcgctcagga cacaagggag    4740
cactcagaac caccagggat agctcaggac caggggc actcggaacc gccaggggc    4800 actcaggaca ctagggggca ctcagaaccc caaggggcg ctcagaagaa caggggtg    4860 ctcagaacac cagagggtgc tcagaagcac caggggcgc tcaggacacc aaagggcact    4920
catgagactg tggcaagggg gtgctgagaa ccacaggatg tgaccaagac caaggggc    4980 actcagaact gccagggggt gctcaggaca ccagaggatt ctcagaacca ccaggggatg    5040
ctcaggaaac tagcgggtgc tcagaaccac cggaggacac tcagaaaacc agggatgct    5100
```

```
caggaaccac caggggggcgc ccacgacacc agagggcagt cagaaccacc ggggcatgct    5160
cagaaccacc aggggggcgct caggacacca ggggatgctc aggacactag gggcgctcag    5220
gaaccaccag gggacgctca ggacactagt agggtctcag aaccaccagg ggatgctcag    5280
gacactaggg ggcgctcagg aaccaccagg ggtcacccag gacaccaggg gtcgctcagg    5340
aaaccagagg gtgcccagga aaccagggga ggttcaggaa ccaccagggg gcactgagga    5400
caccaagggg tgctcagaac caccaggggg cgctcaggaa ccaccagggg gcgctcagga    5460
cactagtagg cactgaggaa ccaccagggg gcgctcagga cactagtagg cactgaggaa    5520
ccaccagggg gggctcagga cactagtagg cactgaggaa ccaccagggg gcgctcagga    5580
cactagtagg cactgaggaa ccaccagggg gggctcagga caccagaggt cgctcagaaa    5640
accagggggt gctcagaacc accaggggggc actcaggaac caccagtggg tgttcaggac    5700
agcaagaatg gctcaggaca ccagggagca ctcaggacct ccaaggggct ctttggaggc    5760
agctccatat caggtacctg gggaggatga ggtttccttt tccaccttgg tgattcctga    5820
cctggtcaag caaaagtctt ccccaggatc tcttacgatg tcttccttgt aactcatggt    5880
ttctttcacc tataaaacat taacttagaa caggggttca attcaacttt taactctgcc    5940
tattttcaga gttatactag caatgatata tctcagtata ttttttttaa ttgtgtatat    6000
tcaatccaaa gtctggctct atgcacaatt ttttgtttt ctgtgctgtc agacacacta    6060
ttgtaaatgc ttttctaaca actcagcata tgcatggggt ccagtttctt ttcctttcat    6120
cggctgtttg tgcagatgaa acaccacttt aagggctcct gtcctccact ttggcccctg    6180
gtgttctgct tctcaaactt tctccatctt ctcttttttct gtcaaaatat tttatcttcc    6240
tcagtctcca tgcaggaaac aggaagtcct tttacttcct gtcctccatg tctggtaaat    6300
cagttcactt cttttcatga tcactgaagc caaccaagtt taggagagta acagttctcc    6360
ttagaataca ctctacctgc agaccctctg ccctcatcac acttttctag ggtcctgcag    6420
acataacccc cacccattcc tcttttttccc taagtaccac agactaggct ctgcaactta    6480
tgctaccctc tgtgtgctca gcccaggggc tcagtagtgc tttcatgaag tccaaatccc    6540
taatgtgttt gcccactctc agaccaccct ccagcaagct gccattgtga ttgaatcctg    6600
caaagcatgg gctgctttca gtttcctatt gctggatgtt ctttattata aaggcatatt    6660
ggcaaataac gactagagtt tgtattgaaa attaacgcca aaaagttttt taaaagtt    6720 ttcaaataga aaagttctat cctgcctagt ttaaaaaaat acaatgttac tttaatcaat    6780
gatttaataa aaatttaagt gatgtttgtc ttattagtta ttcaatttat taataactga    6840 ctgatatttta aaaagtaaat actggctggg cgcagtggct cacgcctgta atctcagcac    6900
tttgggaggg tgaggtgggt ggatcacctg aggtcgggaa ttcgagacca gcctgaccaa    6960
catggagaaa ccccctctct actaaaaata caaaattagc tgggcgtggc ggggaagctg    7020
aggcaggaga atcgcttgaa cctgggaggc ggaggttgcg gtgagccgag aacacgccat    7080
tgcactccag cctgggcgac aagaccaaaa ctctgtctca aaaaaaaaaa aaagtaaata    7140
ccattgtaca cttaagtaat atatttggca agaatggcat ttacattcat tcaaaaatga    7200
aactgcaaat acgagttaca ttcaattaaa taattaaaat aatatagaaa aaatgggtg    7260 tgttgtttttg gtgtttaata tacattcatt tttgcatgga cgggtatatg tgtcattgct    7320
gggctgttgt gtatgtgtgc gtgtgtgtgt gtgtctgtgt gtacaactat gaagtttaaa    7380
atatattatt aaattacgta gttatattaa tccaaattta tcatgttaaa atattaggaa    7440
```

```
aaaaacacca gtagagaaat tacagagaac atcagcaatg cctacagcat ttacaagagt      7500
cacattaata acaaacaaac tagttcaaat gtttagatat gacacatgca gtagaaaacg      7560
ttcacatggt attaacacaa aaatggtgca caactgagga aattataata cgttcatgat      7620
attggctaca taaatgctta tgatagtaat gcttttcatc catcaaatgc ttatgataat      7680
gcttttcatc catcatatta tagatgataa acaactcta taaacacttc catcactagc      7740
gtttaatatg agatgcctca catctttttc tgaaataaat aaacatctgt ccaccacttc      7800
gatgatcatt tcaggattat cctctgaaat aattatccat aataatttta gtaacaatat      7860
tattttcaga agcctatttt ataaggtctt tgaactatta tttttatgat tgttacttta      7920
tattttacac actttttatt tggaataatt ataggttatc agaacaattg taaggaaaat      7980
acagtgtgtt cacatccatc tccaagtttt cactaaagtt aatatgtcaa aaaaaacatg      8040
ggacatggga ctaatatatt tacattgata agtttctgtt tattcagctc tgggatttat      8100
ttgaattttg ccaattttta acagtttcct ttttttcctt ttcttttctt tttgagataa      8160
ggtgtcactt tcctattgct ttttgttgt ttctttgttc aacccacgta accacatcaa       8220
attcagtcac catgttcctc tcatatcttc tggttaatca cagtttgggt tcctgctgtc      8280
ttcccattga atattctata aatgaaacta gtcaaataag ttgattctgg tcacttatat      8340
atttacctat tttatcacgt ttgttttgtc aatcacagta agtgtcgaat tcgctatctg      8400
ttatagatgt tagcctattt tctatcccag atccattggt taaatctttg gtgatgcctt      8460
ttagaaaact gatcccttta ccctatgtaa tatgccccctt gattcctgaa agtcttatgt      8520
ctaccttgtc tgaatttaac atagctaagc acgctttctt ttcgttcata ttttcatggt      8580
ccatgttttc ctgtatttaa cttttctatg tagagcaaat ttctgtacag agctagtagt      8640
tgggtcttgc ttttttaaatc aactataata attctatttt aaaactggta ttactatttt    8700
tctgttaatt tctgttttaa tttggcattt tatgatcatg tttatttctc tattaactta     8760
ttgtttagtt catcttttat gaatattgta ttggcccctaa gatatacaat aagaattgtg    8820
tataatcaga ttctaattca aataacgtaa aacctcttca taggttgtag agctattata    8880
acttattctt ctaaacactc tttctcatcc gttgtcttag tttattctca gtttgcactt     8940
atatgtgcta taaaatataa tatgtgcatt tttatcatta catagacata tattagaaca     9000
attaaaaata taaaaactac atttcaactt catttttttca ttcttgacca catgttttat    9060
ttggatagat tcatgtttcg gatgtatatc atatggctac tcaccctggc agaaaatttg     9120
ccaaagcacc tactgaagga tgaatgcact agcaataaat tttctcagaa tcgatttgtc     9180
ttacagggta ttcatttgac tttcgcttta aatgaaattt ttaatatata tagaattcca     9240
gtttgacttt aatttgtaat ttattttctt gtactcatgt attcattatt ttcttcctga    9300
agatggtcac acattccatt ctgctgggcc ttcattatag atatttgtgt gtatctattc    9360
agggctatat ttgcaattta tggatgccac aattatcaga gttgaagtca gcttctgctg    9420
tccacagaga tttcaagttc ctcccatgat acttgctttt gtgtccctgt ttgatcctgg    9480
gtctttatat ttagttttcc ccagggaggc tgtctgtttc agctgtggaa agtgcaccct    9540
actgacagtt taaattgatg actgtgtggt gaaggaggtt ggacaaagcg ggacttcctc    9600
caaccttctg actgagtctc cttcttatgc aggagtagta agcatagttc tggggagtgg    9660
ccttccacat tgtcctgtcc ttaactcttt ccccagggct ggaacgtctt ttcccagaca    9720
caactgtttt tcaccagtgt ccccagcttt ttacccacta tccttaccct aaagagtaag    9780
gatttctttc ctgaggaagg agatgggagg tgtttctgga tcaagtttcc ttggtgtcgt    9840
```

```
ctgtttcctt tgtttctgt tgacttcacc acagctcata tgacacatgc tttggtggat    9900
ttcccctgga ggtagtggag gtgcattcag gcattccaca ggagctgctg ttcttttccc    9960
cagtcaacac cacaagacac cagatgagga agttgtccgt ggattttca  agttctctag   10020
gaaaagcttg caagcactag gccaatctaa caccattagt acatgcatac taaaaaaaaa   10080
aaagtcatta agtatttcta ggttagtctg tttctatctc aaatgccatc cagtggcacc   10140
tgccctacgt acactagcag gtaggtcctg gttctctctg caggctccta tcttctcaga   10200
tttcagtttt cttgtttgct tggtgaaatc aactcagata tgttgaatgt ttttctctc    10260
ttttatttgt agctgttcag cttcgttgtt aatgaggtca gaataaaatc acagttttct   10320
cattttttc  acattcccac actgaatagc tgctttccgt ataaaagcca gaaactgaga   10380
gaacacattg aatatccatt acaggtgaat gttaaacaat tgagatatg  tttgtgtact   10440
ggaataaaat gctgcattac aatcaagtca tcactcattc acataaaaca tggccacatt   10500
ctcaaataat gtagggacct gagtgcccct ccatctactg gcctctcctg gggccctagc   10560
ctggccacac cttcttgcag ggcagtcttg gacgccctgg gatcccgcac caaaatttct   10620
gccctggcag aacatgcctg actggtggag agctccaatc gggcagccct catgtgcaca   10680
caccagctta cacacttcct ccgaatactg taggttcacc caggcccacg taacttccca   10740
catcactttg cagtcacatg tctgtatagg tgggttttgc ttttcttgtc ccaccattgc   10800
gtggagtgca gtcccctccc cccaccccaa ccaccatggc agaggaagct ttggtgggga   10860
aaaagccagg gccgctcctg tcagcgtccc gcacttgcgc taattctgca cagagaatag   10920
cagatcatct cacacattca gaaatcactc ctgcttgtgg ggcatgaata cggcacccgg   10980
gcctgtgccc acaagtgtcc catccctgag ccaacacctc ctccagtgtg accttgaaca   11040
cagtcaccaa cagggcccca cagacgcaat gcctctgcca ctgtgcgaa  cacctgcagg   11100
gaggcaggca cccagacacc cactagcact ctgccacagc tgccacacct caacagccc   11160
aggacagtgg attcctaacc ttaaggagcc ggagaaccaa gtcagggact agtataactt   11220
cccccagagt cagagcacac agtctaggtg ttgggagctg agcactggcc acctaaattt   11280
ttccagaaat gaagccagtt ggctgaatcc accttatacc acaatcaaac cctcaaggtc   11340
atccaatagg gtaaaagaaa ataaaaatgt atccaaaggt cagcaacttc aaagattgaa   11400
ggtggataag cccacaaaga tgagaaagaa ccagtgcaaa agtcctgaaa acaaaaaggg   11460
cgccctcttt cctccaaaca accacagcac ctcttcaaca gcagttctga atggggctga   11520
gatggctgaa atgacagaaa cagaactcag aatatggaga gtgaaaatgt agatgaatac   11580
agctatttat ggagaatact ataaatgttc ctcaaaaaat aaagaaacaa aatctactgt   11640
agaatccagc agtctcactg ctggctatgt atccaaagga aatgaaatca acatgtcaaa   11700
gagatatctg cactccatgt tcacgttcat tgcagcatta tttaaaatag taaagatatg   11760
gaaacatcct aaaattccat gaatggatga atgaataaag aaaatgcata cagacacaac   11820
agagtaatgt tcatccttaa ataagaagga aaccctgcct ctgtgacagc atgcatgaat   11880
ctagaggacc ttatgccaag tgaaacaagc caggaacaga ggaagagtca ttcatgattt   11940
cactgtatat attaaagcag tagacttgca gaggtagagt agaatgttgg ttaccaggc    12000
ctagaggggt ggactgggaa agggagatgt gggttaaagt gcacaacgtt ccagttagac   12060
cggaggtata agttatgcct ttctaatgca cagcatgtca actatagctg ataaggtagt   12120
atatatttca aaattactaa aaaaataaac attagaattt ccccactaag aaatgataaa   12180
```

```
tttgtgaggt gatgaatata agcggcttga gttacccagt tcataatgta tacatgtatc  12240
ataactaaac aacatatgtc ataaatatat gcaaaaatta tttgtaattt ataataaaat  12300
aagtttcata tttaaataat tacattaaga aaatgaacag aaactttcag atttcaagaa  12360
tattttatat atatatatat atatcttaaa acaaacttgc aacagaatat agaaataagt  12420
tttacgactc aatggaaaag aacagaattc aataaaaact ggctaaaaga aacaacagct  12480
gcatcattat agaaaattct ggaataatca gccatataaa gattctcact ctcttagaac  12540
tagaattccg taggacttgt aattcctcct gacctgggtg ggaggcaaaa ggaagaacag  12600
ctaatggtga ttcagtgagt tttatacctg tgtgtacttc tgtgctcact cagcagaaag  12660
aaaagaagaa aagaaagaaa gagagaaaga aagaaacaga aagaaagaaa gaagaagaa  12720 agaaagaaag aaagaaagaa agaagaaag aaagaaagaa agaaagaaga agaaagaaga  12780
aggaagaagg aaggaaagaa aagaaagaaa gaaagagaga gagggagaga gggaaggaag  12840
ggacagcaga agtcattgtg gtgtgtgtga aagcacaatc cttgggctcc cccacatcca  12900
tctctactcc agtcccatca atgtccagca atacattttt ctaagatgaa gtattttaaa  12960 cttttctaaat cctgctagaa aaccccctcag ctctttcagt tttgctctat cacttgaatt  13020
attgaattaa atctagtttt tgtgggccta tcaataccat aagccaaaat aacacatgaa  13080
gaaattgcac tgagacacat gaaaaccttc tgaaagctcc ataatttcag atctgcattc  13140
ttatttcccc gaacctaaat cactgaatag agactcagaa cgagttgatc ttgttcctga  13200
acgtgcacag agccaaggac atcctgtctg tctggaacag ctcaggtttg ttcctgtttc  13260
tcctagagga tataaaatct tgagttaggg aaaaacagcc agggacaccc tgggctttgt  13320
tcttctctcc cctggaggca ggatgtcctt cagagctttg tcccagtggg taacacagct  13380
gctgaggtgt acaacccacg tggcctcgtt ttggtcactt ttgcatggtg agcctgcttt  13440
gcaccatggc ctacaatatg cgtgtgtaac taatctgtct ccatcttcaa aatgacatta  13500
ttccacatca aatctagtgc aggtgcctca cacagaacat tctcaattac ctccatcatt  13560
cataaaattg atgccattaa tttcaagtat acatacatca gactcattta acgtattgtt  13620
attctcattg tttgaaacat aacttttaga tcaaataatt aacaataata aaaatataaa  13680
ttttgaagtc aggtaatgtg atttctctag ttgtgttctc tttgctcaga atggcttggg  13740
ctgttctgca tcttttgttt ttccacatat attttaggat ttttttaaaaa tttctgtgaa  13800 gaatatcatt gttgttttca tagggattgt actgagtctg tagattgctt taagtattat  13860
ggacatttta acaatattga atctttgaat tcataaacat ggaatattgt tccatcttgt  13920 gtcctctttta tttcctcaat gttttataga tttattgtag tttttttttta ctttgttcat  13980 tacacattgt atgcctgtac caaaacatca catatacccca acaaatagaa atatatatac  14040
tattatgtgc ttataacaat taaaaattat gtatgtatat tgaatctatt caaaatcaga  14100
aactatttct ttttactgtt tgtaaggtct tgtctctagg ctataaaaag aatttgtaaa  14160
actcaacaga aagcataata taaacagaat tctaaaatga gtgaaaatct gaacaaacac  14220
ctcaccaaga aaaatgttta tctgaaaata agaatatata aaattgttca gtatcaattg  14280
tcataaactg atactcatat ttaccaaata caaaagtaaa catgatgtat ttcaacagaa  14340
ttgattctca aatatttgta tactcataca gtggaatact atcagtcata aaaactatgg  14400
gttattaatt cagaagacaa catttttaaca tttttttctaa gtgaaggaag atggacaaaa  14460
gagactaagt attgtacaat tccattcatg agacctgcta aatacagtaa aattaaaagg  14520
attttaaaaa caggtttgtg ataggcaggg cttttgggga aagacaagag actgacttgg  14580
```

-continued

```
caaagctcag gggatatttt tagggtaaaa caaactgtgt gccattgtga tatgcctaat      14640
ttcttattat atttgttcag agttaatagt gtacgtttca accaactcgg tgattttata      14700 ttttctatttt gctgatagag acatgttcat ttttgtcaat cactttgcta aatgtggctg     14760
agaggctgtt gaaatgaacg ctgagcaaat gtattcacca aatctacaag agcaaattat      14820
ttgccaattg ctgattgagt ggggtctata atgtatttga gattgggtgt ggggatgtta     14880
ttgtgtgaga tcatgatgtt tagaccatga cactctctgg tgagggatca ctcattcatt     14940
gcacatttaa tgaaaggcag gtaggaggag cagaagggga tgagtcacac tcctgaccac      15000
agccacaggt tattgaaggc agaactgatg taatccccta aggtagacca ctgcccctcc      15060
aaggtgacct tatcctagag ttgacacaca tcctgggaca ccagagacaa ctccttctct      15120
cccctttctc tgcacttcag ctggaagcaa ctgtctcacc gagcaccttg tgttaaggaa      15180
tgagagttcc tgttccaggt gtgagggccc aggtgcatcc acttgatcca gcacaagagc      15240
aagaacagct ttccagaaaa tgacatcgcc tgaggtataa ccagctctca cctgctgcag      15300
cttcctctga ataaaaagga aactgttgaa acttcctcat aagtgtcctg ctgtgccatt      15360 cccttttgtcc ccacatgttc agttgtgtct gtccagatgt cacttttgtg tagggagatt    15420 aggggttctgc ttccagtacc agaacacaca tgacctctta ggggacttca gggttttgct   15480
gacatatgtg atgatcttaa aagtcattag ctccatttct acatcaaaaa acatctgaac     15540
caaaggagca cataggctca ggcctgtaat cccagcactt gggaagcca aggcagagga      15600 atcacttgag gtcaggaatt tgagaccagc ctggtgaaca tggtgaaacc ccgtctctac     15660 taaaaatat atacaaaaat tagccaggcg tggtggcact agcctgtaat cccagctact      15720
tgaaaggctg aggcaggaga attgcttgaa cccaggaggt ggagattgaa gtgagctgag    15780
atcgcaccac ttcactccag cctgggcgac agagtgagcc tccatctaaa aaaaaaaaaa    15840
atttatatat atatatatat atatatatat ataataaaata tatattatat atcatatata    15900
tattttatat aatatatatg tatattttta tatattatac atacatatca atatatgata     15960
tataatatgt atatataata tataatatgt atattcatat attatataat atgtatattg     16020
atatatatta cacatatata ttttgatata tatatatctc caaaccatct aaatatcaag    16080 tatttttttaa tccatctaag agctgaaatt gctgaaaaaa ctactccctc caaaagctgt   16140
agagacaggc acatccacag tcacagcaga gacttgctga cttggaagag aagctcctgg     16200
agacacattg gtgagaacat ttacctggtg attatgctga atgtctggag gacaaatgtg    16260
gactaggggg agggtgagca ctcctagagg ctgtacaccc cacacttgtg tggacttgcc    16320
ctccagggcc ttcaggttct cgtggaagca attaaaatag attccctata gccatgaact    16380
ggggaggagt aatcacggag aaaagatgca caaaagact tttctagaaa gctcatccaa     16440
gggaaggtat tctccaaaat cttagtttat gtgggggaag gaaatacttc caaattacag    16500
acccctcctc ctcagccttc ctctatcacg caaatgataa aattagccaa gaggagtcag    16560
attcaaggcg gtagccctgg gtgcagcatc tgcagaaggg aggaaagaga gaaaatcagc    16620
tgtatcactg gagattcctt gtgaaggtca ctgctcagga gaagaggca accaaaccag      16680 ggagagtcaa ctgtaagaac ataccatgct cccctgcccc acacattacc tcctcaacag    16740
catcattaat atggattaaa gagggcagtg tgattgcttt agatctgttt gagaaagaaa    16800
gtcacatact gaggcctagg gtcagggtcg gcggcacttc ccgtgagtaa gatactacga    16860
agaaggaaaa attaggggtc cataactgtg aaaatcagcc acagtgtgtg tgagaatgtt    16920
```

```
tgtgtttgtg tttctgtgtg tttgagtagg agttattgga acagcggacg tggagtgagc    16980
tttaatccac atccatctgc agcttcaggt attctcagat gcagtattca tctgcaagag    17040
ccgaaatgag aaaagagcca cctccaaccc ccccagagtt ttagcctccc tttgtttcca    17100
gtgatccagt gcatctagac ctccaggaag tggactccct ggtgatttta gcgattcttc    17160
tcttggagcc accctgaaga ggacattggg tttccaaagg cccattcact atttcaagaa    17220
gtggtgccat cagctcatgt tgtcactgaa ggagcattct gagccagggc acagtcactt    17280
cctagtgagc tacagaggct gagagaaaaa tgctctgtga cccaatggg  aagctccct    17340 gcagtgcaag gtctgggtgg cagggagcgc tagggcctcg cccagcacag gctgcagccc    17400
tggagcaggt gcagggagg  ctgggagggg ttcctccca  gggtctgatg tcttccttt    17460 ctcggacaaa catgctttaa taagttaaac aagactttag taaagactat tgatgtgtct    17520
ttgtgtcttt cagtatacag ttctatttgt aggatttatc taacctaaca agtcaatgag    17580
aatcacatgt aaaaggagaa atttctagga ttttcagata tcttaatagg taggagatgg    17640
agaaaaggga tggttttatt aattcagtgc ttgccaatct taacagagac agtagtaaga    17700
catgcagaaa gcaaagccca gaaaagtatg aaggtgtcaa agtgccattt aagtatgggt    17760
tcacttggag gaccatgttc tgcgggaact tgttttcagc agacaatcta ttttagcaga    17820
gttctgggca tacaaggga  cacacatcat taaacaagga ttgggacagg gacttcagcg    17880
tcccactgtt gcatggccca taaattatgt gtgttctctt tctcatcttg gatcaagtct    17940
agagctatga aatagtatcc ctcatgaata tgcaaataac ctgagattta ctgaagtaaa    18000
tacagatctg tcctgtgccc tgagagcatc acccagcaac cacatctgtc ctctagaaa    18060 tcccctgaga gctccgttcc tcaccatgga ctggacctgg aggatcctct tcttggtggc    18120
agcagccaca ggtaagaggc tccctagtcc cagtgatgaa aaagagattg agtccagtcc    18180
agggagatct catccacttc tgtgttctct ccacaggagc ccactcccag gtgcagctgg    18240
tgcagtctgg ggctgaggtg aagaagcctg ggcctcagt  gaaggtctcc tgcaaggctt    18300
ctggatacac cttcaccggc tactatatgc actgggtgcg acaggcccct ggacaagggc    18360
ttgagtggat gggatggatc aaccctaaca gtggtggcac aaactatgca cagaagtttc    18420
agggcagggt caccatgacc agggacacgt ccatcagcac agcctacatg gagctgagca    18480
ggctgagatc tgacgacacg gccgtgtatt actgtgcgag agacacagtg tgaaaaccca    18540
catcctgagg gtgtcagaaa cccaagggag gaggcagctg tgctgggggct gagaaatgaa    18600 agggattatt attttttaatg ttgtttacag tatgtcatta ataaattgaa aaaaagtaac    18660
aatagaagta tatactctaa ttatatggga actttgtttt ttcagttttt tcattttttt    18720
tttttttttt ggtttgtttg tgacagagtc tcactctgcc acccaggctg gagtgtaacg    18780
gcacaatctc agctcactac aacctccacc tcccaggttc aagcaattct cctgcctcgg    18840
cctccagagt agttgggatt acaggcaccc gccaccatgc ccggtgaatt tttgtatttt    18900
tagtagagac gggggtttcac catgttagct aggctggtct caaactgctg atctcaggtg    18960
atctaccctc ctcagcctcc caaagtcctg ggattacagg cgtgagccac tgcgcctggc    19020
ccaattatat gggaattgtt tatataatta tcaccctata agcaaaattc atggaggagg    19080
aaaagctcta ctgaagaaag ctgataccgg cattcccatg aaagtatctg tgtagaagta    19140
agtattaaaa tcagttgaat aggcaaggca tggtggctca cgcctataat cccagcactt    19200
tgggagaccg aggcaggtgg atcacaaggt aaggagttca agatcagcct gcccaagatg    19260
gtgaaacccc ttctctacta aaaatacaaa gaattagctg ggcgtggtgg tgggtgcctg    19320
```

```
taatcgcagc tattcgggag gctgaggcag agaattgctt gaacctggga ggtgaaggtt   19380
gcagtgagcc gagatcacgc cactgcactc cagcctgggc gacagagtga aactccatct   19440
caaaacaaaa caaaacaaaa caaaacaaaa aaacagttga ataaagtacc ttagagtcat   19500
ctgttcaatt aacatgttta actccaaaga aatactgaaa atattttcca aaaaggaagt   19560
gccattttac gttcctacca acagtgaata agattttctt ttctggagcc ttgtcagtat   19620
tcactaatgc tttgctgtgc agccgttgta atatttatagt aaatgagtag cagtatttaa   19680
tggttgtttt aaatatacat attcttaata caaagtcttg atgaacactt ttttatacat   19740
tgttttatga ggtgtgtgtt cagatctatg tatgccagaa atgcctggca gcgttaattt   19800
aagcacactg tgagaatgac cctatagttt atgaagaatg tatgttcaga gctctgagct   19860
aagaaatcca ggagctgtca acccagaagt ttattccttg tctgtgaagg acatctgaat   19920
ccctggccta tcccttggaa cacaggatgt ccaggtgatt gatgctcttt gttaaatctg   19980
gaggttgcta ggtagagggt gctaagtgaa aatcataata taaactacac gtgttttaca   20040
aatggtagtg gttttcctgt ccaacacact tttcctgggc cacattgtat gcaagtcctc   20100
aatacaccct aggtcttgtt catgggctcc aggtctcctc ttcagccttt tggacatggt   20160
gccatgccta ttacagtcaa tagggtcta gcatgacaac tggtaggccc agaacaaggt   20220
caaagaaaat cctgcaagct cttagacaac agtgtcaagg aaggggagac ctgtggggaa   20280
atcccaggca ggccatgcac atctctgtgg gcccaacagc tgcaatcctt gatggatggg   20340
gcccgctgca tgtgtacggg gatgcctcca aaatgccaaa agttctggag gacctgttgc   20400
ctgaggtgga tgtgacaatg tgacaaagtg acagtcagat tcctgagctg tggcagctgt   20460
tggccactcc tgactgcact ctgagcaacc actgaggcag agctcattgc acaggctagg   20520
gtgtgtcagc cacgagaaca gttgtaacta taatgagatg ccgcctgtag ggataggata   20580
gcaaattgga gaccattgtt tatttggtag gccatttaaa gtgttgctga ctgccacacc   20640
aatgcattag gactactatg actacgtcat cctgggagcc taagtcctgg cgtccgatgt   20700
agagctccag tgggaaggag atgaaggtta ggatgagtcc ataaaggttc ttgctctgca   20760
gccctgctt tgctgtctca cttggtgaac agagaatggg aggtcaatgc ggacaaagtc   20820
cagggtccag gcttatcagt caaatacttg gtgtcatctg gttacataag actatagtta   20880
ttccatattt catcatagat aagataagat gcaggtctac tcatgtccca ccacaccaaa   20940
gcagttggaa acctcccaag gcctcctggg acattggcga tcctttattc cccatttcgg   21000
caaacccctt gggcccccat ggcacttaga caagaaggtg ccccactgcg actgttccaa   21060
aagggaggat gagggctctg aagaagctga agtcacagtg aaatgaatac aaaccttggg   21120
agttctagtg cagggacagc cctgtgaatt ggatgtagtc agttaccctg aggggtttag   21180
gtggggactg tgttaaaggc aaggacataa gtgtgtgtcc ctaagaccct ggtctcaaag   21240
acagaaggaa gctgaagtga gatatactgt ttaggagtag caactgcact acatgtcatg   21300
ccttacgagt gtaggatgtg acaaagaggg ccactccaca tccggaacaa cctttagcag   21360
gctggctaaa ggatgccttc cagacacaaa agccttggaa tgccaggaca cagtctgtag   21420
ccaaatggta cttgtggtgg tcaccaccaa cataaaagtg ggccaactgt gccagcagaa   21480
gttagcccca cagaactttc ccccacctaa gagaaggcag tgcaccacaa tgcggaattc   21540
caccactgtg gaattggggg agcttagaat tggattcaga cacaagggga gagagtggat   21600
cacagggtgg cttctctatg ggataggggg tggagagtat tatactctct ggactcaaga   21660
```

```
tgagtaaaat gacacccatc acaaaccatc cagccctatg atggcacctt tatggtaagt    21720
ggttgcaggc tccaagggg ccgggtccaa tgaggaagat gccccacag ctcgttctca      21780 atggcagact atagaagagt tgcaggatat cttctgggag tcgagatgag gcatgctaat    21840
tatgctgaga attattgaag tcccaacaat gaattgttta ctgcaaaata aaagctacag    21900
ttatgtattc agtgcctacc caatggcatg gtgcactgat ttccacgtta agcccctgg     21960 gagggcagcc aacatttcat gtgcccagg tagttgctga cttaggagaa aagaagaaac     22020
tgagtaagca agggatgcac cctactgtga tgaagaacaa tggcaccaaa ggaagagaga    22080
cagccaagga gccagtcagg gtggccagac aacgaatgtg ctctaactgg caacacctac    22140
cagttctctg ggcccatagc ggcaataggt ggttatggaa gggccacgga agtcagaccg    22200
gttgaactag tgatacgacc tgggggactg ccacccagac cctgtgtagt atacacagct    22260
tccatcctag aacacatgag aatggatatc ttcttaggcg tgaccctcca aacaacggcc    22320
agggaattcc aacggagagt tagagtggtg atatgtgtga ccaagcagaa ggcaaactgg    22380
atgccagtag agctgccaac ccatgggag tcccacagct ggagcaacac cacccgccct    22440
gggaggggaa gatgatccaa tcatgaagat tgttaaggag ctagcccagg taggcattag    22500
gaggccactg catggttcct acaacagacc tgcatggccc atgcagaggc cagttgagac    22560
atggagaatg acagtagatt actgggagtt aaataaggtg gtctcccgag tgaatgcagc    22620
tgttcctaat atctcctcca gtctgacgag aataggagag gtgttagcca cgtagcattt    22680
ccttatcagt ttagtcaata ccttcttcag catttctgtt gccccagagt caagatcaat    22740
ttgcattaac ctaaaaagaa caatggactt ttactgtctt gttccaggga tatttacaca    22800
gcccaaatct cacagcctag tgacctccaa cctcagtcga tgggctgacc caaggggat    22860 acatgttttc cactacattg gtgttatcat gataacctct gagtcttttt tcagcttata    22920
aattacagcc cctgtcttgc tgtctcactt gctgaataga ggatgggagg ttaatacaga    22980
caaaatccag ggtccaggct tatcagtcaa atagttggtg tcatctggtt gggtaaaact    23040
aaagtcattc catctgccat catagataag gtgcaggcct acccacgtcc caccacaaca    23100
aagcagctgc aaactctcaa ggccttctgg agcatcagtg tccttttatt ccttttattt    23160
gacatccctg aaggaggctg ctaggggaga ctgtgtccct cctaaattca tgtgctgaag    23220
tcccaaccct tggtccttca gaatgaaatc atacttggat tagtgtcctt taaagaggtg    23280
aataagttaa agtgagattc ctggagtggg gccctaatgc aatctgactg ttgttataag    23340
aagaggaagc aggagggagg gtgcacaggc cccgagggac ggccatgtta ccacagaaca    23400
gtgagaaggc gccatctgca tgccagggag cgagacctca gaggaaaccc acccagctgg    23460
cagcttgatc ttaggctttc atcctccata agtgtgagga aattggtttt gtattgtaag    23520
ccatccgatc tgtggtattt cgttataaaa gccctataaa atgaatacag taggtaatag    23580
gagagcttct atacattgaa aaagtcggat ggccagaaaa acctagacac tcctgttcag    23640
acctgagcag ggtgatggac ctgctttggg acaggagagg ggaagagatg aacccagcac    23700
ccagacccag ctgagcccat tcctcagcag gccgtccctg gccggagct tgcacaggtg     23760 tgaaagagcc tgtcttggtc ttcagggggct catggagttg gacggagaat ggtgtagact    23820
caagaacacg tcatcggtgt gcccgtgttt atctgaatgg gatgtgtttc tagggtgtgc    23880
tcatccccaa agaagaatta atcaggtctc ttgggctaaa aagaggttgt ggcatttgtg    23940
tgtattaata actgtggtcg gacagtaaat tatgttaaac tgcttatggg aaggcacaat    24000
ggaaagaaac actttgttac agaaggaaaa aaaaggtgat tatttaaatg aggtgccttt    24060
```

```
gaaggtcacc atgccaagag gagcccatca catgatagtg ctggctttca tgttcaggag   24120
atcaggaggg tccgtccgct ggcttttatg acaccctaga cagagctgag agtgtaatgt   24180
atgaatggag gggaagtgga gagagggag gccaaatgtt tggtgggaat ggagggtcac    24240
tattggagcc attaggaaat acacaagcat gaattatgct ggaggacaga acagtgttcc   24300
tggggaatat tgtgttgctt tgggagctgc tgaacataca ggagtttcac tgttcctagt   24360
tctcaaattc tctagactct ctggacaacc cagttttaaa tattgggaat ataggtaaga   24420
cacattcgtt attaaaaatt attaagagaa gatgtaggaa gaaatttaaa gtaatccatt   24480
tggttatgaa aatttagtta cagcgaactg tgatgtccgt ttcttacttg gaataatgga   24540
atgtaagtca ttagtcatct caacggttca tttttccata accatcaatt acaaaactgc   24600
tgagtaattt cctgaattgc ccaccataga aactgacctc acatttcctc aatgagaaac   24660
tgccagtccc gttgatccag cctcgttctt cccatcaggg attttgtatc tctgtggacg   24720
tgtggcacag tgctgcatat ccatcggcat atggcctcag gaaaggcgcc agcctatcca   24780
tgcatgatga agcttactta ggggatgaag cccgcatgct gggtgagcca gtgccaacag   24840
ctgaaagaat caactgcctg gtgtatgatg cttttatgaa aacaagccca gggcctcttg   24900
cattcttctg tattagattc tctggtgaag attttttattc atttctgcct gaaattgcca   24960
catataatta cctggaagca ttacaataaa ctgatttgga agttaactga cttcctggtg   25020
aggttaaaat gagtgtcagg tgcatagtga gacagaccgg agacatggat gcatagcaaa   25080
cttgtgctca ccatggtttc tatcttagtt agggaaactt ctgtaccttc cttagatgtt   25140
caggcactcc attgaggacc ctggcataac attatttatt gacagaccat agctcaaagt   25200
atagaactgg atactaccaa ggaggatata ctattactat tttatcttta tcttaaaata   25260
tactcttcca tctgaggtga aaattaatcc agatggtaga acttattgca gttactacag   25320
cattttagca aatcaaaagc cgcagaacaa acatatggac agatggcagg tatgttttcg   25380
gaatcgtaaa caagttcgtg atgactgtaa aaccaagggg tgtctcacga gggctggaaa   25440
cctctcacaa tgaaacaaca caatgaggat ctttgaaaag tactctgacc tcctggtgag   25500
ctggctgata tggaggctga gctccatgta gaaagccaaa ggaatttctg caggacgtca   25560
tcatgccaag cacagccgta acctgggtcc cagccctttt cacacgctca atggttagat   25620
cttgggaggg aatcaaagaa gccatagtaa aatatcaaaa tttaaacccc gatttttgaat  25680 ttaaaagtg ttaaaatatg gttgtggcct acactcagaa aatctgtgtc cttcagatgg    25740
tttctcagtg gcaccagatg gtttcaagtg gctattcatt aagtttctca gtgaaattac   25800
cagacataga ataaataaat tgtcactgtc ttaaatcaac ccatgggaaa ggaaaactgt   25860
gtaaatacag cagagaggaa acattgctca agggaaaaac aatctccaga agtattgtt    25920 aaagaaacag aggccctctt tccagccagc gccgagcgat gggcacctct cgggacaact   25980
ggcacaaggg ccgcaaagct gggggcaaga gaaggccctg ccacaagaag cggaagtatg   26040
agttggggcg cccagctgcc aacagcaaga ctgacccgtg ccgcatccac acagtccgtg   26100
tgcgaggagg taacaagaaa tactgtgccc cgaggctgga cgtggggaat ttctcctggg   26160
gctcagaatg ctgcgctggt gaaacaaggg tcatcgatgt tgtctacaat gcatccaata   26220
acgagctggt tcgtaccaag accgtggtga agaattgcat cgtgcccatc gacagcacgc   26280
cctaccgaca gtggtacgag tcccactgtg cactgccct gggccgcaag aagggagcca   26340
agctgactcc tgaggaagaa gagattttaa acaaaaaacg atctaaaaaa attcagaaga   26400
```

```
aatatgatga aaggaagaag aatgccaaaa tgagcagtct cctggggag cagttccagc    26460
agggcaagct tcttgcgtgc atggcttcaa ggccgggaca gtgtggccga gcagatggct    26520
atgtgctaga gggcaaagag ttggagttct atcttaggaa aatcaaggcc cagaaaggca    26580
aataaatcct tgttttgtct tcacccatgt aataaaggtg tttattgttt tgttcccaaa    26640
aaaaaaaaag aaagaaaaag aaacagaggc atcacactta ctagaaaaac atattctatt    26700
tcatatatta tggggatatg acgtgatgtt ttgacatatg cggcattgt gaaattatta     26760
aatcaagtaa ataaacatgt ccatcacctc acatacttat tttttatggt gtaaacgtgt    26820
aaaatctact ctcttatcag ttttcaagta tatagtacat tagtatcatg gaagtcacca    26880
tgctgtgcaa tagatcttca aacgaattcc ttctatctaa ccaaaactct gtacccttc     26940
accaacgtct cagctttcac atgcccctga cgccagcccc tggtaggcac cattctactc    27000
tctactctga gttcaacatt tttagattgc atgtgtaagt gagatcatgg agtaatttt     27060
tatacctggc ttatttcact caacataaag agtcaaatgc tcaacatcac taatcatcag    27120
ggaaatgcaa attaaaacca cgataagata tcacctcaca catgttacaa tggcttagtc    27180
tcagtctgtc ttttgttac tataaccgaa taccagagac tgggcaattt ctaaagaaaa     27240
ggaatttatg ctttatggtg cttgagtcag agaagtctaa tatcaaggca ctggcatctc    27300
acaagggcct tctcactgcc tcatctcaca gcagaggtgg gtgagcaaga gaccatttgt    27360
ccacgagaga aaagagacca tcttttatta gaaattcact cctataataa ctaacccact    27420
ccattgatag tgacagtaat ccattcatga ggacagagcc ttcatgactt gatcacataa    27480
taaaggtccc acctctcaac actgttgcat taaagattat ttccagatcc taaactttgg    27540
gagacacatt taaaccatag cattccattc ctaatatcaa aatttatgtc cttatcacaa    27600
tgcaaattac attcattcca tcccaattgt ctccaaagtc ttatccagca tcagtgcaaa    27660
agtctgaagt ccaaagtctc atctaaatca gatatgagtg tgactcgagg cacaatttag    27720
cctgatataa attgttttcca tctgcgagcc tataaagtca aaacaagtta tctactttca   27780
aatacagtga acaatggggc aggtatggga tagaaattcc cattccaaag ctcagagaga    27840
ggcaaggaga aagcggtgcc tagttcaaaa cccaacaggg aaaaaaacat taagtcttat    27900
agctggaaaa tcatcctctt taacggcatc ttgtgcacac tggggagggg gatgggcccc    27960
caaggcctcc ggcagtcttg cctctatata tttctgggt tcagtccact cagccgctct     28020
cacaggtggg actctcaggc ctctagctct cctaggctga ctggaaactc tttgtggtac    28080
ctccaaaccc acatttctgc ttggcattgt gctaagggcc cagtgtggtg actctgtctc    28140
tgcaacaagt cactgcccga gaccttaggc tgtccttagg ctgcccgaga ccttaggccg    28200
tccacagcat tctttgaaat ctaggtggag aaagccatgc cctcgtggtt cttgtattct    28260
gcacacctgc agaattaaca acacatggat gccatggaag ttgatgactt gtaccattaa    28320
agtgatggct tgagccacac ctaggtcctc ctgagccaca gcatgggcag ccaaggagtg    28380
ctgtgcctgg acaccgggaa cagagtccta aagtgcctgc tagaagtcag gccatagatt    28440
tccttcaaat ttctcccacc atataacctc gttcatggct ctgaacttcc accttacaga    28500
aggacctagg gatgaacaca attcagccac gttctttgcc actttatggc aaggatggcc    28560
tttgctccat tttccgatga gctattcttc tttttctcct gagacctcat cagaacggcc    28620
tttattgtcc acggttctac tgacattcta atggtcatca cctaaataat ctctaagaag    28680
tttcagaatt tcctcacagc tctcttcttc tgagtcctca aaagaatcac ctctagtgtt    28740
ctattcaggg caatccagac ttttttatagt ctgatcctcc aaattattcc agtctttgtg   28800
```

```
cattactaca tccacttcta cattttgggg tatttgttat cgcaacagcc ccacctcttg   28860
atactgattt ttcgtcttag tccactttgt ggtgcaatga gtgaatacca cacactggct   28920
aaagtataag gaaaagaaat ttattttctc gcagctctag aggctgggaa gtcaatatca   28980
aggtgttagc atctggcaag agccttcttg ctgtgatgtc catgtggaag gcaggagagc   29040
aggtgcgaag gatggaaagg ggtttaaact cattttttaa tgaggaaccc aggcctgtag   29100
taactaatct gctaccacaa tgagtaacct actctgacga taatggcatt cattgcttca   29160
tgagggcaga gccctcatga cctaatcatt tcttaacatt cccacctctg gacactatgg   29220
aatttgggat taagtttcca atacacatcc tttctaaaca gcaggggctt tttaataggt   29280
tgaccaccca aggctgcagg aggctctgaa gcagtggcct gaggttggct gtcctttgtg   29340
agaatggaga gaagtgaact gactcatgga gacacaagta gatgaggtaa aggcattcat   29400
tgcttcatta catggatggt gaggtcgatt gaaggcatta acggattaaa gatggtggca   29460
aaaccgtctg aggtggagac cacggggagt ccatcagaaa tggaggacac gtcccaataa   29520
atggtgcttc atttccctgc aaagcagaag aaagcaaaga acaaaacaca acatcatagt   29580
gtacactgag cagtggattg agagaagagt ttcctaaggc ataactgaca gagtggagaa   29640
gacacacaaa tctttgcatg atgctaacat ttggactgtg gcttcattat ttcttattaa   29700
tattttactg aaatatcgct agaaggagac tgaaaatgaa gtgtgaaaag ttaaatggga   29760
tttctgctct atgtcctttt cagatgagag gaactaggga attccaggga agaaacaata   29820
atagctgctg agcaaggctt ttgcagggca ggacaaggaa tccccaaaga gaaaacggaa   29880
acctcagctt cactttgcat ctgctcctga gccaggtcct gagcgacccc tgtaggtcct   29940
gagtgcccct ccgtaggttc tgagcatccc ttggttgctg ggcgccctct ggtggtgtct   30000
gagcccctct ggtggtttct gagcccccccg ccttatgtct gatcctccct ggtggtgtcc   30060
gagtgcccct gctagtgtct gagcccccctg gtggtgtctg agtccccttc ttagtgtctg   30120
agccacccta ttagtgtctg aggaccctg atggtgtctg agccccagt tagtgtctga   30180 gccaccctat tagtgtctga gcccccctgg tggtgtctga gcacaggaga gctcctctga   30240
aggaagggtc tacatgggga caggcgtgct tgtctcaggg aagggtccat gtggggacag   30300
gtgtgcttgt ctgaaggaag gttccacatg gagacaggtg tgcttgtctc agggaagggt   30360
ccacatgggg acaggtgagc ctgtctgagg ggacagaagt gcttgtctca aggaagggtc   30420
ctcatgtgga caggtgagct cttttgaggg aagggttgac ctggggacag gcatgcttgt   30480
ctgaggtaag ggtcctcctg gggacaggtg tgcttctctc agggaagggt ccacgtgggg   30540
acagaggtgc ttgtctaagg caagaatcca agtagggaca ggtgagctcg tctcagggaa   30600
gggtccaggt ggggacagtt gtgctcatct gagagaagcg ttgaagtggg gacaggtgtg   30660
cttgtctcaa ggaagggtcc atgtggggac aggtgtgcta gtatcaagaa agggtccaca   30720
tagggacagg tgtgcttctc tcagggaagg gtgcatgtgg ggacaggtgt gcacatcgga   30780
gagaatggtc cacctgggga caggtgttct tgcctcaggg aagagtccac cttctcaggg   30840
aagaagtgtg ctcctctgag ggaagggtgc acatggggac aggtgtgctt gtctcaggga   30900
agggtccatg tgggaacagg tgagctcatc tgagggaaga gtccacgtgg ggacaggtga   30960
gctcatctga gggaagggtc cacatgggga caagtgacct cgtctgaggg aagggtccac   31020
gtggggacag gtgagctcgt ctgaaggaag ggtccacttg ggaccggtg tgctcctctg   31080 agggaagggt ccacgtgggg acaggtgtgc tcctctggag ggaagggtcc acgtggggac   31140
```

```
aggtgagttc atctgaagga agggtccaca tggggacagt tatgctcctc tgagggaagg    31200
gtccatgtgg ggacaggtgt gcttgtctca gggaaaggtc cacgtgggga caggtgtgct    31260
caccttgggg aagaggacag atgagctcat ctcagggaag gggccatgtg gggacaggac    31320
caagggttgg gacttcagca caagaattta ggaggaacac agtcttccct agcagcctcc    31380
ttcagggatg tcaaatattt tccttctgtt ccctgtgaaa gccttaaagg ggtagggaaa    31440
gggcgttcaa cctgcacact cgtagagggg aaaccagctt cattagtaat cgttcatctg    31500
tggtaaaaag gcaggatttg aagcgatgga agatgggagt acgggcgtt ggaagacaaa     31560 gtgccacaca gcgcagcctt cgaaacacac cacggtcacg ttaagtttaa atggagtgac    31620
cacattcgcc aggaaaggga aatatttaca cttttgaaga aacagtaatt tgtgtttctg    31680
attatgatct ggccttggat tttccctccc ctcataagca atgacagaat tggcagaaat    31740
atgtgaaacg ttagttctca gacatgagac acccacagag ggcccctgt gcccttccct     31800 gagagctgat cagctcctgc atctgaagaa atgaccaaag accaggagag aaccacacag    31860
aagcatcgga gggacagcac ctgggctct gatgggtca ggaatagcat ctgttcccaa      31920
tagatggact aagtaaaaag tatcataatt cacaagagtt ttacatagca cagaagaaaa    31980
agttacccta tatcaactgt tgatcttgtg aatccaggaa ctctggattc aaggtggtcg    32040
ggcacatctt gatttacgca tttcagggac acatgagaca tcagtcaata taagtaagaa    32100
ggacattagt tccatccaga aaggctgaga caactcaaag caagtcctcc ccacttaggg    32160
cttccaggtc acaggtaggt gagagacaga tggttgcatt cttttgagtt tctgataagt    32220
gtttgcaaag gaggccatga ggatatgcac ctgtctctgt gagcagaggg acaactttaa    32280
atagactggg aggcagattt gtcctgagtg gtttccagct tgacggggcc caagatattt    32340
tcctttcaca atctggtaac ttcaaacaaa acttcaaagc cacaacaaaa caacacaaca    32400
acaaaaagaa taagacatgg gtacttatta agagtagaaa aacattcagt ccccaaggaa    32460
aatattggca gtgtctacct ccacatgaca aaggagtaag cagtgtgagc cacagaaagg    32520
agcactatta acccacagag caaccgagaa taacacgggt gatgcgaggg cattggacgc    32580
acatcattgc attttgtaga ttcagaaaga acggaaaag attgacggtg gtaaaagaga    32640
cagccctgct tccctctccc ttttccctcc ccgatgaggc ctcacagcca tgaccctcag    32700
cctcatcccg cagtgcagca gctgccgtcc tgtccaggcc cacccctgc cccgccctgg    32760 gactgttacc tcattccctc ccggagtcca ggtgccccc ggggtgtggt gcgggagcct     32820
ggggaggccc tttgttctct gtcagggtct ccctgggagg gacgcagcca ccgcagctgg    32880
ttggggcctg gcttcgccca ggacagtcct ttcctttccc attgtctttg gatgactatc    32940
gctgggctgg gacatgaggc gggcagaggc gcggtcacc cttaggaccc ccctcttgct     33000
gctggggctc tgggcgctcc tggctccggt ccggtgttct caaggccgtc ccttgtggca    33060
ctatgcctcc tccgaggtgg tgattcccag gaaggagaca caccatagca aaggccttca    33120
gtttcccggc tggctgtcct acagcctgtg ttttggggtc aaagacacgt cattcacatg    33180
cggaggaaac accttctttg gcctagacat ctgctggtga caactcagga tgaccaagga    33240
gtcttgcaga tgggtgaccc ctacatccct ccagactgct agtacctcgg ctacctggag    33300
gaggtgcctc tgtccatggt caccgtcgac acgtgctatg gggacctcag aggcatcatg    33360
aggctggacg accttgcgta cgaaatcaaa cccctccagg attcccgcag gtttgaacat    33420
gttgtttttc agatagtggc cgagcccaac gcaacagggc ccacatttag agatgatgac    33480
aatgagacag accccctgtt ctctgaagca aatgacagca tgaatcccag gatatctaat    33540
```

```
tcgctgtata gttctcatag aggcaatata aaaggccacg ttcaatgttc caattcatat    33600
tatcgcatat atggcaatat tacaacttgt tccaaagagg tggtccagat gttcagtctc    33660
attgacagca ttgctcaaaa tattgatctg cggtactata tttatctttt gaccatatat    33720
aataatcgtg acccagcccc tgtgaatgaa tatcgaattc agagtgcaat gtttacctat    33780
tttaaaacaa cttttttttga tacttttcat gttcattcat ccacactact tattaaatac    33840
gtgccacatg aatctaacta tgaacctgaa aggtataact tctgttcccg tatagccctg    33900
ttacacattg gtactccagg cagacattat ttattggtag ccgtcataat aacccagaca    33960
cagatgagaa gtattggtct ggagtatgat gataactact gcacatgtca gagaagggcc    34020
tcctgcatta tgcagcgatt tcctgggatg acagatgcgt tcagtaactg ttcttatgga    34080
catgcacaaa attgttttat acattcaggc cggtgtgttt ttgaaacact tgctcctgtg    34140
tataacgaaa ccatgacaac ggttcgctgt ggaaacctca tagtggaggg gagggaggaa    34200
tgtgactgtg gctccttcaa gcagtgttat gccagttatt gctgccaaag tgactgtcac    34260
ttaacaccgg ggagcatctg ccatatagga gagtgctgta caaactgcag cttctcccca    34320
ccagggactc tctgcagacc tatccaaaat atatgtgacc ttccagagta ctgtcacggg    34380
accaccgtga catgtcccgc aaacgtttat atgcaagatg aaccccgtg cactgaagaa    34440 ggctactgct atcgtgggaa ctgcactgat cgcaatgtgc tctgcaaggc gatctttggt    34500
gtcagtgctg aggatgctcc cgaggtctgc tatgacataa atcttgaaag ctaccgattt    34560
ggacattgta ttagacaaca aacatatctc agctaccagg cttgtgcagg aatagataag    34620
ttttgtggaa gactgcagtg taccaatgtg acccatcttc cccggctgca ggaacgtgtt    34680
tcattccatc actcagtgag aggagggttt cagtgttttg gactggatga acaccatgca    34740
acagacacga ctgatgttgg gcgtgtgata gatggcactc cttgtgttca tggaaacttc    34800
tgtaataaca cccagtgcaa tgtgactatc acttcactgg gctacaactg ccaccctcag    34860
aagtgcggtc atagaggagt ctgcaacaac agaaggaact gccattgcca tataggctgg    34920
gatcctccac tgtgcctaag aagaggtgct ggtgggagtg tcaacagcgg gccacctcca    34980
aaaagaacac gttccgtcaa acaaagccag caatcagtga tgtatctgag agtggtcttt    35040 ggtcgtatttt acgccttcat aattgcactg ctctttggga cagccaaaaa tgtgcgaact    35100
atcaggacca ccaccgttaa ggaagggaca gttactaacc ctgaataaca ctaattcagc    35160
ctcccgatcc ctgtaaagat acagagaata taacagcaaa atctatgaaa caggatcagg    35220
ggaagggatg gcaaagctca agtccacatt tcttgaagtc cacaggaagc acagggtcct    35280
gtttcacatc acagggaaac gggaggcatt ggcttctgtc ccaggttctt gtaggtcgct    35340
gatgctcact ctgaaataaa tcttcaaaaa cacacattgg tgccttccac attttcttag    35400
actcctctgg gagcccaaac ttggccagaa cctcttgcct ggagagacat gaatgagcat    35460
ctggctcttg tcctgaggtc tctggtccca gaattaacgg aagttgccac cagctcctta    35520
cagggaacat tcatgacatt tctccagaag agagctccag agcaatgagc ttcctcattc    35580
cccaggtaat ctgtccttct ctaaacccga agtcagttta gggtgatcca gggctactcc    35640
ctgttccctg tctgttcctc acgggggtgc tgtgggcttt gcagtgagag ggacttgggt    35700
tcaaatcccc caccaagcaa atcccctac ctggggccga gcttcccgta tgtgggaaaa    35760
tgaatccctg aggtcgattg ctgcatgcaa tgaaattcaa ctagaaaat aggtagacgt    35820 gagggcaag ctgtctgtca tttagtgtga gctctgtgag tggcagctgc ccccttcctt    35880
```

```
cctgccccca catttccttg aactgaaaca ggaagggaag ctgagtaagt cgtgatgagg    35940
aagagaaacc aggcttgtag cagcacaggc tggtccgggt ggaaaacagg gctaggtgta    36000
tcactgagtt attgtaaagg aaaatggaag ttaaatgtat aaataactga atgagataac    36060
attttatttt aacttaaaat tcacactaat attgactttt aaaatgcagt gtagatatgt    36120
cagagagaat ttcaaaggca agcccaccg acggaagaaa tcaccctccc cataccatcc     36180
acagaaaact gttggtattc tagggtagta ctgagatcta gcattttcct gaatacatct    36240
gtggttctag atgtcctgct tccatagata ttgtttagaa ttcccacccc tttctccaaa    36300
cacagcttga tatcctttct ctgaacctgt tagaaatttc ctccattcag ctgtcataaa    36360
gatgcgagca atccattcct gtgcctctgt cagtgtgttc tattattttg tggctgaacg    36420
ctaatggaca gttaagtgtg aggtcagtga atacagtgcc ctccctctat gtgtccttcg    36480
ggtgtgaggg gttttgctga tagagcagca ggccccatcc caccctttat gcatctccgc    36540
cccccacctc acgctccagc tgacctctcc cctgtggcct ggggcgttcc ccaggggaa     36600 tgacctctcc tctctccagg gcccacccac tcagtgcccg tgcaagacca ccacgcttgg    36660
cacggcccca cctcgtgtca gggcctgtgt cccctgcccc acccctaaa cagatgggaa     36720 ccactgggac tctgctcagg gcaggggcg gaggtatgtg tgaaaggaag gcaaatgtgc     36780
actctgttgg agaaatatta taggtagttt gagcaaaaaa tctaatgcca tgggaacttt    36840
tagaatgata cgtattttaa caagaacat gaccaataga gtttgtattg aagccaggaa     36900
aacactattt agagcaacag caatatcaaa aacacaagcc aacagttcac caagaaaaac    36960
caccattaac cccatggaaa tggtcttcca agagcatcgg cacttaaatc ctggaaatct    37020
gcctgcctca gcacctgttg tcctgacctg ccctcctgtg tgtcctaatc actcccaaac    37080
acggggcctg cactgtggga gattcacact gtgccaggtg gagggagcag acaactgct    37140 aacaggttgt tggtgtggat gccgaggcca cccaagcagg tgtaaactcc cacctgtggg    37200
gcagggaaga gtgcacggga gacatgtccc gggcataggg tgaggagag ctgtgggggc    37260 tctgggttct gaagtgggtt ctgaagaggg ttctggcctg gcagggataa gaccaaccag   37320
catgtgaggc caggctggag tctggacctc tgaagctgca agggtcatgg gctgcttggc   37380
cccaggggct gtcctggttc tctatggagt actttcaaac attctttctt cttccaatcc   37440
ccctccttct ctcccaaagc ctgcatctcc caaatcctct ttgtcggatc ctcggcttca   37500
ctctgcatcc gtcctgagca tcgatcttcc aattccatcc tcttctcttc tgctatgtct   37560
aagctgctgt gaagccacct gctgtaattt actgctttat atttaatatt gtaccgtaca   37620
tctgttctgt ttccctcatc ataaatgctt catttcatgc tcagcatctg agaacacaag   37680
gccttgtcag ctgtcacctc cttccgttct ctgtttcctt cctcctatcc ccatattgct   37740
catcatgtcc agtctcctgc catcctgaat gcttctgatg gaaggtctga gatgtctcat   37800
gagcactgtg aagattcttt gtaatgtgag cttgttccag gcaggaattc tccttcaccc   37860
agccctggaa gccaagtata ggcagatggc catgctcaat caaagactga gctaacttaa   37920
cagtggcttt ggttttaagg tttctccaat ccccagggca caggatttca gggaattcag   37980
gtgagagtct gggtgttacc cttcaggagg ctgtaaactc catttcacct agtctacacc   38040
acagactatg gaaactatat atatatatag ttctgtccct ctagagaaac ctaatatgta   38100
tatatacaat atataatacg tattatatat tatatataat acgtattata tattatatat   38160
attatatata tattagagtt tattgaggag tattaaactc acaatcacaa ggtcccacag   38220
taggccatct gcaagctgag gagcaaggaa gccagtccga gtcccaaagc tgaagaattt   38280
```

```
gaagtctgat gttcgacggc aggaagcatc cagcacagga gaaagatgta ggctgggagg    38340
ctaagccagt ctagtctttt cacgttttc tgcctgcttt atatcctggc cacactggca    38400
gctgattaga tggtgcccac ctagattaag ggtgggtctg cctttcccag tttactggct    38460
caaatgttaa tctcctttgg caacaccctc acagacacac ccaggatcaa tactttgcat    38520
gcttcaatcc aatcaagttg acactcagta tcaaccatca caagtccacc ccttgtcaac    38580
ttgaacccat acaaatctcc tgagatcata cataatcttc aaataaagac aataataagg    38640
tcataattac acctaatgta atacaactat cttttgtaca accagaaatg caccaatccc    38700
caacccaaat gctattatgt aaagttaaga acacttaaat gctgatatga agtcaataaa    38760 tttatgtca catgataaag gaaaaagaa atgaaggaat tttcttagta caagtgtgta    38820
catgcacaaa catgttttta acaaagaag aggaaatac tgatgacaat acagtcctc    38880 atttctgcaa ctgatcacgt ggttgtagct ggtattgatg actaccttct tctactaccc    38940
attctgtatt ccctttgcct tcagcaagca tcacagcagg tagagttttt tctcctagtg    39000
gagtgatgca aaccttcatt cctgaagggt ctgggccatt tgtagtcctg cctggattgg    39060
gctgttgtag tttcccgttg accttaatga cagggcatgg taatgttaag agacgcccta    39120
atggatctcc tgtattccat acatattctt ccttacctcc attgtggagt aatagactga    39180
ttgcatcttg atagtccagg tcaatcagcc cagccaacac tgtaactccc ctcttagcct    39240
gtggacttaa aggtaggagg ggcccaaagt ggccaggtgg aaatctttac ttccagttta    39300
atggaattgt tgttgtttct cctgatggca gcattattcc cactggaact aagacctcta    39360
ggccaacaga atgtaatgtc atgggaccag gaagcaaaaa ttttgctagt ggatcactag    39420
gggtgatggt gaatggtgcc atttccactt ccaccccttg attcctggat ccatgaatta    39480
tggctatggg agaaagagta ccatatattg gatgctgatt tggagcatac atggccttt    39540 ggagagcttt gccccagccc tgcaaagtat tggagcctag ttgacattgt aattgtgact    39600
ttgaaaggcc attccattct tctatcaatc cagctgcttc aggatgatgg ggaaaatggt    39660
aagacaagtg aatcccatga gcatgagccc actgccacac ttctttagcc gtaaagggag    39720
tgccttggtc agaggcaatg ctatgtggaa tactgtgaca gtggataagg cattccatga    39780
ctccacagat ggtagtcttg gcagaagcat tgcatgcata tctgcagtaa gtgtctattt    39840
cagtgaggac aaacctctgc cctttccagg atggaagagg tccaatataa tccaacctgc    39900
catcaggtag ctcactgatc accctgagga atggtgtcat ttgggtagag acccagagcc    39960
aaaccagatc acgccaccca acccctccca aatctcatgt cctctttgca tttcaaaacc    40020
aatcatgcct tcccaacagt cccccaacat cttaactcat ttcagtatta actcaaaagt    40080
ccaaatccaa agtcacattg gagacaaggc aagtcccttt catctatgaa cctgtaaaat    40140 gaaaacaag tcagttactt ccaagacaaa atgggggtac aggcattaga tacatgctcc    40200
catttcagtt gggagaaatg agccagaata aaggggcttc aggtcacatg caagcccaaa    40260
ctccagtggg gcagtcatta aatcttaaag cttcaaaata atctcctttg actccattcc    40320
tcacattcag gcatgctta tgcaaagtgg gggctcctac aaccttggga agctctcacc    40380
ctgtggcttt gcagctctga ccccatggct gctctcatgg gctttgcaga gttcagccct    40440
cctggctgct ctcattgagt gcatgcagct tttccaggtg cacagtgcaa gccgttaatg    40500
gatctaccat tctgggggtct gaaagatggt ggccctcttc tcacagcccc attagtcact    40560
gtctccagtg gggactctgt gtggggggctc caaccccaca tttcccttct gcactgccct    40620
```

```
agcagaggct ctccatgaag gctttgcccc tggcgcagac ttctggctgg acatccagtc   40680
atttctataa atcctctgag atctgggtgg aggatcacaa agctgaactc ttctcttccg   40740
cacatcccta ggcccaacat catgtagaag ccaccaatga ttggggcttt ctgaagcaat   40800
ggcctgagct gtacattgga cttttttagc cacagctaga cctggagcag ctgggacaca   40860
gggcaccaag tcccaaggct ccaaagagaa gctgggccct ggacccagcc catgaaaaca   40920
tttttccctg ataggcctcc aggcctgtga ttggaagggc tgctgcaaag atctccgaca   40980
tgccctggaa acattttccc cattgtcttg attattaata ttcatctctt cattacttat   41040
gcaaatttct gcagccaact tgaatttctc cctagcaaat gtgttttttct ttactaccac   41100
atggccaggc tgcaaatttt ccaaactttt atgctctgtt tccctttaa aaataagttc   41160
ctatttcaga tcatctctct caagggcaaa gttccacaga tttctagggc agggacaaaa   41220
ttccatcaag cttggtttta tacattttag agaggcatga gacatcaatc aaatacattt   41280
aagagacaca ttggtttggt ccagaaaggt ggaacaactc aaagctaggg cttccaggct   41340
ataggtgaat ttaaatattt tctggttgac aattggttga gtttgtctaa agacctggga   41400
tagatagaaa ggtaatgttc aggttaagat aaagattgta gagtccaaag ttcttttgaa   41460
gtcttatagt ggctgcccctt agagataata ggtgacaaat gtttcctatt caaatcttag   41520
ttgaactctt taggattggg aggttctaga agaaaaagat ctagctatgt taatagagat   41580
tctttacaga tgcaaatttt ccccacaaa gaacagcttt gcagggccct ttcttttcttt   41640
ctttctttct ttcttttcttt cttttcttctt ttctttcttt cttttcttct tttttagatg   41700
gagttttgct cttgttgccc aggctagagt ataatggcac gatcttgtct caccacaacc   41760
tccacctcct gggttcaagt aattctcctg cctcagtctc ccgagtagct atgattacag   41820
gcatgcacca ccacacccgg ctaattctgt attttttagta gacacagggt ttctccatgt   41880
tggtgaggct ggtctcgaac tcccaacctc aggtgatccg cccacctcag cctcccaaag   41940
tgctgggatt acaggcatga gccaccatgc ccggcctgca gggccatctc agagtatggc   42000
aaagaaacat gttttggggt aaaatatttt gatttcttta tttgtctcat aatgttatgc   42060
cagagtcagt ttgaaagta aatcatgata tataggttta aataaaaccc atctgatgag   42120
aatttatgat ttgtagagca tgcctcccca gactctttag ataggaattt gggcaagatg   42180
aaaaaaaaat cagagtttag tcctcactac ctaagaccag ctcagcttgg acttcactgt   42240
tcatgtcact atcagcattt tagtcaaaac cactcaataa gtctctagga agttccaaac   42300
tttcccacat cttcccttct cctttcaagt tctccaaact gttccaaccg ctgccaggag   42360
gtacccagtt ccaaagttgc ttccagattt tgagttatct ttatagcagt tccccactcc   42420
tggtaccaat ttactatatt agtctgtttc cacagtgcta taagaactg cccgaaagtg   42480
gttaatttgt aaagaaaaga ggtttaattg actcacagtg ctgtgtggtt agggtcggag   42540
gctcaggaaa cttgcaatca tggtggaagt ggaagcaggc atgtgacaca tggcagcagg   42600
tgagagagag aaagagagag agagggaatg aaggaggaac caccatacat ggataaaacc   42660
atcagatctc atgagaactc actcactatc aggagaacat gaggacagca tgggggaaac   42720
caccccctatg acccagtcac ctcccaccag gtccaccccct tgacacataa ggattactat   42780
ttgagatgag atttgtttaa tgcacacagag ccaaaccaca tcagcatgtg acaaaggtct   42840
aatatcaaga atctatgagg gggcagttcc aaaatggctg aataggaaca gctccagtct   42900
acagctccca gcatgagcta cacagaagac aggtgatttc tgcatttcca actgaggtac   42960
tgggttcatc tcacgggggc ttgttggaca gtgggggcag gacagtgggt gcagcccacc   43020
```

```
aagagtgagc tgaagcaggg cgaggcattg cctaacccag gaagtgcaag gggtcaggga   43080
attcccgttc ctagccaagg gaagcggtga tggacggcac ctggaaaatc cggtcactcc   43140
caccctaata ctgcactttt ccaacggtct tagcaaatgg cacaccagga gattatatcc   43200
tatgcctggc ttggaggttc ccatgccac ggaacctcgc ttattgctag cacagcagtc    43260
tgagatcaaa ctgcaaggtg gcagtgaggc tgggggaggg gtgcccacaa ttgctgaggc   43320
ttgagtaagt aaacaaagtg gctgggaagc tcaaactggg tggagtccac tgcagctcaa   43380
ggagacctgt ctgcctctgt agactccacc tctgggggca gggcatagct gaacaaaagg   43440
cagcagaaac ctctgcagac ttaaatgtcc ctgtctgaca gctttgaaga gagtagtgtt   43500
tctcccacat ggactttgag atctgagaat ggacagactg cctcctcaag tgggtccctg   43560
acccccgagt agcctaactg ggaggcaccc tccagtaggg gcagactgac accttacacg   43620
gctgggtgcc cctctgagat gaagcttcca gaggaattat caggcagcaa catttgctgt   43680
tcagcaatat tcgctgttct gcagcctctg ctgctgatac ccaggaaaat agggtctgca   43740
gtagacctcc agcaaactcc aacagacctg cagctgaggg tcctgactgt cagaaggaaa   43800
actaacaaac agaaaggaca tccacatgaa aaccccatct gtacatcacc attatcaaag   43860
acaaaaggta gataaaacca caaagatggg gaaaaaacag ggcagaaaag ctgaaaattc   43920
taaaaatcaa agtgcctctc cccctccaaa ggaatgcagc tcctcgccag caatggaaca   43980
aagctggatg gagaatgact ttgatgagtt gagagaaggt ttcagatgat caaacttctc   44040
cgagctaaag gaggaagttg gaacccattg caaagaagct aaaaaccttg aaaaaagatc   44100
agatgagtag ctaactagaa taatcagtgt agagaagtcc ttaaatgacc tgatggagct   44160
gaaaaccatg gtatgagaac tacgtgatga atgcacaagc ttcagtagcc gattcgatca   44220
actggaagaa agggtatcag tgattgaaga tcaaatgaaa gaaatgaagg gagaagagaa   44280
gtttagagga aaaaaagta aaagaaaga aacaaaccct ccaagaaata tcagactatg    44340
tgaaaagacc aaatctatgt ctgattggtg cacctgaaag tgacagggag aatggaacca   44400
agttggaaaa caccctgcag tatattatcc agcagaactt ccccaaccta gcaagacagg   44460
ccaacattca aattcaggaa atacagagaa ccccacaaag atactcctcg agaagagcaa   44520
ctccaagaca cataattgtt agattcacca aagttgaaat gaaggaaaaa atattaaggg   44580
cagccagaga gaaaggtcgg gttaccctca aagggaagcc catcgacta acagctgatc    44640 tctcagcaga aactctacaa gccagaagag agtgggggcc aatattcaac attcttaaag   44700
aaaagaaatt tcaacccaga atttcatatc catccaaact aagcttcata agtgaaggag   44760
aaataaaatc ctttacagac aaacaaatgc tgatagattt tgtcatcacc aggcctgccc   44820
tacaggagct cctgaaggaa gcactaaaca tggaaaggaa caactggtac cagccactgc   44880
aaaaacatgc caaatcataa agaccaccaa agcgaggaag aaactgcatc aactaacgag   44940
ccaaataacc agctaacatc ataatgacag gatcaaattc acacataaca atattaacct   45000
ttaatgtaaa tgggctaaat gctccaatta aaagacacag actggcaaat tggataaaga   45060
gtcaagaccc atcagtgtgc tgtattcagg agacccatct cacatgcaga gacacacata   45120
ggctcaaaat aaaggcatgg aggaagatct accaagcaac tggaaaacaa aaaaaggcag   45180
gagttgcaat cctagtctct gataaaagag actttaaacc aacaaagatc aaaagagacg   45240
aagaagacca ttcataatg gtaaagggat caattcaaca agaagagcta actatcctaa    45300
atatatatgc atccaataca ggagcaccca gattcataaa gcaagtcctt ggagacctac   45360
```

```
aaagagactt agattcccac acaataataa tgggagactt aacacccca ctgtcaacat    45420 tagacagatc aacgagacag aaagttaata aggatatcca gcaactgaac tcggctctgc    45480
accaagcaga cctaatagac atctacagaa ctctccaccc caaatcaaca gaatatacat    45540
tcttttcagc accacaccac acctattcca aaattgacca catagatgga agtaaagcac    45600
tcctcagcaa atgtaaaaga acagaaatta aacaaactg tctctcagag cacagtgcaa    45660
tcaaactaga actcaggatt aagaaactca ctcaaaacca ctcaactaca tggaaactga    45720
acaacctgct cctgaatgac tactgggtac ataatgaaac gaaggcagaa ataaagatgt    45780
tctttgaaac cagtgagaac aaagacacaa cataccagaa tctctgggac acattcaaag    45840
cagagtgtag agggaaattt atagcactaa atgcccacaa gagaaagcag gaaaaatcta    45900
aaattgacac cctaacatca caattaaaag agctagagaa gcaagtgcaa acacattcaa    45960
aagccagcag aaggcaagac ataactaaga tcagagcaga actgaaggaa acagagacac    46020 aaaaaaccc ttcaaaaaat caatgaatcc aggagctggt ttttgaaaa gatcaacaaa    46080 attgatagac cactagcaag actaataaag aagaaaagag agaagaatca aatagatgca    46140
ataaaaaatg ataaagggga tatcaccacc gatcccacag aaatacaaac taccatcaga    46200
gaatactata aacacctcta cggaaataaa ctagaaaatc tagaagaaat ggataaattt    46260
ctcgacacat acaccatccc aagactaaac caggaagaag ttgaatctct gaatagacca    46320
ataacaggct ctgaaattga ggcaataatt aatagcttaa caaccaaaaa aagtccagga    46380
acagatggat tcacagccga attctaccag agctacaagg aggagctggt accattcctt    46440
ctgaaactat tccaatctat agaaaagag ggaatcctcc ctaactcatt ttatgaggcc    46500
agcatcatcc taataccaaa gcctggcaga gacacaacaa aaaaaagag aattttaggc    46560 caataaccct gatgaacatc aatgcaaaaa tcctcaataa aatactggca aaccgaatcc    46620
agcagcacat caaaaagctt atccaccatg atcaagtggg cttcatccct gggatgcaag    46680
tctggttcaa catacgcaaa tcaataaacg taatccagca tataaacaga accaacgaca    46740 aaaacacat gattatctca atagatgcag aaaaggcctt tgacaaaatt caacaacact    46800
tcatgctaaa aactctcaat aaattagata ttgatgggac gtatctcaaa ataataagag    46860
ctatctatga caaacccaca gccaatatca tactgaatgg gcaaaaacta caagcattcc    46920
ctttgaaagc tggcacaaga cagagacacc ctctctcacc actccattc aacatagtgt    46980 tggaagttct ggccagggca atcaggcagg agaaggaaat aaagggtatt caattaggaa    47040
aagaggaagt caaattgtcg ctgtttgcag atgacatgat tgtatatcta gaaaccccca    47100
tcgtctcagc ccaaaatctc cttaagctga taagcaactt cagcaaagtc tcaagataca    47160
aaatcaatgt gcaaaaatca cacgcattc tataacccaa taacagacaa acagagagcc    47220
aaatcatgag tgaactccca ttcacaattg cttcaaagag aataaaatac cttggaatcc    47280
aacttacaag ggacgtgaag gacctcttca aggagaacta caaaccactg ctcaatgaaa    47340
taaaagagga tacaaacaaa tggaaaaaca ttccatgctc atgggtagga aggatcaata    47400
tcctgaaaat ggccatactg cccaaggtaa tttatagatt caatgacatc cccatcaagc    47460
taccaatgac tttcttcaca gaattgggaa aaactgcttt aaagttcata tggaaccaaa    47520
aaagagcctg caatgtcaag tcaatcctaa gccaaaagaa caaagctgga ggcatcacgc    47580
tacctgactt caaactatac tacgaggtta cagtaaccaa aacagcatgg tactggtacc    47640
aaaacagaga tacagaccaa tggaacagaa cagagccctc agaaataatg ccgcatatct    47700
acaactatct gattttggc aaacctgaca aaaacaagaa atgggaaaac gattccctat    47760
```

```
ttaataaatg gtgctgggaa aactggctag ccatatgtag aaagctgaaa ctggatccct    47820
tccttacaca ttatacaaaa attaattcaa gaggattaaa gacttaaatg ttagacctaa    47880
aaccataaaa accctagaag aaaacctagg caataccatt caggacatag gcatgggcaa    47940
ggacttcatg tctaaaacac caaaagcaat gacaacaaaa gccaaaattg acaaatggga    48000
tctaattaaa ctaaagagct tctgcacagc aaaagaaact accatcagag taaacaggca    48060
acctacagaa tggagaaaaa tttttgcaat ctacttatct gacaaagggc taatatccag    48120
aatctacaat gaactcaaac aaatttacaa gaaaaacaaa caaccccatc aaaaagtggg    48180
caaaggatat gaatagacac ttctcaaaag aagacattta tggagccaaa agacacatga    48240
aaaaatgctc atcatcacta gccatcagag aaatgcaaat caaaaccaca atgagatacc    48300
atctcacacc agttagaacg gcgatcatta aaaagtcagg aaacaacagg tgctggagag    48360
gatgtggaga aataggaaca cttttacact gttggtggga ctgtaaacta gttcaaccat    48420
tgtggaagtc agtgtggcga ttcctcaggg atctagaact agaaatacca tttgacccag    48480
ccatcccatt actgggtata tacccaaagg attataaaac atgctgctat aaagacacat    48540
gcacacgtat gtttattgcg gcactattca caatagcaaa gacttggaac caacccatat    48600
gtccaacaat gatagactgg attaagaaaa tgtggcacat atacaccatg gaatactctg    48660
cagccataaa aaaggatgag ttcatgtcct ttgtagggac atggatgaag ctggaaacca    48720
tcattctcag caaactatca caaggacaaa aagacaaaca ctgcatgttc tcattcatag    48780
gtgggaattg aacaatgaga acacttggac acaggaaggg gaacatcaca caccagggcc    48840
tgttgtgggg tgggggagt ggggagggat agcattagga gatataccta atgttaattg    48900
atgagtttat gggtgcagca caccaacatg gcacatatat acatatgtaa caaacctgca    48960
cgttgtgcac atgtacccta aaacttaaag tataataaaa aaattttttaa aaaaagaaac    49020 acctgctttt ttctgttttc catttgctta gtagattttt ctccatcctt ttactttgag    49080
cctggggatg tcattgcatg tgagatgggt ctcttgaaga cagcatacat ttgggtcttg    49140
cttctttctc caacttggca attctctgcc ctttaattgg ggcatttagc ccatttacat    49200
tcaaggttaa tattgatatg tgcatatttc atcctgttat catgttgtta gctgctcaat    49260
atgcagattt gattgtatag ttgatttata gtggcaatcg ttatgtactt aagtgtgttt    49320
ttgtggtggc cagtaacgtt cttccattat catatttagc aatcccttaa gggcctcttg    49380
taaggcaatc tagtggtgat gaatacccctt agcatttgct tgtctgaaaa ggatcttatt    49440
tctccttcac ttgtgaagct tcatttggct agatatgaaa ttcttgcttg gaatttcttt    49500 tcttttaagaa tgctgaatat aggcccccaa tctcttctgg attgtacagt ttctgctgaa    49560
acctccattg ttagcctcat tgggttccct ttgtatgtga cctgaacctt ctttctagct    49620
gcctctaata tttttttttcc tttcaacctt taagagtctg atgtctgatg gctatatgtc    49680
ttagggatgg ttgtcatgta taatatcatg cagaggttat ttgcatttct tgaatttgaa    49740
tgttggcctc tctggtgagg ttggagaaat tttcatggag gatagcctga aatgttttttc    49800 aagtttcttt ttttctcttt ctcttcttaa gggataccaa tgtgtcatag atctggtctt    49860
tttacataat tgcacatttc tctgaggttt tatgccttct tttttattct tgttctttta    49920
tttttgtctg actgagttaa ttcagagaat cagttttttaa gctctgtgat tctttcctca    49980
gcttggtcta ttctgctgtt aatacttgta attgtattct gaaattcttg aagtgagttt    50040
tttagctcta tcaaatcagt ttggttcttt cttaaaatgg ccatttcatc tttcagcttc    50100
```

```
tgtatcattt tactttattt cttagctccc ttggattggg tttcaacatt ctcctgaatc    50160
tcagtgatct tctttcctgt gcatattctg aattctatgt ctgtcatttc agccatttca    50220
gtcaggttaa gaaccattgc tgggaaacca gtgtgattat ttggaggtaa gaagacactc    50280 tggatttttag agttgcagag tttcttgcat taattctttc tcatctttgt gggctgtttc    50340 tttaatctttt gaagtggctg tcctttggat gttttttgtct tttttgttgt ttttggtgt    50400 gtgttttttgt ttgtttgttc atttgtttgt ttttgctct tatcttcttt gatactcttg    50460
caggtttgat tgtggtataa agtggattca gttagctgtg tttcttgaaa atcttagagg    50520
gtccaggctc acctcagcac tcttgtggtg tgttctctgc tctgggactg ggcccctggc    50580
tttattctct ggcccttga gtttagaaac ttgctgcatt ggaggggctg aggtgttccc    50640
agtccattgg ccacaacact atagtagggg gtgccggcca aagcacttca ttagagtggt    50700
ggcagtggga tccattctta ctcatgggtg ccagcagttg tggagtcatg gcagggtgca    50760
catgcatctg ctggggtggg ggtactggca ggagcagagt ggcagcatcc ctacataggt    50820
tcctgctggc agtcacagcg cagtgaggtg cccgtgtgtt ggcagggaca gggtggtggg    50880
gcacacatgc acatgcttgc tggtggtaga gggagttgtg atctgctgtg cactcatgcc    50940
agcaaagcag ttgggaggta ctatgggtgg actggtgcac atcagcagag gctggcctgc    51000
tggaggtctc caatggttag gcatggtctg ctggcaaagg agctatgatg agggccccca    51060
ggaaacaccc tggttgggct tccaaggctg tactgcaagc aggcacagcc agcctggggc    51120
cccaggagag gccagaaggc aaggaaattc tcatttcaga tgggccctgt cccatggaca    51180
agaccaccct gctttattca ggtcccatag tcactctaag gttaaaatct cctagaggag    51240
gttggtgagc cttgggggat gggtgtcccc tggctgtgct ccactacagc cattctcatg    51300
tcaaacactc tgggctttac acagactgga gtcctgcccc tggcatctct ctaagcagct    51360
gtcccttcca gcacaagtgt ccatgggggt catgggtgtct cctgctgcta ggattctgga    51420
ggcccatggc aacagcaggc cactcctcac ctgttcaact caacctttcc ccaggagttg    51480
ctgggagcca ggaatgagtc ctggtgcttg gcatccccat gcagggttcc catcttcctc    51540 cacctcagc tcagcatctg tgtcctcccc cgtctactct caatccactc tcaatgcctc    51600
cccttcaaag atctgcttgg aaagcacccg tcttcctgat gtctcactcc ctccatggca    51660
gatattcctc ctggctgcat ctagtcagcc atcttgactc gcctccaaag tcttttaat    51720 taccacttcg gttaaattag taactatcat tttacaatgg cctgtgattc tgttttgatc    51780
aaatattttg agcctttag catctataac aaatgttctc aaaaatcaaa atcctaaatc    51840
aagtctctgc cttagtctta tttctgggc ttattaaggc tataaaaatt aatcaccata    51900
aggttgtaca agcttttttac agcttccagt caggctatga actccagtat caccacctcc    51960
agcctgataa ttacatatat tggaagaaaa tcagttaaag gactccctct agacccttga    52020
aagggtgtga gagacaacat ggtttcgcct gccttcatgt gtcccagtcc atccctgtgg    52080
ctgcctctgt ccacctcagc ttgcccactg tctttccttc ccaactgtct gccctgctga    52140
cttctggcct cagtgacaga tgcaaagaca aggcgacagc cccacataga ccgtttaacc    52200
agtcccacat ttgcataagc taaatggtca tgtcacagtc tgttgcccag gctggtctca    52260
aactcctggg ctcaagtgat ccacccacct tgaccccaa ggtgctggga ttacaggctt    52320
gagccacagt gcccagccaa gaacccgttt tgagtgggc accttggcac acacctgtaa    52380
acgcaacact ttgggaggcc aaggtgggag tgtggcttga ggccaggagg ttgaggttgc    52440
agtgagctat gatggcacca cctcactcca gcgtgggtgg cagagtgaga tcctttagaa    52500
```

```
aaaaaaaaaa aaaaaacttg ttttctctgc agccgggctc cgtgaccaaa cacaaacaca   52560 aacttccoct ccagagggtc caggaggggc tgggctgcag gaggtgctta gggcctctta   52620
gggaatggta agtgaccacc caacgcaggc actcagcccc aggggcatat gcagagagag   52680
ggtccaggag gagctgggct gcaggaggtg cttagggcct cttagggaat ggtaagtgac   52740
cacccaacgc aggcactcag ccccaggggc atatgcagag agagggtcca ggaggagctg   52800
ggctgcagga ggtgattagg gcctcttagg gaatggtaag tgaccatcca acgcaggcac   52860
tcagccccag gggcatatgc agagagaggc tgggaggaca ctttcagtga ctgggttac    52920 aaaccccaac cataagacat tgctggctct gtgagccgcc acctccagaa atctcccact   52980
tagttcttag cacttatcca ctcttccctt ttcctactct caattcctgg aggatgccct   53040
cctttctcag gctcagacca acctaccagc tccactctag acctgaacac atgactcctc   53100
cctctgtctc cacctggaaa tctcatcagt gcctcacatt tacactcctg aaaatcaggt   53160
cctgcctacc caccctcttg ctccacctga ttcctgccct gtttcagcca gagaccttgc   53220
agtctccttt aactctcaaa cccacccatg tcgtgtgagc atactgactg tgttctatgc   53280
aagaaagagc agtttcttgg tggtcctgcg gttttattag tccagaggca aagcgttggc   53340
agagctggtt tcttctgaac cctggggaggg agattctgtt ttcatgcctt ttccagattc   53400
tagaacccat attccttgct ctgtgtcccc ttcttccatc ttcaaaggcc atcctctcat   53460
ctctgtgtcc atcatcacat caccttcccc ctgactctgg ttctcctgct tccacttata   53520
agcacccttg tgattacatc atacccaccc agacaatgca gggccatatt ctcccctctc   53580
gagattaatt taatcacatc tacaaagttc ctcgtgccat atgaggtcac taaaccacat   53640
gttctggggg tttgaatgta aacatttggg ggatgcatta ttcagccacc cacaagcact   53700
gctccccact ggccacacac tatgcacagc cgagatcatg caagtgaggc acgttcatca   53760
acagcagctt cagcaggaaa ctatatgctc cactttcctg ccatttgtat ctggattttt   53820
ttttcgctat cattgtagaa agagtggtat tgtaaaatta aagatggatt attttctttc   53880
tagaacactt tggcaatcta tccaacatta tttatcccct tctgagtgtc aagtgtgagg   53940
tcattctttc attgagagct caatgcctac aattatgata atgcatattg ggtactttca   54000
cacatcagaa agttcttctt tcttaaaatc tgttcttgaa ttattcattc ttctctagct   54060
ttttgttgat ctatttata attttagaaa aatcagaaag taacttgaag tatctgtcat   54120
ctctacaggt ttacctccct ctttgtggcc ttcagaatgt catgacacgc ttttcccttg   54180
ctcatcacat ggtttctatg tatgagacct catcacagga gctgtggtcc cccgggagca   54240
ggcatctgtg gatggtgcct tgctcctggc tgctgggacc tgtgtgctgc cagtggcact   54300
ccacgacagt gatttcccag ctcagttttg cagctccaga tggtgggtga gacactagga   54360
ccactttgtg aacagcgagg gcttgggggtt tgcttttcta ccatgtccag ggctgctgtt   54420
catgagggaa tgtttctaac ctgacatcat ggctgaagcc aacttagaac ctctctagcc   54480
gtatggggag taggtgagtg atacagatgt taattagctc agtggagcca ctcccctatg   54540
tagacatgtt acaaaacatt atgctgtaca gaataaatat aggtcatttt tatgtgtcaa   54600 tcaaagaga aactaattat ttaaaaaaaa aaaaaaacc tctctactca agccgaaacc    54660
tcagctccag tcccacaagt cacacaaggc tgctcccgtc ctgtgtatgt taaacctacc   54720
tcagaaatgc aaggggggcat tcaggtttca ttctcaattc aaatgcccctt tttaattttg   54780 tctattccta gcacctggca acttccagct cttttttttcg gggctcattc attatttaaa   54840
```

| | |
|---|---|
| gcacgtataa tttttcaccc acattctaac acatgtagta ctgtagagaa tccttcccta | 54900 |
| ggaggatcta cagcattaga aaagaattaa gaactccaat atttacaaga aggaaaaagc | 54960 |
| aaaaagagat caaaaaatgg gcaacttcta gaaatagaaa accctcatga gtatgatgat | 55020 |
| aaatcgctgg cacacatgtg aatagttact tgatgcttat agtgatgtct gggaaaataa | 55080 |
| catgaaatac ttataatctg tttctcacac atgtaattca aaagaataga gagaagatga | 55140 |
| tttgaaatat tcttaagttt gtaggaaaaa agctacttcc atatgcataa ttgcatgtat | 55200 |
| tttgatactg ccattattaa gaactatcta agagggtcca ttaaaataa aatttcttgg | 55260 |
| ctgggcacag tggctcatgc ctgtatccca gcactttgga aggccgaggc aggtggctca | 55320 |
| cctgaggtca gaagttcaaa accagcctgg ccaacatggt gaaacgctgt atctaccaaa | 55380 |
| aatacaaaaa ttagctgggc atggtggcat gcacctgtag tctgagctac ttgggggggct | 55440 |
| gaggcaggat aatcgtttga acccaagagg tgtaggttgc agtgagctaa gatcatacca | 55500 |
| ccgcactcca gcctgacaga caaagcaaga ctctgtctca aaatattaa aataaaattt | 55560 |
| ctcattccta ttacagagta atttaattca ttaatgccct gccctgttac aaaactcatt | 55620 |
| tgtaaaatac taattgtaat tgtgaaaaaa tggcaattga tactaatttt aaattctaaa | 55680 |
| aacagggcac ccatattaaa gattattctg cagtaagaga attagctata acattttgta | 55740 |
| ataaggtgga gaaacattc tccaacttac aatggttggt gagaagaaag tttccagcac | 55800 |
| ggtagatgga cccctaagagc ccttgttgaa ataataagac aaaaagatat acagagagat | 55860 |
| gagccagatg aagggagaca gagagagaga gagagagaga gagagaggca cagaaatgag | 55920 |
| agatacaaag tgaaagaggg caacctgtgg ggtcatcaga tatttgtttt ctgttttgtt | 55980 |
| tattctaaca taaaggcagt ggtgggtcat cgatgtattt agagtttgca caatcactgt | 56040 |
| ggaacacaga cagacacagg ggaagaggag aaacacaggg cggtggcttg cccttggact | 56100 |
| gttcttagtt cctcaaaacg taacagcttt gcccaaccta agggaacttt cagcagctgc | 56160 |
| tcttctgcca taggcctctt tcctgccttg ttttcatgtg gctgactgtt tctgttcctg | 56220 |
| caggtcttag ctcatcagac aggcatttat tacctctgtg tcaacagtgg gagcttccat | 56280 |
| tactctctag catgacactc cccttcctct tttaggaaat ttaacatgga agtgagtttg | 56340 |
| ccatcggcct tctccccaca gtgttaacag tggtgaggaa gccagcctgt tccaccttgc | 56400 |
| ccctcccatg attccaacac tgagttcaga cttgtcacat ggaacttatc tttgcatgtt | 56460 |
| tgtggcacag acagatggac ccaaccatgg attagtggat ggatggatgg atggatggat | 56520 |
| ggatggatgg atggatggat ggatagatgg atggatggat ggctgagtag gtgtgtggat | 56580 |
| ggaagagtga aaagatagat ggatgcatgt atgggtggat gggtaggttg atggatgcat | 56640 |
| ggatgggtgg atggatgggt gagtggatga atgggtgggt agtgggtgg ctacatgcat | 56700 |
| ggatgagtac ttggatagat aagtgagtgg atggatggat ggatggatga atgggtatgt | 56760 |
| gaagggatgg atgtattaga gtgggtagtt aggcaggcat gagctgatag tcaagtgatt | 56820 |
| gttaaactgc ctctctaaaa taataattgg tctcggctgg acgcggtggc tcatgtctgt | 56880 |
| aatcccaaca ctttgggagg ctgaggtggg cggatcacaa ggtcaagaga ttgagaccat | 56940 |
| cctgaccaac atggtgaaac cctgtcttta ctaaaaatac aaaaattagc tgggcgtggt | 57000 |
| ggcgtgcatc tatagttcca gctactcggg aggctgaggc aggagaattg cttgaacctg | 57060 |
| ggaggaagag gctgcagtga gctgagattg tgccactgca ctccagcctg gtgacagagc | 57120 |
| aaagctctgt ctcaaataat aataataata ataaataata attgatctca gccagcgcca | 57180 |
| agaaaaggca gtctcccaat agatagaaaa caccgaaac tggtcatcag cagcttcctg | 57240 |

```
ataagatctc aggcattggg tgagtgggct caagcatatg cactaagagg caaagtggca   57300
gagtttaact ggcacataat cttcctctag gaacactcta atagtaagag aaggacacct   57360
caaatgagca tgtgcacatt tcattaaacc cactgtgtat gcagcccctc ccaagtgctg   57420
gcaggccact gtacatgtgg gcagcccact ccaaggaagg aatcaaggga gaagaaatac   57480
aaatcccaga accatgtcaa tgtataaaac cccaagtcaa gggccggaca gagcacttag   57540
atctctcaag tcgcccactt agccctcttc caagtgtact ttacttcctt tagttcccac   57600
tttaaaactt taataaacat ttactcctgc tctaaaactt gcttgggtct ctcactcttc   57660
tgtatgcccc ttggccaaat tctttcctcc aaggaggcga gaatcaagtt gctgcagacc   57720
tgtatggatt cgctcctgct aacagatagc tggatgggtg gacagatgca tgaattagtg   57780
gatgacgtt tggatgtgtg ggtgggtggg tggattgtgg gatggctgga tgaatgcatg   57840
gctggatggg tggacagatg catgaattag tggatggatg tttggatgtg tgagtgggtg   57900
ggtggattgt gggatggctg gatgaatgca tggctggatg ggtggacaga tgcatgaatt   57960
cgtggatgga cgtttggatg tgtgggtggg tgggtggatt gtgggatggc tggatgaatg   58020
catggctgga tgggtggaca gatgcatgaa ttcgtggatg gacgtttgga tgtgtgggtg   58080
ggtgggtgga ttgtgggatg gctggatgaa tgcatggctg gatgggtgga cagatgcatg   58140
aattcgtgga tggacgtttg gatgtgtggg tgggtgggtg gattgtggga tggctggatg   58200
aatgcatggc tgggtgggtg gatggatgca tggataagtg gtggacggat ggacgggtga   58260
gtggatgggt ggatgtgtgt gtggatgggt ggataggaaa gccctctaat tgattacagg   58320
gctcagtgtg tgcttcaaca tcatgatggc atcatcacat tggtccctgt atgaagcagt   58380
gggggaggag agtgtaccag gggagcagga atgacttttc tccagaatcg acctctccca   58440
ccctgcagcc tgggctgtgc aggccacatt ggagaaggtg cggtcgacta ctcctaaatg   58500
ttgttgtgtc caatggcttg ttgacgttga tgtaggaatg agcctacatc tccaccatag   58560
atggaactgt ttgggtcccc aaagcagaaa gcctcttctg ttgcaggtgc tgaagtttcc   58620
atcttcttct gcttatacgg aagctcacgc atcccttgga tggcaggcgt caggttcctg   58680
tgcgcactga gttccccct tacatgcttt ggacagaagt gtgagacaca caagattgct   58740
gcaggaagtc cacctgtggg gatgctgcga cttctccagc aagaacacga gtctgctcat   58800
tgaccatcac cacacataac aaattaagtg tcccttttt gataacacgt cattgtttca   58860
cagagtattc tttaaagtg tataagttga ctgcagttat tattttttac ttctgttact   58920
aatttactca taattaggca caatttacac ttaagaaatt tcttaatagt ttttcctcc   58980
ttaaggtgaa ctacagtcag ataacatact tatcaattgt ctctagctct tgtcagaaaa   59040
acatatagat gtgtgtgtgc gtgtgtcttg gcctttccaa tgatgaatta agatgtgcat   59100
tgagaaggca ttcactttat ttgacgttaa ggaagtacca agaagacgct ctccacagac   59160
cctgggaaag ccagcagctg caccccgagg ctgtgccagg cagggaacaa ggaggcagca   59220
ccacctgctg ggcagggaaa atgtcctccc agtccctgcc gcttctctgc agaggcacaa   59280
agagctgccc cttctcctgg gccttctcct gggctgatga gattgctccc cgatatgcca   59340
aatcagggtt gtgcatctga ggctctgtct agactctcag ctccttccta ctcctgcaaa   59400
gtgaagaaaa caatgccaag gggtcctgga ggcgtctcta cccctggaga gttttgactc   59460
tcttcaatag tctccactac cctgcccctca ctccatgtcc tccgtttctc cctaaagcgg   59520
tgcccagtct gattgcactg tggcagggat aacgagggc caggacatca ggggagagaa   59580
```

```
gtttctacct gagtcacagc agcggctgcc ctgcagactc ctgaagacac aagacacatt    59640
tccatcccag agacccagcg aaatgcaacc tcaggctaga gacagccagt tattttttct    59700
tgttctgtcc tggagaggcc actgagaaag tcgagcccct tgttgaggaa aacatgagat    59760
ctctgtgtgt cgtcctctgc ctgatggctg tacctccatg tgagtgtctc agagatttca    59820 gaacggggc tgtgggctgt ggtgtccgct tgtgactcat ctctttgctt cttgtccctg     59880
agtgtcctgc atcagatgca gctactggag tcatgcccag ggctggtgag gtcctcacag    59940
acctctgggc ctggacccag cagccctctg ggaaggcgct ggggcacctc agctccaggg    60000
gcagcacaca cttcagccca gccttctgg gccaactctc catctgtaga gacacatcca     60060
aggcccagtt atccctgcag ctgagctccg tgatggccaa gggcagggcc gcacattccc    60120
gtgggagaca gaatgggac ctcagcgtga gcccagacac aaacctccct gcagggaagc     60180
acaagaccac caggcggcgc tccagaccac acagcggccc cagaagcagg ttttaggggg    60240
cggggcagac gtgtccgcgt tgagtcaggt cattggtttt actttccctg agcaaacggc    60300
ctctgccaag gactcactgc acctctcacc ttcacagttg tttttttttt tttttaatc    60360 accctgtaga gttttgctag ctaatttaga tattgaggag tgcttcatac ttccttgggc    60420
ctctgcttgc agaaacatag caattgtaag gaggcacgtg ggaaagcccc ggctcggtga    60480
cccgggggat gctgctgtgg ccctggcaag agggcgtcgg gccgcagtaa caaaggtgca    60540
gacggctctc agcctgcgcc cgcggagtac aacacataag ggctgtaacc taacgaaaaa    60600
agaatcgcag tgcaactgtc ctgcatttga gttgtgatc agttttgccc tttgtcttta     60660
acaggttcta acataaaatt ttgaatgttg gttcaagccc tgtgggtaaa atgcacttac    60720
ccacattcct taaacaaata gaacactgag gtggaaatgt tttgaaaaag tagttttcag    60780
acatttggaa acaagcatca caggatcata acccctgaga aaagaaaaac aaatgaacga    60840
atcctgctat tgcctgaaag cagctgccag gacacacgga aaggcttagt gagctgagcg    60900
gacagagagc agagttcaag gcagcagcag cccgagggga ggagcaccgg ggagcaggct    60960
gctgtgcagc caggatgggc cggggtgggg cgggggggaga acagctggag acttgccgca    61020
gggaggggga tccctcaggt ttggggctga gaactgactt atgcctgact tatgcctgca    61080
tgaaaagaaa ctactcgata tcaggggaa atcaccagaa acctgtggac ccaaaactac     61140
acagagccta cacaaggaaa gcattgtttg tgttctccca gccagggtgg aaagaccttg    61200
agatatgtaa agcttcaagc aatcttccga agtaatctcg tgagtagtgg tgccacatta    61260
attcaggact aaaggctgct ctgaactgaa cctaagaaat gcttcaagtg tagcctggag    61320
cccgggtgca gtggctcaca cctgtaatcc cagcactgtg ggaggccgag gcaggcggat    61380
cacttgaggt caggactttg agaccagcct ggccaacatg gcaaaacctg tctctactaa    61440
aaacacaaaa attagctggg cgtggtggca gatgcctgta atcacctccc acctgggccc    61500
ttccttgata catcagaatt acaactagag atgagattgg ggtggggaca cagagccaaa    61560
ccgtatcaca taggaaccta aaaggataat aaagtaggaa aacttcccac atcagtaacc    61620
ctttatccga tagtaatccc aatctgcaaa gtaaaactgt gtgattttac taagataacg    61680
gaatcttctc tacagaagga cttttccagtg caaaagctcc ccacccctcac catgaaatgc    61740 acgtgaccat ttccaatttg tgtaaagtcc tcagttagta ctgagacttc ggaaggttag    61800
aaatcccttt gctcatgctg catggtccgg atgagatgta agaatcatta gctaatagac    61860
atgcaacagc ttttgtgtga aagatgttat gagacattta aggtatttgc ttgtgattac    61920
taagcattca ttgtatcatt ggagcacatg tgcttttata ccctggagaa attccagtaa    61980
```

-continued

```
ttgaattgct gggttgaatg ggattttgat ttggattaaa tttaaactat agattttatt   62040
tagggaaaac tggcatctta attatgttat tgggggggccc ttgctcccag agctcccaag   62100
atggtggcag gccgcttcca aaatgaccgc aggccacttc caagatggtg gcaagcctca   62160
tgttctctga cctggggttc ttggcctcac ggattccaag gaatgaagc ttgggccatg    62220
cagtgagtgt tatagctcta ttagaagccg tgggtcacgg aagagaaccg tggaacccag   62280
tgactagtgt tcagctcgat taggacgaac ccaggcactt agccgtgcag gaacaatggc   62340
gagcatttgg cccgatcgag agtggcaatg ggcgcctcgc tggatcagga gcacagcgga   62400
taccctgatg gatccggagg gatggaagcc agcggtgggt ctcccacggg ggcaaacagc   62460
agtggtggac ggtgagcgaa agcgaagctc gagccgtaac aaacatggac cagaagagtg   62520
cagttgcaag atttagtaga gtgaagacag agctcccata caaagggagg ggacccaaag   62580
agggtagctg ttaccggctc gaatgcctgg gtttatatcc cgatcattgt ccctcccgct   62640
gtgctctcag gtgatagatg attggctatt tctttacctc ctgcttttgc ctaattagca   62700
ttttagtgag ctctctttac tatctgattg gtcgggtgtg agctgagttg caagccccgt   62760
gtttaaaggt ggaagtggtc accttcccag ctgggcttag ggattcttag tcggcctagg   62820
aaatccagct agtcctgtct ctcaattaca ctgagttttc caatccatgc atccaatatg   62880
tggtgtatct cttcatatgt tcatagcctc tgagcaatgt tttacaattt tctgtgtaaa   62940
gaactccaca tcgtttttatg tttcttctaa ggtatatcct gattgctttt tatgtcttca   63000
caagttttttt cctttcaaaa ttaattttcc aattgtttgg tgctaatatg ctcaaatgtc   63060
cttgattttc ttagtttgaa cagtccgttt ttgttttggg gatttatttt tttttcagat   63120
tctttaagat tttctatgtc tataaccata taatctctga acagagacag ttttgctttt   63180
tcctttcaac ttgaggtagg ttttctgggt agttcaggac gcgcaggcac tgggtgggtg   63240
gtgttagcag ctgcacgatg ccttggagag gacactctcg ggggactgtg gccgctgctc   63300
agctgtgacc gttcttatag caccagcagc tgcggccacc attcttatcc aatttccaaa   63360
gccacaccac aggccctctc aagaacgagg cgtggaggct atgccctctc ctggacacat   63420
catcattccc aagcccacg atgtgggccc catgggacgc acacctttgt ctgtccagac    63480
ctcagcccca cctcctcatc ctgcaccaga actcttcaga gcccagtgca tgaaatgggc   63540
taccaaggaa atgagggtag gttcctgaga ggaaactggc cctgcatttg ggagctagga   63600
gtctgctaat tcgcctggca gccctgtgca gccctccgtg gctacagtcc accccgtgcc   63660
catcagtgcc tccttcctgt gcaagcctgg acctcgccct gggctcagga tgggctgtag   63720
accgagaatg caggcgggaa agtctttgtc tatcggggcc atagtcaggt tctacagtga   63780
gtcagggaaa gacctgtgga ggtgtggatg aggacaatgg gtccaccatc aacaggagga   63840
cacgggttcg accccttgca gaggcacagt cccacatcac tgggaggcag ccacactcac   63900
tgcctcgccc tctcctcaca cagtgcagtt tccacgttca cagccccagc cagtcaccag   63960
gaatgccctg ggggcggcct ttccccagtg cactccgagc cctcccttgg ctgtgcggtg   64020
agctccatgc ccaggagata tccacccata gtcctccgga aagcagctga cctgccatgc   64080
cctggaacca caaatcccca cagatcagcc agcctgcagt gggccttgga tgtggtgagg   64140
agtggtggca ccccgttcc caccccacag atgcaacgcc tgtgggtgac gcatgtgagt    64200
actgaggagt agagggtaga actgtaggcc ccgagaacca cagaaactcg ggtgttacac   64260
tctggggcca tgtaaggaga aagtgtcact ggacagaaac aggcccctcc tagacactgt   64320
```

| | | | | |
|---|---|---|---|---|
| gtgcgccata | gtcacctgtc | attagctctc | actcttgcag | attcatgatt gaggtggtta | 64380 |
| aaaaaaaaaa | agctcctact | cacccatcca | accccatcct | gggtgtttc caccaccctt | 64440 |
| ggggtttggg | atgagctgcc | cttgcccact | gtgctctgtg | gacctcccectt tagaagctca | 64500 |
| cagctccctg | cactcggctc | catcctgccc | caccacacag | aagcaaaacc cctctccttt | 64560 |
| ccactgcagg | cttttcctgg | accagaatgc | tgacctgctg | cccttcactc ccgaagtggt | 64620 |
| gggactgcct | ggggtggtgt | gggtgttgag | ccttcttact | ctagggacct ggcacctggc | 64680 |
| cccaggggca | cagggatggt | gcatctgcct | agggatgcct | cctcatgcca gggggtgggg | 64740 |
| gttagtacca | tcggccctca | ggatttgttg | catgaatgag | tgaatgggtg aataaatgaa | 64800 |
| ggggatctga | tctatgaata | agggtatata | gactttggtt | gatgtaggac gccaaatgct | 64860 |
| ggaatttcag | agtcatcaca | cccaggggcc | ctgcctctga | gctcctcttt gcatccaatc | 64920 |
| tgctgaagaa | catggctcta | gggaaaccca | gttgtagacc | tgagggcccc ggctcttcaa | 64980 |
| tgagccatct | ccgtcccggg | gccttatatc | agcaagtgac | gcacacaggc aaatgccagg | 65040 |
| gtgtggtttc | ctgtttaaat | gtagcctccc | ccgctgcaga | actgcagagc ctgctgaatt | 65100 |
| ctggctgacc | agggcagtca | ccagactcga | gtgccatttc | attacctctt tctccgcacc | 65160 |
| cgacatagat | tctcactcac | ctgtgccatc | tccgggaca | gtgtctctag caacagtgct | 65220 |
| gcttggaact | ggatcaggca | gtccccatcg | agaggccttg | agtggctggg aaggacatac | 65280 |
| tacaggtcca | agtggtataa | tgattatgca | gtatctgtga | aaagtcgaat aaccatcaac | 65340 |
| ccagacacat | ccaagaacca | gttctccctg | cagctgaact | ctgtgactcc cgaggacacg | 65400 |
| gctgtgtatt | actgtgcaag | agacacagtg | agggaagtc | agtgtgagcc cagacacaaa | 65460 |
| cctccctgca | gggatgctca | ggaccccaga | aggcacccag | cactaccagc gcagggccca | 65520 |
| gaccaggagc | aggtgtggag | ttaagcaaaa | atggaacttc | ttgctgtgtc ttaaactgtt | 65580 |
| gttgttttt | tttttttttt | ggctcagcaa | cagagatcat | agaaaaccct ttttcatatt | 65640 |
| tttgaaatct | gttcttagtc | taatggagat | tctctaatat | gtgacaatgt ttttctcttg | 65700 |
| ctgtttttgg | aattctttgt | ctttgacttt | tgacaacttg | acttttgaca gtgtgcctca | 65760 |
| aagaagttct | atttttgggtt | ctgtgaacct | cctggatctg | ggaagttttc agctatgatt | 65820 |
| tcattaaacg | tgttttctac | accatttccc | tactcttttg | gaatacccat aatgcaaata | 65880 |
| tttgttcact | taattgtgtc | ccataaatgc | tggggatttt | cttcattcct ttttactctt | 65940 |
| tttttctttt | tattcatctg | cctgaattat | ttcaaaagat | ctgtcttcaa cttcagaaac | 66000 |
| tcttttgctt | ggcctagtct | aatcttgaag | gtctcaattg | tacttttaat ttcattcatt | 66060 |
| gaattcttca | actctggaat | ttctgttggt | tcttttttat | gatacttatc tctttgttga | 66120 |
| attcctcatt | caaatgataa | attgttttcc | tgatttcact | gaattttcta tctgtacact | 66180 |
| attgtatctc | cctgagtttc | ttagagatta | tccttttgaa | ttatttttct gacattctgt | 66240 |
| atatttcctt | atgattgggg | tctgctactg | gagaatgact | gttgtctttt tcaggtgtcg | 66300 |
| tgtttcctgg | ccttttcatg | ttttatgtgt | tcctacgttg | atttctacac atctggcgga | 66360 |
| ccagtcatcc | cttgcaattt | aatggagtag | gttttgcagg | aaaagacttc ctagtacaga | 66420 |
| cgggtctcag | ggtgtcagtg | tggcggggcg | tgctggcttt | agttctaggt tgacgcagta | 66480 |
| gcgtagtctc | catgtcgttt | cttcagctgc | cgtccacatt | ggtgacgttt gcgagtgtct | 66540 |
| cagtggcctg | ggctgagagg | tttgtggcag | tggaagtgca | acgttgctag aggtggactc | 66600 |
| accaggctgt | ttctgaggtc | gaggcacatg | catgcacatg | gtggattgac caacttggtg | 66660 |
| ccaggctcac | tagggttggg | gacatggggc | tgtttctcag | gcccaggatg caaacacaag | 66720 |

```
tctctttggc tggcctgggg gtgtggcttc tgagggcaat ccacagggct gtttctcagg   66780
ttcaggacac aagtgcatgg ccgctcaact ggcctgggca tgtgtctccc agggccaccc   66840
catgggctct ttctcagacc caggacatgg ccacatggct tcctcagctg gcctgggtgt   66900
gtgtctgctg gggggctgca ggggcacagg gttatttctc aggccggggt catgggcgca   66960
cagctgcttg ctggcttata ggagtgcctg ccaggggtgg cccatgatgc tgtttctcag   67020
gcctaatttc aggtgcagag cctttgggca ggtcaacggc atacctgtgg aaattggagt   67080
ggatgccaca gggctatttc tcaggtgcct gagtgtgggc acatatccac tctgccagcc   67140
tggagttagt atcaggtgct cggtggctca ggggcctctc ctgctcaggg gagggccctc   67200
agcagcttgg ccaaatcaat ggtggattca ccctgggcag gcctggcagg ctcttcctcc   67260
agctggatgt gcagcagcag gggttgggtt ttttgctgtg cagggccaga gtcacggcca   67320
atcctcagcc taggctctgc acagccaggg ttgtggcatt cagccaccca gatatgggca   67380
tcctgaagat ggagccccaa tgctagaaag gggcagtggc taccagcctc agggcaggat   67440
gcactccaga ggcggctccg gtctcaaggt ggcgctgggc tgcagcagct aggctcacag   67500
tggatgaatg ggggcaggga gtacacacct tgtgctccta atctgggatc attcctggca   67560
gctcccaaac ttggctgagg gcttgcaaaa cctgtggaat tcctgttg caagggctgt   67620 agatgtttgc agtggcagtg ggtgctggcg ggaaatctgc ttacctttc cctacatggg   67680 aagtccctcc tgtgtccaga ccaatccgat ctgggtgggg aagacaaggc tgcaaaggcc   67740
aggtgcctcc atgctgccct ccgatcacca cgggtgcgtt tccacacctc cactgcactc   67800
cgtcagtctc ccttcaacac tccagtcaaa ccttagctgt ttcttctttg ccttattcct   67860
tcctcatggg gagggtgtgg gtgaacacca ggcttctcta agttcttcat ccatcttgct   67920
gatgtcattc tccatccagg catgggtttt taagaagtag tgaatactga aatttcagca   67980
gaggacacct ctataaaaat tctgcaactg gaaaacctcc ttaaattggc tgattgtcat   68040
tacaattgga ggaaaactgc caataatttc aaatttagaa ggctgagact ctataaacaa   68100
agactaacaa tatgttttct gatattttc cccaaaataa tacttttcca agacgaaaat   68160
ttttccaggg tatataagca catgtgctcc aatgatacaa caaatactta ctaatcataa   68220
gcaaatacct taaatgtctt ataacatctt tcacacaaaa gctgttgcat gtctattagc   68280
taaaaattct tatgtctcgt ccagatcatg cagcatgagc aaagggattt ttgaccttca   68340
aaagtctcag tactaactga ggactttaca caaattggaa atggtcacct gcatttcatg   68400
gtggtggtgg ggagcttttg cactggaaaa tccttctgta gagaagattc cattatcttg   68460
gtaaaattac atagttttat tttgcagatt gggattacca actgataaag ggttactgat   68520
gtggaagttt tcctacttta ttctcctatt aggttcctat gtgatatggt ttggctctgt   68580
gtccccaccc caatctcatc tccaattgta attcccatgt gtccagggag ggtccaggtg   68640
ggagtgatta gatcaagggt ggttttcc aggctgtttt catgataggg tgttatcatg   68700
agatatgatg gtttaaaagt ggcaggttcc cctgctctct ctctcgcctg ctgccacata   68760
agacgtgcct tgctttccct tcaccttctg ccatgattgt aagtttcctg aggcctcccc   68820
agccatgcgg aactatgagt caattaaacc tcctctcttt ataaattacc cagtctcagg   68880
tagtatcttt atagcggtgt gaaaatggac taatacacta tggctttgaa ttaataattt   68940
aaaatttgtc agcttggcaa taaaacatcc tgttgacatt tatttttag gtaatatttt   69000 aaattggcag tttcattcat gttttacaa attcttattt tcagggtgtt taaggccttt   69060
```

```
gctttgaact tggtggttcc ttacactcca tgctgttagt gaagagggac caggttggga    69120
ggcattggtt tgggtggtgg tcaggaaggg cagagtgatt tgagtagggt ctgagtggat    69180
aatagctcat cagtttggaa tttataaatg accagggatg atttaaggag attcctgcca    69240
gacacctatg ccatggccat gccctatctg gatctccagc cgtgagatga aacccagcc     69300
atgcggggga gtctgttcgt tctgctcaat gttgtaagtg gcacatgcta ttggataatg    69360
tagaattgaa tggatatcat tttattatta taatttacaa acttcctaca ataaacttat    69420
cacctttata catagaaaca aatataagta cattttccct ccctatgtc attttgagcc     69480
ctctctccaa accatcctcc cactctgcga ctcactgtcc tgcatttggc tatgctctgg    69540
caagtcctgc ttagacaagc actcaccaga ccacctactc agcctcsctt cagcgcccac    69600
ctggcccacc tgctcaaata catgttgagt ggtcacacac atggactgaa caccatctat    69660
tccatgcact gccccagtga ccgcactgag cagcaagaga gaaatgatcg cattagctat    69720
caattatgcc aattcaaatg ctggagtctt tctcagatac ttttcaatgt tcaagaattg    69780
ttgattgtga attctatacc caatgaaact atccttcaga aatgagcaga aaatggatac    69840
cttctcaaat aaacaaaaac taaaagaatt cttgctacaa gatgtactct taaagactgg    69900
ctaaaggaag ttcttcaaac agcaaggaaa ttgaattgat cttatgtcct gcacacttgc    69960
taaatttcct ctcaatttta gcagcactgt ttagattcca taggattttc atacaaaca    70020
gtcatgtggt ctatatatag agacagattt tcctcttttc cagtggggat aaatttatgt    70080
cttttctctt ctgtgttaca gcaggtagga cctccagtac aatgttaaac agaagtggtg    70140
aaaacagaca ttcttgcctg tttcctaacg ttggagtttg gtcttttact atggtgtcag    70200
atgttagctg tagggttttt ataaatgccc ttcatcacat tgaggaagtt tgctcctatg    70260
cctaattttc tgagagtctt ttaatgtgac actcatgcta gaatttatta aatgctttct    70320
gtctactaag atgattatgc agttcttata ttaacatgaa taattacatt tatttattct    70380
ttaatatcaa ggcaattttg cattcctgag acaaacccca tttagtcatc atgtgttgtt    70440
attgttacat attgttggat tcaattttcct caaaatttgt taagaattgt tacatctatg    70500
tttacaagga agattagtct gtagggtatt ttttcttata ataactttgc ctagttttgc    70560
aatcagggta atgctggact cacagaatga gttgggaagc tatttcctcc tcttcatttt    70620
tctgaaagaa tttgtataaa attggaatta tatcttcctt aaaggtttgc aagatttcat    70680
aatgaagtca ttggcctaga gttttctttg tgggaaagtc tttgtttgtt tgttttgtgg    70740
tttgggtttt tttttaagag acacagtctc actctgttgc ccaggctgga atgcagtggt    70800
gtaatcatag ctcacagcag cctcaacctc ctgggctcaa gcaatcctcc tacctcagcc    70860
ttcagagtag ctgggactac gggcatgtac caccacaccc agctgtttgt ttgtttgttt    70920
atcgctttgt cttgtttttg aggtcttatt atgttgccca ggctggtctt gaactcctgg    70980
cctcaagtaa tcctcatgcc tcagcctccc acagtgctgg aattacaggc atgagccact    71040
gcacacagac tgtgggaaag tttttaacta aaaattcaat tttctcttcc ttttccagtg    71100
agctttccag tgtctttcaa ttaatgtatc tattttatct aagttgttga atttattgtc    71160
aaaattttt taaacaatat tcctctctta gaggttgaac atctgtagaa tctgtagtga    71220
tggcacctct taaatccctg atcttgctca tctgtgtcgt ctctctttct ctaatcagta    71280
tgcctaaagt ttaatttcat tgattttctt aaaaaactgg ttttggtttt attgattttt    71340
ttccctagtt ttttgtgtta catttcattg acttctgctc tgatatttac tatttccttt    71400
ctactgccta cagtaagttt aatttgctat tttcttagtt tcctaaagtg gaagctaagt    71460
```

```
ttattgactt gaggcctttc ctctgtctgg atgcggatat ttgctgctaa acatttccct   71520
ccaacaccat gctgtgagtt ttagttacag cgggcttgga gttggcctga gaaattctac   71580
ttaaacagct gcacctatca tgtaagtgat aaatgatgta cctgcctggc cctcacccct   71640
ggtcaaagaa tgggatgtac taatgagcaa tgttgctgcg tagctgtgga tttcaaggta   71700 tttctgtgt ggttttatca tcagcattgt ttgttgatga ctgcaagact gatgatttgc   71760
acctggcctc ggtgagatcc ccgaaagacc ctgcagatgg gctggttact tagcagaaaa   71820
tatgacaacg tggccagcag gaaacaggaa ggtacaatcg gctgcaggtg agctgttgga   71880
agtaagttcc aattttccta ttttgtattt gcattttaat agtgagactg cgcttatgtt   71940
atttgtgtga aacagcttta ttcatagcac tgtaatttaa agagaaaacc cattcatggg   72000
aacaacaaac gacctagaca ccaaggtagc tcatgccatc caaggctata ctgtgcagtg   72060
attgggaaaa tgggcactgg tcccagaagt ctgatcgaca ctctgccact ggctagtccc   72120
gtgctggggg gcgaggatcc acactctgcc actggttagt cccatgctgg ggacaagtat   72180
ccacactctg ccactggcta gtcccgtgct gggggcgag gatccacact ctgccactgg   72240
ttagtcccat gctggggaca agtatccaca ctctgccact ggctagtccc gtgctggggg   72300
gcaaggatcc acactctgcc actgattagt gttgtgaaga tttaaataaa gaacccacac   72360
catattcttt gacttgtgct ttccgtatac tgagagatag taagagtaca ttattattat   72420
ttataaagta aactagaaag cacatgggaa gacaagaaga aaacctgaat aaacatgaat   72480 tacccccattt tcctcaggag aaaactttca cactctgaag gtacacaaat tagcctacaa   72540
atttaatgta aagcaaatag actgttgtag gtaccaattc tcaatgtcac agtgttacat   72600
ggaaagtaaa atacacaaga acagcccaaa agatggaaac aatggacgtg gtcaaatgac   72660
atcagtacaa catccatatg gtcctaagta gccatcttta aaatgggtta gaaatgcctt   72720
caatcattca cacagacaca tgcattgaac aaactctaag aagtgttctt acacgggaaa   72780
agcaagttac agatgcatgg gcatgatatg gatgtagatg tgtgtatgtg catcccactc   72840
atacacaaaa tacccagcat cgcccacatg cctgctgtgt gcgtaagtgt gagcgagtgc   72900
acagacaaca gcgtgcagaa attcaaacca agctgtgggt acttgttacc actgggaagg   72960
gagtcggtca cagagggaaa gagaaacagg acatcagcct ttgacttcag aactgttcct   73020
gccttttcac atcctgtgct gttttcagca tcatcggagc ccttaacaca catcacggga   73080
gtaagagtgt gttagaggga gcattcggtg ggacagatat tgccatggct tgtggataga   73140
gttcacagtc cttaataatc cccgagatgg cagccaagag ctacgttctc aatcacgcag   73200
cttcacccca gaaactgaca gaaacccaac aaccaaaagg tgtccattct gacagcctca   73260
gcctgtgctg gctcagatga gcaaaaatgt acagatatta ataatgatgt tgatttgaag   73320
agcacagagg ggggtatgca tgataagggt ccaaattttt accttaaaaa agaatacatt   73380
tacttctcaa tcacctacat aacgatcatt ttttaaaaaa ctgatcaaat ttggtgttac   73440
aagggcacgt tgcaaattct tctggctact tttctctgac tattctaatt acgttaccgt   73500
gttttctcct gtatgtgccc gttcatgtga atgtcatttc tggctacttt tctctgacta   73560
ttctaattac gttaccgtgt tttctcctgt atgtgcccgt tcatgtgaat gtcatttctg   73620 gctactttc tctgactatt ctaattacat taccgtgttt tcctgtatgt gcccgttcat   73680
gtgaatgtca tttctggcta cttttctctg actattctaa ttacgttacc atggtttctc   73740
ctatatgtgc ccgttcatgt gaatgtcatt tctggctact tttctctgac tattctaatt   73800
```

```
acgttaccgt gttttctcct gtatgtgccc gttcatgtga atgtcatttc tggctacttt    73860
tctctgacta ttctaattac attaccgtgt tttcctgtat gtgcccgttc atgtgaatgt    73920
catccaggca gatttcccaa atccggcttc ctgtaaccaa gggctgaaag agggaacggt    73980
ttcctgggaa tccttttttgc agtttatttt acccggaggc agaagcccac ggttccgtga   74040
agagtctatt gctctcccct ctctcctttt gtgtctctat ttttaattga caaaaagca    74100 aatgtgaaga ttcctggggt acaatgcaaa gtgacaatgc ctgtctatat tgtgggatga    74160
ttaaaacaag gtaagtggca tatccatcac ctcacacact tatcattttg tggtgagaac    74220
atttaaaatc tcatctttta gcaattttga aatagtcatt attgttaact atagtcacca    74280
tgctgtgcaa cagatcaaaa gaactgactc ctcccatcag cagaaacttc atgccctttg    74340
accagcatct ctcctttccc cgtccacgac taacccccag cccaagagaa cagccaacac    74400
ccacctcgct gctgccacac gacatgtcgg gctttgatgg gatggaggtg agggtgggga    74460
agacaattcc aaagctggag cactggcctc acagctcaga cactcttcta cttatcctga    74520
gagaatgatg tgctgagacc aactaaacct ccccctgctct tcccacatgg cagaaaagag    74580
gcaacccagg gaagccattg ccaggacatc atggtcaccc aaccctttgtg cagaaaggaa    74640 gcacctgccc aggatgccat agcacccaac cctcatcccc aaggaaacac agcccagggc    74700
accatggaca cccaaccgtc atccccaggg gaggacacag cccagggcac catggacacc    74760
caaccctcat ccccagggga ggacacagcc agggtatct tggacaccca gccctcattc    74820
ctaggggagt acacagccca gggcatcttg gacatccaac cctcatcccc agggaaggac    74880
acagcccagg gcatcttgga cacccaaccc tcattcccat aagagcacac agcccagggc    74940
atcgtggagg cccgaccctc atccctaggg gaggacacag cccagggcac catggacacc    75000
caaccctcat ccccagggga agacacaacc caggccacca ttaacaccca atcatgtgca    75060
gggagggtgt ccttggagcc tgggactctt gccagtgaag cggtggacaa gaaactgagg    75120
atgcgatcag cacacagaaa tctcaggcag cctaggatac atgaggcctc tcaccctgg    75180 gaacactgag cagccaccag gagcccacac cttgaggtac agcaggagcc atgcgctctt    75240
gctcttgctc actcacactc ctgcacacag ccactgacac acgccctcgt gcacgttgca    75300
gattaactcc actggccttg cacttgcaac gctggaggct gagaggtatc cccaggttct    75360
tttctcgtga gaggggcagg ctgactttca ctctcctcca tgtgctagag gcagctccac    75420
caacactggc tgccctgagt ggatgcacct ggctctggaa ttcctgtcat ttgctttgga    75480
tccaggagcc cctgcctcat gtagctactt aacagaaagg aggaatccac ccaggacatg    75540
cccagacggg agcctcacag gatggacagt ggtgtctggg gtcacgggca gccctgaccc    75600
agcagcgcca gcaccagcac acccagtggg aaggcgggg aggcccaaac gccacccaca    75660
gtttgttact ccactgggtg ggacccggca cccctgcctt cctgacaccc tggagtccct    75720
gcctcctcct agagccccca agcccatctg cctcagagca tccagagaca gacctgggga    75780
gccatttcct caggccctgg acaaggaaac agggaattcc aggttatggg tgcctggggc    75840
aggtctcagg caggtgctgg gaaccagaga gagggtcac cgcgaggcct caggcctggc    75900
accagcactt tgagcctcag tttaccagcc cacgaggtgc tgagtctgga ctggatgacc    75960
ttcccacccc cagtgacctc tgccctttcc cgagcatgtc agctctgctc cagcatcctg    76020
gtgtgagcgc aatgccactt tttttctcaa caaatacgaa aggaggaagg tgccccagg    76080 gccctgtgcc ctgaggatgc ctgtgtggag gggtccattt catcactggt gtcactcaca    76140
ggaagggacg aagccacctg ccttgacgga gcttactcca cctccgccga aggccgggga    76200
```

```
ggtccctcac agagaacctg aggcccagca ggctgcagag gtgctggcat ggaatgactg    76260
ctcagacgcc cggggccggc agagaggacg gatgtggggg aggtgcacac tgaggagcct    76320
ctccttggag gtggagacac gtgcaccaca tggaccagga cacagtccac gaagcctcgc    76380 atcccctga gctgcagctc aagggcctct ctctgagccc agagtccac ccctgggagg     76440 cagctgcccc agctctgagg gaggagggca tccaccaggc cctccatctc ctggggcac    76500 cagcccagcc cagaggctct gcaggactct gcacctccaa ttcatggcca ggactttctg    76560
gatgtatctt aaggactgag gactccacat cagggaccac acaagaccgg ggtcccggac    76620 acggggggttg ggggtgagca tgtcaccggg atgggctgtg gcgtcactct ggtacttcat   76680
ccggacagcc agggaccaaa gccacgccct cagccccacc ccaccctgc ctcacatggc     76740 aacgcagggt ctgcagatgc aggagagtga gaagcatggt agccaggcag actagaggac    76800
ccgagctggg gttgagcacc tccctgtcta cccagggcat ggcctgtgag actgcaggtg    76860
gcctagtgtg tgctgcaggc tcaaggtcct gccccaggga gcatgacatt caggcccaga    76920
aattgcatcg tgctgcacac agtccaaggg gataaccctg tgaagttcag gtcaccagca    76980
ggcttggggt caagaccgag ctgcagagga caggtttctg gaaggcacag catcatgggt    77040
ggagggactt ggagcaaggt ccttagcccc gggaccagtg aatgtgtgcc cttataggga    77100 aaggggggtct gtgcagaagc aagttagctg aaaatcatga agtggagagg ctcccctgga   77160
ttaaaggggt gagccctaat gtaatcacaa gtgtccttct aggaggttgg cagagggaga    77220
ctgacataga cagaagccag gtgaggtggg aagcggaggc agaggccgag agagcagacg    77280
ctacgccctg gccctgaaga cggaggagga gccgagagct cagggatgga gagactggag    77340
gaggcaggga agttctcccc gcaagcctgg agggagcatg gcctccagca cccccagacc    77400
ttggccctgc aggattcatc tggacctgtg gtataaatgg tgtttaagcc actgggctgt    77460
gcaaattgtc atagcagcca tggcgcattc ctagagggag ccctggtggg gacccagcag    77520
gcagcgacgg ggccctcaca agcctgtgag ccactcagag ccgcgagagt ggctaggctt    77580
ggtgaggtgc aggccacgcg cacctccact aaggcagcct tagggcccac acttcctctc    77640
tctctctctc tctctctatc tctctcctc cctccttccc tccctcccgc tctcttggtt     77700
ggacagctct ccatcatccc cctggacatg accacctccc aaggccgagc tggggcgctt    77760
tgctcgaggt gagcactgac atcctggggg tgtgaggggc acctgcccag cggcccgtg    77820 tgcaggatgg gcggtgggcc ctagctggca ctgggcatat ggcccggctg gtgcctgcag    77880
gctgcagctt ttctggggtg gctgggatca gtgaaggcc ccagagtctg ggcctgggat    77940
ccctgcagtg ctggctgagg acaggcgggg ctgggcagtg agggcactgg gtcactatca    78000 ccacccacg tttattactt cactaggtgg gacctggcac ccctgccttc ctgacaccct     78060
ggaatccctg cctcctccta cagcccccaa gcccatctcc ctcagagcct ccagagacag    78120
acctggggag gcatttcttc tgcccccagc agaagcccgg gaggccggga aggcacagtg    78180
ggtctaaagg agaggatccc aggactgcct gaggggtgac tccgacgagg caagcataga    78240
gcccactgag aagcggggtg ggagcccac cagggatggg ctagttcctc atgaaggacc    78300
aggacccagg aaggacaagg gggcctgctg ggcagggtc tgctatgccg gagtccctgt    78360
gagcctggcc cagacctgcc tctctctttc ctcattggtc cccacaggtc cgtggtggtt    78420
gccgtatcgg gaggccccat ggtggcaggg gtgggacacc tggtatacgt cgccaggtgt    78480
gtccaatagg ctcatgctca caccttctcc tggcacctgg gcaaagcctg agcacccagg    78540
```

```
cactgaagtg agggcaaggc ctcggggccc cacaggatgg ccgaggagac agctgcaggg    78600
cgcctgggac ccctgggctc aggaggtaga aggatacagc ctgaaaaccc acaccacaag    78660
ctcaccggcc agtgcaggcc cacagagctc gaggaggcag ccctgagcct cccagggaga    78720
gatgctctgt gcacgccggc acaggccctg ggttacaaac cctaggcaca gcccaggaga    78780
ggcccaggcc ccagtccagc aaggggttgc aggaagcaag aggtccccgg ccacagcatg    78840
agataagccc atcaagccag gccaggtgg gcaatgggag gcaggcaggg cttggggtg     78900
agtccctgct gcagcgccgt ccactgtcga ccggaggagt ttcttccctg tgcggagtcc    78960
acgggcctcc tgtgagtgtg tgcatgggca caagtgtgtg tgtggctctg ctgtgtgtct    79020
gtacacacat atgttttggg ttttttttgtg tctcagacca cagagtctgc ccctcccacc   79080
aaagcccagg cagaaggatg aacccacgcc cctggggccc aggcctcagc agcctctgcg    79140
ggatcattgt tcccagttgt cacttgcctt tgccacagcc ctatttctcc acaattcctt    79200
aaagtcctca acatgcattt aaggcacaaa ggtgaaactg cccagaaaca tctgactccg    79260
ccgtggaacc caggagcaag ctgggttagc taaggagcgg ggccgttggc agaggctggg    79320
gatccaggct gaactttgga ggaggcatgt cccagcatgg gctcctgact atgtcctcct    79380
gggacaaacc caaacccgct cttgaatat gggagggact ttgctggccc cggccctgac    79440
cgcagcactt ggaaactgag gagtggtcgc ctcctccgtg tcacagctgc ccgttcacca    79500
tcatagaagc aactctgtca cctccatggg ccctctgtg gctgctgcct gggtccaagc    79560
tgagcccagc tgcccaggcc cagaaggaaa gcccaggcca ggtgcccagc acagaggcag   79620
tcacataccc cggggagagc cacagcaagc agccaatatt gcccaggaga ggagtagctg    79680
acaaggcaga acgtgagctg ccatcggctc gagaggcttt gctggtcctc ctggggctct    79740
ggacatgacc aggaggagcg agggaagaag tcgcatggtg gtcccatcct gggtggggcc    79800
tgatggcagc tggccacccg tcccagagtg gcagccagat gccagcgcca ttcccacagt    79860
cacatcattg gtcacagaat gcaggacata gagtgtcttc tttccatcac agtgctgtcc    79920
agacccatag cctagggtag acctggaaga ttcaatgtcc acacccgggg ctggagcgta    79980
gccatgagca acgcccccctg cccgtgcatg gaaagccagc ccaagctctg ctccatccct   80040
agccaaagtc agtgtccttt cccctcctcc caagtgagct ctagccacct gcctaccctg    80100
ccatctgagg atgacagcct tcattccatt ggaacctggc tctgccacca gcaggcttgc    80160
agtcctgggc agactccgtc acctctctat gcctcagcct ttccatctgc acaggaggaa    80220
gatgatgatg tggtgatga tgatggcgat ggtttccttt tgcatctgag gcaaggacta    80280
attgagatga tacacatcag gcactgggta tggtgctggt ccttcctgag cactcaatct    80340
atgtgagctg tccttgtgaa atgggtgtca ccacatttcc ccacgcagaa catcctttgt    80400
ctgccatact tgaaacgtct gccccaatac taacagctcc tcatggaaga tgtgcacacc    80460
cacccacccct catactccca aaggtgcccg tgctttatca agccaaagtc cagccaggaa    80520
ctttacagca gcatcccttt ccctctccaa gcaccaagga gcaaggcaaa gcactacatc    80580
ttccatctgg aggcaatgcc accctcttct cccattttca ctgccatccc taagaggcag    80640
tgcttccccca aaaggttcca tagcagcctg cctacagcaa ctctgttcac acgagtttca    80700
gcatccttgc agtggctccc ctgccatgct gtggctcttc attcaccctc ttctcctgct    80760
ccccgtgaca ggcatagatt ctgagtgatc tggatacatt gctttgttta ataacattac    80820
agcttctgtg ctgaaaaaga tacagcagat agagaaggca attgttgaac acaaaatagt    80880
gacagcagag atgacggcaa gttggcattt ttcttttcta gcaataaaac ttaaagctga    80940
```

```
ctcaaggaga aatggaaatc ataattggaa cagtaatcct caagaaagca ttaagattat   81000
taaataattg ccctcacaga tgacttcagg ccaagatggc tttatgggtg aagtttagac   81060
tttcacaaaa ctaatcagtt cccataagaa ctgctccagg atttggagga acatgggaaa   81120
gtctattaaa gggatcacaa ttcacagtcc ccagagtaaa acatgggcta acttgcattt   81180
tggcaaagag ccaaatgtta taaatgacat cctagaaggc caaattctgt ccatctcgtt   81240
gaacaaggac ttacaccagg aatttagaac tatttatagc tcatcccacc actcaggcca   81300
atgatgaccc atgatcatct caccagaaat ggaaagactc agatgattaa tagagtctca   81360
atttctctga gacatctaag agcccagccc aagcccagac ccaggagggc acccaggcct   81420
ggacagagaa cactgatatc acaccagccc tccagaggga agcagagact ccttcaagct   81480
ctggaaacac aggcccagac agctgcccaa agttgggcag gcttcactgc aaacccaaat   81540
catgaagcta ggtaacacct ttacagattc tttacattta aaaatcatca aaacaagagt   81600
aaataataaa ctcaaataat attaatctaa tatgtaaagg tcttgtacca ttattatgca   81660
aacaacatac ataagctaat aagaaaaaga acaaatccct taagaaatcg gcaaaaagga   81720
tataacacaa tttctaaaag aaaacaaatg gctagcacac ataaggaaaa cactttgtga   81780
acagacattc ttcagaacat tatttataat tataaaatag ttgaaagcaa gatagtgcct   81840
gaagaaatta tggtgcatac attagtggga ctattctgca aacattccca attatacttg   81900
tcacatatct gtgataacgt gacagccagc attcatgggg tgacctcatt tggtaaaagg   81960
gtgcaaagct caacacgcat tgtgagatga ctgtggtgta aaattagtgg gattattccg   82020
caaacattcc caattatact taccgcatat ctgtgataac atgacagcat tcatggggtg   82080
acctcatttg gtaaaagggt gcaaagctca acacgcattg tgagatgact ggtgtaaata   82140
caaagaccaa actgtgaaaa ggagtccatc aattaatcga tgcttacctt cagttttggg   82200 ctaatttttta aagtatgcta taagcatatg ctcctgttat aacagaatgg agggattatg   82260
agagatgatg caggtgtgtc ctgggcctcc cctggcccac tgggccctag agatgccttc   82320
ccaggcatcg ctgtcagggc ttccctcaga gggagtcctg tattgacctc accaccaagg   82380
tctggagcag gggatcctta gatattggtt ggggttatct cacttaggt ctgaatatgg   82440 ggttgtctta gactgttttg tgctgttaga atagaatacc caagactggg aaatttatac   82500
tgaacggaaa tttatttctc acagttctag aggctgtgaa gtccaagagc acaggtgcca   82560
gagcaagtcc aagagcaagg gaaagtccaa agcaagtcca ggagcatctg gcgaggacct   82620
tcttgctgtg tcatcacatg gcggaaggca agaaagagag caagaggggg ccgaactcac   82680
ccttttataa cagcaccaat cccacccatg aggtggggac cttatgacct aatcactctt   82740
catactgtta caatggcaat gaaatttcaa catgagtttt ggaggagaga agcattcaaa   82800
ccacagcaag ggtgctccta cctcctctct cagggcatct gcagaaagag ctgcaactgc   82860
acgtccttcc tccgtccatc ctccatccct tcccaatgtc cgtgcatatc ctgtgaccca   82920
ggaggtctgg catagggggt gctcctgcct taggtctgag ccctgtctg aagagggta   82980 ggtgaggagg ccatctgatg gtctgggcca agacagtcac aggacgcatc atttatcatc   83040
aaggaggctg agggttgagt ctccaggtcc agggaactcc ccacaaagtg gaaccctgc   83100 ccagctccac acagcctctg ctgggggacc ctgctctggt gcagagcctg ggacaggtc   83160 ttgagctcag ccagagtctg cctccctgtc atttaggaac taaaccaagc ggcaggatgc   83220
tggagcccag cccccatctg accttacagg gccaaggctg gggccctggg ttcccctcaa   83280
```

```
ggcgcagcag gactggagcc ccaggcagtg caggagtggc caaagctggg gcttcctcca    83340
gagcccccaa gcatcacggc accaagaagg gtaggaccct ggcctgagga attggcacca    83400
aagcccagga aactaccctg acaccatggg agagaggcct ggaggggaag caccaggcac    83460
tgcctcccct tctgatccca cctgaggtgg ctgccaagcc cagagagccg ctctgatgtc    83520
ccccagccct gcagcccagg gatacctgta ctgtgcccct gggggacccc tggccagtct    83580
gtgcaaagaa gtcaccaccc tacactcaga gacagtgggg gtcctcgtcc cacatcctca    83640
gagcatggcc cggctgctgc agggatggtc tcctggtcct cagagcatgg cccggctgct    83700
gcagggatgg tctcctggtc ctcagagcat ggcccagctg ctgcagggat ggtctcctgg    83760
aggcccccca gtgctctatt gtcagggctc cctccacccc ccgcaccaa gagagagcca    83820 gaccccagca aggcttccag tggcttcagg tcacacccct aggctgaccc cagcccatt    83880 aacacctgcc tgagaaagct ccacgcacca gaactgaccg tctgctccaa ctcttgacct    83940
cccgttctca gggcgtctgc tgaaaaggct gcaactgcac atccttcctc cgtccgttcc    84000
cgatgtccgt gtgtctcctg tggccaggaa ggtcttttctc gggacctgag agccgctccc    84060
tgaagtgtcc ccattgggaa ggatggggcc tgtgtctcca ggctctggga ggacagaatc    84120
ctgacctcaa cagtggccgg cacggacaca actggcccca tcccggggac gctgaccagc    84180
gctgggcaac ttttcccttc cccgacgact gagccccgag caccctccct gctcccctac    84240
cacctccctt tacaaggctg tggcctctgc acagatgata atggagcttg gctcattccc    84300
ctagagtcgg tagggagtta aggacaaaac tcagtttcct ccacctgaac tcaagtctgc    84360
ctatgtttac ctaatcacac ctggtggaca gtttggacaa acttgcacac tcagagacac    84420
agacacttct agaaatcatt atctccctgc cccggggacc ccactccagc agaagtctgc    84480
taggcactgg cctgggccct cctgctgtcc taggaggctg ctgacctcct gcctggctcc    84540
tgtccccagg tccagagtca gagcagactc cagggacgct gcaggctagg aagccgcccc    84600
ctccaggcca gggtctagtg caggtgccca ggacaagaaa gattgtgaat gcaggaatga    84660
ctgggccaca cccctcccgt gcacgccccc tcttgccctg caccccacag cccagccccc    84720
cgtgctggat gccccccccac agcagaggtg ctgttctgtg atccccctggg aaagacgccc    84780 tcaacctcca ccctgtccca cggcccaagg aagacaagac acaggccctc tcctcacagt    84840
ctccccacct ggctcctgct gggaccctca aggtgtgaac agggaggatg gttgtctggg    84900
tggcccctag gagcccagat cttcactcta cagaccccaa cccaagcacc cccttctgca    84960
gggcccagct catccccctc ctcctccctc tgctctcctc tcgtcgcctc tacgggaaat    85020
ccgggactca gcagtaaccc tcaggaagca gggcccaggc gccgtttaat aggaggcttc    85080
ctcacaatga aacttttaga aagccttgac tacaatgatg accttggtgt ggctgtgaac    85140
actgtcagct cccacagctg ctgcagcaaa aaatgtccat agacagggtg ggggcccggg    85200
gtcgtctgct gtcctgctca gcccacagca cgcatggagg atctgaggtg ccacacctga    85260
cgcccaggcc agaacatgcc tccctccagg gtgacctgcc atgtcctgca ttgctggagg    85320
gacaggggca gcctatgagg atctggggcc aggagatgaa tcctattaac ccagaggaaa    85380
actaacagga cccaagcacc ctcccgttg aagctgacct gcccagaggg gcctgggccc    85440
accccacaca ccggggcgga atgtgtacag gccccggtct ctgtgggtgt tccgctaact    85500
ggggctccca gtgctcaccc cacaactaaa gcgagcccca gcctccagag ccccgaagg    85560 agatgccgcc cacaagccca gccccatcc aggaggcccc agagctcagg gcgccggggc    85620
agattctgaa cagccccgag tcacggtggg tacaactgga acgaccaccg tgagaaaaac    85680
```

```
tgtgtccaaa actgtctcct ggccctgct ggaggccgcg ccagagaggg gagcagccgc   85740
cccgaaccta ggtcctgctc agctcacacg accccagca cccagagcac aacggagtcc   85800
ccattgaatg gtgaggacgg ggaccagggc tccagggggt catggaaggg gctggacccc   85860
atcctactgc tatggtccca gtgctcctgg ccagaactga ccctaccacc gacaagagtc   85920
cctcagggaa acgggggtca ctggcacctc ccagcatcaa ccccaggcag cacaggcata   85980
aaccccacat ccagagccga ctccaggagc agagacaccc cagtaccctg ggggacaccg   86040
accctgatga ctccccactg gaatccaccc cagagtccac caggaccaaa gaccccgccc   86100
ctgtctctgt ccctcactca ggacctgctg cggggcgggc catgagacca gactcgggct   86160
tagggaacac cactgtggcc ccaacctcga ccaggccaca ggcccttcct tcctgccctg   86220
cggcagcaca gactttgggg tctgtgcaga gaggaatcac agaggcccca ggctgaggtg   86280
gtgggggtgg aagaccccca ggaggtggcc cacttccctt cctcccagct ggaacccacc   86340
atgaccttct taagataggg gtgtcatccg aggcaggtcc tccatggagc tcccttcagg   86400
ctcctccccg gtcctcacta ggcctcagtc ccggctgcgg gaatgcagcc accacaggca   86460
caccaggcag cccagaccca gccagcctgc agtgcccaag cccacattct ggagcagagc   86520
aggctgtgtc tgggagagtc tgggctcccc accgcccccc cgcacacccc acccacccct   86580
gtccaggccc tatgcaggag ggtcagagcc cccatgggg tatggactta gggtctcact   86640
cacgtggctc ccctcctggg tgaaggggtc tcatgcccag atccccacag cagagctggt   86700
caaaggtgga ggcagtggcc ccagggccac cctgacctgg accctcaggc tcctctagcc   86760
ctggctgccc tgctgtccct gggaggcctg gactccacca gaccacaggt ccagggcacc   86820
gcccataggt gctgcccaca ctcagttcac aggaagaaga taagctccag accccccaaga  86880
ctgggacctg ccttcctgcc accgcttgta gctccagacc tccgtgcctc ccccgaccac   86940
ttacacacgg gccagggagc tgttccacaa agatcaaccc caaaccggga ccgcctggca   87000
ctcgggccgc tgccacttcc ctctccattt gttcccagca cctctgtgct ccctccctcc   87060
tccctccttc aggggaacag cctgtgcagc ccctccctgc accccacacc ctggggaggc   87120
ccaaccctgc ctccagccct ttctcccccg ctgctcttcc tgcccatcca gacaaccctg   87180
gggtcccatc cctgcagcct acaccctggt ctccacccag accctgtct ctccctccag   87240
acaccctcc caggccaacc ctgcacatgc aggccctccc ctttctgct gccagagcct   87300
cagtttctac cctctgtgcc tacccctgc ctcctcctgc ccacaactcg agctcttcct   87360
ctcctgggc cctgagcca tggcactgac cgtgcactcc cacccccaca ctgcccatgc   87420
cctcaccttc ctcctggaca ctctgacccc gctcccctct tggacccagc cctggtattt   87480
ccaggacaaa ggctcaccca agtcttccc atgcaggccc ttgccctcac tgccccggtta  87540
cacggcagcc tcctgtgcac agaagcaggg agctcagccc ttccacaggc agaaggcact   87600
gaaagaaatc ggcctccagc accctgatgc acgtccgcct gtgtctctca ctgcccgcac   87660
ctgcagggag gctcggcact ccctgtaaag acgagggatc caggcagcaa catcatggga   87720
gaatgcaggg ctcccagaca gcccagccct ctcgcaggcc tctcctggga agagacctgc   87780
agccaccact gaacagccac ggagcccgct ggatagtaac tgagtcagtg accgacctgg   87840
agggcagggg agcagtgaac cggagcccag accatagggg cagagaccag ccgctgacat   87900
cccgagcccc tcactggcgg ccccagaaca ccgcgtggaa acagaacaga cccacattcc   87960
cacctggaac agggcagaca ctgctgagcc cccagcacca gccctgagaa acaccaggca   88020
```

```
acggcatcag agggggctcc tgagaaagaa aggaggggag gtctccttca ccagcaagta   88080
cttcccttga ccaaaaacag ggtccacgca actcccccag gacaaaggag gagcccctg    88140 tacagcactg ggctcagagt cctctcccac acaccctgag tttcagacaa aaaccccctg   88200
gaaatcatag tatcagcagg agaactagcc agagacagca agaggggact cagtgactcc   88260
cgcggggaca ggaggatttt gtgggggctc gtgtcactgt gaggatattg tagtagtacc   88320
agctgctata cccacagtga cacagcccca ttcccaaagc cctgctgtaa acgcttccac   88380
ttctggagct gaggggctgg ggggagcgtc tgggaagtag ggcctagggg tggccatcaa   88440
tgcccaaaac gcaccagact ccccccccaga catcacccca ctggccagtg agcagagtaa  88500
acagaaaatg agaagcagct gggaagcttg cacaggcccc aaggaaagag ctttggcggg   88560
tgtgcaagag gggatgcggg cagagcctga gcagggcctt ttgctgtttc tgctttcctg   88620
tgcagatagt tccataaact ggtgttcaag atcgatggct gggagtgagc ccaggaggac   88680
agtgtgggaa gggcacaggg aaggagaagc agccgctatc ctacactgtc atctttcaag   88740
agtttgccct gtgcccacaa tgctgcatca tgggatgctt aacagctgat gtagacacag   88800
ctaaagagag aatcagtgaa atggatttgc agcacagatc tgaataaatt ctccagaatg   88860
tggagccaca cagaagcaag cacaaggaaa gtgcctgatg caagggcaaa gtacagtgtg   88920
taccttcagg ctgggcacag acactctgaa aagccttggc aggaactccc tgcaacaaag   88980
cagagccctg caggcaatgc cagctccaga gccctccctg agagcctcat gggcaaagat   89040
gtgcacaaca ggtgtttctc atagccccaa actgagaatg aagcaaacag ccatctgaag   89100
gaaaacaggc aaataaacga tggcaggttc atgaaatgca aacccagaca gccagaagga   89160
caacagtgag ggttacaggt gactctgtgg ttgagttcat gacaatgctg agtaattgga   89220
gtaacaaagg aaagtccaaa aaatactttc aatgtgattt cttctaaata aaatttacag   89280
ccggcaaaat gaactatctt cttaagggat aaactttcca ctaggaaaac tataaggaaa   89340
atcaagaaaa ggatgatcac ataaacacag tggtcgttac ttctactggg gaaggaagag   89400
ggtatgaact gagacacaca gggttggcaa gtctcctaac aagaacagaa caaatacatt   89460
acagtacctt gaaaacagca gttaaaattc taaattgcaa gaagaggaaa atgcacacag   89520
ctgtgtttag aaaattctca gtccagcact gttcataata gcaaagacat taacccaggt   89580
tggataaata aacgatgaca caggcaattg cacaatgata cagacataca ttcagtatat   89640
gagacattga tgatgtatcc ccaaagaaat gactttaaag agaaaaggcc tgatatgtgg   89700
tggcactcac ctcccctgggc atccccggac aggctgcagg cacactgtgt ggcagggcag  89760
gctggtacct gctggcagct cctggggcct gatgtggagc aggcacagag ccgtatcccc   89820
ccgaggacat ataccccaa ggacggcaca gttggtacat tccggagaca agcaactcag    89880
ccacactccc aggccagagc ccgagaggga cgcccatgca cagggaggca gagcccagct   89940
cctccacagc cagcagcacc cgtgcagggg ccgccatctg gcaggcacag agcatgggct   90000
gggaggaggg gcagggacac caggcagggt tggcaccaac tgaaaattac agaagtctca   90060
tacatctacc tcagccttgc ctgacctggg cctcacctga cctgacctca acctggcctg   90120
gacctcacct ggcctagacc tcacctctgg gcttcacctg agctcggcct cacctgactt   90180
ggaccttgcc tgtcctgagc tcacatgatc tgggcctcac ctgacctggg tttcacctga   90240
cctgggcttc acctgacctg ggcctcatct gacctgggcc tcactggcct ggacctcacc   90300
tggcctgggc ttcacctggc ctcaggcctc atctgcacct gctccaggtc ttgctggaac   90360
ctcagtagca ctgaggctgc aggggctcat ccagggttgc agaatgactc tagaacctcc   90420
```

```
cacatctcag ctttctgggt ggaggcacct ggtggcccag ggaatataaa aagcctgaat   90480
gatgcctgcg tgatttgggg gcaatttata aacccaaaag gacatggcca tgcagcgggt   90540
agggacaata cagacagata tcagcctgaa atggagcctc agggcacagg tgggcacgga   90600
cactgtccac ctaagccagg ggcagacccg agtgtccccg cagtagacct gagagcgctg   90660
ggcccacagc ctcccctcgg tgccctgcta cctcctcagg tcagccctgg acatcccggg   90720
tttccccagg cctggcggta ggtttggggt gaggtctgtg tcactgtggt attacgattt   90780
ttggagtggt tattataccc acagtgtcac agagtccatc aaaaacccat ccctgggaac   90840
cttctgccac agccctccct gtggggcacc gccgcgtgcc atgttaggat tttgactgag   90900
gacacagcac catgggtatg gtggctaccg cagcagtgca gcccgtgacc caaacacaca   90960
gggcagcagg cacaacagac aagcccacaa gtgaccaccc tgagctcctg cctgccagcc   91020
ctggagacca tgaaacagat ggccaggatt atcccatagg tcagccagac ctcagtccaa   91080
caggtctgca tcgctgctgc cctccaatac cagtccggat ggggacaggg ctggcccaca   91140
ttaccatttg ctgccatccg gccaacagtc ccagaagccc ctccctcaag gctgggccac   91200
atgtgtggac cctgagagcc ccccatgtct gagtaggggc accaggaagg tggggctggc   91260
cctgtgcact gtccctgccc ctgtggtccc tggcctgcct ggccctgaca cctgggcctc   91320
tcctgggtca tttccaagac agaagacatt cccaggacag ctggagctgg gagtccatca   91380
tcctgcctgg ccgtcctgag tcctgcgcct ttccaaacct cacccgggaa gccaacagag   91440
gaatcacctc ccacaggcag agacaaagac cttccagaaa tctctgtctc tctccccagt   91500
gggcaccctc ttccagggca gtcctcagtg atatcacagt gggaacccac atctggatcg   91560
ggactgcccc cagaacacaa gatgcccac agggacagcc ccacagccca gcccttccca   91620 gaccccctaaa aggcgtccca cccctgcat ctgcccagg gctcaaactc caggaggact   91680
gactcctgca caccctcctg ccagacatca cctcagcccc tcctggaagg gacaggagcg   91740
cgcaagggtg agtcagaccc tcctgccctc gatggcaggc ggagaagatt cagaaaggtc   91800
tgagatcccc aggacgcagc accactgtca atggggggccc cagacgcctg gaccagggcc   91860
tgcgtgggaa aggcctctgg gcacactcag gggcttttg tgaagggtcc tcctactgtg   91920
tgactacagt aactaccaca gtgatgaacc cagcagcaaa aactgaccgg actcccaagg   91980
tttatgcaca cttctccgct cagagctctc caggatcaga agagccgggc ccaagggttt   92040
ctgcccagac cctcggcctc tagggacatc ttggccatga cagcccatgg gctggtgccc   92100
cacacatcgt ctgccttcaa acaagggctt cagagggctc tgaggtgacc tcactgatga   92160
ccacaggtgc cctggcccct tccccaccag ctgcaccaga cccgtcatg acagatgccc   92220 cgattccaac agccaattcc tggggccagg aatcgctgta gacaccagcc tcttccaac   92280 acctcctgcc aattgcctgg attcccatcc cggttggaat caagaggaca gcatccccca   92340
ggctcccaac aggcaggact cccacaccct cctctgagag gccgctgtgt tccgtagggc   92400
caggctgcag acagtccccc tcacctgcca ctagacaaat gcctgctgta gatgtcccca   92460
cctggaaaat accactcatg gagccccag ccccaggtac agctgtagag agagtctctg   92520
aggcccctaa gaagtagcca tgcccagttc tgccgggacc ctcggccagg ctgacaggag   92580
tggacgctgg agctgggccc atactgggcc acataggagc tcaccagtga gggcaggaga   92640
gcacatgccg gggagcaccc agcctcctgc tgaccgagg cccgtcccag agcccaggag   92700
gctgcagagg cctctccagg gggacactgt gcatgtctgg tccctgagca gcccccacg   92760
```

```
tccccagtcc tgggggcccc tggcacagct gtctggaccc tctctattcc ctgggaagct    92820
cctcctgaca gccccgcctc cagttccagg tgtggttatt gtcaggggt gtcagactgt     92880 ggtggataca gctatggtta ccacagtggt gctgcccata gcagcaacca ggccaagtag    92940
acaggcccct gctgtgcagc cccaggcctc cagctcacct gcttctcctg gggctctcaa    93000
ggctgctgtt ttctgcactc tcccctctgt ggggagggtt ccctcagtgg gagatctgtt    93060
ctcaacatcc cacggcctca ttcctgcaag gaaggccaat ggatgggcaa cctcacatgc    93120
cgcggctaag atagggtggg cagcctggcg ggacaggac atcctgctgg ggtatctgtc     93180
actgtgccta gtggggcact ggctcccaaa caacgcagtc cttgccaaaa tccccacggc    93240
ctcccccgct aggggctggc ctgatctcct gcagtcctag gaggctgctg acctccagaa    93300
tggctccgtc cccagttcca gggcgagagc agatcccagg ccggctgcag actgggaggc    93360 cacccctcc ttcccagggt tcactgcagg tgaccagggc aggaaatggc ctgaacacag      93420
ggataaccgg gccatccccc aacagagtcc accccctcct gctctgtacc ccgcaccccc    93480
caggccagcc catgacatcc gacaaccca caccagagtc actgcccggt gctgccctag      93540
ggaggacccc tcagccccca ccctgtctag aggactgggg aggacaggac acgccctctc    93600
cttatggttc ccccacctgg ctctggctgg dacccttggg gtgtggacag aaaggacgct    93660
tgcctgattg gccccagga gcccagaact tctctccagg gacccagcc cgagcacccc      93720 cttacccagg acccagccct gcccctcctc ccctctgctc tcctctcatc accccatggg    93780
aatccagaat ccccaggaag ccatcaggaa gggctgaggg aggaagtggg gccactgcac    93840
caccaggcag gaggctctgt ctttgtgaac ccagggaggt gccagcctcc tagagggtat    93900
ggtccaccct gcctatggct cccacagtgg caggctgcag ggaaggacca gggacggtgt    93960
gggggagggc tcagggcccc gcgggtgctc catcttggat gagcctatct ctctcaccca    94020
cggactcgcc cacctcctct tcaccctggc cacacgtcgt ccacaccatc ctaagtccca    94080
cctacaccag agccggcaca gccagtgcag acagaggctg gggtgcaggg gggccgactg    94140
ggcagcttcg gggagggagg aatggaggaa ggggagttca gtgaagaggc cccctcccc     94200 tgggtccagg atcctcctct gggaccccg gatcccatcc cctccaggct ctgggaggag     94260
aagcaggatg ggagaatctg tgcgggaccc tctcacagtg gaatacctcc acagcggctc    94320
aggccagata caaagccccc tcagtgagcc ctccactgca gtgctgggcc tgggggcagc    94380
cgctcccaca caggatgaac ccagcacccc gaggatgtcc tgccagggg agctcagagc      94440 catgaaggag caggatatgg gaccccgat acaggcacag acctcagctc cattcaggac      94500
tgccacgtcc tgccctggga ggaaccccttt tctctagtcc ctgcaggcca ggaggcagct    94560
gactcctgac ttggacgcct attccagaca ccagacagag gggcaggccc ccagaaccca    94620
gggatgagga cgccccgtca aggccagaaa agaccaagtt gcgctgagcc cagcaaggga    94680
aggtccccaa acaaaccagg aagtttctga aggtgtctgt gtcacagtgg agtatagcag    94740
ctcgtcccac agtgacactc gccaggccag aaacccatc ccaagtcagc ggaatgcaga     94800
gagagcaggg aggacatgtt taggatctga ggccgcacct gacacccagg ccagcagacg    94860
tctcctgtcc acggcaccct gccatgtcct gcatttctgg aagaacaagg gcaggctgaa    94920
gggggtccag gaccaggaga tgggtccgct ctacccagag aaggagccag gcaggacaca    94980
agccccctcc ccattgaggc tgacctgccc agagggtcct gggcccaccc aacacaccgg    95040
ggcggaatgt gtgcaggcct cggtctctgt gggtgttccg ctagctgggg ctcacagtgc    95100
tcaccccaca cctaaaacga gccacagcct ccggagcccc tgaaggagac cccgcccaca    95160
```

```
agcccagccc ccacccagga ggccccagag cacagggcgc cccgtcggat tctgaacagc   95220
cccgagtcac agtgggtata actggaacta ccactgtgag aaaagcttcg tccaaaacgg   95280
tctcctggcc acagtcggag gccccgccag agagggagc agccacccca aacccatgtt    95340
ctgccggctc ccatgacccc gtgcacctgg agccccacgg tgtccccact ggatgggagg   95400
acaagggccg ggggctccgg cgggtcgggg caggggcttg atggcttcct tctgccgtgg   95460
ccccattgcc cctggctgga gttgacccct ctgacaagtg tcctcagaga gtcagggatc   95520
agtggcacct cccaacatca accccacgca gcccaggcac aaaccccaca tccagggcca   95580
actccaggaa cagagacacc ccaatacccct ggggaccccc gaccctgatg actcccgtcc  95640
catctctgtc cctcacttgg ggcctgctgc ggggcgagca cttgggagca aactcaggct   95700
taggggacac cactgtgggc ctgacctcga gcaggccaca gacccttccc tcctgccctg   95760
gtgcagcaca gactttgggg tctgggcagg aggaacttc tggcaggtca ccaagcacag    95820
agcccccagg ctgaggtggc ccaggggga accccagcag gtggcccact acccttcctc    95880
ccagctggac cccatgtctt ccccaagata ggggtgccat ccaaggcagg tcctccatgg   95940
agcccccttc aggctcctct ccagacccca ctgggcctca gtccccactc taggaatgca   96000
gccaccacgg gcacaccagg cagcccaggc ccagccaccc tgcagtgccc aagcccacac   96060
cctggaggag agcagggtgc gtctgggagg ggctgggctc cccaccccca ccccacctg    96120 cacacccac ccaccctgc ccgggccccc tgcaggaggg tcagagcccc catgggatat     96180
ggacttaggg tctcactcac gcacctcccc tcctgggaga aggggtctca tgcccagatc   96240
cccccagcag cgctggtcac aggtagaggc agtggcccca gggccaccct gacctggccc   96300
ctcaggctcc tctagccctg gctgccctgc tgtccctggg aggcctgggc tccaccagac   96360
cacaggtcta gggcaccgcc cacactgggg ccgcccacac acagctcaca ggaagaagat   96420
aagctccaga cccccaggcc cgggacctgc cttgctgcta cgacttcctg ccccagacct   96480
cgttgccctc cccgtccac ttacacacag gccaggaagc tgttcccaca cagaccaacc    96540
ccagacgggg accacctggc actcaggtca ctgccatttc cttctccatt cacttccaat   96600
gcctctgtgc ttcctccctc ctccttcctt cgggggagca ccctgtgcag ctcctccctg   96660
cagtccacac cctggggaga cccgacccetg cagcccacac cctggggaga cctgacccte  96720 ctccagccct ttctccccccg ctgctcttgc cacccaccaa gacagcctg gggtcctgtc   96780 cctacagccc ccacccagtt ctctacctag acccgtcttc ctccctctaa acacctctcc   96840
caggccaacc ctacacctgc aggccctccc ctccactgcc aaagaccctc agtttctcct   96900
gcctgtgccc accccgtgc tcctcctgcc cacagctcga gctcttcctc tcctagggcc    96960
cctgagggat ggcattgacc gtgccctcgc acccacacac tgcccatgcc ctcacattcc   97020
tcctggccac tccagcccca ctcccctctc aggcctggct ctggtatttc tgggacaaag   97080
ccttacccaa gtctttccca tgcaggcctg ggccttacc ctcactgccc ggttacaggg    97140
cagcctcctg tgcacagaag cagggagctc agcccttcca caggcagaag gcactgaaag   97200
aaatcggcct ccagcgcctt gacacacgtc tgcctgtgtc tctcactgcc cgcacctgca   97260
gggaggctcg gcactccctc taaagacgag ggatccagga agcagcatca caggagaatg   97320
cagggctacc agacatccca gtcctctcac aggcctctcc tgggaagaga cctgaagacg   97380
cccagtcaac ggagtctaac accaaacctc cctggaggcc gatgggtagt aacggagtca   97440
ttgccagacc tggaggcagg ggagcagtga gcccgagccc acaccatagg gccagaggac   97500
```

```
agccactgac atcccaagcc actcactggt ggtcccacaa caccccatgg aaagaggaca   97560
gacccacagt cccacctgga ccagggcaga gactgctgag acccagcacc agaaccaacc   97620
aagaaacacc aggcaacagc atcagagggg gctctggcag aacagaggag gggaggtctc   97680
cttcaccagc aggcgcttcc cttgaccgaa gacaggatcc atgcaactcc cccaggacaa   97740
aggaggagcc ccttgttcag cactgggctc agagtcctct ccaagacacc cagagtttca   97800
gacaaaaacc ccctggaatg cacagtctca gcaggagagc cagccagagc cagcaagatg   97860
gggctcagtg acacccgcag ggacaggagg attttgtggg ggctcgtgtc actgtgagga   97920
tattgtacta atggtgtatg ctatacccac agtgacacag ccccattccc aaagccctac   97980
tgcaaacgca ttccacttct ggggctgagg ggctggggga gcgtctggga aatagggctc   98040
aggggtgtcc atcaatgccc aaaacgcacc agactcccct ccatacatca cacccaccag   98100
ccagcgagca gagtaaacag aaaatgagaa gcaagctggg gaagcttgca caggcccaa    98160 ggaaagagct ttggcgggtg tgtaagaggg gatgcgggca gagcctgagc agggcctttt   98220
gctgtttctg ctttcctgtg cagagagttc cataaactgg tgttcgagat caatggctgg   98280
gagtgagccc aggaggacag cgtgggaaga gcacagggaa ggaggagcag ccgctatcct   98340
acactgtcat ctttcgaaag tttgccttgt gcccacactg ctgcatcatg ggatgcttaa   98400
cagctgatgt agacacagct aaagagagaa tcagtgagat ggatttgcag cacagatctg   98460
aataaattct ccagaatgtg gagcagcaca gaagcaagca cacagaaagt gcctgatgca   98520
aggacaaagt tcagtgggca ccttcaggca ttgctgctgg gcacagacac tctgaaaagc   98580
cctggcagga actccctgtg acaaagcaga accctcaggc aatgccagcc ccagagccct   98640
ccctgagagc ctcatgggca aagatgtgca caacaggtgt ttctcatagc cccaaactga   98700
gagcaaagca aacgtccatc tgaaggagaa caggcaaata aacgatggca ggttcatgaa   98760
atgcaaaccc agacagccac aagcacaaaa gtacagggtt ataagcgact ctggttgagt   98820
tcatgacaat gctgagtaat tggagtaaca aagtaaactc caaaaaatac tttcaatgtg   98880
atttcttcta aataaaattt acaccctgca aaatgaactg tcttcttaag ggatacattt   98940
cccagttaga aaaccataaa gaaaccaag aaaaggatga tcacataaac acagtggtgg   99000
ttacttctgc tggggaagga agagggtatg aactgagata cacagggtgg gcaagtctcc   99060
taacaagaac agaacgaata cattacagta ccttgaaaac agcagttaaa cttctaaatt   99120
gcaagaagag gaaaatgcac acagttgtgt ttagaaaatt ctcagtccag cactgttcat   99180
aatagcaaag acattaaccc aggtcggata aataagcgat gacacaggca attgcacaat   99240
gatacagaca tatatttagt atatgagaca tcgatgatgt atccccaaat aaacgacttt   99300
aaagagataa agggctgatg tgtggtggca ttcacctccc tgggatcccc ggacaggttg   99360
caggctcact gtgcagcagg gcaggcgggt acctgctggc agttcctggg gcctgatgtg   99420
gagcaagcgc agggccatat atcccggagg acggcacagt cagtgaattc cagagagaag   99480
caactcagcc acactcccca ggcagagccc gagaggacg cccacgcaca gggaggcaga   99540
gcccagcacc tccgcagcca gcaccacctg cgcacgggcc accaccttgc aggcacagag   99600
tgggtgctga gaggaggggc agggacacca ggcagggtga gcacccagag aaaactgcag   99660
acgcctcaca catccaccct cagcctcccct gacctggacc tcactggcct gggcctcact   99720
taacctgggc ttcacctgac cttggcctca cctgacttgg acctcgcctg tcccaagctt   99780
tacctgacct gggcctcaac tcacctgaac gtcctgac ctgggtttaa cctgtcctgg   99840
aactcacctg gccttggctt cccctgacct ggacctcatc tggcctgggc ttcacctggc   99900
```

```
ctgggcctca cctgacctgg acctcatctg gcctggacct cacctggcct ggacttcacc    99960
tggcctgggc ttcacctgac ctggacctca cctggcctcg ggcctcacct gcacctgctc   100020
caggtcttgc tggagcctga gtagcactga gggtgcagaa gctcatccag ggttggggaa   100080
tgactctaga agtctcccac atctgacctt tctgggtgga ggcagctggt ggccctggga   100140
atataaaaat ctccagaatg atgactctgt gatttgtggg caacttatga acccgaaagg   100200
acatggccat ggggtgggta gggacatagg gacagatgcc agcctgaggt ggagcctcag   100260
gacacaggtg ggcacggaca ctatccacat aagcgaggga tagacccgag tgtccccaca   100320
gcagacctga gagcgctggg cccacagcct cccctcagag ccctgctgcc tcctccggtc   100380
agccctggac atcccaggtt tccccaggcc tggcggtagg tttagaatga ggtctgtgtc   100440
actgtggtat tacgatattt tgactggtta ttataaccac agtgtcacag agtccatcaa   100500
aaacccatgc ctggaagctt cccgccacag ccctcccccat ggggccctgc tgcctcctca   100560
ggtcagcccc ggacatcccg ggtttcccca ggctgggcgg taggtttggg gtgaggtctg   100620
tgtcactgtg gtattactat ggttcgggga gttattataa ccacagtgtc acagagtcca   100680
tcaaaaaccc atccctggga gcctcccgcc acagccctcc ctgcagggga ccggtacgtg   100740
ccatgttagg atttttgatcg aggagacagc accatgggta tggtggctac cacagcagtg   100800
cagcctgtga cccaaacccg cagggcagca ggcacgatgg acaggcccgt gactgaccac   100860
gctgggctcc agcctgccag ccctggagat catgaaacag atggccaagg tcaccctaca   100920
ggtcatccag atctggctcc gaggggtctg catcgctgct gccctcccaa cgccagtcca   100980
aatgggacag ggacggcctc acagcaccat ctgctgccat caggccagcg atcccagaag   101040
cccctccctc aaggctgggc acatgtgtgg acactgagag ccctcatatc tgagtagggg   101100
caccaggagg gagggctgg ccctgtgcac tgtccctgcc cctgtggtcc ctggcctgcc   101160
tggccctgac acctgagcct ctcctgggtc atttccaaga cagaagacat tcctggggac   101220
agccggagct gggcgtcgct catcctgccc ggccgtcctg agtcctgctc atttccagac   101280
ctcaccgggg aagccaacag aggactcgcc tcccacattc agagacaaag aaccttccag   101340
aaatccctgc ctctctcccc agtggacacc ctcttccagg acagtcctca gtggcatcac   101400
agcggcctga gatccccagg acgcagcacc gctgtcaata ggggccccaa atgcctggac   101460
cagggcctgc gtgggaaagg cctctggcca cactcgggct ttttgtgaag ggccctcctg   101520
ctgtgtgact acagtaacta ccatagtgat gaacccagtg gcaaaaactg gctggaaacc   101580
caggggctgt gtgcacgcct cagcttggag ctctccagga gcacaagagc cgggcccaag   101640
gatttgtgcc cagaccctca gcctctaggg acacctgggt catctcagcc tgggctggtg   101700
ccctgcacac catcttcctc caaataggggg cttcagaggg ctctgaggtg acctcactca   101760
tgaccacagg tgacctggcc cttccctgcc agctataccca gaccctgtct tgacagatgc   101820
cccgattcca acagccaatt cctgggaccc tgaatagctg tagacaccag cctcattcca   101880
gtacctcctg ccaattgcct ggattcccat cctggctgga atcaagaagg cagcatccgc   101940
caggctccca acaggcagga ctcccgcaca ccctcctctg agaggccgct gtgttccgca   102000
gggccaggcc ctggacagtt cccctcacct gccactagaa aaacacctgc cattgtcgtc   102060
cccacctgga aaagaccact cgtggagccc ccagcccag gtacagctgt agagacagtc   102120
ctcgaggccc ctaagaagga gccatgccca gttctgccgg gacccctcggc caggccgaca   102180
ggagtggacg ctggagctgg gcccacactg ggccacatag gagctcacca gtgagggcag   102240
```

```
gagagcacat gccggggagc acccagcctc ctgctgacca gaggcccgtc ccagagccca   102300
ggaggctgca gaggcctctc cagggagaca ctgtgcatgt ctggtaccta agcagccccc   102360
cacgtcccca gtcctggggg cccctggctc agctgtctgg gccctccctg ctccctggga   102420
agctcctcct gacagccccg cctccagttc caggtgtggt tatttgtcag cgatgtcaga   102480
ctgtggtgga tatagtggct acgattacca cagtggtgcc gcccatagca gcaaccaggc   102540
caagtagaca ggcccctgct gcgcagcccc aggcatccac ttcacctgct tctcctgggg   102600
ctctcaaggc tgctgtctgt cctctggccc tctgtgggga gggttccctc agtgggaggt   102660
ctgtgctcca gggcagggat gattgagata gaaatcaaag gctggcaggg aaaggcagct   102720
tcccgccctg agaggtgcag gcagcaccac ggagccacgg agtcacagag ccacggagcc   102780
cccattgtgg gcatttgaga gtgctgtgcc cccggcaggc ccagcccctga tgggaagcc   102840 tgtcccatcc cacagcccgg gtcccacggg cagcgggcac agaagctgcc aggttgtcct   102900
ctatgatcct catccctcca gcagcatccc ctccacagtg gggaaactga ggcttggagc   102960
accacccggc cccctggaaa tgaggctgtg agccagaca gtgggcccag agcactgtga   103020 gtacccggc agtacctggc tgcagggatc agccagagat gccaaaccct gagtgaccag   103080
cctacaggag gatccggccc cacccaggcc actcgattaa tgctcaaccc cctgccctgg   103140
agacctcttc cagtaccacc agcagctcag cttctcaggg cctcatccct gcaaggaagg   103200
tcaagggctg ggcctgccag aaacacagca ccctccctag ccctggctaa cagggtgg   103260 gcagacggct gtggacggga catattgctg gggcatttct cactgtcact tctgggtggt   103320
agctctgaca aaacgcaga ccctgccaaa atccccactg cctcccgcta ggggctggcc   103380
tggaatcctg ctgtcctagg aggctgctga cctccaggat ggctccgtcc ccagttccag   103440
ggcgagagca gatcccaggc aggctgtagg ctgggaggcc acccctgccc ttgccgggt   103500 tgaatgcagg tgcccaaggc aggaaatggc atgagcacag ggatgaccgg gacatgcccc   103560
accagagtgc gccccttcct gctctgcacc ctgcaccccc caggccagcc cacgacgtcc   103620
aacaactggg cctgggtggc agccccaccc agacaggaca gacccagcac cctgaggagg   103680
tcctgccagg gggagctaag agccatgaag gagcaagata tggggccccc gatacaggca   103740
cagatgtcag ctccatccag gaccacccag cccacaccct gagaggaacg tctgtctcca   103800
gcctctgcag gtcgggaggc agctgacccc tgacttggac ccctattcca gacaccagac   103860
agaggcgcag gcccccaga accaggggttg agggacgccc cgtcaaagcc agacaaaacc   103920 aagggggtgtt gagcccagca agggaaggcc cccaaacaga ccaggaggtt tctgaaggtg   103980
tctgtgtcac agtggggtat agcagcagct ggtaccacag tgacactcac ccagccagaa   104040
accccattcc aagtcagcgg aagcagagag agcagggagg acacgtttag gatctgagac   104100
tgcacctgac acccaggcca gcagacgtct cccctccagg gcaccccacc ctgtcctgca   104160
tttctgcaag atcaggggcg gcctgagggg gggtctaggg tgaggagatg ggtcccctgt   104220
acaccaagga ggagttaggc aggtcccgag cactctcccc attgaggctg acctgcccag   104280
agagtcctgg gccaccccca cacccggggg cggaatgtgt gcaggcctcg gtctctgtgg   104340
gtgttccgct agctggggct cacagtgctc accccacacc taaaatgagc cacagcctcc   104400
ggagcccccg caggagaccc cgcccacaag cccagccccc acccaggagg ccccagagct   104460
cagggcgccc cgtcggattc cgaacagccc cgagtcacag cgggtataac cggaaccacc   104520
actgtcagaa tagctacgtc aaaaactgtc cagtggccac tgccggaggc cccgccagag   104580
agggcagcag ccactctgat cccatgtcct gccggctccc atgacccca gcacgcggag   104640
```

```
ccccacagtg tccccactgg atgggaggac aagagctggg gattccggcg ggtcggggca 104700
ggggcttgat cgcatccttc tgccgtggct ccagtgcccc tggctggagt tgacccttct 104760
gacaagtgtc ctcagagaga caggcatcac cggcgcctcc caacatcaac cccaggcagc 104820
acaggcacaa accccacatc cagagccaac tccaggagca gagacacccc aatacccctgg 104880
gggaccccga ccctgatgac ttcccactgg aattcgccgt agagtccacc aggaccaaag 104940
accctgcctc tgcctctgtc cctcactcag gacctgctgc cgggcgaggc cttgggagca 105000
gacttgggct taggggacac cagtgtgacc ccgaccttga ccaggacgca gacctttcct 105060
tcctttcctg gggcagcaca gactttgggg tctgggccag gaggaacttc tggcaggtcg 105120
ccaagcacag aggccacagg ctgaggtggc cctggaaaga cctccaggag gtggccactc 105180
cccttcctcc cagctggacc ccatgtcctc cccaagataa gggtgccatc caaggcaggt 105240
gctccttgga gccccattca gactcctccc tggacccac tgggcctcag tcccagctct 105300
ggggatgaag ccaccacaag cacaccaggc agcccaggcc cagccaccct gcagtgccca 105360
agcacacact ctggagcaga gcagggtgcc tctgggaggg gctgagctcc ccaccccacc 105420
cccacctgca cacccccaccc acccctgccc agcggctctg caggagggtc agagcccac 105480
atggggtatg gacttagggt ctcactcacg tggctcccat catgagtgaa ggggcctcaa 105540
gcccaggttc ccacagcagc gcctgtcgca agtggaggca gaggcccgag gccacccctg 105600
acctggtccc tgaggttcct gcagcccagg ctgccctgct gtccctggga ggcctgggct 105660
ccaccagacc acaggtccag ggcaccgggt gcaggagcca cccacacaca gctcacagga 105720
agaagataag ctccagaccc ccagggccag aacctgcctt cctgctactg cttcctgccc 105780
cagacctggg cgccctcccc cgtccactta cacacaggcc aggaagctgt tcccacacag 105840
aacaacccca aaccaggacc gcctggcact caggtggctg ccatttcctt ctccatttgc 105900
tcccagcgcc tctgtcctcc ctggttcctc cttcggggga acagcctgtg cagccagtcc 105960
ctgcagccca caccctgggg agacccaacc ctgcctgggg ccctccaac cctgctgctc 106020
ttactgccca cccagaaaac tctggggtcc tgtccctgca gtccctaccc tggtctccac 106080
ccagacccct gtgtatcact ccagacaccc ctcccaggca aaccctgcac ctgcaggccc 106140
tgtcctcttc tgtcgctaga gcctcagttt ctcccccctg tgcccacacc ctacctcctc 106200
ctgcccacaa ctctaactct tcttctcctg gagcccctga gccatggcat tgaccctgcc 106260
ctcccaccac ccacagccca tgccctcacc ttcctcctgg ccactccgac cccgccccct 106320
ctcaggccaa gccctggtat ttccaggaca aaggctcacc caagtctttc ccaggcaggc 106380
ctgggctctt gccctcactt cccggttaca cgggagcctc ctgtgcacag aagcagggag 106440
ctcagccctt ccacaggcag aaggcactga agaaatcgg cctccagcac cttgacacac 106500
gtccgcccgt gtctctcact gcccgcacct gcagggaggc tccgcactcc ctctaaagac 106560
aagggatcca ggcagcagca tcacgggaga atgcagggct cccagacatc ccagtcctct 106620
cacaggcctc tcctgggaag agacctgcag ccaccaccaa acagccacag aggctgctgg 106680
atagtaactg agtcaatgac cgacctggag ggcaggggag cagtgagccg gagcccatac 106740
catagggaca gagaccagcc gctgacatcc cgagctcctc aatggtggcc ccataacaca 106800
cctaggaaac ataacacacc cacagcccca cctggaacag ggcagagact gctgagcccc 106860
cagcaccagc cccaagaaac accaggcaac agtatcagag ggggctcccg agaaagagag 106920
gaggggagat ctccttcacc atcaaatgct tcccttgacc aaaaacaggg tccacgcaac 106980
```

```
tcccccagga caaaggagga gcccctata cagcactggg ctcagagtcc tctctgagac 107040
accctgagtt tcagacaaca acccgctgga atgcacagtc tcagcaggag aacagaccaa 107100
agccagcaaa agggacctcg gtgacaccag tagggacagg aggattttgt gggggctcgt 107160
gtcactgtga ggatattgta gtggtggtag ctgctactcc cacagtgaca cagacccatt 107220
cccaaagccc tactgcaaac acacccactc ctggggctga ggggctgggg gagcgtctgg 107280
gaagtagggt ccaggggtgt ctatcaatgt ccaaaatgca ccagactccc cgccaaacac 107340
caccccacca gccagcgagc agggtaaaca gaaaatgaga ggctctggga agcttgcaca 107400 ggcccccaagg aaagagcttt ggcgggtgtg caagagggga tgcaggcaga gcctgagcag 107460
ggccttttgc tgtttctgct ttcctgtgca gagagttcca taaactggtg ttcaagatca 107520
gtggctggga atgagcccag gagggcagtc tgtgggaaga gcacagggaa ggaggagcag 107580
ccgctatcct acactgtcat cttttcaaaag tttgccttgt gaccacacta ttgcatcatg 107640
ggatgcttaa gagctgatgt agacacagct aaagagagaa tcagtgagat gaatttgcag 107700
catagatctg aataaactct ccagaatgtg gagcagtaca aagcaaaaca cacagaaagt 107760
gcctgatgca aggacaaagt tcagtgggca ccttcaggca ttgctgctgg gcacagacac 107820
tctgaaaagc cttggcagga tctccctgcg acaaagcaga accctcaggc aatgccagcc 107880
ccagagccct ccctgagagc gtcatgggga aagatgtgca gaacagctga ttatcataga 107940
ctcaaactga gaacagagca aacgtccatc tgaagaacag tcaaataagc aatggtaggt 108000
tcatgcaatg caaacccaga cagccagggg acaacagtag agggctacag gcggctttgc 108060
ggttgagttc atgacaatgc tgagtaattg gagtaacaga ggaaagccca aaaaatactt 108120
ttaatgtgat ttcttctaaa taaaatttac accaggcaaa atgaactgtc ttcttaaggg 108180
ataaactttc ccctggaaaa actacaagga aaattaagaa aacgatgatc acataaacac 108240
agttgtggtt acttctactg gggaaggaag agggtatgag ctgagacaca cagagtcggc 108300
aagtctccaa gcaagcacag aacgaataca ttacagtacc ttgaatacag cagttaaact 108360
tctaaatcgc aagaacagga aaatgcacac agctgtgttt agaaaattct cagtccagca 108420
ctattcataa tagcaaagac attaacccag gttggataaa taaatgatga cacaggcaat 108480
tgcacaatga tacagacata catttagtac atgagacatc gatgatgtat ccccaaagaa 108540
atgactttaa agagaaaagg cctgatgtgt ggtggcactc acctccctgg gatccccgga 108600
caggttgcag gcacactgtg tggcagggca ggctggtaca tgctggcagc tcctggggcc 108660
tgatgtggag caagcgcagg gctgtatacc cccaaggatg gcacagtcag tgaattccag 108720
agagaagcag ctcagccaca ctgcccaggc agagcccgag agggacgccc acgtacaggg 108780
aggcagagcc cagctcctcc acagccacca ccacctgtgc acgggccacc accttgcagg 108840
cacagagtgg gtgctgagag gaggggcagg gacaccaggc agggtgagca cccagagaaa 108900
actgcagaag cctcacacat ccacctcagc ctcccctgac ctggacctca cctggtctgg 108960
acctcacctg gcctgggcct cacctgacct ggacctcacc tggcctgggc ttcacctgac 109020
ctggacctca cctggcctcc ggcctcacct gcacctgctc caggtcttgc tggaacctga 109080
gtagcactga ggctgcagaa gctcatccag ggttggggaa tgactctgga actctcccac 109140
atctgacctt tctgggtgga ggcatctggt ggccctggga atataaaaag ccccagaatg 109200
gtgcctgcgt gatttggggg caatttatga acccgaaagg acatggccat ggggtgggta 109260
gggacatagg gacagatgcc agcctgaggt ggagcctcag gacacagttg gacgcggaca 109320
ctatccacat aagcgaggga cagacccgag tgttcctgca gtagacctga gagcgctggg 109380
```

```
cccacagcct cccctcggtg ccctgctgcc tcctcaggtc agccctggac atcccgggtt   109440
tccccaggcc agatggtagg tttgaagtga ggtctgtgtc actgtggtat tatgattacg   109500
tttgggggag ttatcgttat acccacagca tcacacggtc catcagaaac ccatgccaca   109560
gccctccccg caggggaccg ccgcgtgcca tgttacgatt ttgatcgagg acacagcgcc   109620
atgggtatgg tggctaccac agcagtgcag cccatgaccc aaacacacag gcagcaggc    109680 acaatggaca ggcctgtgag tgaccatgct gggctccagc ccgccagccc cggagaccat   109740
gaaacagatg gccaaggtca ccccacagtt cagccagaca tggctccgtg ggtctgcat    109800 cgctgctgcc ctctaacacc agcccagatg gggacaaggc caaccccaca ttaccatctc   109860
ctgctgtcca cccagtggtc ccagaagccc ctccctcatg gctgagccac atgtgtgaac   109920
cctgagagca ccccatgtca gagtaggggc agcagaaggg cggggctggc cctgtgcact   109980
gtccctgcac ccatggtccc tcgcctgcct ggccctgaca cctgagcctc ttctgagtca   110040
tttctaagat agaagacatt cccggggaca gccggagctg ggcgtcgctc atcccgcccg   110100
gccgtcctga gtcctgcttg tttccagacc tcaccaggga agccaacaga ggactcacct   110160
cacacagtca gagacaaaga accttccaga aatccctgtc tcactcccca gtgggcacct   110220
tcttccagga cattcctcgg tcgcatcaca gcaggcaccc acatctggat caggacggcc   110280
cccagaacac aagatggccc atggggacag ccccacaacc caggccttcc cagaccccta   110340
aaaggcgtcc caccccctgc acctgcccca gggctaaaaa tccaggaggc ttgactcccg   110400
cataccctcc agccagacat cacctcagcc ccctcctgga ggggacagga gcccgggagg   110460
gtgagtcaga cccacctgcc ctcgatggca ggcggggaag attcagaaag gcctgagatc   110520
cccaggacgc agcaccactg tcaatggggg ccccagacgc ctggaccagg gcctgcgtgg   110580
gaaaggccgc tgggcacact cagggggcttt ttgtgaaggc ccctcctact gtgtgactac   110640
ggtgactacc acagtgatga aactagcagc aaaaactggc cggacaccca gggaccatgc   110700
acacttctca gcttggagct ctccaggacc agaagagtca ggtctgaggg tttgtagcca   110760
gaccctcggc tctagggac accctggcca tcacagcgga tggctggtg ccccacatgc    110820 catctgctcc aaacagggc ttcagagggc tctgaggtga cttcactcat gaccacaggt    110880
gccctggccc cttccccgcc agctacaccg aaccctgtcc caacagctgc cccagttcca   110940
acagccaatt cctggggccc agaattgctg tagacaccag cctcgttcca gcacctcctg   111000
ccaattgcct ggattcacat cctggctgga atcaagaggg cagcatccgc caggctccca   111060
acaggcagga ctcccgcaca ccctcctctg agaggccgct gtgttccgca gggccaggcc   111120
ctggacagtt cccctcacct gccactagag aaacacctgc cattgtcgtc cccacctgga   111180
aaagaccact cgtggagccc ccagcccag gtacagctgt agagagactc cccgagggat    111240
ctaagaagga gccatgcgca gttctgccgg gaccctcggc caggccgaca ggagtggaca   111300
ctggagctgg gccacactg gccacatag gagctcacca gtgagggcag gagagcacat    111360
gccggggagc acccagcctc ctgctgacca gaggcccgtc ccagagccca ggaggctgca   111420
gaggcctctc cagggggaca ctgtgcatgt ctggtccctg agcagccccc cacgtcccca   111480
gtcctggggg cccctggcac agctgtctgg accctccctg ttccctggga agctcctcct   111540
gacagccccg cctccagttc caggtgtggt tattgtcagg gggtgtcaga ctgtggtgga   111600
tacagctatg gttaccacag tggtgctgcc catagcagca accaggccaa gtagacaggc   111660
ccctgctgtg cagccccagg cctccacttc acctgcttct cctggggctc tcaaggtcac   111720
```

```
tgttgtctgt actctgccct ctgtggggag ggttccctca gtgggaggtc tgttctcaac   111780
atcccagggc ctcatgtctg cacggaaggc caatggatgg gcaacctcac atgccgcggc   111840
taagatagggg tgggcagcct ggcggggggac agtacatact gctgggtgt ctgtcactgt   111900
gcctagtggg gcactggctc ccaaacaacg cagtcctcgc caaaatcccc acagcctccc   111960
ctgctagggg ctggcctgat ctcctgcagt cctaggaggc tgctgacctc cagaatgtct   112020
ccgtccccag ttccagggcg agagcagatc ccaggccggc tgcagactgg gaggccaccc   112080
cctccttccc agggttcact ggaggtgacc aaggtaggaa atggccttaa cacagggatg   112140
actgcgccat ccccaacag agtcagcccc ctcctgctct gtaccccgca ccccccaggc   112200
cagtccacga aaaccagggc cccacatcag agtcactgcc tggcccggcc ctgggcgga   112260
ccccctcagcc cccaccctgt ctagaggact tgggggaca ggacacaggc cctctcctta   112320
tggttccccc acctgcctcc ggccgggacc cttgggtgt ggacagaaag gacacctgcc   112380
taattggccc ccaggaaccc agaacttctc tccaggacc ccagcccgag cacccccta   112440
cccaggaccc agccctgccc ctcctcccct ctgctctcct ctcatcaccc catgggaatc   112500
cggtatcccc aggaagccat caggaagggc tgaaggagga agcggggccg tgcaccaccg   112560
ggcaggaggc tccgtcttcg tgaacccagg gaagtgccag cctcctagag ggtatggtcc   112620
accctgcctg gggctcccac cgtggcaggc tgcggggaag gaccagggac ggtgtgggg   112680
agggctcagg gccctgcggg tgctcctcca tcttcggtga gctccccct tcacccaccg   112740
tcccgcccac ctcctctcca ccctggctgc acgtcttcca caccatcctg agtcctacct   112800
acaccagagc cagcaaagcc agtgcagaca aaggctgggg tgcaggggg ctgccagggc   112860
agcttcgggg agggaaggat ggagggaggg gaggtcagtg aagaggcccc cttccctgg   112920
gtccaggatc ctcctctggg accccggat cccatccct cctggctctg gggagagaag   112980
caggatggga gaatctgtgc gggaccctct cacagtggaa tatcccaca gcggctcagg   113040
ccagacccaa aagcccctca gtgagccctc cactgcagtc ctgggcctgg gtagcagccc   113100
ctcccacaga ggacagaccc agcaccccga agaagtcctg ccaggggag ctcagagcca   113160
tgaaagagca ggatatgggg tccccgatac aggcacagac ctcagctcca tccaggccca   113220
ccgggaccca ccatgggagg aacacctgtc tccgggttgt gaggtagctg gcctctgtct   113280
cggaccccac tccagacacc agacagaggg gcaggccccc caaaaccagg gttgaggat   113340
gatccgtcaa ggcagacaag accaaggggc actgaccca gcaagggaag gctcccaaac   113400
agacgaggag gtttctgaag ctgtctgtat cacagtgggg tatagcagtg gctggtacca   113460
cagtgacact cgccaggcca gaaaccccgt cccaagtcag cggaagcaga gagagcaggg   113520
aggacacgtt taggatctga ggccgcacct gacacccagg gcagcagacg tctcccctcc   113580
agggcaccct ccaccgtcct gcgtttcttc aagaatagg gcggcctgag ggggtccagg   113640
gccaggcgat aggtcccctc taccccaagg aggagccagg caggacccga gcaccgtccc   113700
cattgaggct gacctgccca gacgggcctg ggcccacccc acacaccggg gcggaatgtg   113760
tgcaggcccc agtctctgtg ggtgttccgc tagctgggc cccagtgct cacccacac   113820
ctaaagcgag cccagcctc cagagccccc taagcattcc ccgcccagca gcccagcccc   113880
tgcccccacc caggaggccc cagagctcag ggcgcctggt cggattctga acagcccga   113940
gtcacagtgg gtataactgg aacgaccacc gtgagaaaaa ctgtgtccaa aactgactcc   114000
tggcagcagt cggaggcccc gccagagagg ggagcagccg gcctgaaccc atgtcctgcc   114060
ggttcccatg accccagca cccagagccc cacggtgtcc ccgttggata atgaggacaa   114120
```

```
gggctggggg ctccggtggt ttgcggcagg gacttgatca catccttctg ctgtggcccc  114180
attgcctctg gctggagttg acccttctga caagtgtcct cagaaagaca gggatcaccg  114240
gcacctccca atatcaaccc caggcagcac agacacaaac cccacatcca gagccaactc  114300
caggagcaga gacaccccaa cactctgggg gaccccaacc gtgataactc cccactggaa  114360
tccgccccag agtctaccag gaccaaaggc cctgccctgt ctctgtccct cactcagggc  114420
ctcctgcagg gcgagcgctt gggagcagac tcggtcttag gggacaccac tgtgggcccc  114480
aactttgatg aggccactga cccttccttc ctttcctggg gcagcacaga ctttggggtc  114540
tgggcaggga agaactactg gctggtggcc aatcacagag cccccaggcc gaggtggccc  114600
caagaaggcc ctcaggaggt ggccactcca cttcctccca gctggacccc aggtcctccc  114660
caagataggg gtgccatcca aggcaggtcc tccatggagc ccccttcaga ctcctcccgg  114720 gacccactg gacctcagtc cctgctctgg gaatgcagcc accacaagca caccaggaag  114780
cccaggccca gccaccctgc agtgggcaag cccacactct ggagcagagc agggtgcgtc  114840
tgggaggggc taacctcccc accccccacc ccccatctgc acacagccac ctaccactgc  114900
ccagaccctc tgcaggaggg ccaagccacc atggggtatg gacttagggt ctcactcacg  114960
tgcctcccct cctgggagaa ggggcctcat gcccagatcc ctgcagcact agacacagct  115020
ggaggcagtg gccccagggc caccctgacc tggcatctaa ggctgctcca gcccagacag  115080
cactgccgtt cctgggaagc ctgggctcca ccagaccaca ggtccagggc acagcccaca  115140
ggagccaccc acacacagct cacaggaaga agataagctc cagacccag ggcgggaccct  115200 gccttcctgc caccacttac acacaggcca gggagctgtt cccacacaga tcaacccccaa  115260 accgggactg cctggcacta gggtcactgc catttccctc tccattccct cccagtgcct  115320
ctgtgctccc tccttctggg gaacaccctg tgcagcccct cctgcagcc cacacgctgg  115380 ggagacccca ccctgcctcg ggccttttct acctgctgca cttgccgccc acccaaacaa  115440
ccctgggtac gtgaccctgc agtcctcacc ctgatctgca accagacccc tgtccctccc  115500
tctaaacacc cctcccaggc caactctgca cctgcaggcc ctccgctctt ctgccacaag  115560
agcctcaggt tttcctacct gtgcccaccc cctaaccccct cctgcccaca acttgagttc  115620
ttcctctcct ggagcccttg agccatggca ctgaccctac actcccaccc acacactgcc  115680
catgccatca ccttcctcct ggacactctg accccgctcc cctccctctc agacccggcc  115740
ctggtatttc caggacaaag gctcacccaa gtcttcccca tgcaggccct tgccctcact  115800
gcctggttac acgggagcct cctgtgcgca gaagcaggga gctcagctct tccacaggca  115860
gaaggcactg aaagaaatca gcctccagtg ccttgacaca cgtccgcctg tgtctctcac  115920
tgcctgcacc tgcagggagg ctccgcactc cctctaaaga tgagggatcc aggcagcaac  115980
atcacgggag aatgcagggc tcccagacag cccagccctc tcgcaggcct ctcctgggaa  116040
gagacctgca gccaccactg aacagccacg gaggtcgctg gatagtaacc gagtcagtga  116100
ccgacctgga gggcagggga gcagtgaacc ggagcccata ccatagggac agagaccagc  116160
cgctaacatc ccgagcccct cactggcggc cccagaacac cccgtggaaa gagaacagac  116220
ccacagtccc acctggaaca gggcagacac tgctgagccc ccagcaccag ccccaagaaa  116280
cactaggcaa cagcatcaga gggggctcct gagaaagaga ggagggagg tctccttcac  116340 catcaaatgc ttcccttgac caaaaacagg gtccacgcaa ctcccccagg acaaaggagg  116400 agcccctgt acagcactgg gctcagagtc ctctctgaga caggctcagt ttcagacaac  116460
```

```
aacccgctgg aatgcacagt ctcagcagga gagccaggcc agagccagca agaggagact  116520
cggtgacacc agtctcctgt agggacagga ggattttgtg ggggttcgtg tcactgtgag  116580
catattgtgg tggtgactgc tattcccaca gtgacacaac cccattccta aagccctact  116640
gcaaacgcac ccactcctgg gactgagggg ctggggagc gtctgggaag tatggcctag  116700
gggtgtccat caatgcccaa aatgcaccag actctcccca agacatcacc ccaccagcca  116760
gtgagcagag taaacagaaa atgagaagca gctgggaagc ttgcacaggc cccaaggaaa  116820
gagctttggc aggtgtgcaa gagggatgt gggcagagcc tcagcagggc cttttgctgt  116880
ttctgctttc ctgtgcagag agttccataa actggtattc aagatcaatg ctgggagtg  116940 agcccaggag gacagtgtgg gaagagcaca gggaaggagg agcagccgct atcctacact  117000
gtcatctttt gaaagtttgc cctgtgccca caatgctgca tcatgggatg cttaacagct  117060
gatgtagaca cagctaaaga gagaatcagt gaaatgcatt tgcagcacag atctgaataa  117120
atcctccaga atgtggagca gcacagaagc aagcacacag aaagtgcctg atgccaaggc  117180
aaagttcagt gggcacccttc aggcattgct gctgggcaca gacactctga aaagcactgg  117240
caggaactgc ctgtgacaaa gcagaaccct caggcaatgc cagccctaga gcccttcctg  117300
agaacctcat gggcaaagat gtgcagaaca gctgtttgtc atagcccaa actatgggc  117360 tggacaaagc aaacgtccat ctgaaggaga acagacaaat aaacgatggc aggttcatga  117420
aatgcaaact aggacagcca gaggacaaca gtagagagct acaggcggct ttgcggttga  117480
gttcatgaca atgctgagta attggagtaa cagaggaaag cccaaaaaat actttttaatg  117540 tgatttcttc taaataaaat ttacacccgg caaaatgaac tatcttctta agggataaac  117600 tttccctgg aaaaactata aggaaatca agaaacgat gatcacataa acacagtggt  117660
ggttacttct actggggaag gaagagggta tgagctgaga cacacagagt cggcaagtct  117720
cctaacaaga acagaacaaa tacattacag taccttgaaa acagcagtta aacttctaaa  117780
tcgcaagaag aggaaaatgc acacacctgt gtttagaaaa ttctcagtcc agcactgttc  117840
ataatagcaa agacattaac ccaggttgga taaataagcg atgacacagg caattgcaca  117900
atgatacaga catacattca gtatatgaga catcgatgat gtatccccaa agaaatgact  117960
ttaaagagaa aaggcctgat gtgtggtggc aatcacctcc ctgggcatcc ccggacaggc  118020
tgcaggctca ctgtgtggca gggcaggcag gcacctgctg gcagctcctg ggcctgatg  118080 tggagcaggc acagagctgt atatccccaa ggaaggtaca gtcagtgcat tccagagaga  118140
agcaactcag ccacactccc tggccagaac ccaagatgca cacccatgca cagggaggca  118200
gagcccagca cctccgcagc caccaccacc tgcgcacggg ccaccacctt gcaggcacag  118260
agtgggtgct gagaggaggg gcaggacac caggcagggt gagcacccag agaaaactgc  118320
agaagcctca cacatccacc tcagcctccc ctgacctgga cctcacctgg cctgggcctc  118380
acctgacctg gacctcacct ggcctgggct tcacctggcc tgggcttcac ctgacctgga  118440
cctcacctgg cctcgggcct cacctggcct gggcttcacc tggcctgggc ttcacctgac  118500
ctggacctca cctggcctgg gcctcacctg acctggacct cacctggcct gggcttcacc  118560
tggcctgggt tcacctggc ctgggcttca cctgacctgg acctcacctg gcctgggctt  118620
cacctgacct ggacctcacc tggcctcggg cctcacctgc acctgctcca ggtcttgctg  118680
gagcctgagt agcactgagg ctgtagggac tcatccaggg ttggggaatg actctgcaac  118740
tctcccacat ctgaccttc tggggtggagg cacctggtgg cccagggaat ataaaaagcc  118800
ccagaatgat gcctgtgtga tttggggca atttatgaac ccgaaaggac atggccatgg  118860
```

```
ggtgggtagg gacagtaggg acagatgtca gcctgaggtg aagcctcagg acacaggtgg    118920
gcatggacag tgtccaccta agcgagggac agacccgagt gtccctgcag tagacctgag    118980
agcgctgggc ccacagcctc ccctcggggc cctgctgcct cctcaggtca gccctggaca    119040
tcccgggttt ccccaggcct ggcggtaggt ttgaagtgag gtctgtgtca ctgtggtatt    119100
actatgatag tagtggttat tactaccaca gtgtcacaga gtccatcaaa aactcatgcc    119160
tgggagcctc ccaccacagc cctccctgcg ggggaccgct gcatgccgtg ttaggatttt    119220
gatcgaggac acggcgccat gggtatggtg gctaccacag cagtgcagcc catgacccaa    119280
acacacgggg cagcagaaac aatggacagg cccacaagtg accatgatgg gctccagccc    119340
accagcccca gagaccatga aacagatggc caaggtcacc ctacaggtca tccagatctg    119400
gctccaaggg gtctgcatcg ctgctgccct cccaacgcca aaccagatgg agacagggcc    119460
ggccccatag caccatctgc tgccgtccac ccagcagtcc cggaagcccc tccctgaacg    119520
ctgggccacg tgtgtgaacc ctgcgagccc ccatgtcag agtaggggca gcaggagggc    119580
ggggctggcc ctgtgcactg tcactgcccc tgtggtccct ggcctgcctg gccctgacac    119640
ctgagcctct cctgggtcat ttccaagaca ttcccaggga cagccggagc tgggagtcgc    119700
tcatcctgcc tggctgtcct gagtcctgct catttccaga cctcaccagg gaagccaaca    119760
gaggactcac ctcacacagt cagagacaac gaaccttcca gaaatccctg tttctctccc    119820
cagtgagaga aaccctcttc cagggtttct cttctctccc accctcttcc aggacagtcc    119880
tcagcagcat cacagcggga acgcacatct ggatcaggac ggcccccaga acacgcgatg    119940
gcccatgggg acagcccagc ccttcccaga cccctaaaag gtatcccac cttgcacctg    120000 ccccagggct caaactccag gaggcctgac tcctgcacac cctcctgcca gatatcacct    120060 cagcccctc ctggagggga caggagcccg ggagggtgag tcagacccac ctgccctcaa    120120
tggcaggcgg ggaagattca gaaaggcctg agatccccag gacgcagcac cactgtcaat    120180 ggggggcccca gacgcctgga ccagggcctg tgtgggaaag gcctctggcc acactcaggg    120240 gcttttgtg aagggccctc ctgctgtgtg actacggtgg taactcccac agtgatgaaa    120300
ccagcagcaa aaactgaccg gactcgcagg gtttatgcac acttctcggc tcggagctct    120360
ccaggagcac aagagccagg cccgagggtt tgtgcccaga ccctcggcct ctaggacac    120420 ccgggccatc ttagccgatg ggctgatgcc ctgcacaccg tgtgctgcca aacagggct    120480 tcagagggct ctgaggtgac ttcactcatg accacaggtg ccctggtccc ttcactgcca    120540
gctgcaccag accctgttcc gagagatgcc ccagttccaa aagccaattc ctggggccgg    120600
gaattactgt agacaccagc ctcattccag tacctcctgc caattgcctg gattcccatc    120660
ctggctggaa tcaagagggc agcatccgcc aggctcccaa caggcaggac tcccacacac    120720
cctcctctga gaggccgctg tgttccgcag ggccaggccg cagacagttc ccctcacctg    120780
cccatgtaga aacacctgcc attgtcgtcc ccacctggca aagaccactt gtggagcccc    120840
cagccccagg tacagctgta gagagagtcc tcgaggcccc taagaaggag ccatgcccag    120900
ttctgccggg accctcggcc aggccgacag gagtggacgc tggagctggg cccacactgg    120960
gccacatagg agctcaccag tgagggcagg agagcacatg ccggggagca cccagcctcc    121020
tgctgaccag agaccegtcc cagagccag gaggctgcag aggcctctcc aggggacac    121080 agtgcatgtc tggtccctga gcagccccca ggctctctag cactgggggc ccctggcaca    121140
gctgtctgga ccctccctgt tccctgggaa gctcctcctg acagcccgc ctccagttcc    121200
```

```
aggtgtggtt attgtcaggg ggtgccaggc cgtggtagag atggctacaa ttaccacagt   121260
ggtgccgccc atagcagcaa ccaggccaag tagacagacc cctgccacgc agccccaggc   121320
ctccagctca cctgcttctc ctggggctct caaggctgct gtctgccctc tggccctctg   121380
tggggagggt tccctcagtg ggaggtctgt gctccagggc agggatgact gagatagaaa   121440
tcaaaggctg gcagggaaag gcagcttccc gccctgagag gtgcaggcag caccacagag   121500
ccatggagtc acagagccac ggagccccca gtgtgggcgt gtgagggtgc tgggctcccg   121560
gcaggcccag ccctgatggg gaagcctgcc ccgtcccaca gcccaggtcc ccaggggcag   121620
caggcacaga agctgccaag ctgtgctcta cgatcctcat ccctccagca gcatccactc   121680
cacagtgggg aaactgagcc ttggagaacc acccagcccc ctggaaacaa ggcggggagc   121740
ccagacagtg ggcccagagc actgtgtgta tcctggcact aggtgcaggg accacccgga   121800
gatccccatc actgagtggc cagcctgcag aaggacccaa ccccaaccag gccgcttgat   121860
taagctccat cccctgtcc tgggaacctc ttcccagcgc caccaacagc tcggcttccc   121920
aggccctcat ccctccaagg aaggccaaag gctgggcctg ccaggggcac agtaccctcc   121980
cttgccctgg ctaagacagg gtgggcagac ggctgcagat aggacatatt gctgggcat    122040 cttgctctgt gactactggg tactggtctt caacgcagac cctaccaaaa tccccactgc   122100 ctccctgct aggggctggc ctggtctcct cctgctgtcc taggaggctg ctgacctcca   122160
ggatggcttc tgtccccagt tctagggcca gagcagatcc caggcaggct gtaggctggg   122220
aggccacccc tgtccttgcc gaggttcagt gcaggcaccc aggacaggaa atggcctgaa   122280
cacagggatg actgtgccat gccctaccta agtccgcccc tttctactct gcaacccca    122340 ctccccaggt cagcccatga cgaccaacaa cccaacacca gagtcactgc ctggccctgc   122400
cctggggagg acccctcagc ccccaccctg tctagaggag ttgggggggac aggacacagg   122460 ctctctcctt atggttcccc cacctggctc ctgccgggac ccttggggtg tggacagaaa   122520
ggacgcctgc ctaattggcc cccaggaacc cagaacttct ctccagggac cccagcccga   122580
gcaccccctt acccaggacc cagccctgcc cctcctcccc tctgctctcc tctcatcact   122640
ccatgggaat ccagaatccc caggaagcca tcaggaaggg ctgaaggagg aagcggggcc   122700
gctgcaccac cgggcaggag gctccgtctt cgtgaaccca gggaagtgcc agcctcctag   122760
agggtatggt ccaccctgcc tggggctccc accgtggcag gctgcgggga aggaccaggg   122820
acggtgtggg ggagggctca gggccctgca ggtgctccat cttggatgag cccatccctc   122880
tcacccaccg acccgcccac ctcctctcca ccctggccac acgtcgtcca caccatcctg   122940
agtcccacct acaccagagc cagcagagcc agtgcagaca gaggctgggg tgcaggggg    123000 ccgccagggc agctttgggg agggaggaat ggaggaaggg gaggtcagtg aagaggcccc   123060
cctcccctgg gtctaggatc cacctttggg accccggat cccatcccct ccaggctctg    123120
ggaggagaag caggatggga gattctgtgc aggaccctct cacagtggaa tacctccaca   123180
gcggctcagg ccagatacaa aagcccctca gtgagccctc cactgcagtg cagggcctgg   123240
gggcagcccc tcccacagag gacagaccca gcaccccgaa gaagtcctgc caggggagc    123300 tcagagccat gaaggagcaa gatatgggga ccccaatact ggcacagacc tcagctccat   123360
ccaggcccac caggacccac catgggtgga acacctgtct ccggcccctg ctggctgtga   123420
ggcagctggc ctctgtctcg gaccccccatt ccagacacca gacagaggga caggcccccc   123480
agaaccagtg ttgagggaca cccctgtcca gggcagccaa gtccaagagg cgcgctgagc   123540
ccagcaaggg aaggccccca aacaaaccag gaggtttctg aagctgtctg tgtcacagtc   123600
```

```
gggtatagca gcggctacca caatgacact gggcaggaca gaaacecccat cccaagtcag   123660 ccgaaggcag agagagcagg caggacacat ttaggatctg aggccacacc tgacactcaa   123720
gccaacagat gtctcccctc cagggcgccc tgccctgttc agtgttcctg agaaaacagg   123780
ggcagcctga ggggatccag ggccaggaga tgggtcccct ctaccccgag gaggagccag   123840
gcgggaatcc cagcccccte cccattgagg ccatcctgcc cagaggggcc cggacccacc   123900
ccacacaccc aggcagaatg tgtgcaggcc tcaggctctg tgggtgccgc tagctggggc   123960
tgccagtcct caccccacac ctaaggtgag ccacagccgc cagagcctcc acaggagacc   124020
ccacccagca gcccagcccc tacccaggag gccccagagc tcagggcgcc tgggtggatt   124080
ctgaacagcc ccgagtcacg gtgggtatag tgggagctac taccactgtg agaaaagcta   124140
tgtccaaaac tgtctcccgg ccactgctgg aggcccagcc agagaaggga ccagccgccc   124200
gaacatacga ccttcccaga cctcatgacc cccagcactt ggagctccac agtgtcccca   124260
ttggatggtg aggatggggg ccggggccat ctgcacctcc caacatcacc cccaggcagc   124320
acaggcacaa accccaaatc cagagccgac accaggaaca cagacacccc aatacccttgg   124380 gggaccctgg ccctggtgac ttcccactgg gatccacccc cgtgtccacc tggatcaaag   124440
accccaccgc tgtctctgtc cctcactcag ggcctgctga ggggcgggtg ctttggagca   124500
gactcaggtt taggggccac cattgtgggg cccaacctcg accaggacac agatttttct   124560
ttcctgccct ggggcaacac agactttggg gtctgtgcag ggaggacctt ctggaaagtc   124620
accaagcaca gagccctgac tgaggtggtc tcaggaagac ccccaggagg gggcttgtgc   124680
cccttcctct catgtggacc ccatgccccc caagataggg gcatcatgca gggcaggtcc   124740
tccatgcagc caccactagg caactccctg gcgccggtcc ccactgcgcc tccatcccgg   124800
ctctggggat gcagccacca tggccacacc aggcagcccg gtccagcaa ccctgcagtg   124860 cccaagccct tggcaggatt cccagaggct ggagcccacc cctcctcatc cccccacacc   124920
tgcacacaca cacctacccc ctgcccagtc cccctccagg agggttggag ccgcccatag   124980
ggtgggggct ccaggtctca ctcactcgct tcccttcctg ggcaaaggag cctcgtgccc   125040 cggtccccccc tgacggcgct gggcacaggt gtgggtactg ggcccagggg ctcctccagc   125100
cccagctgcc ctgctctccc tgggaggcct gggcaccacc agaccaccag tccagggcac   125160
agccccaggg agccgcccac tgccagctca caggaagaag ataagcttca gaccctcagg   125220
gccgggagct gccttcctgc caccccttcc tgccccagac ctccatgccc tcccccaacc   125280
acttacacac aagccaggga gctgtttcca cacagttcaa ccccaaacca ggacggcctg   125340
gcactcgggt cactgccatt tctgtctgca ttcgctccca gcgcccctgt gttccctccc   125400
tcctccctcc ttcctttctt cctgcattgg gttcatgccg cagagtgcca ggtgcaggtc   125460
agccctgagc ttggggtcac ctcctcactg aaggcagcct cagggtgccc aggggcaggc   125520
agggtggggg tgaggcttcc agctccaacc gctccactag ccgagactaa ggaagtgaga   125580
ggcagccaga aatccagacc attccatagc aaatggattt cattaaagtt accagacttc   125640
agtgtaagta acatgagccc catgcacaac aatccccttat gaaggggaag tcagtgtcgc   125700
ctcggatttc ttgaaaaaca caaaaactta tcaatgcctg taaaagtctg ttggaaagaa   125760
aatatgattc aagaatgtta tgcccaacaa agctggcata ttttctaccc ggacacactc   125820
agggaatgtg gtcccttgag tgcttctctc actgcgtaaa tcctacgtgg tgtttaagca   125880
tattcataaa tgtgtatgtc tatttttatg tgtaagatgg ttcattttta ttttatttat   125940
```

```
tcaatatgta caataaagaa tattgacaaa taggctggac atggtggctc ccacctgtaa   126000
tcccagccct tgggaggcc gaggcgggca gatcacctga ggtctggagt tcgagaccag    126060
cctggccaac atgatgaaaa cccatctcta ctaaaaatac aaagattagc caggcatggt   126120
ggtgcatgcc tgtaatccca gccactcagg aggctgagac aggagaaatg cgtgaacccg   126180
gaaggcggag gttgcagtga gccgagatca caccactgca ctccagcctg gcgacagagc   126240
aagattccat ctcaaaaaaa aaaaaagaca aagaaatttg ttttttttgaa taaagacaaa   126300
tttcatcaca cgaagataaa gatgcaaagc tccagacagg aaggcacgga cagcacagtg   126360
aagcccggag cgggcgctgg ggggccaggg gcatggcggg ggtgccagcg tctctcggtt   126420
cctaccatgg ccactccagc ctgtgttctc acgaggatgg ctgtgcaatg ctaggagcgt   126480
gttcgaagct ctagggcaac cactggaagt gaggctgagg agcagagccc agaggcccgt   126540
ggagctgatg aaaagaaagc tggagaaagt gtttgctgcc tcccaacatg gtaagaaaag   126600
atagaaagag agagcacacg gcaaagggag cttgctgagg gactctttac aatggcttgc   126660
acagagctca gggggtctgg gaggctaggg ccctgcgcag ggcagtcacc ccagcctgct   126720
gaccaaggtt tgctgcaggc agctctgggg gtggttgagg cgcggtccct ggagccaccc   126780
ctcaagggaa cgaggcagca gagtgggcca aggcccaggt cggctgcaag gctgcccagg   126840
acttggggtc cttacatcag cagccactga tgcagctggc ccagagagag gcgccgagca   126900
ggttgcctcc aggggacaaa ccaggtcgga gagggtgagg cagtggatgg agccacaaca   126960
accccgggca cgggtgacac gcacgttcat gcacatctga cccttcctcc ctcaccaaac   127020
aggtccccct gccttcccca tggttgcgaa aaagcaaaat gtagacgttt tttctttttt   127080
aattcatgtt ttaattgaca aatgaagccg tatatattta ttgtgtacaa catgatgctt   127140
taaaatatgt atacatcgtg gaacagcaac gttgagctaa tttaacacgc attacttcac   127200
atacttgtca tcttttgtgg cgagaatgct taaaatccac tctcttagta tttttttaaga  127260
atgcaataca ttgttgtcaa ctgtggtcac cgtcatgcat agccaagctc ccgacctcac   127320
cctcctgcca gctcaggctg tgcatccttt caccagcatc ccccaccccg gccctggcc    127380
ctggtaacta ccactctata ctctacgtat gagttcagct ttttaagatt ccacagatga   127440
atgagatcat acagtatttg cttctatgc ctggcttatt ttagttaaca cactgtcctc    127500
cagatccatc cgttgttgca aatgacaggg tttcattctt tttaaagtct aaagagtatt   127560
ccattgtgtc aatggacctc atttgctttta tccatgcatc aactatggac atttaggttg   127620
attccatttc ttagctgttg tggatggtgc tgcagtaaac atggggctgc agatgtctct   127680
tcaacatact gacatcatgt cctttggata aatacccagt agtgggatcg ctggatcaca   127740
atgtacagtt ttttttttaa tggaaacttt catttttggg tgaaattagg aaaacagata   127800
aaccccacag aatccaaaat atatgtgaag atgccaaaaa cagttgacat tgggcagagg   127860
tcacatggaa ggaagtgaat acatgacggg gtgtgagggc ccagaggcag ctgaaatacg   127920
cttttctaaac acaaggacct cttctgagag ggcagaagtt ttatcctgca catgcaatga   127980
ccagcacagc taaaatacac tttctaaaca tgaggacctc ttctgagagg gcagctttat   128040
cctgcaaatg caatgaccag cacaggaccc agaataaaga gagttgccag cggacgcctg   128100
gtgtccatgt gtccaggtga gttcgagatg cggacggcgc tggccagcca gtcacaccct   128160
aagtcaatct gctgcatgca tttgtccttg ccacagcaga aaacgagaaa gcctttgggc   128220
tgcaaagctt cacaggctcc tcttctcccg actccatgga aacagctaca aagagcaggc   128280
ccagtagagc ttaattcatg aaaatgagta ataaacttga actggaacag tatcgacttt   128340
```

```
ttagaaacgg cagcaaagtg tataaaaaat attcaccaga acaatatttc caaacgatga    128400
gatgagaatt tcagccaagt aatcctccat ggatagaaaa taatgaaggg attggattta    128460
tgaaggaaaa tcatggagct caaatacaag aaaagagaat caaaaatgaa caggaggaga    128520
taaaatatgg tttggccaaa gttacaaaat aaatttttta aaaacccttc atcatggcaa    128580
gtagaaagag cgagaggaaa aacagatccc gtggaagaca caaataggac atggggagaa    128640
aaatgaatga gatgaaacag agcagaaata aaattttacg gaactaaaga caagtgatct    128700
gaacctgcct ggggcctggg ggacctcgcc accctgaagg gaaagaacat gcctggctgg    128760
ctttgccacc tgctcattgc agagccccac agcttgcaac aaacataggc ggtagccagg    128820
gagtggttac agcaggcctt gagcaagacc cagtgttgtg ctgacttcag gtctgaccca    128880
gcactgtcat agtggtggtg tccatagtgg tagtgggggt gcttgtgtca ctccaccccc    128940
atctccagga ggctcagaac agacagagag agactccatt tgtttgggag aaagtaaggg    129000
atgagaacaa gagtctctgc ctggtaatcc agagaattat tctagatctt ggccaagatt    129060
atcaaagcag tacctctatg agtcttttgg gcttggagtc cccctaaagc agatatagct    129120
aagatcacaa cacccaagtc cttttgaata tgtgggaaga cttcccaagg acaggagcaa    129180
acaaacaagc ccagactgca aaaaacaag ccgagactgc aataaacacc tcactcttca    129240
atgcccaggc actgaagaac atctcctagc agcaacacca tccaggaaaa catgccctca    129300
accagtgaac taaataaggc accagggacc agtctcggag aaatagaggt atgttatctt    129360
tcagagaatt caaagtagct tgttgagga aactcaaaga aattcaagat aacacagtga    129420
aggaattcag aatcctatcc gataaattta acagagattg aagcaattaa aaagaattaa    129480
gcagaaatta tggagctgaa aaatgcaatt ggcatactga aaaatgcatc agagtatttt    129540
catagcctca tatatcaagt agaagaaaga attagtgagc ttgaaaacag gctatttgga    129600
aaagcacgat aaaaggagac aaaagagaaa agaataaata acaatgaagc atatctacag    129660
gatctagaaa atagcctcaa aaggccaaat ctaagaatta ttagccttaa agaggaggta    129720
gagaaagagg gatggagagt ttattcaaag ggataataac agaaaacttc ccaaacctag    129780
agaaagatat caatatccaa atgcaagaag gatgtagtac accaaggaga tttaatgcaa    129840
agaagactac ctcaaggcat tcaatactca aactcccata tgacaaggac tttaaaaaga    129900
tcctaaaagc agcaaaagaa aagaaatgaa taaaatacta tggagctcca atatgtctgg    129960
cagcagactt ttcagtgaag actttatatg ccaggagaga gtgtcataat ggatttaaag    130020
tgctgaagga aaaaactttt accctcgaac agtatagctg gtgaaattat ccttcaaaca    130080
tgaaggagaa ataatttgtt tccagacaaa tgttgaggga tttcatgaac accagacctg    130140
tcttttaaga aatgctaaag ggagtacttc aatcagaaag aaacacgtta gtgaacaata    130200
agaaatcatc tgaaggcaca aaactcaccg gtaatagtaa gtacacagaa aaacacagaa    130260
tattataaca ctgtaactgt ggtgtgtaaa ctccttttgt ttgtttgttt gtttgtttgt    130320 ttgttttttgt ttttagacgg agttttgctc cagcccaggc tggagtgcaa tggcacaatc    130380
tcagctcact gcaacttcca cctcccgggt tcaagcaatt ctcctgcctc agcctcccaa    130440
gtagctggga ttacaggcat gtgctaccat gtccagctaa ttttgtattt tagtagagac    130500
ggtgtttcac catgttggtc aggctagcct tatcttgagt agaaaaacta aatgatgaag    130560
caatgaaaaa taataactac aacttttcaa gacatagtac aataagatat aaatcataac    130620
aaaaagttaa aaggtggagg gatgaagtta aggcatagag tctttattag ttttctttt    130680
```

```
acttgtctgt ttatgcaaac agtgttaagt tgtcatcagt ttaaaataat gggtcataag    130740
atactatttg caagcctcat ggtaacgtca aaccaaaagc aatacaacag atacacaaaa    130800
aacaaaaagc aagaagctaa attacgtcat cagagaaaat caccttcact aaaaggaaga    130860
cggagaaaag aatgaagaga gagaagacca aaagcaaata gcaatatggc aggagtaagt    130920
ccttacttat caataatacc attgaatgta aatggactaa actctccaat caaaagacat    130980
agagtggctg aatcaattaa agaaaaaaca agacccattg atctgttgtc cacaagaaac    131040
acactttatc tataaagaca cacatagact gaaaacaaag ggatggaaaa agatactcca    131100
cgccaatgga aaccaaagaa agagcaggag tagctacact tatatcaggc aaaatagatt    131160
tcaagacaaa aactataaga agagacaagg tcactaatga taaacaggtc aattcagcaa    131220
gaggatataa caattgtaaa tatatatgca cccaatgctg gagcacccag atatataaag    131280
caagtattta ctagagctaa agagagaaat agactccaat gcaataatag ctggagattt    131340
caacatccca ctttcaacat tgaacagatc ctccagatag aaaatcaaca aagaaatatt    131400
ggacttaatc tgcactatcg accaaatgga tctaacagat atttacagaa catttcatcc    131460
aacagctgca gaacacacat tcttttcctc agcacataga tcattctcaa ggatagacca    131520
tatgttgggt cacaaaacaa gttttaaaat attcaaatac attgaaataa tatcaagcat    131580
cttctgtgac cacaatggac taaaactaga aatcaataac aagaggaatt ttggaaacta    131640
tataaatata tggaaattaa tgaatgctga gtgggtcaat gaagcaatta agaaggaaac    131700
tgaaattttt cttggaacga atgatcatgg aaacagaaaa taccaaaacc tatgggatac    131760
agcaaaagca gtactaagag ggaagtttac agctacaaat gcttacatta aaaagaaga    131820 aaaacttcaa taaaaaaacc taacaatgca tcttaaagaa ctagaaaagc aagaggaaat    131880
caaatccaaa attagtagaa gaaaacagta aaggtcagag cagaaataag taaaattgaa    131940
atgaagaaaa caatacaaaa gatcaataaa acaacaggtt gttttcttga aaagttaaac    132000
aaaattgaca aacctttagc cagactaaga aaaaagaca gaagatccaa ataaataaaa    132060
tcagagatga aaaaggtgac attacaactt acaccacaga aattcaaagg atcattagtg    132120
gctactataa gcaactatat gccaataaat tggaaaatct agaagaaatg cagaaattcc    132180
tagacacata caacctccca agattaaacc aagaagaaat tcaaaacctg aacagactga    132240
taacaagtaa tgagatcaaa gccgtaataa aaagcctccc agtaaagaga agcccaggac    132300
ccgacggctt cactgctgaa ttctaccaaa catttaaagt agaactaata ccaatcctac    132360
tcaaactatt ccaaaaaata gaggtggaag gaatacttca aaactcatta tacgaggcca    132420
gtattaacct gacaccaaaa ctagacaaag acacatgaaa aaagaaaac tacaggccaa    132480 tatgtctgat gaatattgac acaaaaatcc tcaacaaaat actagcaaac caaattcaac    132540
tacacattag aaagttcact catcatgacc aagtggaatt tatctaactt gggatgcaaa    132600
gatggttcaa catatgcaaa tcaatcaatg tgatacatca tatcaacaga atgaacaaca    132660
aaaccatttt gatcatttaa ttgatactga aaaagcattt gataaaattc aacattcctt    132720
cataataaaa attctcttct atactaggta caaagaaac ttacctcaac ataataaagc    132780
catatatgac agtcccacag tatgatacta aatgaggaaa aactgagagc ctttcctcta    132840
cgatctggaa catgacaaag atgcccactt tcatcactgt tattcaacat agtactggaa    132900
gtcctagctg gagcgatcag acaagagaaa gatataaaag acatccaaat tggaaaggaa    132960
taagtcaaat tatcctcatt tgcatatggt atgatcttct atttagagct aactaaagac    133020
tccaccaaaa aaagttatta gaactgacga acaaattcag taaagctgca ggatacaaaa    133080
```

```
tcaacataca aaaatcagta gcatttctat atgccaacaa tgaccaatgt gaaaagaaa  133140 ttaaaaagta accctattta caataaccac aaataaacac ctaggaatta accaaagagg  133200
taaaagattt ctgtaatgaa aactataaaa cactgatgaa agaaattgaa gagtacacca  133260
aaaaatggaa agcaattgca tgttcatgga ttagaagaat cagtgttgtt ataatgtcca  133320
tactatccaa agcaatctac agattcaatg caatccttat caaaataccaa atgacatcat  133380 tcacagaaat agaaaaaaaa aatcctaaaa tttacgtgga accacaaaga cccagaatag  133440
ccaaagctct cctaagcaaa agaacgaaa ctgtaggaat gacattgcct gtcttcaaat  133500
tctactacag agctatagat agtaaccaaa acagcgtggt actggcataa aaacagacac  133560
agagacaaac agaacaaaat ttaaaaaccc agaaataaat ccacacacct acagcaaatt  133620
catttttgac aaagttgcca agaacatact ctggggaata gataatgata tctcttcaat  133680
aaatagtgtg gggaaaactg gatatccata tacataacag tgaaactaga cccctctctc  133740
tctcactata tacaaaaatc aaatcaaaat tgtttaagga cttaaatcta agacctcata  133800
ctatgaaacc actgcaagac aaccttggcg gaaactctcc aagacatcag tccaggcaaa  133860
gatttcttga gtaatatccc acaagcacag acaaccaaag caaaaatgga caaatgggat  133920
cacatcaagt taaaagctt ctgcacagta agggaaacaa ccaacaaaat gaagagacaa  133980
cccacagaat gggagaaaat atttgaaaaa tacccatctg gcaagggatt aaaaaccaga  134040
atatatgcag aatatataag gagctcaaac agtgctatag aaaaaaaaat ctaataatct  134100
gatttaaaaa tgggaaaaat gttagaatag acatttctta aaataagaca tacagatggc  134160
aaaccgacat ggaacggtgc tcaacatcat ggattatcac agaaacacaa tcaatcaaaa  134220
ctaaaactaa aatgtgctat catctcaccc cagttaaaat ggctgatatc cagaagacag  134280
gcaataacaa atgctggcaa ggatgtgggg aaaagggagc ccccatacac tgttgctggg  134340
attgtaaatt agtacaacca ctgtggagag cagcatgaaa gttcctcaaa aaactgaaag  134400
aaagctacca taggatccag caatcccact gctgtgtata tactacaaaa gaaaggaagt  134460
cagtatatga agaggtatct gcactccat gtttgttgca gccctgttca caacagccaa  134520
gatttggaag caacctaagt gtccatcagc agttgaatgt ataagaaaa tgtggtgcat  134580 atacacaatg gagtattatt caataataaa aaggaatgag attgagtcat ttgcaacaac  134640
atggatggaa ctggagatca ttatgtgaag tgaaataagc caggcacaga aagacaaaca  134700
ttacaatgtt cttacttatt aatgagatct aaaaatcaaa acaattgcac ccatgttcat  134760
aaagagtaaa aggatggtta ccagatgctg agaacggtgg tgggggggata gggaaaggtg  134820 gcagtggtta acgggtacaa aaaaatagaa agaatgaata agacttgcta cttgatagca  134880
cagcaaggtg gctatagtca gtaatttagt tgtatatttt taataatgaa aggtgtataa  134940
ttggattgtt tctaacacaa aggataatgc ttaagaggat ggatacccca ttttccatga  135000
tgtgattatt tcacattgca cgcctagatc aaaacatcca atgtaccccca taatatata  135060 catcttctat gtacccataa aaattctgta aaataaaata tataaaaaga ggtgacagat  135120
atggaagaca ggcaaagaag agacgacatc cacataatcc gagtacctaa gaagaatgg  135180 agtccagtgc atctcaggag ccaccattct aagccaattt tctctggttc tctcagtcac  135240
cctaccaata cgtgggcaat cttgttttat ttcaggatag agttttttgaa attatagatt  135300 taagtatgct ttctgttcta ttacttttgg taattaattt tagaaagaac taatttgggc  135360
acaaatttga aaaaattcta aatccaaaaa aaaaagaaa aaaacacaca cacaatcatc  135420
```

```
tataaggggg atgatgacca gtcctagatt tctcaccagc cacattcaag atcagtaaat   135480
ggtaggacaa aacctgtagg gtccttaagg gggaaagaag tagtggatag tccagagtct   135540
atatacagcc aactgttctt gaagaaaaaa ggctgctgaa aaggagttcc aaacattcta   135600
taatccataa tctcatgatg aaactactag aggaagacca ccagccatca aaaggtgctt   135660
ggagaaccca gggccaagaa ccaaaagtaa atattaagtg tccttaactg cgagactaag   135720
atagaaatga ctgtgggga ccatgtggcc tcaacagagg tgaaatggtg tctgcctgac   135780
aaagtggaca ttttacaatg atcaaaacac agaatatgag atagagagca cttctgaatt   135840
actgcctcac tccaaataac tctcagccaa aggacttcag taaaaccaaa ttgggcatat   135900
tagacagtac aaacaaattc taagaaaata atattactga ttacaatcac atgatgctag   135960
agatggaggg gaaaggaag aggaaaccag gtaatttcat actcgtatat agtaaagaac   136020
taaagtacat tgtccaaaga agaacaaaga atattttgga aagttataaa ggtagccact   136080
acacatagaa gatagcaaag aacaagaaaa cttaagatgg aaaacttttt ggaagcataa   136140
gaatagaaaa tataaactac taagataaga ttgaagccaa acagatctat gaaaacaaca   136200
aacatcaatg gccttaactt gcctattaaa aggaagagac tttcaaattg gaccacaaga   136260
taaaacccaa ctctatatag catatgagta ttacacacaa aatgggaaaa gctgaaaaaa   136320
cttgggcaaa attcacccca agcaaattcc actgtttcct ttgggacaaa atgccaagct   136380
ccatgccagg gaagatgatt ctcctcagac ctttctcctca ctctcccagt cctcttaggg   136440
aaggaattgg gtgttagagg agggagactc tgtcgattat cagctgaagc agtggtgtgc   136500
tcctgcgttg cttctgacct gggaaatgaa gcagcaagac tctttctgct gtgtctttgc   136560
ccagaagggc catcccccca gagcagagta cccaggccgg caggagcagt ggtggaagcg   136620
tggaaaccac gtctcctaca gcagagacca tcagaagcgg agcctcgggt ataagggaaa   136680
caacgcgttc tccctaacct gggagtgaca gacagcgtca ttcctcacag tgatacccctg   136740 tgttctagcc atctggccca tgacagagcc agcccagagc cagcccagag ccagcccctc   136800
accatcctgg agcctggcca gctcgccaag ctgcaccata ggcctggaag gcgtggagac   136860
ctgcggcagt gccctgtcct cccgtgaggc ctgccatccc tgccaggggt cgcctctggc   136920
ttctccttct ccaggaccgc acggtccaga ggctcagtgc ctggagtagg tgttgcctcc   136980
ctgcttctag gcccagaccc tcccttgttc ctgaccccgg gcctttccct ctggcttgga   137040
catccagggc cctgtctcag ctggggagct gctcctgctc aaggactgtc ttccgcggga   137100
tcgaaaggcc gcgtcctgaa caatgcgtgg gccacgtaag cggagcaggc tctaaaggcc   137160
gcgtcctaaa cagtgcgtgg gccacgtgag cggagcaggc tctaaaggcc gcgtcctaaa   137220
cagtgcgtgg gccacgtgag cggagcaggc tctaaaggcc gcgtcctaaa cagtgcgtgg   137280
gccacgtgag cggagcaggc tctaaaggcc gcgtcctaaa cagtgcgtgg gccacgtgag   137340
cggagcaggc tctaaaggcc gcgtcctaaa cagtgcgtgg gccacgtgag cggagcaggc   137400
tctaaaggcc gcgtcctaaa cagtgcgtgg gccacgtgag cggagcaggc tctaaaggcc   137460
gcgtcctaaa cagtgcgtgg gccacgtgag cggagcaggc tctaaaggcc gcgtcctaaa   137520
cagtgcgtgg gccacgtgag cggagcaggc tctaaaggcc gcgtcctaaa cagtgcgtgg   137580
gccacgggag cggagcagac tctaaaggcc gcgtcctaaa cagtgtgtgg gccacgtgag   137640
cggagcgccc tctccactgc cctcggggcc gcagctccca gctcagctcc cagccctgct   137700
cagggcagcc aggccaggag gtaccatcca ggctaagtga ccctcagggg ggacaggtgc   137760
cccaggagat gccagctgtt gggagaggct gggggaccaa ctcgacctgg cctgtgggcc   137820
```

```
ctgccctggc cacccattgt aggatccagc cgccacgcct gtgacactcg tgtgctttcc   137880
ctggtgtgtg cttgtggcag gtgggggcag agggtcctca ggccagagag ccactcccccc  137940
agcgccagac caccctcttc ctcactcccc cacctcaccc cctcacaggt gcctcccagg   138000
ccatcagggc ccaaccaccc ctaaacaaat gggttctcgg cccctcgtgg ctggaggtgg   138060
gttctctcac cattcccagc ctaagactcc atccccatgc tggcagctgt caaccatgt    138120
ctagagagat ccactgtccc agacagcacc tcagggtccc ccgtcctgcc tggaaccctg   138180
taggaaactc cacaaaccgc cgccattctg tccacacccc tacaggagcc caaccctct    138240
ccccacatcc aggcttccct cccagacccc tcatccctgc ccgcacggtg cctgaggggg   138300
ccttcttggg cagcgcctaa gcaagccccc agcacccttc ggccccttca aggcacacag   138360
gccccctttc cacccagcct caggaaacca cctgtgtcct ccaacgacag gtcccagcct   138420
cccagccttt gccttgcctg ttcctctccc tggaactctg ccccgacaca gaccctcccc   138480
agcaagcccg caggggcacc tcccctgccc ccagacaccc tgtgcccgtc agttcatccc   138540
cagcagaggc cctcaccagg cacaccccca tgctcacacc tggccccagg cctcagcctc   138600
cctgagggcc ccacccagcc cgcgtctggc cagtggtgcg tgcaaagccc ctcacccaga   138660
ctcggcggaa ggcagccagt gcaggcctgg ggaggggctc tccttagacc accttgcacc   138720
ttccctggca cccaccatgg gaagagctga gactcactga ggaccagctg aggctcagag   138780
aagggaccca gcactggtgg acacgcaggg agcccacgcc agggcgccgt ggtgagtgag   138840
gcccagtgcc acccactgag gcctcccgtt cagtgggacg acggtgaaca ggtgaaccca   138900
accaggcaac ccccgccggg ccccacagac gggatcagag caggaaaggc ttcctgcccc   138960
tgcaggccag cgaggagccc tggcgggggc cgtggccctc caggcgagga ggctcccctg   139020
gccaccgcca cccgggcctc tctgctgctg ggaaaacaag tcagaaagca agtggatgag   139080
aggtggcgtg acagacccag cttcagatct gctctaattt acaaaagaaa aggaaaaaca   139140
cacttggcag ccttcagcac tctaatgatt cttaacagca gcaaattatt ggcacaagac   139200
tccagagtga ctggcagggt tgagggctgg ggtctcccac gtgttttggg gctaacagcg   139260
gaagggagag cactggcaaa ggtgctgggg cccctggac ccgaccccgcc ctggagaccg    139320
cagcccacatc agcccccagc cccacaggcc ccctaccagc cgcagggttt ggctgagct    139380
gagaaccact gtgctaactg gggacacagt gattggcagc tctacaaaaa ccatgctccc   139440
ccgggacccc gggctgtggg tttctgtagc ccctggctca gggctgactc accgtggctg   139500
aatacttcca gcactggggc cagggcaccc tggtcaccgt ctcctcaggt gagtctgctg   139560
tctggggata gcggggagcc aggtgtactg gccaggcaa gggctttggc ttcagacttg    139620
gggacaggtc tcagcaaag gaggtcggca ggagggcgga gggtgtgttt ttgtatggga    139680
gaagcaggag ggcagaggct gtgctactgg tacttcgatc tctggggccg tggcaccctg   139740
gtcactgtct cctcaggtga gtcccactgc agccccctcc cagtcttctc tgtccaggca   139800
ccaggccagg tatctggggt ctgcagccgg cctgggtctg gctgaggcc acaccagctg    139860
ccatccctgg ggtctccgcc atgggctgca tgccagagcc ctgctgtcac ttagccctgg   139920
ggccagctgg agccccaag acaggcagg gaccccgctg gcttcagcc ccgtcaggga     139980
ccctccacag gtagcaagca ggccgagggc agggacggga aggagaagtt gtgggcagag   140040
cctgggctgg ggctgggcgc tggctgttca tgtgccgggg accaggcctg cgctttagtg   140100
tggctacaag tgcttggagc actggggcca ggcagcccg gccaccgtct ccctgggaac    140160
```

```
gtcacccctc cctgcctggg tctcagcccg ggggtctgtg tggctgggga cagggacgcc    140220
ggctgcctct gctctgtgct tgggccatgt gacccattcg agtgtcctgc acgggcacag    140280
gtttgtgtct gggcaggaac agggactgtg tccctgtgtg atgcttttga tatctggggc    140340
caagggacaa tggtcaccgt ctcttcaggt aagatggctt tccttctgcc tcctttctct    140400
gggcccagcg tcctctgtcc tggagctggg agataatgtc cgggggctcc ttggtctgcg    140460
ctgggccatg tggggccctc cggggctcct tctccggctg tttgggacca cgttcagcag    140520
aaggcctttc tttgggaact gggactctgc tgctggggca aagggtgggc agagtcatgc    140580
ttgtgctggg gacaaaatga ccttgggaca cggggctggc tgccacgcc ggcccgggac     140640 agtcggagag tcaggttttt gtgcacccct taatggggcc tcccacaatg tgactacttt    140700
gactactggg gccagggaac cctggtcacc gtctcctcag gtgagtcctc acaacctctc    140760
tcctgcttta actctgaagg gttttgctgc attttggggg ggaaataagg gtgctgggtc    140820
tcctgccaag agagcccgg agcagcctgg ggggctcagg aggatgccct gaggcaacag     140880
cggccacaca gacgaggggc aagggctcca gatgctcctt cctcctgagc ccagcagcac    140940
gggtctctct gtggccaggg ccaccctagg cctctgggt ccaatgccca acaaccccg      141000 ggccctcccc gggctcagtc tgagagggtc ccagggacgt agcggggcgc cagttcttgc    141060
ctggggtcct ggcattgttg tcacaatgtg acaactggtt cgaccctgg ggccagggaa     141120 ccctggtcac cgtctcctca ggtgagtcct caccaccccc tctctgagtc cacttaggga    141180
gactcagctt gccagggtct cagggtcaga gtcttggagg catttggag gtcaggaaag     141240 aaagccgggg agagggaccc ttcgaatggg aacccagcct gtcctcccca agtccggcca    141300
cagatgtcgg cagctggggg gctccttcgg ctggtctggg gtgacctctc tccgcttcac    141360
ctggagcatt tcaggggct gtcgtgatga ttgcgtggtg ggactctgtc ccgctccaag     141420
gcacccgctc tctgggacgg gtgccccccg gggttttttgg actcctgggg gtgacttagc   141480
agccgtctgc ttgcagttgg acttcccagg ccgacagtgg tctggcttct gaggggtcag    141540
gccagaatgt ggggtacgtg ggaggccagc agagggttcc atgagaaggg caggacaggg    141600
ccacggacag tcagcttcca tgtgacgccc ggagacagaa ggtctctggg tggctgggtt    141660
tttgtggggt gaggatggac attctgccat tgtgattact actactacta cggtatggac    141720
gtctggggcc aagggaccac ggtcaccgtc tcctcaggta agaatggcca ctctagggcc    141780
tttgttttct gctactgcct gtgggggtttc ctgagcattg caggttggtc ctcggggcat   141840
gttccgaggg gacctgggcg gactggccag gaggggacgg gcactggggt gccttgagga    141900
tctgggagcc tctgtggatt ttccgatgcc tttggaaaat gggactcagg ttgggtgcgt    141960
ctgatggagt aactgagcct ctagactgag cattgcagac taatcttgga tatttgtccc    142020
tgagggagcc ggctgagaga agttgggaaa taaactgtct agggatctca gagcctttag    142080
gacagattat ctccacatct ttgaaaaact aagaatctgt gtgatggtgt tggtggagtc    142140
cctggatgat gggataggga ctttggaggc tcatttgagg gagatgctaa acaatcctaa    142200
tggctggagg atagttggg gctgtagttg gagattttca gttttagaa taaaagtatt       142260 agctgcggaa tatacttcag gaccacctct gtgacagcat ttatacagta tccgatgcat    142320
agggacaaag agtggagtgg ggcactttct ttagatttgt gaggaatgtt ccacactaga    142380
ttgtttaaaa cttcatttgt tggaaggaga gctgtcttag tgattgagtc aagggagaaa    142440
ggcatctagc ctcggtctca aagggtagt tgctgtctag agaggtctgg tggagcctgc      142500
aaaagtccag ctttcaaagg aacacagaag tatgtgtatg gaatattaga agatgttgct    142560
```

```
tttactctta agttggttcc taggaaaaat agttaaatac tgtgactttta aaatgtgaga 142620 gggttttcaa gtactcattt ttttaaatgt ccaaaattct tgtcaatcag tttgaggtct 142680
tgtttgtgta gaactgatat tacttaaagt ttaaccgagg aatgggagtg aggctctctc 142740
ataacctatt cagaactgac ttttaacaat aataaattaa gtttcaaata tttttaaatg 142800
aattgagcaa tgttgagttg gagtcaagat ggccgatcag aaccagaaca cctgcagcag 142860
ctggcaggaa gcaggtcatg tggcaaggct atttggggaa gggaaaataa aaccactagg 142920
taaacttgta gctgtggttt gaagaagtgg ttttgaaaca ctctgtccag ccccaccaaa 142980
ccgaaagtcc aggctgagca aaacaccacc tgggtaattt gcatttctaa aataagttga 143040
ggattcagcc gaaactggag aggtcctctt ttaacttatt gagttcaacc ttttaatttt 143100
agcttgagta gttctagttt ccccaaactt aagtttatcg acttctaaaa tgtatttaga 143160
attcattttc aaaattaggt tatgtaagaa attgaaggac tttagtgtct ttaatttcta 143220
atatatttag aaaacttctt aaaattactc tattattctt ccctctgatt attggtctcc 143280
attcaattct tttccaatac ccgaagcatt tacagtgact tgttcatga tcttttttag 143340 ttgtttgttt tgccttacta ttaagacttt gacattctgg tcaaaacggc ttcacaaatc 143400
tttttcaaga ccactttctg agtattcatt ttaggagaaa gacttttttt ttaaatgaat 143460
gcaattatct agacttattt cagttgaaca tgctggttgg tggttgagag gacactcagt 143520
cagtcagtga cgtgaagggc ttctaagcca gtccacatgc tctgtgtgaa ctccctctgg 143580
ccctgcttat tgttgaatgg gccaaaggtc tgagaccagg ctgctgctgg gtaggcctgg 143640
actttgggtc tcccacccag acctgggaat gtatggttgt ggcttctgcc acccatccac 143700
ctggctgctc atggaccagc cagcctcggt ggctttgaag gaacaattcc acacaaagac 143760
tctggacctc tccgaaacca ggcaccgcaa atggtaagcc agaggcagcc acagctgtgg 143820
ctgctgctct taaagcttgt aaactgtttc tgcttaagag ggactgagtc ttcagtcatt 143880
gctttagggg gagaaagaga catttgtgtg tcttttgagt accgttgtct gggtcactca 143940
catttaactt tccttgaaaa actagtaaaa gaaaaatgtt gcctgttaac caataatcat 144000
agagctcatg gtactttgag gaaatcttag aaagcgtgta tacaattgtc tggaattatt 144060
tcagttaagt gtattagttg aggtactgat gctgtctcta cttcagttat acatgtgggt 144120
ttgaattttg aatctattct ggctcttctt aagcagaaaa tttagataaa atggatacct 144180
cagtggtttt taatggtggg tttaatatag aaggaattta aattggaagc taatttagaa 144240
tcagtaagga gggacccagg ctaagaaggc aatcctggga ttctggaaga aaagatgttt 144300
ttagttttta tagaaaacac tactacattc ttgatctaca actcaatgtg gtttaatgaa 144360
tttgaagttg ccagtaaatg tacttcctgg ttgttaaaga atggtatcaa aggacagtgc 144420
ttagatccga ggtgagtgtg agaggacagg ggctggggta tggatacgca gaaggaaggc 144480
cacagctgta cagaattgag aaagaataga gacctgcagt tgaggccagc aggtcggctg 144540
gactaactct ccagccacag taatgaccca gacagagaaa gccagactca taaagcttgc 144600
tgagcaaaat taagggaaca aggttgagag ccctagtaag cgaggctcta aaaagcacag 144660
ctgagctgag atgggtgggc ttctctgagt gcttctaaaa tgcgctaaac tgaggtgatt 144720
actctgaggt aagcaaagct gggcttgagc caaaatgaag tagactgtaa tgaactggaa 144780
tgagctgggc cgctaagcta aactaggctg gcttaaccga gatgagccaa actggaatga 144840
acttcattaa tctaggttga atagagctaa actctactgc ctacactgga ctgttctgag 144900
```

```
ctgagatgag ctggggtgag ctcagctatg ctacgctgtg ttggggtgag ctgatctgaa    144960
atgagatact ctggagtagc tgagatgggg tgagatgggg tgagctgagc tgggctgagc    145020
tagactgagc tgagctaggg tgagctgagc tgggtgagct gagctaagct ggggtgagct    145080
gagctgagct tggctgagct agggtgagct gggctgagct ggggtgagct gagctgagct    145140
ggggtaagct gggatgagct ggggtgagct gagctgagct ggagtgagct gagctgggct    145200
gagctggggt gagctgggct gagctgggct gagctgggct gagctggggt gagctgagct    145260
ggggtgagct gagctgagct ggggtgagct gagctgagct ggggtgagct ggggtgagct    145320
gagctggggt gagctgagct gagctggggt gagctgagct ggggtgagct gagctgagct    145380
ggggtgagct gagctgagct gagctgagct gagctggggt gagctgagct gagctgagct    145440
ggggtgagct ggggtgagct gagctgagct ggagtgagct gagctgggct gagctggggt    145500
gagctgggct gagctggggt gagctgagct gagctgagct gagctggggt gagctgagct    145560
gagctggggt gagctgagct ggggtgagct gggctgagct gagctgagct gagctgagct    145620
gagctgagct gagctgagct gagctgagct gagctgagct gagctgagct gagctgagct    145680
ggggtgagct gagctgagct gggctgggtgt ggggtgagct gggctgagct gggctgagct   145740
gggctgagct ggggtgagct gagctggggt gagctgagct gagctgggct gagctgagct    145800
gagctggggt gagctgagct gagctggggt gagctgagct gagctgagct ggggtgagct    145860
gagctgagct gggctgagca gggctgagct ggggtgagct gagctgagct ggggtgagct    145920
gggctgagct gggctgagct gagctgagct gggctgagct gggctgagct gggctgagct    145980
gggctgagct gggctgagct ggggtgagct gagctggggt gagctggggt gagctgagct    146040
ggggtgagct gagctggggt gagctgagct gagctggggt gagctgagct ggggtgagct    146100
gagctgagct ggggtgagct gagctgagct ggggtgagct gagctagggt gaactgggct    146160
gggtgagctg gagtgagctg agctgaggtg aactggggtg agccgggatg ttttgagttg    146220
agctgggta agatgagctg aactggggta aactgggatg agctgtggtg agcggagctg    146280
gattgaactg agctgtgtga gctgagctgg ggtcagctga gcaagagtga gtagagctgg    146340
ctggccagaa ccagaatcaa ttaggctaag tgagccagat tgtgctggga tcagctgtac    146400
tcagatgagc tgggatgagg taggctggga tgagctgggc tagctgacat ggattatgtg    146460
aggctgagct agcatgggct ggcctagctg atgagctaag cttgaatgag cggggctgag    146520
ctggactcag atgtgctaga ctgagctgta ctggatgatc tggtgtaggg tgatctggac    146580
tcaactgggc tggctgatgg gatgcgccag gttgaactag gctcagataa gttaggctga    146640
gtagggcctg gttgagatgg ttcgggatga gctgggaaaa gatggactcg gaccatgaac    146700
tgggctgagc tggttgggaa gaccatgaat tgagctgaac tgagtgcagc tgggataaac    146760
tgggttgagc taagaataga ctacctgaat tgtgccaaac tcggctggga tcaattggaa    146820
attatcagga tttagatgag ccggactaaa ctatgctgag ctggactggt tggatgtgtt    146880
gaactggcct gctgctgggc tggcatagct gagttgaact aaatgagga aggctgagca    146940
aggctagcct gcttgcatag agctgaactt tagcctagcc tgagctggac cagcctgagc    147000
tgagtaggtc taaactgagt taaaaatcaa caggggataat ttaacagcta atttaacaag    147060
cctgaggtct gagattgaat gagcagagct gggatgaact gaatgagttt caccaggcct    147120
ggaccagtta ggctaggacc tcgttctata gaggcagact gtgtgctaca gtggagtttc    147180
aagatgattc catgagtcct ccccgcccccc aacataaccc accttcctcc taccctacac    147240
gcctgtctgg tgtgtaaatc ccagctttgt gtgctgatac agaagcctga gcccctcccc    147300
```

```
cacctccacc tacctattac tttgggatga gaatagttct cccagccagt gtctcagagg 147360
gaagccaagc aggacaggcc caaggctact tgagaagcca ggatctaggc ctctccctga 147420
gaacgggtgt tcatgcccct agagttggct gaagggccag atccacctac tctagaggca 147480
tctctccctg tctgtgaagg cttccaaagt cacgttcctg tggctagaag gcagctccat 147540
agccctgctg cagtttcgtc ctgtatacca ggttcaccta ctaccatatc tagccctgcc 147600
tgccttaaga gtagcaacaa ggaaatagca gggtgtagag ggatctcctg tctgacagga 147660
ggcaagaaga cagattctta cccctccatt tctcttttat ccctctctgg tcctcagaga 147720
gtcagtcctt cccaaatgtc ttcccctcg tctcctgcga gagcccctg tctgataaga 147780
atctggtggc catgggctgc ctggcccggg acttcctgcc cagcaccatt tccttcacct 147840
ggaactacca gaacaacact gaagtcatcc agggtatcag aaccttccca acactgagga 147900
caggggcaa gtacctagcc acctcgcagg tgttgctgtc tcccaagagc atccttgaag 147960
gttcagatga atacctggta tgcaaaatcc actacggagg caaaaacaaa gatctgcatg 148020
tgcccattcc aggtaagaac caaaccctcc cagcagggt gcccaggccc aggcatggcc 148080
cagagggagc agcggggtgg ggcttaggcc aagctgagct cacaccttga cctttcattc 148140
cagctgtcgc agagatgaac cccaatgtaa atgtgttcgt cccaccacgg gatggcttct 148200
ctggccctgc accacgcaag tctaaactca tctgcgaggc cacgaacttc actccaaaac 148260
cgatcacagt atcctggcta aaggatggga agctcgtgga atctggcttc accacagatc 148320
cggtgaccat cgagaacaaa ggatccacac cccaaaccta caaggtcata agcacactta 148380
ccatctctga aatcgactgg ctgaacctga atgtgtacac ctgccgtgtg gatcacaggg 148440
gtctcacctt cttgaagaac gtgtcctcca catgtgctgc cagtgagtgg cctgggctaa 148500
gcccaatgcc tagccctccc agattaggga agtcctccta caattatggc caatgccacc 148560
cagacatggt catttgctcc ttgaactttg gctccccaga gtggccaagg acaagaatga 148620
gcaataggca gtagaggggt gagaatcagc tggaaggacc agcatcttcc cttaagtagg 148680
tttgggggat ggagactaag cttttttcca acttcacaac tagatatgtc ataacctgac 148740
acagtgttct cttgactgca ggtccctcca cagacatcct aaccttcacc atcccccct 148800
cctttgccga catcttcctc agcaagtccg ctaacctgac ctgtctggtc tcaaacctgg 148860
caacctatga aaccctgaat atctcctggg cttctcaaag tggtgaacca ctggaaacca 148920
aaattaaaat catggaaagc cctcccaatg gcaccttcag tgctaagggt gtggctagtg 148980
tttgtgtgga agactggaat aacaggaagg aatttgtgcg tactgtgact cacagggatc 149040
tgccttcacc acagaagaaa ttcatctcaa aacccaatgg taggtatccc cccttccctt 149100
cccctccaat tgcaggaccc ttcctgtacc tcatagggag ggcaggtcct cttccaccct 149160
atcctcacta ctgtcttcat ttacagaggt gcacaaacat ccacctgctg tgtacctgct 149220
gccaccagct cgtgagcaac tgaacctgag ggagtcagcc acagtcacct gcctggtgaa 149280
gggcttctct cctgcagaca tcagtgtgca gtggcttcag agagggcaac tcttgcccca 149340
agagaagtat gtgaccagtg ccccgatgcc agagcctggg gccccaggct tctactttac 149400
ccacagcatc ctgactgtga cagaggagga atggaactcc ggagagacct ataccctgtgt 149460
tgtaggccac gaggccctgc cacacctggt gaccgagagg accgtggaca agtccactgg 149520
taaacccaca ctgtacaatg tctccctgat catgtctgac acaggcggca cctgctattg 149580
accatgctag cgctcaacca ggcaggccct gggtgtccag ttgctctgtg tatgcaaact 149640
```

-continued

```
aaccatgtca gagtgagatg ttgcatttta taaaaattag aaataaaaaa aatccattca   149700
aacgtcactg gttttgatta tacaatgctc atgcctgctg agacagttgt gttttgcttg   149760
ctctgcacac accctgcata cttgcctcca ccctggccct tcctctacct tgccagtttc   149820
ctccttgtgt gtgaactcag tcaggcttac aacagacaga gtatgaacat gcgattcctc   149880
cagctacttc tagatatatg gctgaaagct tgcatgcctg caggtcgact ctagaggatc   149940
cccgggtacc gagctcgaat tcgccctata gtgagtcgta ttacaattca ctggccgtcg   150000
ttttacaacg tcgtgactgg gaaaaccctg gcgttaccca acttaatcgc cttgcagcac   150060 atccccctttt cgccagctgg cgtaatagcg aagaggcccg caccgatcgc ccttcccaac   150120
agttgcgcag cctgaatggc gaatggcgcc tgatgcggta ttttctcctt acgcatctgt   150180
gcggtatttc acaccgcata tggtgcactc tcagtacaat ctgctctgat gccgcatagt   150240
taagccagcc ccgacacccg ccaacacccg ctgacgcgaa ccccttgc                150288
```

```
<210> SEQ ID NO 71
<211> LENGTH: 23
<212> TYPE: DNA
<213> ORGANISM: Artificial Sequence
<220> FEATURE:
<223> OTHER INFORMATION: synthetic

<400> SEQUENCE: 71
ggaaggtgtg cacaccgctg gac                                                23

<210> SEQ ID NO 72
<211> LENGTH: 23
<212> TYPE: DNA
<213> ORGANISM: Artificial Sequence
<220> FEATURE:
<223> OTHER INFORMATION: synthetic

<400> SEQUENCE: 72
ggaaggtgtg cacaccactg gac                                                23

<210> SEQ ID NO 73
<211> LENGTH: 23
<212> TYPE: DNA
<213> ORGANISM: Artificial Sequence
<220> FEATURE:
<223> OTHER INFORMATION: synthetic

<400> SEQUENCE: 73
ggaaggtgtg cacactgctg gac                                                23

<210> SEQ ID NO 74
<211> LENGTH: 23
<212> TYPE: DNA
<213> ORGANISM: Artificial Sequence
<220> FEATURE:
<223> OTHER INFORMATION: synthetic

<400> SEQUENCE: 74
agactgtgcg cacaccgctg gac                                                23

<210> SEQ ID NO 75
<211> LENGTH: 22
<212> TYPE: DNA
<213> ORGANISM: Artificial Sequence
<220> FEATURE:
<223> OTHER INFORMATION: synthetic

<400> SEQUENCE: 75
```
tcttatcaga cagggggctc tc                                          22

<210> SEQ ID NO 76
<211> LENGTH: 22
<212> TYPE: DNA
<213> ORGANISM: Artificial Sequence
<220> FEATURE:
<223> OTHER INFORMATION: synthetic

<400> SEQUENCE: 76
aagaagcaca cgactgaggc ac                                          22

<210> SEQ ID NO 77
<211> LENGTH: 22
<212> TYPE: DNA
<213> ORGANISM: Artificial Sequence
<220> FEATURE:
<221> NAME/KEY: variation
<222> LOCATION: (12)...(12)
<223> OTHER INFORMATION: w = a or t
<220> FEATURE:
<223> OTHER INFORMATION: synthetic

<400> SEQUENCE: 77
agtggataga cwgatggggg tg                                          22

<210> SEQ ID NO 78
<211> LENGTH: 22
<212> TYPE: DNA
<213> ORGANISM: Artificial Sequence
<220> FEATURE:
<223> OTHER INFORMATION: synthetic

<400> SEQUENCE: 78
agtggataga ccgatggggc tg                                          22

<210> SEQ ID NO 79
<211> LENGTH: 22
<212> TYPE: DNA
<213> ORGANISM: Artificial Sequence
<220> FEATURE:
<223> OTHER INFORMATION: synthetic

<400> SEQUENCE: 79
aagggataga cagatggggc tg                                          22

<210> SEQ ID NO 80
<211> LENGTH: 22
<212> TYPE: DNA
<213> ORGANISM: Artificial Sequence
<220> FEATURE:
<223> OTHER INFORMATION: synthetic

<400> SEQUENCE: 80
ggaagacatt tgggaaggac tg                                          22

<210> SEQ ID NO 81
<211> LENGTH: 22
<212> TYPE: DNA
<213> ORGANISM: Artificial Sequence
<220> FEATURE:
<223> OTHER INFORMATION: synthetic

<400> SEQUENCE: 81
ggaagatgga tacagttggt gc                                          22

RESTRICTED IMMUNOGLOBULIN HEAVY CHAIN MICE

CROSS-REFERENCE TO RELATED APPLICATIONS

This application is a continuation application of U.S. application Ser. No. 13/653,456, filed Oct. 17, 2012 (now U.S. Pat. No. 10,246,509), which application claims the benefit under 35 U.S.C. § 119(e) of U.S. Provisional Application Ser. No. 61/658,459, filed Jun. 12, 2012, U.S. Provisional Application Ser. No. 61/597,969, filed Feb. 13, 2012, and U.S. Provisional Application Ser. No. 61/547,974, filed Oct. 17, 2011, which applications are hereby incorporated by reference in their entirety.

FIELD

Non-human animals that are genetically engineered at an immunoglobulin heavy chain variable (V) region locus (or in a transgene) to make antibodies from a restricted number of immunoglobulin heavy chain variable ($V_H$) segments (or a single $V_H$ segment) and/or variants thereof. Non-human animals that have a human heavy chain variable domain derived from a single immunoglobulin heavy chain variable gene segment, e.g., human immunoglobulin $V_H$1-69 gene segment or human $V_H$1-2 gene segment. Methods for making antibody sequences in non-human animals that are useful for binding pathogens, including human pathogens.

BACKGROUND

Non-human animals, e.g., mice, have been genetically engineered to be useful tools in methods for making antibody sequences for use in antibody-based human therapeutics. Mice with humanized variable region loci (e.g., $V_H$, $D_H$, and $J_H$ genes, and $V_L$ and $J_L$ genes) are used to generate cognate heavy and light chain variable domains for use in antibody therapeutics. Other mice are available that generate fully human antibodies with cognate heavy and light chains.

Human antibody therapeutics are engineered based on desired characteristics with respect to certain pre-selected antigens. Humanized mice are immunized with the pre-selected antigens, and the immunized mice are used to generate antibody populations from which to identify high-affinity cognate heavy and light variable domains with desired binding characteristics. Some humanized mice, such as those having a humanization of just variable regions at endogenous mouse loci, generate populations of B cells that are similar in character and number to wild-type mouse B cell populations. As a result, an extremely large and diverse population of B cells is available in these mice from which to screen antibodies, reflecting a large number of different immunoglobulin rearrangements, to identify heavy and light variable domains with the most desirable characteristics.

But not all antigens provoke an immune response that exhibits a very large number of rearrangements from a wide selection of variable (V) segments. That is, the human humoral immune response to certain antigens is apparently restricted. The restriction is reflected in clonal selection of B cells that express only certain V segments that bind that particular antigen with sufficiently high affinity and specificity. Some such antigens are clinically significant, i.e., a number are well-known human pathogens. A presumption arises that the V segment expressed in the human immune response is a V segment that, in combination with a human D and a human J segment, is more likely to generate a useful high affinity antibody than a randomly selected V segment that has not been observed in a human antibody response to that antigen.

It is hypothesized that natural selection, over millennia, has selected the most efficient foundation or base from which to design a most effective weapon for neutralizing human pathogens—a clonally selected V segment. There is a need in the art for more and superior antibodies that bind and/or neutralize antigens such as the pathogens discussed above. There is a need to more rapidly generate useful sequences from selected V segments, including polymorphic and/or somatically mutated selected V segments and to more rapidly generate useful populations of B cells having rearrangements of the V segments with various D and J segments, including somatically mutated versions thereof, and in particular rearrangements with unique and useful CDR3s. There is a need for biological systems, e.g., non-human animals (such as, e.g., mice, rats, rabbits, etc.) that can generate therapeutically useful antibody variable region sequences from pre-selected V segments in increased number and diversity than, e.g., can be achieved in existing modified animals. There is a need for biological systems engineered to have a committed humoral immune system for clonally selecting antibody variable sequences derived from restricted, pre-selected V segments, including but not limited to cognate human heavy and light chain variable domains, useful in the manufacture of human antibody-based therapeutics against selected antigens, including certain human pathogens.

There is a need in the art for therapeutic antibodies that are capable of neutralizing viral antigens, e.g., HIV and HCV, including antigen-specific antibodies containing heavy chains derived from a single human variable segment, and for a system that produces a diverse source of antibodies from which to select therapeutic antibody sequences. There is also a need for further methods and non-human animals for making useful antibodies, including antibodies that comprise a repertoire of heavy chains derived from a single human $V_H$ segment and having a diverse set of CDR sequences, and including such heavy chains that express with cognate human light chain variable domains. Methods are needed for selecting CDRs for immunoglobulin-based binding proteins that provide an enhanced diversity of binding proteins from which to choose, and enhanced diversity of immunoglobulin variable domains, including compositions and methods for generating somatically mutated and clonally selected immunoglobulin variable domains for use, e.g., in making human therapeutics.

SUMMARY

Genetically modified immunoglobulin loci are provided that comprise a restricted number of different heavy chain variable region gene segments (i.e., V genes, $V_H$ genes, $V_H$ gene segments, or V gene segments), e.g., no more than one, two, or three different V genes; or no more than one V gene segment family member present, e.g., in a single copy or in multiple copies and/or comprising one or more polymorphisms.

Loci are provided that are capable of rearranging and forming a gene encoding a heavy chain variable domain that is derived from a $V_H$ gene repertoire that is restricted, e.g., that is a single $V_H$ gene segment or selected from a plurality of polymorphic variants of the single $V_H$ gene segment. Modified immunoglobulin loci include loci that comprise human immunoglobulin sequences are provided, e.g., a human V segment operably linked to a human or (or human/non-human chimeric) non-human immunoglobulin constant sequence (and in operable linkage with, e.g., a D and/or a J segment). Modified loci that comprise multiple copies of a single $V_H$ gene segment, including wherein one or more of the copies comprises a polymorphic variant, are provided. Modified loci that comprise multiple copies of a single $V_H$ segment, operably linked with one or more D segments and one or more J segments, operably linked to a non-human immunoglobulin constant sequence, e.g., a mouse or rat sequence, are provided. Non-human animals comprising such humanized loci are also provided.

Non-human animals are provided that have a reduced immunoglobulin heavy chain variable gene segment complexity (i.e., a limited number of heavy chain variable gene segments, or a limited heavy chain variable gene repertoire), wherein the reduced immunoglobulin heavy chain variable gene segment complexity is characterized by the presence of no more than one or no more than two heavy chain variable gene segments, and wherein the heavy chain variable genes present are operably linked to a human or non-human constant region sequence.

Non-human animals are provided that have a reduced immunoglobulin heavy chain variable gene segment complexity (e.g., a single $V_H$ gene segment, or a limited number of $V_H$ gene segments that are polymorphic variants of a single $V_H$ gene segment), wherein the reduced immunoglobulin heavy chain variable gene segment complexity is characterized by the presence of a single $V_H$ gene segment or a plurality of $V_H$ gene segments that are polymorphic forms of a single $V_H$ gene segment (e.g., $V_H$ gene segments associated with high copy number and/or polymorphism in humans), and wherein the heavy chain variable genes present are operably linked to a human or non-human constant region sequence. In various embodiments, the heavy chain variable genes present are operably linked to one or more D and/or one or more J gene segments in the germline of the non-human animal.

Non-human animals are provided that comprise an immunoglobulin heavy chain variable locus (e.g., on a transgene or as an insertion or replacement at an endogenous non-human animal heavy chain variable locus) that comprises a single $V_H$ segment operably linked to a D and/or J gene segment. In various embodiments, the single $V_H$ gene segment is operably linked to one or more D and/or one or more J gene segments at the endogenous immunoglobulin heavy chain variable gene locus of the non-human animal.

Non-human animals are provided that are modified at their immunoglobulin heavy chain variable region loci to delete all or substantially all (e.g., all functional segments, or nearly all functional segments) endogenous immunoglobulin $V_H$ segments and that comprise a human $V_H$1-69 segment (or a human $V_H$1-2 segment) operably linked to a D and J segment or a J segment at the endogenous immunoglobulin heavy chain variable region locus of the non-human animal.

Non-human animals are also provided that are modified at their immunoglobulin heavy chain variable region loci to render the endogenous variable region loci incapable of rearranging to form a functional heavy chain comprising endogenous variable region gene segments; wherein the non-human animals comprise a single human variable gene segment (a human $V_H$1-2 or a human $V_H$1-69 gene segment) operably linked to a D and a J segment or a J segment at the endogenous immunoglobulin heavy chain variable region locus of the non-human animal.

Non-human animals are provided that comprise a restricted number (e.g., no more than one, or no more than two) of heavy chain gene segments operably linked to a human or non-human constant region sequence. In one embodiment, the no more than one or no more than two heavy chain gene segments linked to the constant region sequence are on a transgene, e.g., are at a position other than an endogenous heavy chain locus.

Methods are provided for making human immunoglobulin sequences in non-human animals. In various embodiments, the human immunoglobulin sequences are derived from a repertoire of immunoglobulin V sequences that consist essentially of a single human V segment, e.g., $V_H$1-69 or $V_H$1-2, and one or more D and J segments or one or more J segments. Methods for making human immunoglobulin sequences in non-human animals, tissues, and cells are provided, wherein the human immunoglobulin sequences bind a pathogen.

Methods are provided for making mice characterized by a restricted immunoglobulin heavy chain locus, wherein the restriction is with respect to the number of immunoglobulin $V_H$ gene segments. In various aspects, the restriction is to one or no more than two, or a single $V_H$ gene family member (e.g., one or more $V_H$ alleles, variants, or polymorphic variants thereof). In various aspects, the heavy chain locus further comprises one or more $D_H$ gene segments and one or more $J_H$ gene segments. In various aspects, the $V_H$, $D_H$ and $J_H$ gene segments are human. In various aspects, the $V_H$, $D_H$ and $J_H$ gene segments are operably linked to a non-human constant region (e.g., an IgM and/or an IgG). In various aspects, the constant region is a mouse or rat constant region.

In one aspect, a method for making a mouse having a restricted immunoglobulin heavy chain locus is provided, comprising introducing a nucleic acid construct as described herein into a mouse embryonic stem (ES) cell, and isolating or identifying a mouse ES cell that comprises the nucleic acid construct.

In one embodiment, the nucleic acid construct comprises a single human $V_H$ gene segment, one or more human $D_H$ gene segments, and one or more human $J_H$ gene segments. In one embodiment, the nucleic acid construct comprises one or more site-specific recombination sites (e.g., a loxP or a Frt site).

In one aspect, a mouse made using a targeting vector, nucleic acid sequence, or cell as described herein is provided. In various embodiments, the targeting vector, nucleic acid sequence or cell comprises a DNA sequence that contains a single human $V_H$ gene segment (or polymorphic variants thereof), one or more human $D_H$ gene segments, and one or more human $J_H$ gene segments operably linked to a non-human constant gene.

In one aspect, a method for making a mouse comprising a restricted immunoglobulin heavy chain locus is provided, comprising replacing a mouse immunoglobulin heavy chain locus with a human genomic sequence comprising a single human $V_H$ gene segment (or polymorphic variants thereof), one or more human $D_H$ gene segments, and one or more human JH gene segments, wherein the human $V_H$, $D_H$ and $J_H$ gene segments are capable of rearranging to form a chimeric heavy chain that contains a human variable domain operably linked to a non-human constant region. In one embodiment, the non-human constant region is a mouse or rat constant region.

In various aspects, the non-human animals are rodents. In various aspects, the rodents are mice and/or rats.

In one aspect, a modified immunoglobulin heavy chain locus is provided that comprises a heavy chain V segment repertoire that is restricted with respect to the identity of the V segment, and that comprises one or more D segments and one or more J segments, or one or more J segments. In one embodiment, the heavy chain V segment is a human segment. In one embodiment, the one or more D segments are human D segments. In one embodiment, the one or more J segments are human J segments. In one embodiment, the one or more D segments and one or more J segments are human D and human J segments.

In one embodiment, the modified locus is a non-human locus. In one embodiment, the non-human locus is modified with at least one human immunoglobulin sequence.

In one embodiment, the restriction is to one V segment family member. In one embodiment, the one V segment family member is present in two or more copies. In one embodiment, the one V segment family member is present as two or more variants (e.g., two or more polymorphic forms of the V segment family member). In one embodiment, the one V segment is a human V segment family member. In one embodiment, the one V segment family member is present in a number of variants as is observed in the human population with respect to that variant. In one embodiment, the V segment family member is selected from Table 1. In one embodiment, the V segment family member is present in a number of variants as shown, for each V segment, in a number of alleles from 1 allele to the number of alleles shown in the right column of Table 1.

In one embodiment, the restriction is to a human $V_H1$-69 gene segment. In one embodiment, the human $V_H1$-69 gene segment is present in two or more copies. In one embodiment, the human $V_H1$-69 gene segment is present as two or more variants (e.g., two or more polymorphic forms the human $V_H1$-69 gene). In one embodiment, the human $V_H1$-69 gene segment is present in a number of variants as is observed in the human population with respect to the human $V_H1$-69 gene segment. In one embodiment, the human $V_H1$-69 gene segment is selected from Table 2. In one embodiment, the human $V_H1$-69 gene segment is present in a number of variants as shown, for each $V_H1$-69 gene segment, in a number of alleles from one allele to the number of alleles shown in Table 2.

In one embodiment, the restriction is to a human $V_H1$-2 gene segment. In one embodiment, the human $V_H1$-2 gene segment is present in two or more copies. In one embodiment, the human $V_H1$-2 gene segment is present as two or more variants (e.g., two or more polymorphic forms the human $V_H1$-2 gene). In one embodiment, the human $V_H1$-2 gene segment is present in a number of variants as is observed in the human population with respect to the human $V_H1$-2 gene segment. In one embodiment, the human $V_H1$-2 gene segment is selected from Table 3. In one embodiment, the human $V_H1$-2 gene segment is present in a number of variants as shown, for each $V_H1$-2 gene segment, in a number of alleles from one allele to the number of alleles shown in Table 3.

In one aspect, a heavy chain immunoglobulin locus is provided that comprises a single functional human V segment. In one embodiment, the single functional human V segment is selected from a $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and a $V_H7$-81 segment. In one embodiment, the single functional human V segment is a $V_H1$-69 segment; in a specific embodiment, the single functional human V segment is present in 1, 2, 3, 4, 5, 6, 7, 8, 9, 10, 11, 12, or 13 polymorphic forms found in the human population. In one embodiment, the single functional human V segment is a $V_H1$-2 segment; in a specific embodiment, the single functional human V segment is present in 1, 2, 3, 4, or 5 polymorphic forms found in the human population.

In one embodiment, the heavy chain immunoglobulin locus is a modified locus of a non-human animal. In one embodiment, the modified non-human immunoglobulin heavy chain locus is present in the non-human animal at a position in the genome in which the corresponding unmodified non-human locus is found in the wild-type non-human animal. In one embodiment, the modified non-human immunoglobulin heavy chain locus is present on a transgene in a non-human animal.

In one embodiment, the single functional human V gene segment is a $V_H1$-69 gene segment. In one embodiment, the $V_H1$-69 gene segment comprises SEQ ID NO: 34. In one embodiment, the $V_H1$-69 gene segment is derived from SEQ ID NO: 34. In one embodiment, the $V_H1$-69 gene segment is at least 80%, at least 85%, at least 90%, at least 95%, or at least 98% identical to SEQ ID NO: 34.

In one embodiment, the single functional human V gene segment is encoded by the nucleotide sequence of SEQ ID NO: 34.

In one embodiment, the single functional human V gene segment is a $V_H1$-2 gene segment. In one embodiment, the $V_H1$-2 gene segment comprises SEQ ID NO: 60. In one embodiment, the $V_H1$-2 gene segment is derived from SEQ ID NO: 60. In one embodiment, the $V_H1$-2 gene segment is at least 80%, at least 85%, at least 90%, at least 95%, or at least 98% identical to SEQ ID NO: 60.

In one embodiment, the single functional human V gene segment is encoded by the nucleotide sequence of SEQ ID NO: 60.

In one embodiment, the single functional human V segment is operably linked to one or more D segments and one or more J segments, or one or more J segments. In one embodiment, the V segment and one or more D and/or J segments are operably linked to an immunoglobulin heavy chain constant region sequence. In one embodiment the immunoglobulin heavy chain constant region sequence is selected from a $C_H1$, a hinge, a $C_H2$, a $C_H3$ sequence, and a combination thereof. In one embodiment, the $C_H1$, hinge, $C_H2$, $C_H3$, or combination thereof are each non-human endogenous constant sequences. In one embodiment, at least one of the $C_H1$, hinge, $C_H2$, $C_H3$, or combination thereof is a human sequence. In a specific embodiment, the $C_H1$ and/or hinge are human sequences.

In one aspect, a modified endogenous non-human immunoglobulin heavy chain locus is provided, comprising a replacement of all functional V gene segments with a single human V gene segment (or a single human V gene segment present in multiple polymorphic forms or copy number), wherein the non-human immunoglobulin heavy chain locus is incapable of rearrangement to form a heavy chain variable gene that is derived from a V gene segment other than the single human V gene segment (or one of the polymorphic forms or copies).

In one embodiment, the single human V gene segment is $V_H1$-69. In one embodiment, the single human V gene segment is $V_H1$-2.

In one embodiment, the locus comprises at least one human or non-human $D_H$ gene segment, and one human or non-human $J_R$ gene segment. In a specific embodiment, the locus comprises a human $D_R$ gene segment and a human $J_R$ gene segment. In a specific embodiment, the locus comprises a human $J_R$ gene segment. In another specific embodiment, the locus comprises a human $V_H1$-69 gene segment (present as a single copy or multiple copies of different polymorphic variants), all functional human $D_R$ gene segments, and all functional human $J_R$ gene segments. In another specific embodiment, the locus comprises a human $V_H1$-2 gene segment (present as a single copy or multiple copies of different polymorphic forms), all functional human $D_H$ gene segments, and all functional human $J_H$ gene segments. In one embodiment, the human V, D, and J gene segments (or V and J gene segments) are operably linked to a mouse constant region gene at an endogenous mouse heavy chain locus. In a specific embodiment, the mouse heavy chain locus comprises a wild-type repertoire of mouse immunoglobulin constant region sequences.

In one aspect, a genetically modified non-human animal is provided, wherein the only functional immunoglobulin heavy chain V gene segment of the non-human animal is selected from a human $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and $V_H7$-81 gene segment. In one embodiment, the heavy chain V gene segment is a human $V_H1$-69 gene segment. In one embodiment, the heavy chain V gene segment is a human $V_H1$-2 gene segment.

In one aspect, a genetically modified non-human animal is provided, wherein the non-human animal comprises a single functional human $V_H$ gene segment (present as a single copy or multiple copies of different polymorphic forms), and wherein the non-human animal is substantially incapable of forming a rearranged immunoglobulin heavy chain variable domain gene that lacks the single functional human $V_H$ gene segment (or one of the polymorphic forms or copies).

In one aspect, a genetically modified non-human animal is provided, wherein the only immunoglobulin heavy chain variable region expressed in the non-human animal is derived from one of a human segment selected from a human $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and $V_H7$-81 gene segment. In one embodiment, the human segment is a $V_H1$-69 segment. In one embodiment, the human segment is a $V_H1$-2 segment. In one embodiment, the only immunoglobulin heavy chain variable region expressed by the mouse is derived from a single V segment family member, and in one embodiment the only immunoglobulin heavy chain variable region is derived from a polymorphic variant of the single V segment family member.

In one aspect, a non-human animal comprising a restricted immunoglobulin heavy chain V gene segment repertoire is provided, wherein the non-human animal further comprises one or more human immunoglobulin κ light chain variable segments (Vκ). In one embodiment, the one or more Vκ segments are operably linked to one or more human J segments. In a specific embodiment, the J segments are human Jκ segments. In another specific embodiment, the non-human animal does not express an immunoglobulin λ light chain. In another specific embodiment, the non-human animal does not comprise a functional human or functional endogenous immunoglobulin λ light chain variable locus.

In one embodiment, the non-human animal is a rodent. In one embodiment, the rodent is a mouse.

In one embodiment, the non-human animal comprises a replacement at the endogenous non-human immunoglobulin Vκ locus of all or substantially all functional endogenous Vκ segments with one or more functional human Vκ segments. In a further specific embodiment, the replacement is with all or substantially all functional human immunoglobulin Vκ segments.

In one embodiment, the non-human animal comprises a replacement at the endogenous non-human immunoglobulin Vκ locus of all or substantially all functional endogenous Vκ gene segments with human Vκ gene segments selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a combination thereof.

In one embodiment, the non-human animal comprises a replacement at the endogenous non-human immunoglobulin Jκ locus of all or substantially all functional endogenous non-human immunoglobulin Jκ segments with one or more functional human immunoglobulin Jκ segments. In a further specific embodiment, the replacement is with all or substantially all functional human immunoglobulin Jκ segments.

In one embodiment, the non-human animal comprises a replacement at the endogenous non-human immunoglobulin Jκ locus of all or substantially all functional endogenous non-human immunoglobulin Jκ gene segments with human Jκ gene segments selected from Jκ1, Jκ2, Jκ3, Jκ4, Jκ5, and a combination thereof.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H1$-69 segment, and the non-human animal further comprises a replacement of all functional non-human $D_R$ segments with all functional human $D_R$ segments, and further comprises a replacement of all functional non-human $J_R$ segments with all functional human $J_R$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H1$-69 sequence, a human $D_R$ sequence, a human $J_R$ sequence, and a mouse constant region sequence.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H1$-2 segment, and the non-human animal further comprises a replacement of all functional non-human $D_H$ segments with all functional human $D_R$ segments, and further comprises a replacement of all functional non-human $J_R$ segments with all functional human $J_R$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H1$-2 sequence, a human $D_R$ sequence, a human $J_R$ sequence, and a mouse constant region sequence.

In one embodiment, a B cell is provided that comprises the rearranged gene. In a specific embodiment, the B cell is from a mouse as described that has been immunized with an antigen of interest, and the B cell encodes an antibody that specifically binds the antigen of interest. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human κ light chain variable region) that specifically binds the antigen of interest.

In one aspect, a non-human animal comprising a restricted immunoglobulin heavy chain V segment repertoire is provided, wherein the non-human animal comprises one or more human λ light chain variable (Vλ) segments. In one embodiment, the one or more human Vλ segments are operably linked to one or more human J segments. In a specific embodiment, the J segments are human Jλ segments. In another specific embodiment, the non-human animal does not express a κ light chain. In another specific embodiment, the non-human animal does not comprise a functional human or non-human κ light chain variable locus.

In one embodiment, the non-human animal comprises a replacement of all or substantially all functional non-human immunoglobulin Vλ segments with one or more functional human immunoglobulin Vλ segments. In a further specific embodiment, the replacement is with all or substantially all functional human immunoglobulin Vλ segments.

In one embodiment, the non-human animal comprises a replacement of all or substantially all functional non-human Vλ segments with a fragment of cluster A of the human λ light chain locus. In a specific embodiment, the fragment of cluster A of the human λ light chain locus comprises human Vλ gene segments Vλ3-27 through Vλ3-1.

In one embodiment, the non-human animal comprises a replacement of all or substantially all functional non-human Vλ segments with a fragment of cluster B of the human λ light chain locus. In a specific embodiment, the fragment of cluster B of the human λ light chain locus comprises human Vλ gene segments Vλ5-52 through Vλ1-40.

In one embodiment, the non-human animal comprises a replacement of all or substantially all functional non-human Vλ segments with a fragment of cluster A and a fragment of cluster B of the human λ light chain locus, wherein as a result of the replacement comprise human Vλ gene segments Vλ5-52 through Vλ3-1.

In one embodiment, the non-human animal comprises a replacement of all or substantially all functional non-human Vλ segments with at least 12 human Vλ gene segments, at least 28 human Vλ gene segments, or at least 40 human Vλ gene segments.

In one embodiment, the non-human animal comprises a replacement of all or substantially all functional non-human immunoglobulin Jλ gene segments with one or more functional human immunoglobulin Jλ gene segments. In a further specific embodiment, the replacement is with all or substantially all functional human immunoglobulin Jλ gene segments. In various embodiments, the functional human Jλ gene segments include Jλ1, Jλ2, Jλ0.3 and Jλ7.

In a specific embodiment, the non-human animal comprises an immunoglobulin heavy chain variable ($V_H$) region locus that comprises only a single $V_H$ segment, wherein the single $V_H$ segment is a human $V_H1$-69 segment or a human $V_H1$-2 segment, and further comprises a replacement of all functional non-human $D_H$ segments with all functional human $D_H$ segments, and further comprises a replacement of all functional non-human $J_H$ segments with all functional human $J_H$ segments, and wherein the $V_H$ region locus is operably linked to a human or non-human constant region gene sequence. In a specific embodiment, the constant region gene sequence is a non-human constant region gene sequence, e.g., an endogenous non-human constant gene sequence. In a specific embodiment, the non-human animal rearranges segments at the non-human immunoglobulin heavy chain locus to form a gene encoding an immunoglobulin heavy chain variable region comprising a human $V_H1$-69 sequence (or a human $V_H1$-2 sequence), a human $D_H$ sequence, a human $J_H$ sequence, and an endogenous non-human constant region sequence.

In one embodiment, a B cell is provided that comprises the rearranged gene. In a specific embodiment, the B cell is from a non-human animal as described that has been immunized with an antigen of interest, and the B cell encodes an antibody that specifically binds the antigen of interest. In one embodiment, the antigen is a human protein selected from a ligand, a cell surface receptor and an intracellular protein. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human λ light chain variable region) that specifically binds the antigen of interest.

In one aspect, a non-human animal comprising a restricted immunoglobulin $V_H$ segment repertoire is provided, wherein the non-human animal comprises a human $V_H1$-69 segment (or a human $V_H1$-2 segment) on a transgene, wherein the human $V_H1$-69 segment is operably linked on the transgene to a human or non-human $D_H$ segment, and/or a human or non-human J segment, and the transgene further comprises a human or non-human constant region gene, or a chimeric human/non-human constant region (e.g., a $C_H1$, hinge, $C_H2$, $C_H3$ or combination thereof wherein at least one sequence is non-human, e.g., selected from hinge, $C_H2$, and $C_H3$ and/or hinge). In one embodiment, the non-human animal is a mouse or rat and the non-human D, J, and/or constant region gene is a mouse or rat gene or chimeric human/mouse or rat.

In one embodiment, the non-human animal comprises a transgene that comprises an immunoglobulin light chain variable region locus that comprises one or more human immunoglobulin Vλ gene segments and Jλ gene segments, or one or more human immunoglobulin Vκ gene segments and Jκ gene segments, and a human immunoglobulin κ or λ light chain constant region gene, such that the transgene rearranges in the non-human animal to form a rearranged immunoglobulin κ or λ light chain gene. In various embodiments, the human Vκ and Jκ gene segments are those described herein. In various embodiments, the human Vλ and Jλ gene segments are those described herein.

In a specific embodiment, the non-human animal comprises a transgene having an immunoglobulin heavy chain variable locus that comprises a single V segment that is a human $V_H$1-69 segment (or a human $V_H$1-2 segment), one or more human D segments, one or more human J segments, and a human constant gene operably linked to the heavy chain variable locus, such that the mouse expresses from the transgene a fully human antibody derived from the $V_H$1-69 segment (or the $V_H$1-2 segment). In one embodiment, the non-human animal does not comprise a functional endogenous immunoglobulin heavy chain variable region locus. In a specific embodiment, the non-human animal comprises a nonfunctional endogenous immunoglobulin heavy chain variable region locus that comprises a deletion of an endogenous non-human $D_H$ and/or endogenous non-human $J_H$ segment, such that the non-human animal is incapable of rearranging the endogenous immunoglobulin heavy chain variable region locus to form a rearranged non-human antibody gene. In a specific embodiment, the non-human animal comprises a deletion of a switch sequence operably linked to an endogenous mouse heavy chain constant region. In a specific embodiment, the switch sequence is a non-human (e.g., mouse) µ switch sequence. In another embodiment, the non-human animal further comprises a lack of a functional endogenous light chain variable locus selected from an immunoglobulin κ locus and an immunoglobulin λ locus. In a specific embodiment, the non-human animal comprises a deletion of a Jκ and/or a Jλ sequence, such that the non-human animal is incapable of rearranging an endogenous non-human immunoglobulin κ light chain and/or an endogenous non-human immunoglobulin λ light chain variable region to form a rearranged endogenous non-human immunoglobulin κ light chain and/or a rearranged endogenous non-human immunoglobulin λ light chain gene.

In one embodiment, the non-human animal comprises a deletion of an endogenous non-human immunoglobulin κ light chain sequence that results in a functional knockout of the endogenous non-human immunoglobulin κ light chain. In one embodiment, the non-human animal comprises a deletion of an endogenous non-human immunoglobulin λ light chain sequence that results in a functional knockout of the endogenous non-human immunoglobulin λ light chain.

In one aspect, the non-human animal comprises a functionally silenced endogenous immunoglobulin heavy chain variable gene locus, and comprises a restricted repertoire of human heavy chain variable gene segments (e.g., no more than one, or no more than two). In one embodiment, the functional silencing comprises a modification of an endogenous non-human heavy chain variable gene locus selected from a deletion, an insertion, an inversion, and a combination thereof.

In one aspect, a rodent is provided that comprises an immunoglobulin $V_H$ repertoire derived from no more than one human $V_H$ segment or one or more polymorphs thereof, from a D segment selected from a repertoire of one or more D segments, and from a J segment derived from a repertoire of one or more J segments. In one embodiment, the rodent rearranges the human $V_H$ segment, a human D segment, and a human J segment and forms a rearranged human heavy chain sequence that is operably linked to a human or a rodent constant region sequence. In one embodiment, the human and/or rodent constant region sequence is selected from a $C_H$1, a hinge, a $C_H$2, a $C_H$3, and a combination thereof. In one embodiment, the rodent expresses an immunoglobulin light chain that comprises a human variable domain, wherein the light chain is cognate with a human heavy chain domain derived from the rearranged human heavy chain sequence. In one embodiment, the rodent does not express a polypeptide sequence selected from a non-human heavy chain variable domain, a non-human light chain variable domain, and a combination thereof.

In one embodiment, the human $V_H$ segment is present in 1, 2, 3, 4, 5, 6, 7, 8, 9, 10, 11, 12, 13, 14, 15, 16, 17, 18, or 19 or more polymorphic variants, wherein each polymorphic variant is operably linked to a D and/or J segment such that each polymorphic variant is capable for rearranging and forming a rearranged heavy chain variable domain with any of the one or more D segments and any of the one or more J segments. In one embodiment, the rodent is a mouse or a rat. In one embodiment, the repertoire of D segments comprises two or more D segments. In one embodiment, the repertoire of J segments comprises two or more J segments. In one embodiment, the D and/or J segments are human segments.

In one aspect, a nucleic acid construct is provided that comprises a sequence encoding a single human immunoglobulin $V_H$ segment and/or polymorphic variants thereof and one or more $D_H$ and one or more J sequences, wherein the construct comprises at least one homology arm homologous to a non-human immunoglobulin heavy chain variable locus, or a recombinase recognition site (e.g., a lox site). In one embodiment, the V segment is a $V_H$1-69 segment or a $V_H$1-2 segment.

In one aspect, a nucleic acid construct is provided; comprising a nucleic acid sequence encoding a single human immunoglobulin heavy chain V segment, wherein the single $V_H$ segment is a $V_H$1-69 (or $V_H$1-2) segment. In one embodiment, the construct comprises a site-specific recombinase recognition site. In one embodiment, the construct comprises a first mouse homology arm upstream of the $V_H$1-69 (or $V_H$1-2) segment and a second mouse homology arm downstream of the $V_H$1-69 (or $V_H$1-2) segment, and wherein the first mouse homology arm is homologous to a region of a mouse chromosome immediately upstream of a mouse immunoglobulin heavy chain variable region but not including a functional mouse immunoglobulin heavy chain variable segment. In one embodiment, the construct comprises SEQ ID NO: 3. In one embodiment, the construct comprises SEQ ID NO: 70.

In one aspect, the restricted single $V_H$ segment is in a non-human animal, or the restricted $V_H$ segment is at a non-human immunoglobulin heavy chain locus (e.g., in situ or in a transgene), and the non-human animal or non-human immunoglobulin heavy chain locus is selected from a mouse, rat, rabbit, pig, bovine (e.g., cow, bull, buffalo), deer, sheep, goat, chicken, cat, dog, ferret, primate (e.g., marmoset, rhesus monkey) locus or animal. In a specific embodiment, the non-human animal or locus is a mouse or a rat locus.

In one aspect, a cell or tissue is provided, wherein the cell or tissue is derived from a non-human animal as described herein, and comprises a restricted $V_H$ segment repertoire. In one embodiment, the $V_H$ segment repertoire is restricted to a single $V_H$ segment family member and/or polymorphic variants thereof. In a specific embodiment, the single $V_H$ segment is a human $V_H$1-69 segment or a human $V_H$1-2 segment. In one embodiment, the cell or tissue is derived from spleen, lymph node or bone marrow of the non-human animal.

In one embodiment, the cell is an ES cell. In one embodiment, the cell is a B cell. In one embodiment, the cell is a germ cell.

In one embodiment, the tissue is selected from connective, muscle, nervous and epithelial tissue. In a specific embodiment, the tissue is reproductive tissue.

In one embodiment, the cell and/or tissue derived from a mouse as described herein are isolated for use in one or more ex vivo assays. In various embodiments, the one or more ex vivo assays include measurements of physical, thermal, electrical, mechanical or optical properties, a surgical procedure, measurements of interactions of different tissue types, the development of imaging techniques, or a combination thereof.

In one embodiment, the non-human animal is a mouse.

In one aspect, a non-human embryo is provided comprising a restricted heavy chain $V_H$ segments as described herein. In one embodiment, the embryo comprises an ES donor cell that comprises the restricted $V_H$ segment, and host embryo cells.

In one embodiment, the non-human animal is a mouse.

In one aspect, a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a nucleus derived from a non-human animal as described herein is provided. In one embodiment, the nucleus is from a diploid cell that is not a B cell.

In one aspect, a pluripotent, induced pluripotent, or totipotent cell derived from a non-human animal as described herein is provided. In a specific embodiment, the cell is a mouse embryonic stem (ES) cell.

In one aspect, a non-human induced pluripotent cell comprising a restricted $V_H$ segment repertoire is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, a lymphocyte of a non-human animal as described herein is provided. In one embodiment, the lymphocyte is a B cell.

In one aspect, mouse cells and mouse embryos are provided, including but not limited to ES cells, pluripotent cells, and induced pluripotent cells, that comprise genetic modifications as described herein. Cells that are XX and cells that are XY are provided. Cells that comprise a nucleus containing a modification as described herein are also provided, e.g., a modification introduced into a cell by pronuclear injection.

In one aspect, an antibody variable domain sequence made in a non-human animal as described herein is provided.

In one aspect, a human therapeutic is provided, comprising an antibody variable domain comprising a sequence derived from a non-human animal as described herein.

In one aspect, a method of obtaining an antibody variable region sequence from a non-human animal is provided, wherein the antibody variable region sequence is derived from a human $V_H$1-69 segment or a $V_H$1-2 segment, wherein the method comprises (a) immunizing a non-human animal with an antigen of interest, wherein the non-human animal comprises a replacement at the endogenous immunoglobulin heavy chain locus of all or substantially all non-human variable segments with a single human variable segment, wherein the single human variable segment is a $V_H$1-69 segment or a $V_H$1-2 segment, and wherein the non-human animal is substantially incapable of forming a immunoglobulin heavy chain variable region sequence that is not derived from a human $V_H$1-69 segment or a $V_H$1-2 segment; (b) allowing the non-human animal to mount an immune response with respect to the antigen of interest; and, (c) identifying or isolating an immunoglobulin heavy chain variable region sequence of the non-human animal, wherein the antibody binds the antigen of interest.

In one embodiment, the single human variable segment is a $V_H$1-69 segment.

In one embodiment, the antibody variable region sequence is derived from SEQ ID NO: 34. In one embodiment, the antibody variable region sequence is at least 75%, at least 80%, at least 85%, at least 90%, at least 95%, or at least 98% identical to SEQ ID NO: 34. In one embodiment, the antibody variable region sequence comprises SEQ ID NO: 34.

In one embodiment, the single human variable segment is a $V_H$1-2 segment.

In one embodiment, the antibody variable region sequence is derived from SEQ ID NO: 60. In one embodiment, the antibody variable region sequence is at least 75%, at least 80%, at least 85%, at least 90%, at least 95%, or at least 98% identical to SEQ ID NO: 60. In one embodiment, the antibody variable region sequence comprises SEQ ID NO: 60.

In one embodiment, the immune response to the antigen is characterized by an antibody titer that is about $6 \times 10^4$ to about $5 \times 10^5$ times greater than two times background as determined in an ELISA assay. In a specific embodiment, the antibody titer is about $1 \times 10^5$ to about $2 \times 10^5$ times greater than two times background as determined in an ELISA assay. In a specific embodiment, the antibody titer is about $1.5 \times 10^5$ times greater than two times background as determined in an ELISA assay. In one embodiment, the antigen is a human cell surface receptor.

In one aspect, a method for generating a repertoire of human antibody variable regions in a non-human animal is provided, wherein the human heavy chain variable regions of the repertoire are derived from the same $V_H$ gene family member and one of a plurality of $D_H$ segments and one of a plurality of $J_H$ segments, wherein the repertoire is characterized by having heavy chain immunoglobulin FR1 (framework 1), CDR1, FR2, CDR2, and FR3 sequences from a single $V_H$ gene family member. In one embodiment, the repertoire is further characterized by having a plurality of different CDR3+FR4 sequences.

In one embodiment, the single $V_H$ gene family is selected from $V_H$ family 1, 2, 3, 4, 5, 6, and 7. In a specific embodiment, the single $V_H$ gene family is $V_H$ family 1. In one embodiment, the single $V_H$ gene family member is selected from $V_H$1-2, $V_H$1-69, $V_H$2-26, $V_H$2-70, and $V_H$3-23. In a specific embodiment, the single $V_H$ gene family member is $V_H$1-69. In a specific embodiment, the single $V_H$ gene family member is $V_H$1-2.

In one embodiment, the repertoire comprises heavy chain FR1, CDR1, FR2, CDR2 and FR3 sequences derived from a $V_H$1-69 segment. In a specific embodiment, the repertoire comprises heavy chain FR1, CDR1, FR2, CDR2 and FR3 sequences derived from SEQ ID NO: 35. In a specific embodiment, the repertoire comprises heavy chain FR1, CDR1, FR2, CDR2 and FR3 sequences of SEQ ID NO: 35.

In one embodiment, the repertoire comprises heavy chain FR1, CDR1, FR2, CDR2 and FR3 sequences derived from a $V_H$1-2 segment. In a specific embodiment, the repertoire comprises heavy chain FR1, CDR1, FR2, CDR2 and FR3 sequences derived from SEQ ID NO: 61. In a specific embodiment, the repertoire comprises heavy chain FR1, CDR1, FR2, CDR2 and FR3 sequences of SEQ ID NO: 61.

In one aspect, a biological (i.e., in vivo) system is provided for generating a plurality of different human CDR3 sequences reflecting a plurality of rearrangements of a single human $V_H$ gene segment with a plurality of human D and J segments, wherein the system generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the single human $V_H$ gene segment is selected from $V_H1$-2, $V_H1$-69, $V_H2$-26, $V_H2$-70, and $V_H3$-23. In one embodiment, the single human $V_H$ gene segment is $V_H1$-69. In one embodiment, the single human $V_H$ gene segment is $V_H1$-2. In one embodiment, the single human $V_H$ gene segment is identified in Table 1. In one embodiment, the single human $V_H$ gene segment is identified in Table 2. In one embodiment, the single human $V_H$ gene segment is identified in Table 3.

In one aspect, an in vivo method for generating a plurality of heavy chain CDR sequences derived from rearrangements of a single human $V_H$ gene segment with a plurality of human D and J segments is provided, wherein the method generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the method comprises exposing a non-human animal as described herein to an antigen of interest, allowing the non-human animal to develop an immune response to the antigen, wherein the immune response generates the plurality of heavy chain CDR sequences derived from rearrangements of the single human $V_H$ gene segment with one of the human D and one of the human J segments, and identifying a set of heavy chain CDRs that bind the antigen. In one embodiment, the method comprises isolating from the animal a nucleic acid sequence that encodes a human $V_H$ domain that comprises the heavy chain CDRs.

In one embodiment, the heavy chain CDR sequences are derived from a rearrangement of a human $V_H1$-69 gene segment. In one embodiment, the heavy chain CDR sequences are derived from a rearrangement of a human $V_H1$-2 gene segment.

In one aspect, a method for generating a plurality of different CDR3 and FR4 sequences in a non-human animal is provided, comprising exposing a non-human animal that comprises an immunoglobulin heavy chain variable gene locus with a $V_H$ segment repertoire restricted to a single $V_H$ segment family member to an antigen of interest, allowing the non-human animal to develop an immune response to the antigen, wherein the immune response generates a B cell repertoire whose heavy chain variable domains are each derived from the single $V_H$ segment family member and that comprise a plurality of different CDR3 and FR4 sequences.

In one embodiment, the singe $V_H$ segment family member is human. In one embodiment, the non-human animal is selected from a mouse, a rat, and a rabbit. In one embodiment, the antigen of interest is selected from a ligand, a receptor, an intracellular protein and a secreted protein. In one embodiment, the antigen of interest is a human pathogen as described herein.

In one embodiment, the single human $V_H$ gene family member is selected from $V_H1$-2, $V_H1$-69, $V_H2$-26, $V_H2$-70, and $V_H3$-23. In one embodiment, the single human $V_H$ gene family member is $V_H1$-69. In one embodiment, the single human $V_H$ gene family member is $V_H1$-2. In one embodiment, the single human $V_H$ gene family member is identified in Table 1. In one embodiment, the single human $V_H$ gene family member is identified in Table 2. In one embodiment, the single human $V_H$ gene family member is identified in Table 3.

In one aspect, a nucleotide sequence encoding an immunoglobulin variable region made in a non-human animal as described herein is provided.

In one aspect, an immunoglobulin heavy chain or immunoglobulin light chain variable region amino acid sequence of an antibody made in a non-human animal as described herein is provided.

In one aspect, an immunoglobulin heavy chain or immunoglobulin light chain variable region nucleotide sequence encoding a variable region of an antibody made in a non-human as described herein is provided.

In one aspect, an antibody or antigen-binding fragment thereof (e.g., Fab, F(ab)$_2$, scFv) made in a non-human animal as described herein is provided.

In one aspect, a mouse having a restricted immunoglobulin heavy chain locus characterized by the presence of a single human $V_H$ gene segment, one or more human $D_H$ gene segments, and one or more human $J_H$ gene segments is provided, wherein the single human $V_H$ gene segment is at an endogenous mouse locus and the $V_H$ gene segment is operably linked to the one or more human $D_H$ gene segments, the one or more human $J_H$ gene segments, and to an endogenous immunoglobulin heavy chain constant gene.

In one embodiment, the mouse further comprises a humanized immunoglobulin light chain locus comprising one or more human $V_L$ gene segments, and one or more human $J_L$ gene segments, wherein the human $V_L$ gene segments and the human $J_L$ gene segments are operably linked to a non-human immunoglobulin light chain constant region gene. In a specific embodiment, the human $V_L$ and $J_L$ gene segments are at an endogenous mouse light chain locus, and wherein the non-human immunoglobulin light chain constant region gene is a mouse gene.

In one embodiment, the humanized immunoglobulin light chain locus is on a transgene, and the constant region gene is selected from mouse, rat, and human.

In one embodiment, the human $V_L$ and $J_L$ gene segments are Vκ and Jκ gene segments. In one embodiment, the human $V_L$ and $J_L$ gene segments are Vλ and Jλ gene segments In one aspect, a non-human animal is provided, wherein the non-human animal has a B cell repertoire that expresses immunoglobulin heavy chain variable domains derived from a single V segment family member. In one embodiment, at least 10%, at least 20%, at least 30%, at least 40%, at least 50%, at least 60%, at least 70%, at least 80%, at least 90, or at least 95% of the B cell repertoire of the non-human animal immunoglobulin heavy chain variable domain expressed in the B cell repertoire is derived from the same V segment family member. In a specific embodiment, the percentage is at least 90%. In one embodiment, the B cell repertoire consists essentially of peripheral (blood) B cells. In one embodiment, the B cell repertoire consists essentially of splenic B cells. In one embodiment, the B cell repertoire consists essentially of bone marrow B cells. In one embodiment, the B cell repertoire consists essentially of peripheral B cells, splenic B cells, and bone marrow B cells.

In one aspect, a genetically modified non-human animal is provided, wherein more than 10%, 20%, 30%, 40%, 50%, 60%, 70%, 80%, or more than 90% of the B cells of the non-human animal that express a heavy chain immunoglobulin variable domain express a heavy chain immunoglobulin variable domain derived from a single $V_H$ gene segment family member. In one embodiment, at least 75% of the B cells of the non-human animal that express an immunoglobulin heavy chain variable domain express an immunoglobulin heavy chain variable domain derived from the single $V_H$ gene segment family member. In a specific embodiment, the percentage is at least 90%. In one embodiment, all of the B cells that express a heavy chain domain that is derived from the single $V_H$ gene family member.

In one aspect, a genetically modified mouse is provided that makes an antigen-specific B cell population in response to immunization with an antigen of interest, wherein at least 10%, 20%, 30%, 40%, 50%, 60%, 70%, 80%, or more than 90%, of said antigen-specific B cell population expresses immunoglobulin heavy chains that are all derived from the same $V_H$ gene segment. In one embodiment, at least 75% of the antigen-specific B cell population expresses immunoglobulin heavy chains derived from the same $V_H$ gene segment. In one embodiment, all of the antigen-specific B cells express a heavy chain that is derived from the same $V_H$ gene segment.

In one aspect, a non-human animal comprising a restricted $V_H$ gene segment repertoire is provided, wherein the restriction is to a human $V_H1$-69 gene segment or a $V_H1$-69 gene segment that is at least about 75.5%, 76.5%, 86.7%, 87.8%, 94.9%, 96.9%, 98%, or 99% identical to a $V_H1$-69*01 gene segment. In a specific embodiment, the restricted repertoire is selected from one or more of the $V_H1$-69 variants of FIG. 15.

In one aspect, a non-human animal comprising a restricted $V_H$ gene segment repertoire is provided, wherein the restriction is to a human $V_H1$-2 gene segment or a $V_H1$-2 gene segment that is at least about 94.9%, 95.9%, 96.9%, 98%, or 99% identical to a $V_H1$-2 gene segment. In a specific embodiment, the restricted repertoire is selected from one or more of the $V_H1$-2 variants of FIG. 18.

In one embodiment, the non-human animal is a mouse.

In one embodiment, the mouse exhibits an immunophenotype having a characteristic of a higher ratio of mature B cells to immature B cells as compared to a wild type mouse. In a specific embodiment, the ratio is calculated from B cells harvested from spleen. In one embodiment, the mouse exhibits a population of mature B cells of about $1\times10^7$. In one embodiment, the mouse exhibits a population of immature B cells of about $0.5\times10^7$. In one embodiment, the mouse exhibits a ratio of mature B cells to immature B cells in the spleen of the mouse that is about 1.5-fold to about 2-fold higher than exhibited by a wild type mouse.

In one embodiment, the ratio is calculated from B cells harvested from bone marrow. In a specific embodiment, the mouse exhibits a population of mature B cells of about $3\times10^5$. In one embodiment, the mouse exhibits a population of immature B cells of about $7\times10^5$. In one embodiment, the mouse exhibits a ratio of mature B cells to immature B cells in the bone marrow of the mouse that is about 3-fold, or about 3.3-fold higher than exhibited by a wild type mouse.

In one embodiment, the mouse exhibits an immunophenotype having a characteristic of a higher number of pro B cells in the bone marrow as compared to a wild type mouse. In a specific embodiment, the mouse exhibits a population of pro B cells in the bone marrow of the mouse that is about 2.5-fold to about 3-fold higher than exhibited in the bone marrow of a wild type mouse. In a specific embodiment, the mouse exhibits a population of pro B cells in the bone marrow of the mouse that is about 2.75-fold higher than exhibited in the bone marrow of a wild type mouse.

In one embodiment, the mouse exhibits an immunophenotype having a characteristic selected from the group consisting of a $CD19^+$ splenic B cell population that is about 80% of a wild-type B cell, a $CD3^+$ splenic T cell population that is about the same as a wild type mouse, and a combination thereof.

In one embodiment, the mouse comprises a lymphocyte population whose % $CD19^+$ B cells in spleen are about the same as a wild-type mouse. In one embodiment, the number of $CD19^+$ B cells per spleen of the mouse is at least about 50% of the number of $CD19^+$ B cells per spleen of a wild-type mouse.

In one embodiment, the non-human animal comprises at least about 75% to about 80% of $CD19^+$ B cells in bone marrow as compared with a wild-type mouse.

In one embodiment, the total number of $CD19^+$ bone cells per femur of the mouse is non less than about 30%, 40%, 50%, 60%, or 75% of the total number of $CD19^+$ bone marrow cells in a wild-type mouse.

In one embodiment, the mouse expresses IgD and IgM at about the same level as observed in a wild-type mouse.

In one aspect, a mouse comprising a restricted human $V_H$ segment repertoire is provided, further comprising a humanized immunoglobulin light chain variable segment locus, wherein the ratio of λ to κ light chains expressed in the mouse is about the same as in a wild-type mouse.

In one aspect, a mouse is provided, comprising a restricted immunoglobulin heavy chain locus characterized by the presence of a single $V_H$ gene segment, one or more $D_H$ gene segments, and one or more $J_H$ gene segments, wherein the single $V_H$ gene segment is a polymorphic $V_H$ gene segment.

In one embodiment, the polymorphic $V_H$ gene segment is a human $V_H$ gene segment that is associated with a high copy number in human populations. In one embodiment, the human $V_H$ gene segment is selected from $V_H1$-2, $V_H1$-69, $V_H2$-26, $V_H2$-70, $V_H3$-23, or a polymorphic variant thereof. In a specific embodiment, the human $V_H$ gene segment is a $V_H1$-69 gene segment. In another specific embodiment, the human $V_H$ gene segment is a $V_H1$-2 gene segment.

In one embodiment, the single $V_H$ gene segment is operably linked to a human, mouse, or chimeric human/mouse immunoglobulin constant region gene. In a specific embodiment, the immunoglobulin constant region gene is a mouse constant region gene. In one embodiment, the immunoglobulin constant gene comprises a human sequence selected from a human $C_H1$, a human hinge, a human $C_H2$, a human $C_H3$, and a combination thereof. In one embodiment, the mouse constant gene is at an endogenous immunoglobulin heavy chain locus.

In one embodiment, the mouse further comprises a human immunoglobulin $V_L$ gene segment operably linked to a J gene segment and a light chain constant gene. In a specific embodiment, the $V_L$ gene segment and/or the J gene segment are selected from a human κ gene segment and a human λ gene segment. In one embodiment, the $V_L$ and/or J gene segments are human κ gene segments.

In various embodiments, the mouse comprises a deletion of all or substantially all endogenous $V_H$ gene segments.

In various embodiments, the non-human animal comprises an inactivated endogenous heavy chain variable gene locus. In various embodiments, the inactivated endogenous heavy chain variable gene locus is not operably linked to an endogenous heavy chain constant region gene.

In one aspect, a mouse is provided, wherein the mouse is characterized by the expression of serum immunoglobulin, wherein greater than 80% of the serum immunoglobulin comprises a human heavy chain variable domain and a cognate human light chain variable domain, wherein the human heavy chain variable domain is derived from a $V_H$ gene segment repertoire consisting essentially of a single human $V_H$ gene segment and/or polymorphic variants thereof.

In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one aspect, a mouse is provided, comprising, in its germline, a replacement at an endogenous immunoglobulin heavy chain locus of all or substantially all endogenous $V_H$ gene segments with a single human $V_H$ gene segment and/or polymorphic variants thereof. In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one embodiment, the mouse further comprises a replacement at an endogenous immunoglobulin light chain locus of all or substantially all endogenous $V_L$ gene segments with one or more human $V_L$ gene segments. In a specific embodiment, the mouse further comprises one or more human $J_L$ gene segments operably linked to the human $V_L$ gene segments.

In one aspect, use of a mouse as described herein to make an immunoglobulin variable region nucleotide sequence is provided. In one embodiment, the sequence comprises a rearranged $V_H$1-69 gene segment. In one embodiment, the sequence comprises a rearranged $V_H$1-2 gene segment.

In one embodiment, the immunoglobulin variable region nucleotide sequence is at least 80%, at least 85%, at least 90%, at least 95%, or at least 98% identical with a human $V_H$1-69 gene segment. In a specific embodiment, the immunoglobulin variable region nucleotide sequence is at least 80%, at least 85%, at least 90%, at least 95%, or at least 98% identical with SEQ ID NO: 34. In various embodiments, the human $V_H$1-69 gene segment is identified from Table 2.

In one embodiment, the immunoglobulin variable region nucleotide sequence encodes an amino acid sequence that is at least 80%, at least 85%, at least 90%, at least 95%, or at least 98% identical with SEQ ID NO: 35.

In one embodiment, the immunoglobulin variable region nucleotide sequence is at least 80%, at least 85%, at least 90%, at least 95%, or at least 98% identical with a human $V_H$1-2 gene segment. In a specific embodiment, the immunoglobulin variable region nucleotide sequence is at least 80%, at least 85%, at least 90%, at least 95%, or at least 98% identical with SEQ ID NO: 60. In various embodiments, the human $V_H$1-2 gene segment is identified from Table 3.

In one embodiment, the immunoglobulin variable region nucleotide sequence encodes an amino acid sequence that is at least 80%, at least 85%, at least 90%, at least 95%, or at least 98% identical with SEQ ID NO: 61.

In one aspect, use of a mouse as described herein to make a fully human Fab or a fully human F(ab)$_2$ is provided. In one embodiment, the fully human Fab or fully human F(ab)2 comprises a heavy chain variable region that comprises a rearranged human $V_H$1-69 gene segment. In one embodiment, the fully human Fab or fully human F(ab)2 comprises a heavy chain variable region that comprises a rearranged human $V_H$1-2 gene segment.

In one aspect, use of a mouse as described herein to make an immortalized cell line is provided.

In one aspect, use of a mouse as described herein to make a hybridoma or quadroma is provided.

In one aspect, use of a mouse as described herein to make a phage library containing human heavy chain variable regions and human light chain variable regions is provided.

In one embodiment, the human heavy chain variable regions are derived from a human $V_H$1-69 gene segment that comprises a sequence selected from SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56 and SEQ ID NO: 58.

In one embodiment, the human heavy chain variable regions are derived from a human $V_H$1-69 gene segment that comprises a sequence selected from SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and SEQ ID NO: 59.

In one embodiment, the human heavy chain variable regions are all derived from a human $V_H$1-2 gene segment that comprises a sequence selected from SEQ ID NO: 60, SEQ ID NO: 62, SEQ ID NO: 64, SEQ ID NO: 66 and SEQ ID NO: 68.

In one embodiment, the human heavy chain variable regions are derived from a human $V_H$1-2 gene segment that comprises a sequence selected from SEQ ID NO: 61, SEQ ID NO: 63, SEQ ID NO: 65, SEQ ID NO: 67 and SEQ ID NO: 69.

In one aspect, use of a mouse as described herein to generate a variable region sequence for making a human antibody is provided, comprising (a) immunizing a mouse as described herein with an antigen of interest, (b) isolating a lymphocyte from the immunized mouse of (a), (c) exposing the lymphocyte to one or more labeled antibodies, (d) identifying a lymphocyte that is capable of binding to the antigen of interest, and (e) amplifying one or more variable region nucleic acid sequence from the lymphocyte thereby generating a variable region sequence.

In one embodiment, the lymphocyte is derived or isolated from the spleen of the mouse. In one embodiment, the lymphocyte is derived or isolated from a lymph node of the mouse. In one embodiment, the lymphocyte is derived or isolated from the bone marrow of the mouse. In one embodiment, the lymphocyte is derived or isolated from the blood of the mouse.

In one embodiment, the labeled antibody is a fluorophore-conjugated antibody. In one embodiment, the one or more fluorophore-conjugated antibodies are selected from an IgM, an IgG, and/or a combination thereof.

In one embodiment, the lymphocyte is a B cell.

In one embodiment, the one or more variable region nucleic acid sequence comprises a heavy chain variable region sequence. In one embodiment, the one or more variable region nucleic acid sequence comprises a light chain variable region sequence. In a specific embodiment, the light chain variable region sequence is an immunoglobulin κ light chain variable region sequence. In one embodiment, the one or more variable region nucleic acid sequence comprises a heavy chain and a κ light chain variable region sequence.

In one embodiment, use of a mouse as described herein to generate a heavy and a κ light chain variable region sequence for making a human antibody is provided, comprising (a) immunizing a mouse as described herein with an antigen of interest, (b) isolating the spleen from the immunized mouse of (a), (c) exposing B lymphocytes from the spleen to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and x light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating one or more lymph nodes from the immunized mouse of (a), (c) exposing B lymphocytes from the one or more lymph nodes to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating bone marrow from the immunized mouse of (a), (c) exposing B lymphocytes from the bone marrow to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences. In various embodiments, the one or more labeled antibodies are selected from an IgM, an IgG, and/or a combination thereof.

In various embodiments, the antigen of interest is a pathogen that afflicts human subjects including, e.g., a viral antigen. Exemplary viral pathogens include, e.g., mainly those of the families of Adenoviridae, bacteria Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Such exemplary viruses typically range between 20-300 nanometers in length. In various embodiments, the antigen of interest is a viral antigen selected from a hepatitis virus (e.g., HCV, HBV, etc.), a human immunodeficiency virus (HIV), or an influenza virus (e.g., H1N1).

In various embodiments, use of a mouse as described herein to generate a heavy and κ light chain variable region sequence for making a human antibody is provided, further comprising fusing the amplified heavy and light chain variable region sequences to human heavy and light chain constant region sequences, expressing the fused heavy and light chain sequences in a cell, and recovering the expressed heavy and light chain sequences thereby generating a human antibody.

In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region comprises a $C_H1$, a hinge, a $C_H2$, a $C_H3$, a $C_H4$, or a combination thereof. In various embodiments, the light chain constant region is an immunoglobulin κ constant region. In various embodiments, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PER.C6™ cell), and a MC3T3 cell. In a specific embodiment, the cell is a CHO cell.

In one aspect, a method for generating a reverse-chimeric rodent-human antibody specific against an antigen of interest is provided, comprising the steps of immunizing a mouse as described herein with the antigen, isolating at least one cell from the mouse producing a reverse-chimeric mouse-human antibody specific against the antigen, culturing at least one cell producing the reverse-chimeric mouse-human antibody specific against the antigen, and obtaining said antibody.

In one embodiment, the reverse-chimeric mouse-human antibody comprises a human heavy chain variable domain fused with a mouse or rat heavy chain constant gene, and a human light chain variable domain fused with a mouse or rat or human light chain constant gene. In a specific embodiment, the human heavy chain variable domain contains a rearranged human $V_H1-69$ or human $V_H1-2$ gene segment.

In one embodiment, culturing at least one cell producing the reverse-chimeric rodent-human antibody specific against the antigen is performed on at least one hybridoma cell generated from the at least one cell isolated from the mouse.

In one embodiment, the antigen of interest is a pathogen that afflicts human subjects as described herein.

In one aspect, a method for generating a fully human antibody specific against an antigen of interest is provided, comprising the steps of immunizing a mouse as described herein with the antigen, isolating at least one cell from the mouse producing a reverse-chimeric rodent-human antibody specific against the antigen, generating at least one cell producing a fully human antibody derived from the reverse-chimeric rodent-human antibody specific against the antigen, and culturing at least one cell producing the fully human antibody, and obtaining said fully human antibody.

In various embodiments, the at least one cell isolated from the mouse producing a reverse-chimeric rodent-human antibody specific against the antigen is a splenocyte or a B cell.

In various embodiments, the antibody is a monoclonal antibody.

In various embodiments, the antibody comprises a heavy chain variable domain that contains a rearranged human $V_H1-69$ or human $V_H1-2$ gene segment.

In various embodiments, immunization with the antigen of interest is carried out with protein, DNA, a combination of DNA and protein, or cells expressing the antigen. In one embodiment, the antigen of interest is a pathogen that afflicts human subjects as described herein.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multi-specific antibody (e.g., a bi-specific antibody), an scFv, a bi-specific scFv, a diabody, a triabody, a tetrabody, a V-NAR, a $V_{HH}$, a $V_L$, a F(ab), a F(ab)$_2$, a DVD (i.e., dual variable domain antigen-binding protein), a an SVD (i.e., single variable domain antigen-binding protein), or a bispecific T-cell engager (BiTE).

In one aspect, a method for making a human antigen-binding protein is provided, comprising exposing a genetically modified non-human animal as described herein to an antigen of interest, allowing the genetically modified non-human animal to mount an immune response to the antigen, obtaining from the genetically modified non-human animal a heavy chain variable domain nucleic acid sequence encoding a human heavy chain variable domain that specifically binds the antigen of interest, cloning the heavy chain variable domain nucleic acid sequence to a human constant region sequence, and expressing in a mammalian cell an antibody comprising the human heavy chain variable domain sequence and the human constant region sequence. In one embodiment, the mammalian cell is a CHO cell. In one embodiment the genetically modified non-human animal comprises a human $V_H$ gene segment repertoire that consists essentially of a single human $V_H$ gene segment, optionally present in two or more polymorphic variants thereof, operably linked to one or more human D and/or J segments. In one embodiment, the human $V_H$ gene segment repertoire is at an endogenous non-human $V_H$ segment locus. In one embodiment, the human $V_H$ gene segment repertoire is at a locus that is not an endogenous $V_H$ segment locus. In one embodiment, the human $V_H$ gene segment rearranges with a human D segment and a human J segment to form a rearranged human VDJ gene operably linked to a constant region sequence, wherein the constant region sequence is selected from a human sequence and a rodent sequence (e.g., a mouse or rat or hamster sequence). In one embodiment, the constant region sequence comprises a sequence selected from a $C_H1$, a hinge, a $C_H2$, a $C_H3$, and a combination thereof; in a specific embodiment, the constant region sequence comprises a $C_H1$, a hinge, a $C_H2$, and a $C_H3$. In one embodiment, the human variable domain and the constant sequence are expressed in the mammalian cell with a cognate human light chain variable domain obtained from the same mouse (e.g., sequence obtained from the same B cell as the human variable domain sequence); in one embodiment the sequence encoding the human light chain variable domain obtained from the mouse is then fused with a sequence encoding a human light chain constant sequence, and the light chain sequence and the heavy chain sequence are expressed in the mammalian cell.

In one embodiment, the antigen of interest is a pathogen that afflicts human subjects as described herein.

In one aspect, a method for making an antibody heavy chain variable domain that binds an antigen of interest is provided, comprising expressing in a single cell (a) a first $V_H$ sequence of an immunized non-human animal as described herein, wherein the first $V_H$ sequence is fused with a $C_H$ gene sequence; and (b) a $V_L$ gene sequence of an immunized non-human animal as described herein, wherein the $V_L$ gene sequence is fused with a human $C_L$ gene sequence; maintaining the cell under conditions sufficient to express an antibody; and, isolating the antibody heavy chain variable domain. In one embodiment, the $V_L$ gene sequence is cognate with the first $V_H$ sequence.

In one embodiment, the cell comprises a second $V_H$ gene sequence of an immunized non-human animal as described herein, wherein the second $V_H$ gene sequence is fused with a $C_H$ gene sequence, wherein the first $V_H$ gene sequence encodes a $V_H$ domain that specifically binds a first epitope, and the second $V_H$ gene sequence encodes a $V_H$ domain that specifically binds a second epitope, wherein the first epitope and the second epitope are not identical.

In one embodiment, the constant region sequences are all human constant region sequences. In one embodiment, the antigen of interest is a pathogen that afflicts human subjects as described herein.

In one aspect, a method for making a human bispecific antibody is provided, comprising making the bispecific antibody using human variable region gene sequences of B cells of a non-human animal as described herein.

In one embodiment, the method comprises (a) identifying a clonally selected lymphocyte of the non-human animal, wherein the non-human animal has been exposed to an antigen of interest and allowed to develop an immune response to the antigen of interest, and wherein the lymphocyte expresses an antibody that specifically binds the antigen of interest, (b) obtaining from the lymphocyte or the antibody a nucleotide sequence that encodes a human heavy chain variable region that specifically binds the antigen of interest, and (c) employing the nucleotide sequence that encodes the human heavy chain variable region that specifically binds the antigen of interest in making the bispecific antibody. In a specific embodiment, the human heavy chain variable region comprises a rearranged $V_H1$-2 or $V_H1$-69 gene segment.

In one embodiment, steps (a) through (c) are performed a first time for a first antigen of interest to generate a first human heavy chain variable region sequence, and steps (a) through (c) are performed a second time for a second antigen of interest to generate a second human heavy chain variable region sequence, and wherein the first human heavy chain variable region sequence is expressed fused with a first human heavy chain constant region to form a first human heavy chain, the second human heavy chain variable region sequence is expressed fused with a second human heavy chain constant region to form a second human heavy chain, wherein the first and the second human heavy chains are expressed in the presence of a single human light chain expressed from a rearranged human Vκ1-39 or a human Vκ3-20 gene segment. In a specific embodiment, the single human light chain comprises a germline sequence.

In one embodiment, the method comprises (a) cloning heavy chain variable regions from B cells of a non-human animal as described herein which has been exposed to a first antigen of interest, and the same non-human animal, or a different non-human animal which is genetically the same and has been exposed to a second antigen of interest; and (b) expressing in a cell the heavy chain variable regions of (a) with the same heavy chain constant region and the same light chain to make a bispecific antibody.

In one aspect, a use of a non-human animal as described herein is provided, to obtain a nucleic acid sequence that encodes a human heavy chain variable domain. In one embodiment, the heavy chain variable domain comprises a rearranged human $V_H$ gene segment selected from $V_H1$-2 and $V_H1$-69.

In one aspect, a use of a non-human animal as described herein is provided, to obtain a cell that encodes a human heavy chain variable domain. In one embodiment, the heavy chain variable domain comprises a rearranged human $V_H$ gene segment selected from $V_H1$-2 and $V_H1$-69.

In one aspect, use of a non-human animal as described herein to make a human antibody variable domain is provided. In one embodiment, the variable domain comprises a rearranged human $V_H$ gene segment selected from $V_H1$-2 and $V_H1$-69.

In one aspect, use of a non-human animal as described herein to make a human antibody is provided, comprising making the antibody using human variable region gene sequences of B cells of a non-human animal as described herein. In one embodiment, the human antibody is a human bispecific antibody. In a specific embodiment, the bispecific antibody comprises one heavy chain variable domain derived from a rearranged human $V_H1$-2 or $V_H1$-69 gene segment. In one embodiment, the human variable region gene sequences comprise a rearranged human $V_H1$-2 or $V_H1$-69 gene segment.

In one aspect, use of a non-human animal as described herein is provided to select a human immunoglobulin heavy chain variable domain. In one embodiment, the heavy chain variable domain comprises a rearranged human $V_H$ gene segment selected from $V_H1$-2 and $V_H1$-69.

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided. In one embodiment, the variable sequence of a medicament comprises a polymorphic human $V_H$ gene segment. In one embodiment, the variable sequence of a medicament comprises a human $V_H1$-69 gene segment. In one embodiment, the variable sequence of a medicament comprises a human $V_H1$-2 gene segment.

In one aspect, a nucleic acid construct encoding an immunoglobulin variable domain made in a mouse as described herein is provided. In one embodiment, the variable domain is a heavy chain variable domain. In a specific embodiment, the heavy chain variable domain comprises a rearranged human $V_H$ gene segment selected from $V_H1$-2, $V_H1$-69, $V_H2$-26, $V_H2$-70, or $V_H3$-23. In another specific embodiment, the heavy chain variable domain comprises a rearranged human $V_H1$-2 gene segment. In another specific embodiment, the heavy chain variable domain comprises a rearranged human $V_H1$-69 gene segment.

In one embodiment, the variable domain is a light chain variable domain. In a specific embodiment, the variable domain is a κ light chain variable domain that is cognate with a human heavy chain variable domain that comprises a rearranged human $V_H1$-69 gene segment. In a specific embodiment, the variable domain is a κ light chain variable domain that is cognate with a human heavy chain variable domain that comprises a rearranged human $V_H1$-2 gene segment.

In one aspect, use of a mouse as described herein to make a nucleic acid construct encoding a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H1$-2, $V_H1$-69, $V_H2$-26, $V_H2$-70, or $V_H3$-23. In a specific embodiment, the heavy chain variable domain comprises a rearranged human $V_H1$-69 gene segment. In a specific embodiment, the heavy chain variable domain comprises a rearranged human $V_H1$-2 gene segment.

In one aspect, use of a mouse as described herein to make a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H1$-2, $V_H1$-69, $V_H2$-26, $V_H2$-70, or $V_H3$-23. In a specific embodiment, the heavy chain variable domain comprises a rearranged human $V_H1$-69 gene segment. In a specific embodiment, the heavy chain variable domain comprises a rearranged human $V_H1$-2 gene segment.

In one aspect, use of a non-human animal as described herein to make a nucleic acid sequence encoding a human heavy chain variable domain is provided. In one embodiment, the human heavy chain variable domain is characterized by having human FR1-CDR1-FR2-CDR2-FR3 sequences that are derived from a polymorphic human $V_H$ gene segment. In a specific embodiment, the human $V_H$ gene segment is selected from a human $V_H1$-2, $V_H1$-69, $V_H2$-26, $V_H2$-70, or $V_H3$-23 gene segment. In one embodiment, the human $V_H$ gene segment is a human $V_H1$-69 gene segment. In one embodiment, the human $V_H$ gene segment is a human $V_H1$-2 gene segment.

In one aspect, a method for making a nucleic acid sequence encoding a human $V_H$ domain is provided, the method comprising immunizing a non-human animal as described herein with an antigen of interest, allowing the non-human animal to mount an immune response to the antigen of interest, and obtaining therefrom a nucleic acid sequence encoding a human $V_H$ domain that binds the antigen of interest. In one embodiment, the method further comprises making a nucleic acid sequence encoding a human $V_L$ domain that is cognate with the human $V_H$ domain, comprising isolating a B cell encoding the human $V_H$ domain and the human $V_L$ domain, and obtaining therefrom the sequence of the heavy and light chain variable domains. In various embodiments, the human $V_H$ domain is derived from a rearranged human $V_H1$-69 or human $V_H1$-2 gene segment. In various embodiments, the human $V_L$ domain is selected from a human Vκ or a human Vλ domain.

In one aspect, use of a non-human animal as described herein to make a human therapeutic is provided, comprising immunizing the non-human animal with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H1$-69 or a human $V_H1$-2 gene segment. In one embodiment, the variable domain is a light chain variable domain. In a specific embodiment, the light chain variable domain is derived from a rearranged human Vκ or human Vλ, gene segment.

In one aspect, a method for making a human therapeutic is provided, comprising immunizing a non-human animal as described herein with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H$1-69 or a human $V_H$1-2 gene segment. In one embodiment, the variable domain is a light chain variable domain. In a specific embodiment, the light chain variable domain is derived from a rearranged human Vκ or human Vλ\, gene segment.

In one aspect, a method for making a human antigen-binding protein is provided, comprising immunizing a non-human animal as described herein with an antigen of interest, allowing the animal to mount an immune response, obtaining from the mouse a nucleic acid sequence encoding an immunoglobulin variable domain that specifically binds the antigen of interest, cloning the nucleic acid sequence in a vector suitable for expression of the nucleic acid, wherein the nucleic acid sequence is cloned in frame with a nucleic acid sequence encoding a human immunoglobulin constant region or functional fragment thereof, and inserting the vector in a mammalian cell, and maintaining the cell under conditions suitable for expressing an antigen-binding protein that comprises the immunoglobulin variable domain and the immunoglobulin constant region or functional fragment thereof. In one embodiment, the antigen-binding protein is a human antibody. In a specific embodiment, the antibody comprises a heavy chain variable domain and a light chain variable domain obtained from a mouse as described herein. In a specific embodiment, the antibody comprises a heavy chain variable domain obtained from a mouse as described herein. In various embodiments, the heavy chain variable domain is derived from a rearranged human $V_H$1-69 or a human $V_H$1-2 gene segment.

In one aspect, a nucleic acid sequence encoding a human antigen-binding domain made in a non-human animal as described herein is provided. In one embodiment, the nucleic acid sequence encodes a human immunoglobulin $V_H$ domain. In one embodiment, the nucleic acid sequence encodes a human immunoglobulin $V_H$ domain and a cognate human $V_L$ domain. In various embodiments, the human $V_H$ domain is derived from a rearranged human $V_H$1-69 or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, fusing the lymphocyte with a myeloma cell to form a hybridoma cell, obtaining from the hybridoma cell a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the cell is a CHO cell. In various embodiments, the human $V_H$ domain is derived from a rearranged human $V_H$1-69 gene segment or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, obtaining from the lymphocyte a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the lymphocyte is derived from the spleen of the non-human animal. In one embodiment, the cell is a CHO cell. In various embodiments, the human $V_H$ domain is derived from a rearranged human $V_H$1-69 gene segment or a human $V_H$1-2 gene segment.

In various aspects, the antigen of interest is a pathogen that afflicts human subjects as described herein. In various aspects, the antigen of interest is a virus that is capable of infecting a human. Exemplary antigens that can be employed in the methods and uses described herein include microbes or microorganisms such as a virus, bacterium, prion, or fungus or any other pathogen that causes disease in humans. A person of skill, upon reading the disclosure, will appreciate those human pathogens that will be applicable for the methods and uses described herein. The various aspects and embodiments are capable of use together, unless expressly noted otherwise or the context clearly prohibits use together.

BRIEF DESCRIPTION OF FIGURES

FIG. 13 shows the nucleotide alignment of the second exon for each of thirteen reported alleles for the human $V_H$1-69 gene. Lower case bases indicate germline nucleotide differences among the alleles. Complementary determining regions (CDRs) are indicated with boxes around the sequence. Dashes indicate artificial gaps for proper sequence alignment. $V_H$1-69*01 (SEQ ID NO: 34); $V_H$1-69*02 (SEQ ID NO: 36); $V_H$1-69*03 (SEQ ID NO: 38); $V_H$1-69*04 (SEQ ID NO: 40); $V_H$1-69*05 (SEQ ID NO: 42); $V_H$1-69*06 (SEQ ID NO: 44); $V_H$1-69*07 (SEQ ID NO: 46); $V_H$1-69*08 (SEQ ID NO: 48); $V_H$1-69*09 (SEQ ID NO: 50); $V_H$1-69*10 (SEQ ID NO: 52); $V_H$1-69*11 (SEQ ID NO: 54); $V_H$1-69*12 (SEQ ID NO: 56); $V_H$1-69*13 (SEQ ID NO: 58).

FIG. 14 shows the protein alignment of the mature heavy chain variable gene sequence for each of thirteen reported alleles for the human $V_H$1-69 gene. Lower case amino acids indicate germline differences among the alleles. Complementary determining regions (CDRs) are indicated with boxes around the sequence. Dashes indicate artificial gaps for proper sequence alignment. $V_H$1-69*01 (SEQ ID NO: 35); $V_H$1-69*02 (SEQ ID NO: 37); $V_H$1-69*03 (SEQ ID NO: 39); $V_H$1-69*04 (SEQ ID NO: 41); $V_H$1-69*05 (SEQ ID NO: 43); $V_H$1-69*06 (SEQ ID NO: 45); $V_H$1-69*07 (SEQ ID NO: 47); $V_H$1-69*08 (SEQ ID NO: 49); $V_H$1-69*09 (SEQ ID NO: 51); $V_H$1-69*10 (SEQ ID NO: 53); $V_H$1-69*11 (SEQ ID NO: 55); $V_H$1-69*12 (SEQ ID NO: 57); $V_H$1-69*13 (SEQ ID NO: 59).

FIG. 15 shows a percent identity/percent similarity matrix for the aligned protein sequences of the mature variable gene for each of thirteen reported alleles for the human $V_H$1-69 gene. Percent identity among the $V_H$1-69 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

FIG. 16 shows the nucleotide alignment of the second exon for each of five reported alleles for the human $V_H$1-2 gene. Lower case bases indicate germline nucleotide differences among the alleles. Complementary determining regions (CDRs) are indicated with boxes around the sequence. Dashes indicate artificial gaps for proper sequence alignment. $V_H$1-2*01 (SEQ ID NO: 60); $V_H$1-2*02 (SEQ ID NO: 62); $V_H$1-2*03 (SEQ ID NO: 64); $V_H$1-2*04 (SEQ ID NO: 66); $V_H$1-2*05 (SEQ ID NO: 68).

FIG. 17 shows the protein alignment of the mature heavy chain variable gene sequence for each of five reported alleles for the human $V_H$1-2 gene. Lower case amino acids indicate germline differences among the alleles. Complementary determining regions (CDRs) are indicated with boxes around the sequence. Dashes indicate artificial gaps for proper sequence alignment. $V_H$1-2*01 (SEQ ID NO: 61); $V_H$1-2*02 (SEQ ID NO: 63); $V_H$1-2*03 (SEQ ID NO: 65); $V_H$1-2*04 (SEQ ID NO: 67); $V_H$1-2*05 (SEQ ID NO: 69).

FIG. 18 shows a percent identity/percent similarity matrix for the aligned protein sequences of the mature variable gene for each of five reported alleles for the human $V_H$1-2 gene. Percent identity among the $V_H$1-2 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "substantial" or "substantially" when used to refer to an amount of gene segments (e.g., "substantially all" V gene segments) includes both functional and non functional gene segments and include, in various embodiments, e.g., 80% or more, 85% or more, 90% or more, 95% or more 96% or more, 97% or more, 98% or more, or 99% or more of all gene segments; in various embodiments, "substantially all" gene segments includes, e.g., at least 95%, 96%, 97%, 98%, or 99% of functional (i.e., non-pseudogene) gene segments.

The term "replacement" includes wherein a DNA sequence is placed into a genome of a cell in such a way as to replace a sequence within the genome with a heterologous sequence (e.g., a human sequence in a mouse), at the locus of the genomic sequence. The DNA sequence so placed may include one or more regulatory sequences that are part of source DNA used to obtain the sequence so placed (e.g., promoters, enhancers, 5'- or 3'-untranslated regions, appropriate recombination signal sequences, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes an immunoglobulin gene or domain, and the DNA fragment encodes one or more human immunoglobulin genes or domains). In various embodiments, an endogenous gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous gene or fragment thereof that is replaced.

Figure 1:
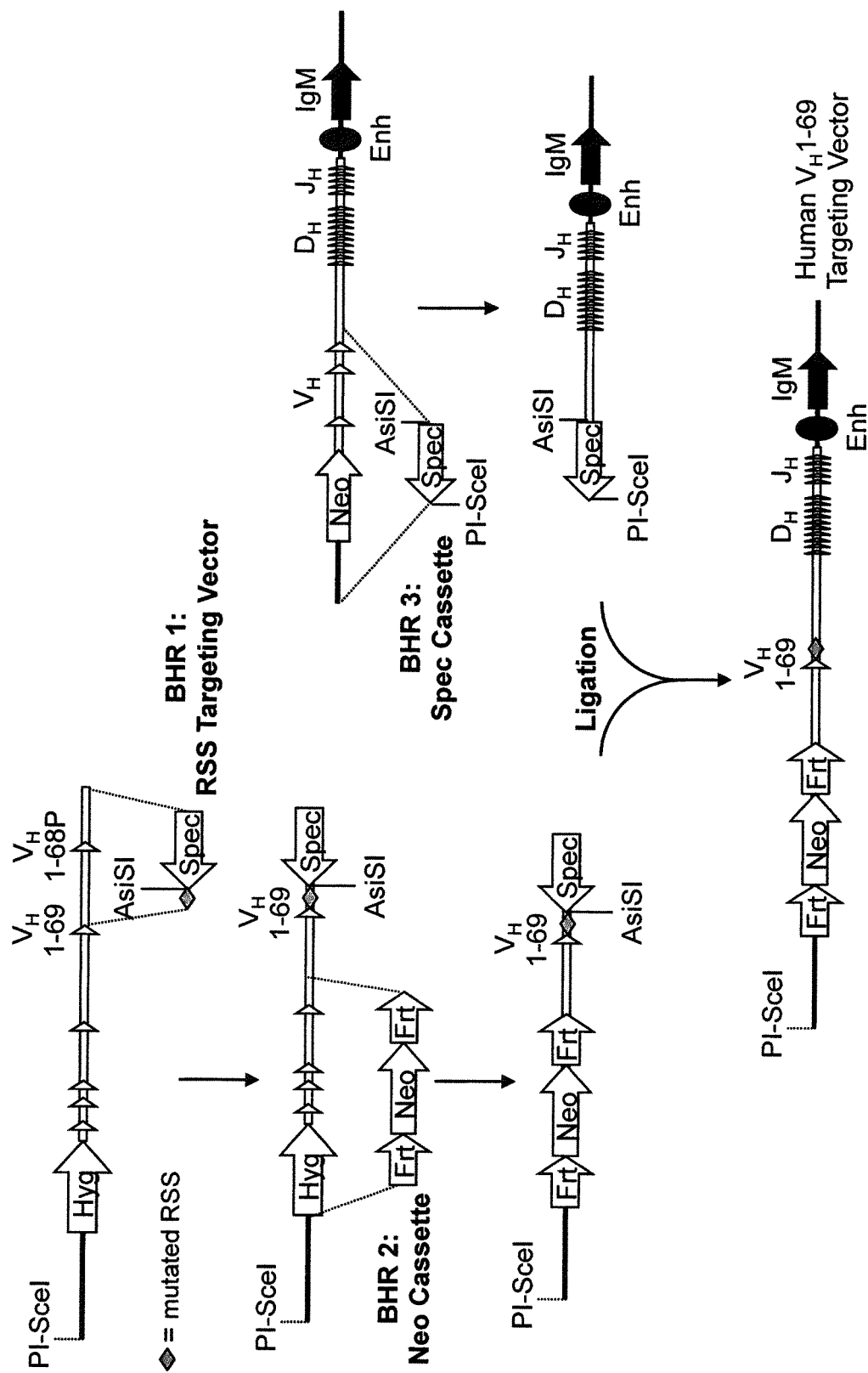
FIG. 1 shows a general illustration, not to scale, of a series of targeting and molecular engineering steps employed to make a targeting vector for construction of a modified heavy chain locus containing a single human $V_H$1-69 gene segment, twenty-seven human $D_H$ and six human $J_H$ gene segments at an endogenous immunoglobulin heavy chain locus.
Figure 2:
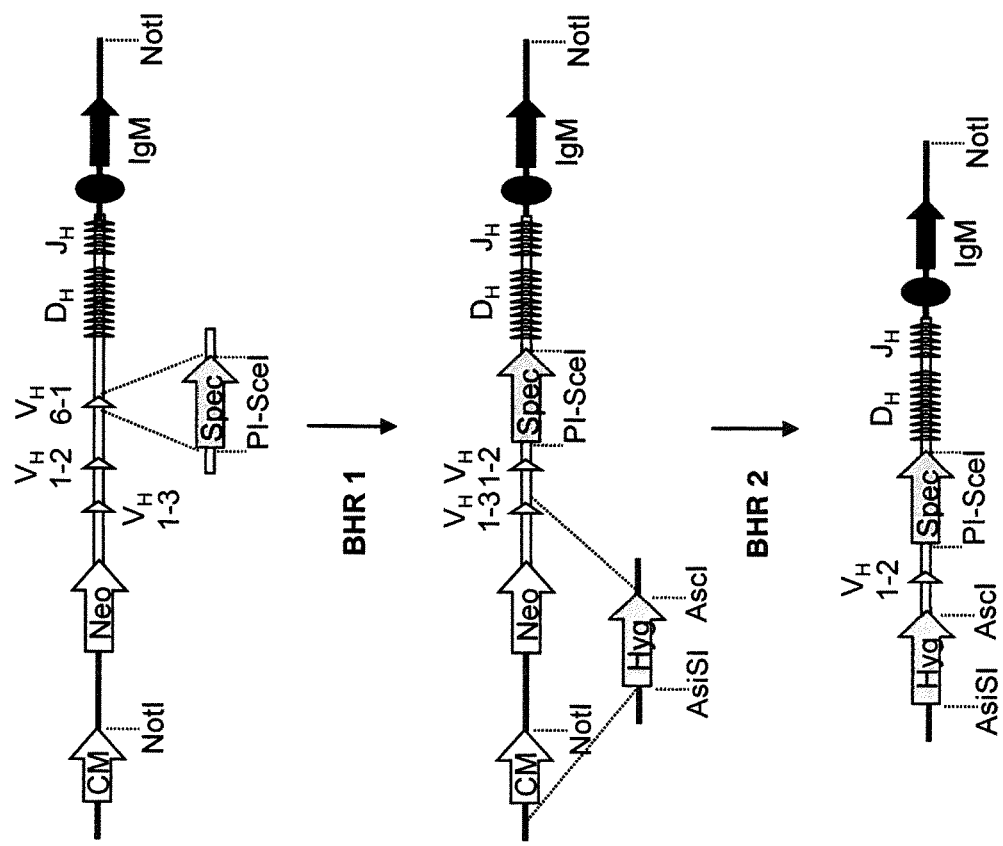
FIG. 2 shows a general illustration, not to scale, of a series of targeting and molecular engineering steps employed to make a targeting vector for construction of a modified heavy chain locus containing a single human $V_H$1-2 gene segment, twenty-seven human $D_R$ and six human $J_R$ gene segments at an endogenous immunoglobulin heavy chain locus.
Figure 3:
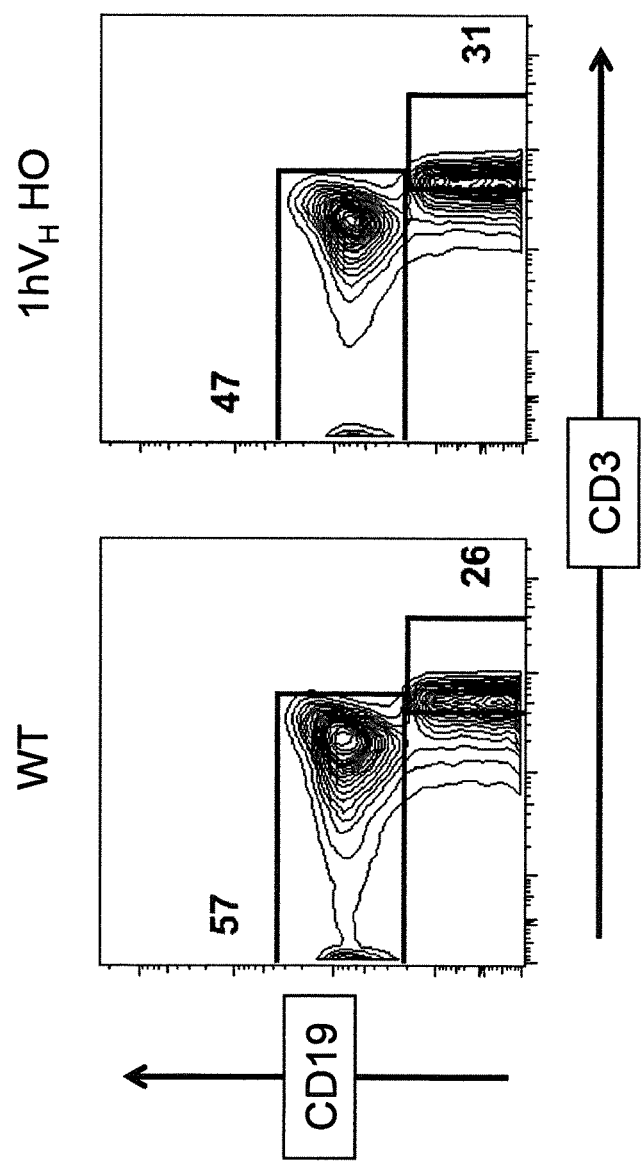
FIG. 3 shows contour plots of splenocytes gated on single lymphocytes and stained for CD19 (B cell) and CD3 (T cell) from a wild type mouse (WT) and a mouse homozygous for a single human $V_H$ gene segment, twenty-seven human $D_H$ and six human $J_R$ gene segments at the endogenous immunoglobulin heavy chain locus (1h$V_H$ HO).
Figure 4A:
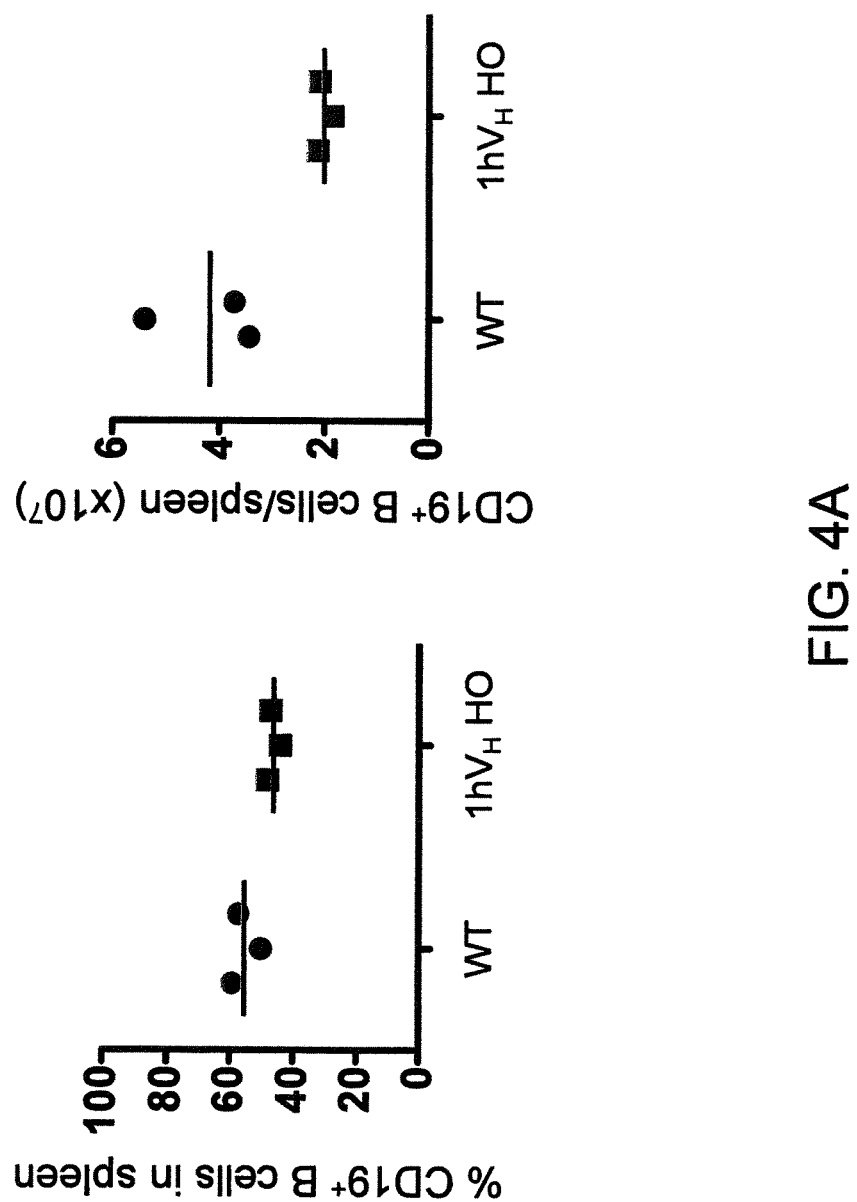
FIG. 4A shows, on the left, the percent of CD19$^+$ B cells in spleens harvested from wild type mice (WT) and mice homozygous for a single human $V_H$ gene segment, twenty-seven human $D_H$ and six human $J_R$ gene segments at the endogenous immunoglobulin heavy chain locus (1h$V_H$ HO). On the right, the number of CD19$^+$ B cells per spleen is shown for both wild type mice (WT) and mice homozygous for a single human $V_H$ gene segment, twenty-seven human $D_R$ and six human $J_R$ gene segments at the endogenous immunoglobulin heavy chain locus (1h$V_H$ HO).
Figure 4B:
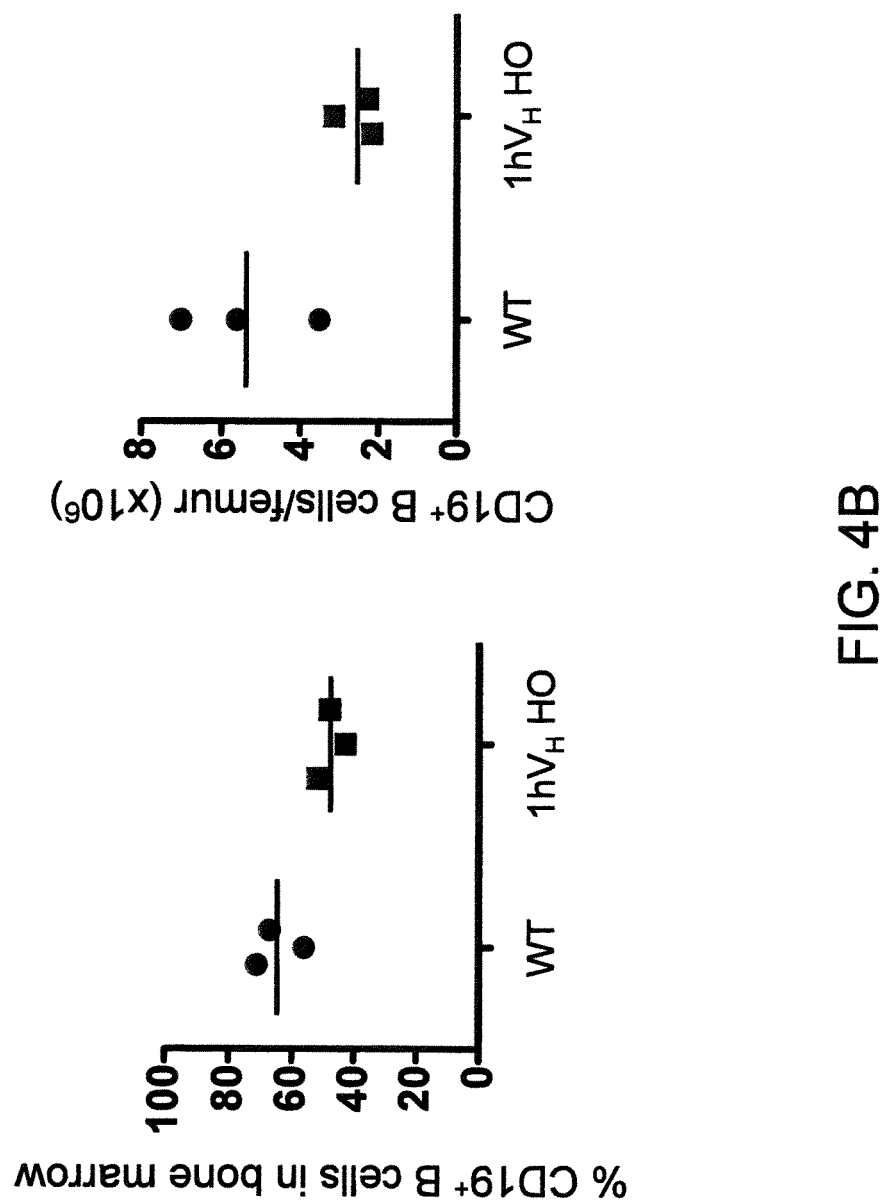
FIG. 4B shows, on the left, the percent of CD19$^+$ B cells in bone marrow harvested from femurs of wild type mice (WT) and mice homozygous for a single human $V_R$ gene segment, twenty-seven human $D_R$ and six human $J_R$ gene segments at the endogenous immunoglobulin heavy chain locus (1h$V_H$ HO). On the right, the number of CD19+ B cells per femur is shown for both wild type mice (WT) and mice homozygous for a single human $V_H$ gene segment, twenty-seven human $D_R$ and six human $J_H$ gene segments at the endogenous immunoglobulin heavy chain locus (1h$V_H$ HO).
Figure 5:
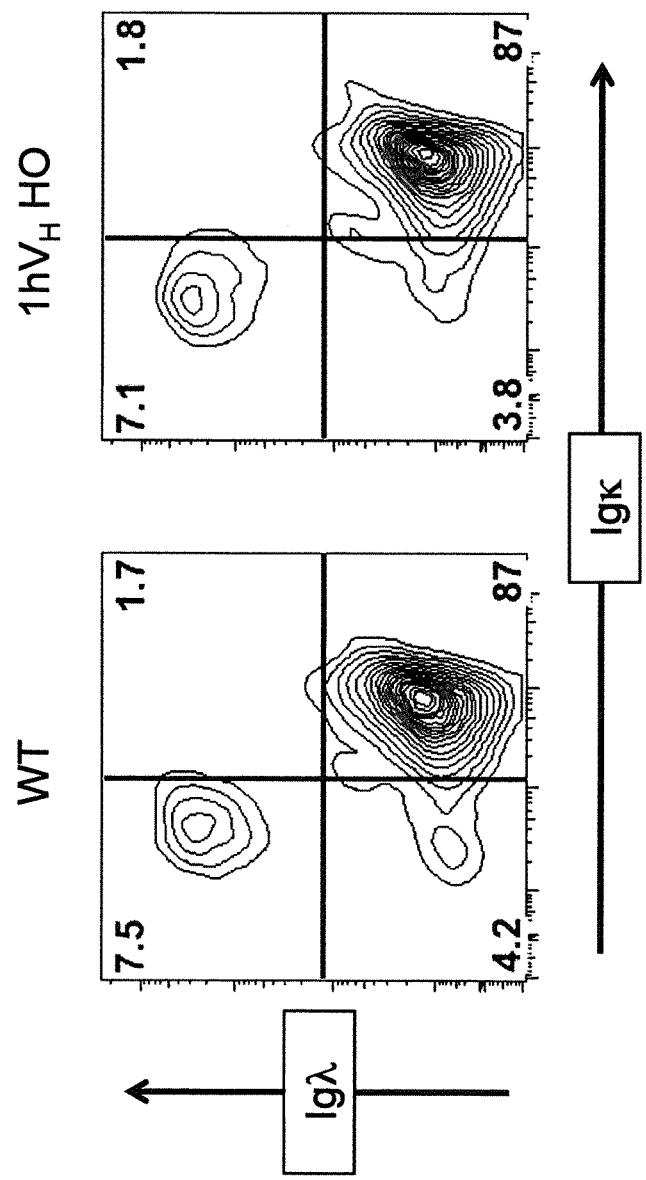
FIG. 5 shows contour plots of splenocytes gated on CD19+ B cells and stained for Igλ+ and Igκ+ expression from a wild type mouse (WT) and a mouse homozygous for a single human $V_H$ gene segment, twenty-seven human $D_R$ and six human $J_R$ gene segments at the endogenous immunoglobulin heavy chain locus (1h$V_H$ HO).
Figure 6:
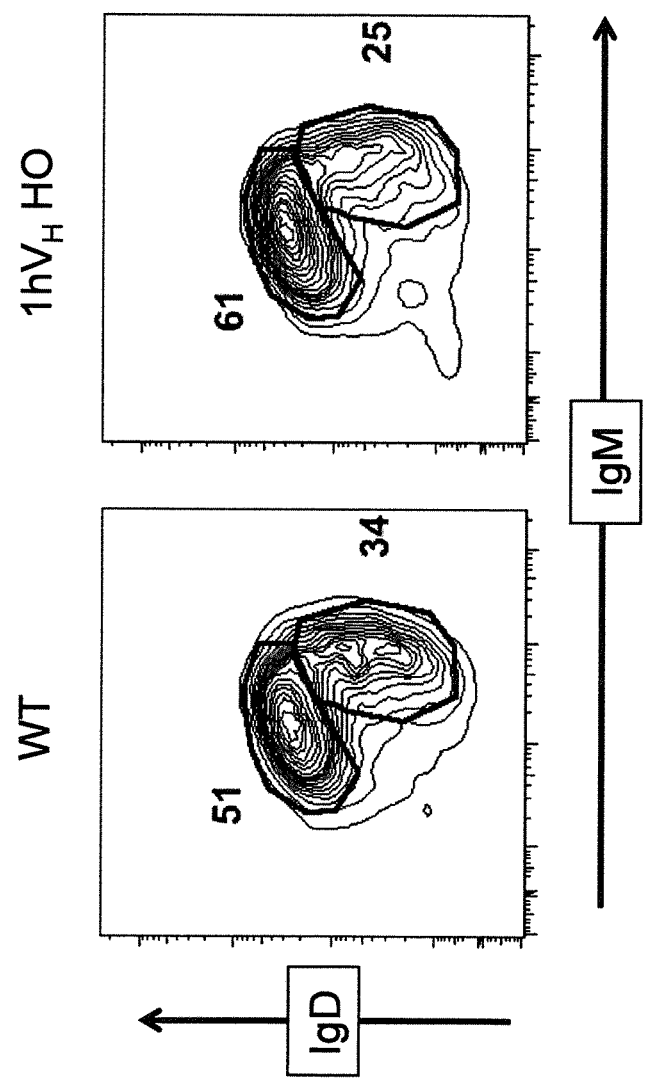
FIG. 6 shows contour plots of splenocytes gated on CD19+ B cells and stained for immunoglobulin D (IgD) and immunoglobulin M (IgM) from a wild type mouse (WT) and a mouse homozygous for a single human $V_H$ gene segment, twenty-seven human $D_R$ and six human $J_R$ gene segments at the endogenous immunoglobulin heavy chain locus (1h$V_H$ HO).
Figure 7:
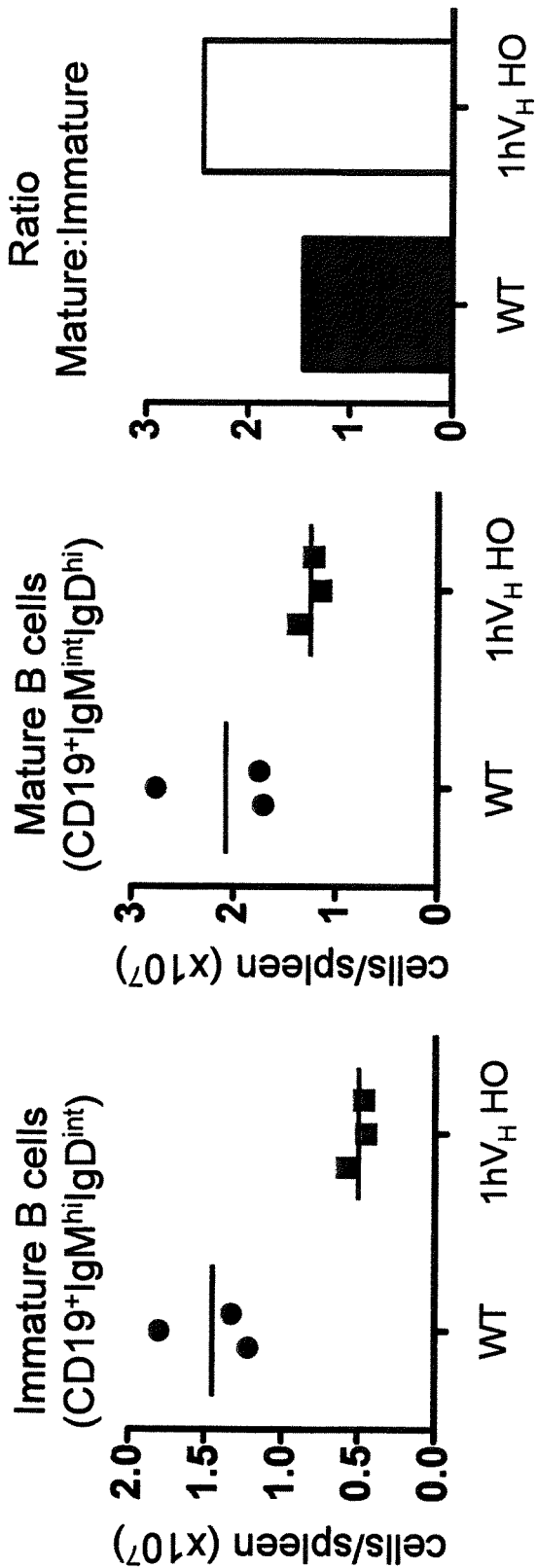
FIG. 7 shows the total number of transitional B cells (CD19+ IgM$^{hi}$IgD$^{int}$), mature B cells (CD19+ IgM$^{int}$IgD$^{hi}$), and the ratio of mature to immature B cells in harvested spleens from wild type mice (WT) and mice homozygous for a single human $V_H$ gene segment, twenty-seven human $D_R$ and six human $J_H$ gene segments at the endogenous immunoglobulin heavy chain locus (1h$V_H$ HO).
Figure 8:
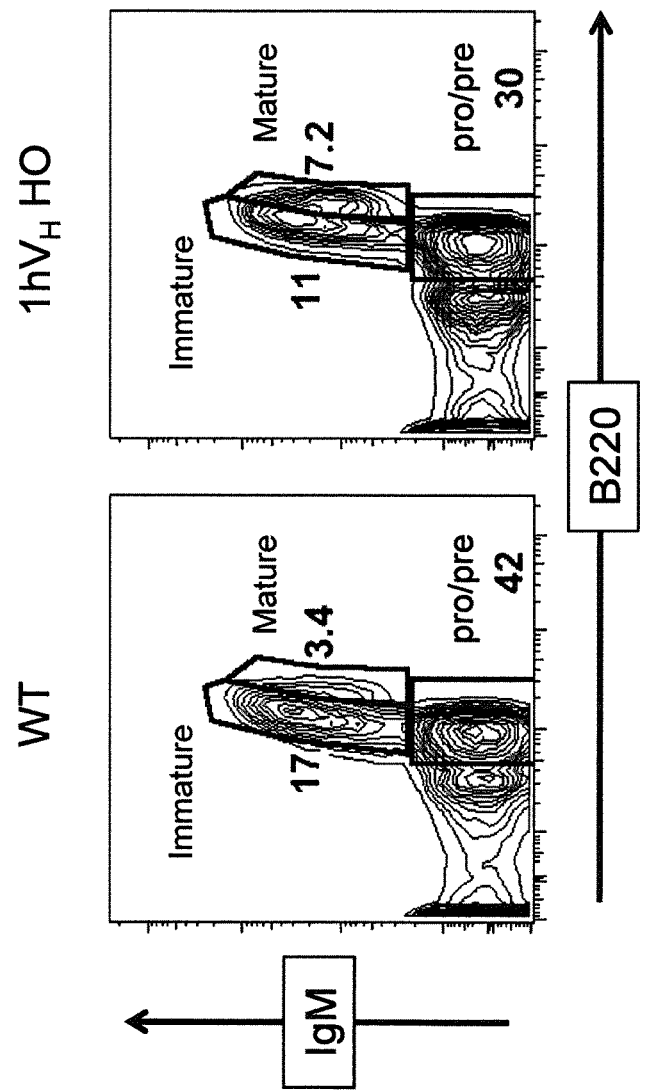
FIG. 8 shows contour plots of bone marrow gated on singlets stained for immunoglobulin M (IgM) and B220 from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 9:
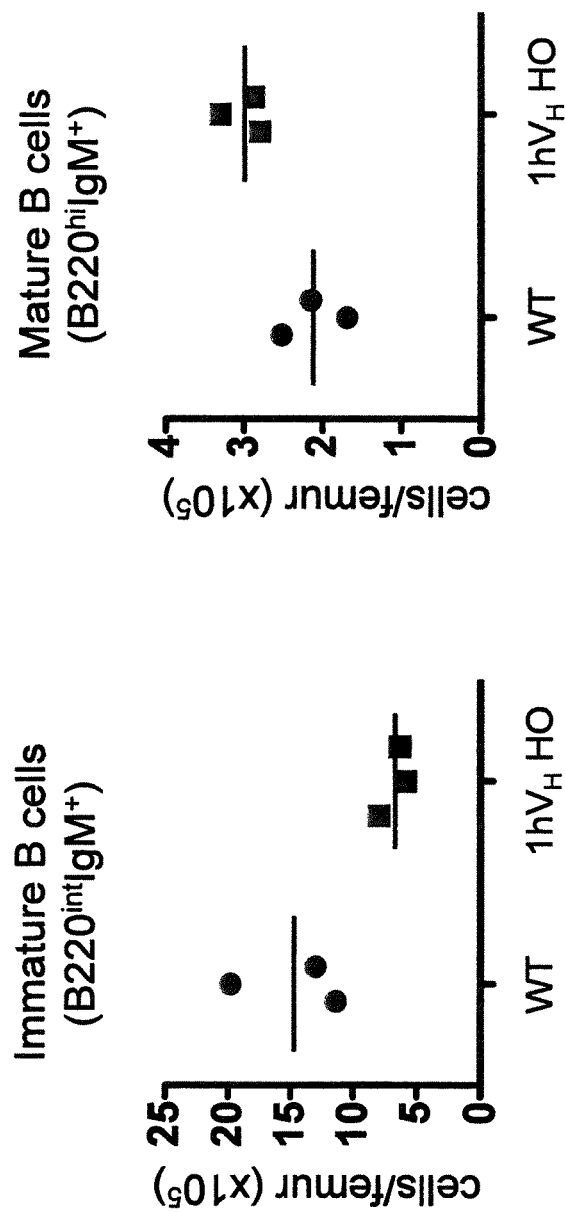
FIG. 9 shows the total number of immature (B220$^{int}$IgM+) and mature (B220$^{hi}$IgM+) B cells in bone marrow isolated from the femurs of wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 10:
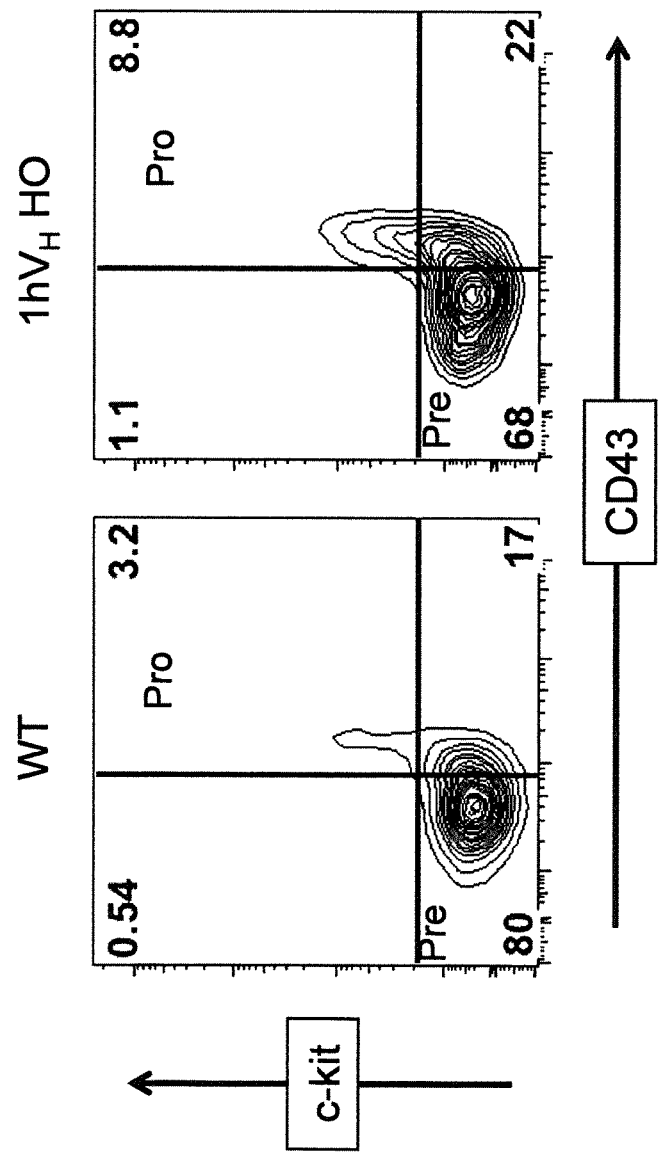
FIG. 10 shows contour plots of bone marrow gated on CD19+ B cells and stained for ckit+ and CD43+ from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 11A:
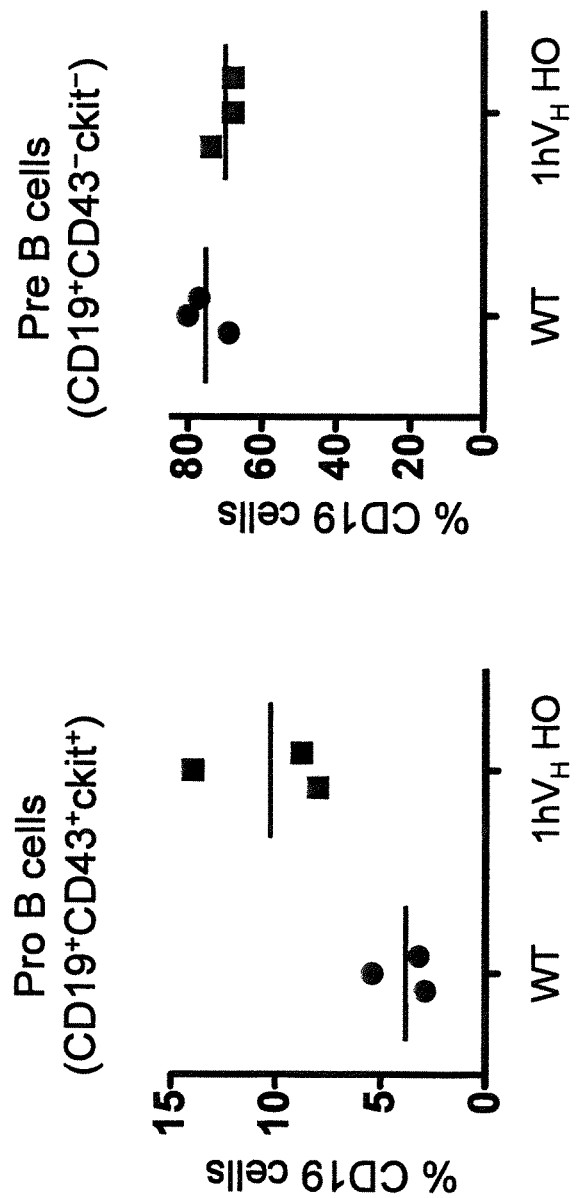
FIG. 11A shows the percent of CD19+ cells in populations of pro B (CD19+CD43+ckit+) and pre B (CD19+CD43−ckit−) cells in bone marrow harvested from the femurs of wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 11B:
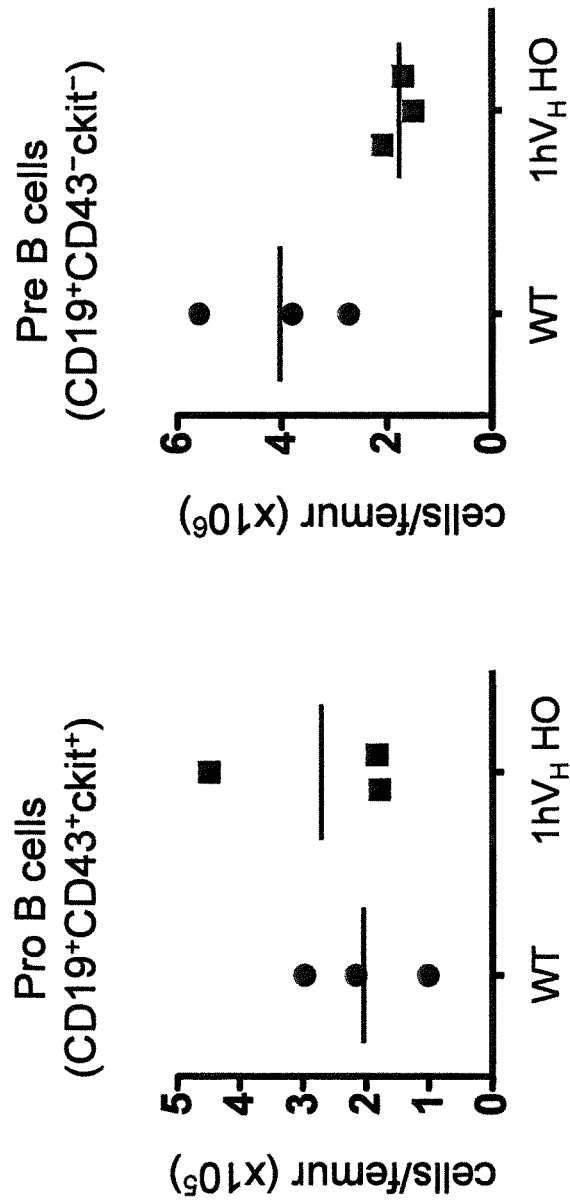
FIG. 11B shows the absolute number of cells per femur in populations of pro B (CD19+CD43+ckit+) and pre B (CD19+CD43−ckit−) cells in bone marrow harvested from wild type mice (WT) and mice homozygous for a single human $V_H$ gene segment, twenty-seven human $D_H$ and six human $J_H$ gene segments at the endogenous immunoglobulin heavy chain locus (1h$V_H$ HO).

A precise, in situ replacement of six megabases of the variable regions of the mouse heavy chain immunoglobulin loci ($V_H$-$D_H$-$J_H$) with a restricted human immunoglobulin heavy chain locus was performed, while leaving the flanking mouse sequences intact and functional within the hybrid loci, including all mouse constant chain genes and locus transcriptional control regions (FIG. 1 and FIG. 2). Specifically, a single human $V_H$, 27 $D_H$, and six $J_H$ gene segments were introduced through chimeric BAC targeting vectors into mouse ES cells using VELOCIGENE® genetic engineering technology (see, e.g., U.S. Pat. No. 6,586,251 and Valenzuela et al., 2003, High-throughput engineering of the mouse genome coupled with high-resolution expression analysis, Nat Biotechnol 21:652-659).

Non-Human Animals with Restricted Immunoglobulin $V_H$ Gene Segments

Non-human animals comprising immunoglobulin loci that comprise a restricted number of $V_H$ genes, and one or more D genes and one or more J genes, are provided, as are methods of making and using them. When immunized with an antigen of interest, the non-human animals generate B cell populations with antibody variable regions derived only from the restricted, pre-selected $V_H$ gene or set of $V_H$ genes (e.g., a pre-selected $V_H$ gene and variants thereof). In various embodiments, non-human animals are provided that generate B cell populations that express human antibody variable domains that are human heavy chain variable domains, along with cognate human light chain variable domains. In various embodiments, the non-human animals rearrange human heavy chain variable gene segments and human light chain variable gene segments from modified endogenous mouse immunoglobulin loci that comprise a replacement or insertion of the non-human unrearranged variable region sequences with human unrearranged variable region sequences.

Early work on the organization, structure, and function of the immunoglobulin genes was done in part on mice with disabled endogenous loci and engineered to have transgenic loci (randomly placed) with partial human immunoglobulin genes, e.g., a partial repertoire of human heavy chain genes linked with a human constant gene, randomly inserted into the genome, in the presence or absence of a human light chain transgene. Although these mice were somewhat less than optimal for making useful high affinity antibodies, they facilitated certain functional analyses of immunoglobulin loci. Some of these mice had as few as two or three, or even just a single, heavy chain variable gene.

Mice that express fully human immunoglobulin heavy chains derived from a single human $V_H$5-51 gene and 10 human $D_H$ genes and six human $J_R$ genes, with human μ and γ1 constant genes, on a randomly inserted transgene (and disabled endogenous immunoglobulin loci) have been reported (Xu and Davis, 2000, Diversity in the CDR3 Region of $V_H$ Is Sufficient for Most Antibody Specificities, *Immunity* 13:37-45). The fully human immunoglobulin heavy chains of these mice are mostly expressed with one of just two fully mouse λ light chains derived from the endogenous mouse λ light chain locus (Vλ1-Jλ1 or Vλ2-Jλ2 only), and can express no κ light chain (the mice are Igκ$^{-/-}$). These mice exhibit severely abnormal dysfunction in B cell development and antibody expression. B cell numbers are reportedly 5-10% of wild-type, IgM levels 5-10% of wild-type, and IgG1 levels are only 0.1-1% of wild-type. The observed IgM repertoire revealed highly restricted junctional diversity. The fully human heavy chains display largely identical CDR3 length across antigens, the same $J_H$ ($J_H$2) usage across antigens, and an initial junctional Q residue, thus reflecting a certain lack of CDR3 diversity. The fully mouse λ light chains nearly all had a Vκ96L substitution in Jλ1 as initial junctional residue. The mice are reportedly unable to generate any antibodies against bacterial polysaccharide. Because the human variable domains couple with mouse light chains, the utility of the human variable regions is highly limited.

Other mice that have just a single human $V_H$3-23 gene, human $D_H$ and $J_H$ genes, and mouse light chain genes have been reported, but they exhibit a limited diversity (and thus a limited usefulness) due in part to mispairing potential between human $V_H$ and mouse $V_L$ domains (see, e.g., Mageed et al., 2001, Rearrangement of the human heavy chain variable region gene V3-23 in transgenic mice generates antibodies reactive with a range of antigens on the basis of $V_H$CDR3 and residues intrinsic to the heavy chain variable region, Clin. Exp. Immunol. 123:1-5). Similarly, mice that bear two $V_H$ genes (3-23 and 6-1) along with human $D_H$ and $J_H$ genes in a transgene containing the human μ constant gene (Bruggemann et al., 1991, Human antibody production in transgenic mice: expression from 100 kb of the human IgH locus, Eur. J. Immunol. 21:1323-1326) and express them in human IgM chains with mouse light chains may exhibit a repertoire limited by mispairing (Mackworth-Young et al., 2003, The role of antigen in the selection of the human V3-23 immunoglobulin heavy chain variable region gene, Clin. Exp. Immunol. 134:420-425).

Other transgenic mice that express $V_H$-restricted fully human heavy chains from a human transgene randomly inserted in the genome, with a limited human λ repertoire expressed from a fully human randomly inserted transgene, have also been reported (see, e.g., Taylor et al., 1992, A transgenic mouse that expresses a diversity of human sequence heavy and light chain immunoglobulins, Nucleic Acids Res. 20(23):6287-6295; Wagner et al., 1994, Antibodies generated form human immunoglobulin miniloci in transgenic mice, Nucleic Acids Res. 22(8):1389-1393). However, transgenic mice that express fully human antibodies from transgenes randomly integrated into the mouse genome, and that comprise damaged endogenous loci, are known to exhibit substantial differences in immune response as compared with wild-type mice that affect the diversity of the antibody variable domains obtainable from such mice.

Useful non-human animals that generate a diverse population of B cells that express human antibody variable domains from a restricted $V_H$ gene repertoire and one or more D genes and one or more J genes will be capable of generating, preferably in some embodiments, repertoires of rearranged variable region genes that will be sufficiently diverse. In various embodiments, diversity includes junctional diversity, somatic hypermutation, and polymorphic diversity in $V_H$ gene sequence (for embodiments where $V_H$ genes are present in polymorphic forms). Combinatorial diversity occurs in the pairing of the $V_H$ gene with one of a plurality of cognate human light chain variable domains (which, in various embodiments, comprise junctional diversity and/or somatic hypermutations).

Non-human animals comprising a restricted human $V_H$ gene repertoire and a complete or substantially complete human $V_L$ gene repertoire will in various embodiments generate populations of B cells that reflect the various sources of diversity, such as junctional diversity (e.g., VDJ, VJ joining, P additions, N additions), combinatorial diversity (e.g., cognate $V_H$-restricted human heavy, human light), and somatic hypermutations. In embodiments comprising a restriction of the $V_H$ repertoire to one human $V_H$ gene, the one human $V_H$ gene can be present in two or more variants. In various embodiments, the presence of two or more polymorphic forms of a $V_H$ gene will enrich the diversity of the variable domains of the B cell population.

Variations in the germline sequences of gene segments (e.g., V genes) contribute to the diversity of the antibody response in humans. The relative contribution to diversity due to V gene sequence differences varies among V genes. The degree of polymorphism varies across gene families, and is reflected in a plurality of haplotypes (stretches of sequence with coinherited polymorphisms) capable of generating further diversity as observed in $V_H$ haplotype differences between related and unrelated individuals in the human population (see, e.g., Souroujon et al., 1989, Polymorphisms in Human H Chain V Region Genes from the $V_H$III Gene Family, *J. Immunol.* 143(2):706-711). Some have suggested, based on data from particularly polymorphic human $V_H$ gene families, that haplotype diversity in the germline is a major contributor to $V_H$ gene heterogeneity in the human population, which is reflected in the large diversity of different germline $V_H$ genes across the human population (see, Sasso et al., 1990, Prevalence and Polymorphism of Human $V_H$3 Genes, *J. Immunol.* 145(8):2751-2757).

Although the human population displays a large diversity of haplotypes with respect to the $V_H$ gene repertoire due to widespread polymorphism, certain polymorphisms are reflected in prevalent (i.e., conserved) alleles observed in the human population (Sasso et al., 1990). $V_H$ polymorphism can be described in two principle forms. The first is variation arising from allelic variation associated with differences among the nucleotide sequence between alleles of the same gene segment. The second arises from the numerous duplications, insertions, and/or deletions that have occurred at the immunoglobulin heavy chain locus. This has resulted in the unique situation in which $V_H$ genes derived by duplication from identical genes differ from their respective alleles by one or more nucleotide substitutions. This also directly influences the copy number of $V_H$ genes at the heavy chain locus.

Polymorphic alleles of the human immunoglobulin heavy chain variable gene segments ($V_H$ genes) have largely been the result of insertion/deletion of gene segments and single nucleotide differences within coding regions, both of which have the potential to have functional consequences on the immunoglobulin molecule. Table 1 sets forth the functional $V_H$ genes listed by human $V_H$ gene family and the number of identified alleles for each $V_H$ gene in the human immunoglobulin heavy chain locus. There are some findings to suggest that polymorphic $V_H$ genes have been implicated in susceptibility to certain diseases such as, for example, rheumatoid arthritis, whereas in other cases a linkage between $V_H$ and disease has been less clear. This ambiguity has been attributed to the copy number and presence of various alleles in different human populations. In fact, several human $V_H$ genes demonstrate copy number variation (e.g., $V_H1$-2, $V_H1$-69, $V_H2$-26, $V_H2$-70, and $V_H3$-23). In various embodiments, humanized mice as described herein with restricted $V_H$ repertoires comprise multiple polymorphic variants of an individual $V_H$ family member (e.g., two or more polymorphic variants of $V_H1$-2, $V_H1$-69, $V_H2$-26, $V_H2$-70, or $V_H3$-23, replacing all or substantially all functional mouse $V_H$ segments at an endogenous mouse locus). In a specific embodiment, the two or more polymorphic variants of mice described herein are in number up to and including the number indicated for the corresponding $V_H$ family member in Table 1 (e.g., for $V_H1$-69, 13 variants; for $V_H1$-2, five variants; etc.).

Commonly observed variants of particular human $V_H$ genes are known in the art. For example, one of the most complex polymorphisms in the $V_H$ locus belongs to the $V_H1$-69 gene. The human $V_H1$-69 gene has 13 reported alleles (Sasso et al., 1993, A fetally expressed immunoglobulin $V_H1$ gene belongs to a complex set of alleles, *Journal of Clinical Investigation* 91:2358-2367; Sasso et al., 1996, Expression of the immunoglobulin $V_H$ gene 51p1 is proportional to its germline gene copy number, *Journal of Clinical Investigation* 97(9):2074-2080) and exists in at least three haplotypes that carry duplications of the $V_H1$-69 gene, which results in multiple copies of the $V_H$ gene at a given locus. These polymorphic alleles include differences in the complementarity determining regions (CDRs), which may dramatically influence antigen specificity. Table 2 sets for the reported alleles for human $V_H1$-69 and the SEQ ID NOs for the DNA and protein sequences of the mature heavy chain variable regions. Table 3 sets forth the reported alleles for human $V_H1$-2 genes and the SEQ ID NOs for the DNA and protein sequences of the mature heavy chain variable regions.

Representative genomic DNA and full-length protein sequences of a $V_H1$-69 gene are set forth in SEQ ID NO: 1 and SEQ ID NO: 2, respectively. FIG. 13 and FIG. 14 set forth DNA and protein alignments of thirteen reported $V_H1$-69 alleles, respectively. Representative DNA and protein sequences of a $V_H1$-2 gene are set forth in SEQ ID NO: 60 and SEQ ID NO: 61, respectively. FIG. 16 and FIG. 17 set forth DNA and protein alignments of five reported $V_H1$-2 alleles, respectively. FIG. 15 and FIG. 18 set forth a percent identity/similarity matrix for aligned protein sequences corresponding to thirteen reported human $V_H1$-69 alleles and five reported human $V_H1$-2 alleles, respectively. In various embodiments, the modified locus of the invention comprises a $V_H$ gene selected from Table 1, present in two or more copy number, wherein the copy number includes up to and including the number of alleles shown in Table 1. In one embodiment, the modified locus of the invention comprises a $V_H1$-69 gene selected from Table 2, present in two or more copy number, wherein the copy number includes up to and including the number of alleles shown in Table 1. In one embodiment, the modified locus of the invention comprises a $V_H1$-2 gene selected from Table 3, present in two or more copy number, wherein the copy number includes up to and including the number of alleles shown in Table 1.

Although embodiments employing a restricted human $V_H$ repertoire in a mouse are extensively discussed, other non-human animals that express a restricted human $V_H$ repertoire are also provided. Such non-human animals include any of those which can be genetically modified to express a restricted human $V_H$ repertoire as disclosed herein, including, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a restricted human $V_H$ repertoire. Thus, in one embodiment a method is provided for editing a non-human animal genome to include a restricted human $V_H$ repertoire, comprising a step of editing the genome employing a ZFN or a TALEN to include no more than one, or no more than two, human $V_H$ gene segments (or polymorphic variants thereof), wherein the no more than one or no more than two human $V_H$ gene segments are operably linked to an immunoglobulin constant gene sequence. In one embodiment, the constant gene sequence is selected from a human heavy chain constant sequence and a non-human heavy chain constant sequence. In one embodiment, the constant sequence is non-human and the no more than one or no more than two human $V_H$ gene segments are operably linked to non-human constant gene sequence at an endogenous non-human immunoglobulin locus.

In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae, In one embodiment, the non-human animal is a rodent that is a mouse of a C57BL strain. In one embodiment, the C57BL strain is selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/01a. In another embodiment, the mouse is a 129 strain. In one embodiment, the 129 strain is selected from the group consisting of 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In one embodiment, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 BioTechniques 29:1024-1032. In another embodiment, the mouse is a BALB strain, e.g., BALB/c strain. In another embodiment, the mouse is a mix of a BALB strain (e.g., BALB/c strain) and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more of a strain selected from the group consisting of Wistar, LEA, Sprague Dawley, Fischer, F344, F6, and Dark Agouti.

TABLE 1

| $V_H$ Family | $V_H$ Gene | Alleles |
|---|---|---|
| $V_H1$ | 1-2 | 5 |
| | 1-3 | 2 |
| | 1-8 | 2 |
| | 1-18 | 3 |
| | 1-24 | 1 |
| | 1-45 | 3 |
| | 1-46 | 3 |
| | 1-58 | 2 |
| | 1-69 | 13 |
| $V_H2$ | 2-5 | 10 |
| | 2-26 | 1 |
| | 2-70 | 13 |
| $V_H3$ | 3-7 | 3 |
| | 3-9 | 2 |
| | 3-11 | 4 |
| | 3-13 | 4 |
| | 3-15 | 8 |
| | 3-16 | 2 |
| | 3-20 | 1 |
| | 3-21 | 4 |
| | 3-23 | 5 |
| | 3-30 | 19 |
| | 3-30-3 | 2 |
| | 3-30-5 | 1 |
| | 3-33 | 6 |
| | 3-35 | 1 |
| | 3-38 | 2 |
| | 3-43 | 2 |
| | 3-48 | 4 |
| | 3-49 | 5 |
| | 3-53 | 4 |
| | 3-64 | 5 |
| | 3-66 | 4 |
| | 3-72 | 2 |
| | 3-73 | 2 |
| | 3-74 | 3 |
| $V_H4$ | 4-4 | 7 |
| | 4-28 | 6 |
| | 4-30-1 | 1 |
| | 4-30-2 | 5 |

TABLE 1-continued

| $V_H$ Family | $V_H$ Gene | Alleles |
|---|---|---|
| | 4-30-4 | 6 |
| | 4-31 | 10 |
| | 4-34 | 13 |
| | 4-39 | 7 |
| | 4-59 | 10 |
| | 4-61 | 8 |
| $V_H5$ | 5-51 | 5 |
| $V_H6$ | 6-1 | 2 |
| $V_H7$ | 7-4-1 | 5 |
| | 7-81 | 1 |

TABLE 2

| IgHV1-69 Allele | Accession Number | SEQ ID NO: (DNA/Protein) |
|---|---|---|
| IgHV1-69*01 | L22582 | 34/35 |
| IgHV1-69*02 | Z27506 | 36/37 |
| IgHV1-69*03 | X92340 | 38/39 |
| IgHV1-69*04 | M83132 | 40/41 |
| IgHV1-69*05 | X67905 | 42/43 |
| IgHV1-69*06 | L22583 | 44/45 |
| IgHV1-69*07 | Z29978 | 46/47 |
| IgHV1-69*08 | Z14309 | 48/49 |
| IgHV1-69*09 | Z14307 | 50/51 |
| IgHV1-69*10 | Z14300 | 52/53 |
| IgHV1-69*11 | Z14296 | 54/55 |
| IgHV1-69*12 | Z14301 | 56/57 |
| IgHV1-69*13 | Z14214 | 58/59 |

TABLE 3

| IgHV1-2 Allele | Accession Number | SEQ ID NO: (DNA/Protein) |
|---|---|---|
| IgHV1-2*01 | X07448 | 60/61 |
| IgHV1-2*02 | X62106 | 62/63 |
| IgHV1-2*03 | X92208 | 64/65 |
| IgHV1-2*04 | Z12310 | 66/67 |
| IgHV1-2*05 | HM855674 | 68/69 |

Antigen-Dependent $V_H$ Gene Usage

Antigen-dependent preferential usage of $V_H$ genes can be exploited in the development of human therapeutics targeting clinically significant antigens. The ability to generate a repertoire of antibody variable domains using a particular $V_H$ gene can provide a significant advantage in the search for high-affinity antibody variable domains to use in human therapeutics. Studies on naive mouse and human $V_H$ gene usage in antibody variable domains reveal that most heavy chain variable domains are not derived from any particular single or dominantly used $V_H$ gene. On the other hand, studies of antibody response to certain antigens reveal that in some cases a particular antibody response displays a biased usage of a particular $V_H$ gene in the B cell repertoire following immunization.

Although the human $V_H$ repertoire is quite diverse, by some estimates the expected frequency of usage of any given $V_H$ gene, assuming random selection of $V_H$ genes, is about 2% (Brezinschek et al., 1995, Analysis of the Heavy Chain Repertoire of Human Peripheral B Cells Using Single-Cell Polymerase Chain Reaction, J. Immunol. 155: 190-202). But $V_H$ usage in peripheral B cells in humans is skewed. In one study, functional V gene abundance followed the pattern $V_H3 > V_H4 > V_H1 > V_H2 > V_H5 > V_H6$ (Davidkova et al., 1997, Selective Usage of $V_H$ Genes in Adult Human Lymphocyte Repertoires, Scand. J. Immunol. 45:62-73).

One early study estimated that $V_H3$ family usage frequency was about 0.65, whereas $V_H1$ family usage frequency was about 0.15; these and other observations suggest that the germline complexity of the human $V_H$ repertoire is not precisely reflected in the peripheral B cell compartment in humans that have a normal germline $V_H$ repertoire, a situation that is similar to that observed in the mouse—i.e., $V_H$ gene expression is non-stochastic (Zouali and These, 1991, Probing $V_H$ Gene-Family Utilization in Human Peripheral B Cells by In Situ Hybridization, *J. Immunol.* 146(8):2855-2864). According to one report, $V_H$ gene usage in humans, from greatest to least, is $V_H3 > V_H4 > V_H1 > V_H5 > V_H2 > V_H6$; rearrangements in peripheral B cells reveal that $V_H3$ family usage is higher than to be expected based on the relative number of germline $V_H3$ genes (Brezinschek et al., 1995). According to another report $V_H$ usage in humans follows the pattern $V_H3 > V_H5 > V_H2 > V_H1 > V_H4 > V_H6$, based on analysis of pokeweed mitogen-activated peripheral small immunocompetent B cells (Davidkova et al., 1997, Selective Usage of $V_H$ Genes in Adult Human B Lymphocyte Repertoires, Scand. J. Immunol. 45:62-73). One report asserts that among the most frequently used $V_H3$ family members are 3-23, 3-30 and 3-54 (Brezinschek et al., 1995). In the $V_H4$ family, member 4-59 and 4-4b were found relatively more frequently (Id.), as well as 4-39 and 4-34 (Brezinscheck et al., 1997, Analysis of the Human $V_H$ Gene Repertoire, J. Clin. Invest. 99(10):2488-2501). Others postulate that the activated heavy chain repertoire is skewed in favor of high $V_H5$ expression and lower $V_H3$ expression (Van Dijk-Hard and Lundkvist, 2002, Long-term kinetics of adult human antibody repertoires, Immunology 107:136-144). Other studies assert that the most commonly used $V_H$ gene in the adult human repertoire is $V_H4$-59, followed by $V_H3$-23 and $V_H3$-48 (Arnaout et al., 2001, High-Resolution Description of Antibody Heavy-Chain Repertoires in Humans, PLoS ONE 6(8):108). Although usage studies are based on relatively small sample numbers and thus exhibit high variance, taken together the studies suggest that V gene expression is not purely stochastic. Indeed, studies with particular antigens have established that—in certain cases—the deck is firmly stacked against certain usages and in favor of others.

Over time, it became apparent that the observed repertoire of human heavy chain variable domains generated in response to certain antigens is highly restricted. Some antigens are associated almost exclusively with neutralizing antibodies having only certain particular $V_H$ genes, in the sense that effective neutralizing antibodies are derived from essentially only one $V_H$ gene. Such is the case for a number of clinically important human pathogens.

$V_H1$-69-derived heavy chains have been observed in a variety of antigen-specific antibody repertoires of therapeutic significance. For instance, $V_H1$-69 was frequently observed in heavy chain transcripts of an IgE repertoire of peripheral blood lymphocytes in young children with atopic disease (Bando et al., 2004, Characterization of $V_H$E gene expressed in PBL from children with atopic diseases: detection of homologous $V_H1$-69 derived transcripts from three unrelated patients, Immunology Letters 94:99-106). $V_H1$-69-derived heavy chains with a high degree of somatic hypermutation also occur in B cell lymphomas (Perez et al., 2009, Primary cutaneous B-cell lymphoma is associated with somatically hypermutated immunoglobulin variable genes and frequent use of $V_H1$-69 and $V_H4$-59 segments, *British Journal of Dermatology* 162:611-618), whereas some $V_H1$-69-derived heavy chains with essentially germline sequences (i.e., little to no somatic hypermutation) have been observed among autoantibodies in patients with blood disorders (Pos et al., 2008, $V_H1$-69 germline encoded antibodies directed towards ADAMTS13 in patients with acquired thrombotic thrombocytopenic purpura, *Journal of Thrombosis and Haemostasis* 7:421-428).

Further, neutralizing antibodies against viral antigens such as HIV, influenza and hepatitis C (HCV) have been found to utilize germline and/or somatically mutated $V_H1$-69-derived sequences (Miklos et al., 2000, Salivary gland mucosa-associated lymphoid tissue lymphoma immunoglobulin $V_H$ genes show frequent use of 1/1-69 with distinctive CDR3 features, Blood 95(12):3878-3884; Kunert et aL, 2004, Characterization of molecular features, antigen-binding, and in vitro properties of IgG and IgM variants of 4E10, an anti-HIV type I neutralizing monoclonal antibody, *Aids Research and Human Retroviruses* 20(7):755-762; Chan et al., 2001, $V_H1$-69 gene is preferentially used by hepatitis C virus-associated B cell lymphomas and by normal B cells responding to the E2 viral antigen, Blood 97(4):1023-1026; Carbonari et al., 2005, Hepatitis C virus drives the unconstrained monoclonal expansion of $V_H1$-69-expressing memory B cells in type II cryoglobulinemia: A model of infection-driven lymphomagenesis, *Journal of Immunology* 174:6532-6539; Wang and Palese, 2009, Universal epitopes of influenza virus hemagglutinins?, *Nature Structural & Molecular Biology* 16(3):233-234; Sui et al., 2009, Structural and functional bases for broad-spectrum neutralization of avian and human influenza A viruses, *Nature Structural & Molecular Biology* 16(3):265-273; Marasca et aL, 2001, Immunoglobulin Gene Mutations and Frequent Use of $V_H1$-69 and $V_H4$-34 Segments in Hepatitis C Virus-Positive and Hepatitis C Virus-Negative Nodal Marginal Zone B-Cell Lymphoma, Am. J. Pathol. 159(1): 253-261).

$V_H$ usage bias is also observed in the humoral immune response to *Haemophilus influenzae* type b (Hib PS) in humans. Studies suggest that the $V_H$III family (the $V_H$IIIb subfamily in particular, $V_H9.1$) exclusively characterizes the human humoral response to Hib PS, with diverse D and J genes (Adderson et al., 1991, Restricted Ig H Chain V Gene Usage in the Human Antibody Response to *Haemophilus influenzae* Type b Capsular Polysaccharide, *J. Immunol.* 147(5):1667-1674; Adderson et al., 1993, Restricted Immunoglobulin $V_H$ Usage and VDJ Combinations in the Human Response to *Haemophilus influenzae* Type b Capsular Polysaccharide, *J. Clin. Invest.* 91:2734-2743). Human $J_H$ genes also display biased usage; $J_H4$ and $J_H6$ are observed at about 38-41% in peripheral B cells in humans (Brezinschek et aL, 1995).

$V_H$ usage in HIV-1-infected humans is reportedly biased against $V_H3$ usage and in favor of $V_H1$ and $V_H4$ gene families (Wisnewski et al., 1996, Human Antibody Variable Region Gene Usage in HIV-1 Infection, *J. Acquired Immune Deficiency Syndromes &Human Retroviology* 11(1):31-38). However, cDNA analysis of bone marrow from affected patients' revealed significant $V_H3$ usage not expressed in the functional B cell repertoire, where Fabs reflecting the $V_H3$ usage exhibited effective in vitro neutralization of HIV-1 (Id.). It might be postulated that the humoral immune response to HIV-1 infection is possibly attenuated due to the $V_H$ restriction; modified non-human animals as described herein (not infectable by HIV-1) might thus be useful for generating neutralizing antibody domains derived from particular $V_H$ genes present in the genetically modified animals described herein, but derived from different $V_H$ genes than those observed in the restricted repertoire of affected humans.

Thus, the ability to generate high affinity human antibody variable domains in $V_H$-restricted mice, e.g., (restricted, e.g., to a $V_H3$ family member and polymorph(s) thereof) immunized with HIV-1 might provide a rich resource for designing effective HIV-1-neutralizing human therapeutics by thoroughly mining the restricted (e.g., restricted to a $V_H3$ family member or variant(s) thereof) repertoire of such an immunized mouse.

Restriction of the human antibody response to certain pathogens may reduce the likelihood of obtaining antibody variable regions from affected humans that can serve as springboards for designing high affinity neutralizing antibodies against the pathogen. For example, the human immune response to HIV-1 infection is clonally restricted throughout HIV-1 infection and into AIDS progression (Muller et al., 1993, B-cell abnormalities in AIDS: stable and clonally restricted antibody response in HIV-1 infection, Scand. J. Immunol. 38:327-334; Wisnewski et al., 1996). Further, $V_H$ genes are in general not present in all polymorphic forms in any particular individual; certain individuals in certain populations possess one variant, whereas individuals in other populations possess a different variant. Thus, the availability of a biological system that is restricted to a single $V_H$ gene and its variants will in various embodiments provide a hitherto unexploited source of diversity for generating antibody variable regions (e.g., human heavy and light cognate domains) based on a restricted $V_H$ gene. Thus, in one aspect, a genetically modified non-human animal is provided that comprises a plurality of polymorphic variants of no more than one, or no more than two, human $V_H$ gene segment family member. In one embodiment, the no more than one, or no more than two, human $V_H$ gene segments are operably linked to one or more human $D_H$ gene segments, one or more human $J_H$ gene segments, and a human or non-human constant region gene segment. In one embodiment the constant region is at an endogenous non-human immunoglobulin constant gene locus. In one embodiment, the non-human animal further comprises a nucleic acid sequence derived from a human $V_L$ sequence, e.g., a rearranged or unrearranged human $V_L$ gene segment or a rearranged human $V_L/J_L$ sequence. In one embodiment, the nucleic acid sequence derived from the human $V_L$ sequence is at an endogenous non-human $V_L$ gene locus; in one embodiment, the nucleic acid sequence derived form the human $V_L$ sequence is on a transgene. In a specific embodiment, the non-human animal is incapable of expressing an immunoglobulin light chain variable domain that itself comprises an endogenous $V_L$ or $J_L$ gene segment, and comprises no more than one, or no more than two, light chain genes that encode rearranged human $V_L$ domains (i.e., from no more than one, or no more than two, rearranged human $V_L/J_L$ sequences).

Genetically modified mice that express human heavy chain variable regions with restricted $V_H$ gene segment usage are useful to generate a relatively large repertoire of junctionally diverse, combinatorially diverse, and somatically mutated high affinity human immunoglobulin heavy chain variable regions from an otherwise restricted repertoire. A restricted repertoire, in one embodiment, refers to a predetermined limitation in the number and/or identity of germline genes that results in the mouse being unable to form a rearranged heavy chain gene that is derived from any V gene other than a preselected V gene. In embodiments that employ a preselected V gene but not a preselected D and/or J gene, the repertoire is restricted with respect to the identity of the V gene but not the D and/or J gene (e.g., the repertoire consists essentially of no more than one, or no more than two, $V_H$ gene segments (and/or polymorphs thereof); and a plurality of D gene segments and a plurality of J gene segments)). The identity of the preselected V gene (and any preselected D and/or J genes) is not limited to any particular V gene.

Designing a mouse so that it rearranges a single $V_H$ gene (present as a single segment or a set of variants) with a variety of human D and J gene segments (e.g., $D_H$ and $J_H$ segments) provides an in vivo junctional diversity/combinatorial diversity/somatic hypermutation permutation machine that can be used to iterate mutations in resulting rearranged heavy chain variable region sequences (e.g., V/D/J or V/J, as the case may be). In such a mouse, the clonal selection process operates to select suitable variable regions that bind an antigen of interest that are based on a single preselected $V_H$ gene (or variants thereof). Because the mouse's clonal selection components are dedicated to selection based on the single preselected $V_H$ gene segment, background noise (e.g., a wide variety of non antigen-binding $V_H$ domains derived from many germline gene segments) is largely eradicated. With judicious selection of the $V_H$ gene segment, a relatively larger number of clonally selected, antigen-specific antibodies can be screened in a shorter period of time than with a mouse with a large diversity of V segments.

Preselecting limited repertoire and restricting a mouse to a single V segment provides a system for permuting V/D/J junctions at a rate that is in various embodiments higher than that observed in mice that otherwise have up to 40 or more V segments to recombine with D and J regions. Removal of other V segments frees the locus to form more V/D/J combinations for the preselected V segment than otherwise observed. The increased number of transcripts that result from the recombination of the preselected V with one of a plurality of D and one of a plurality of J segments will feed those transcripts into the clonal selection system in the form of pre-B cells, and the clonal selection system is thus dedicated to cycling B cells that express the preselected V region. In this way, more unique V region rearrangements derived from the preselected V segment can be screened by the organism than would otherwise be possible in a given amount of time.

In various aspects, mice are described that enhance the junctional diversity of V/D/J recombinations for the preselected V region, because all or substantially all recombinations of the immunoglobulin heavy chain variable locus will be of the preselected V segment and the D and J segments that are placed in such mice. Therefore, the mice provide a method for generating a diversity of CDR3 segments using a base, or restricted $V_H$ gene repertoire.

In one aspect, a non-human animal is provided, wherein the B cell population of the non-human animal expresses immunoglobulin heavy chains that are derived from no more than one, or no more than two human $V_H$ gene segments. In one embodiment, each of the no more than one, or no more than two, human $V_H$ gene segments are present in two or more polymorphic forms. In one embodiment, the human $V_H$ gene segment is present in three, four, five, six, seven, eight, nine, 10, 11, 12, 13, 14, 15, 16, 17, 18, 19 or 20 polymorphic forms. In one embodiment, the non-human animal expresses a human light chain variable domain derived from a human $V_L$ gene segment.

In one aspect, a method is provided for generating a B cell population in a non-human animal, wherein the B cell population expresses human heavy chains derived from a single germline human $V_H$ gene segment and two or more human D gene segments and two or more human J gene segments; the method comprising a step of immunizing a non-human animal as described herein with an antigen of interest, and allowing the non-human animal to mount an immune response to the antigen of interest, wherein the immune response comprises expressing the human heavy chains on the surface of B cells in the B cell population In one embodiment, the non-human animal is a rodent (e.g., a mouse or rat). In one embodiment, the human $V_H$ gene segment, human $D_H$ segment, and human $J_H$ segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a method for making a non-human animal that expresses an immunoglobulin population characterized by the immunoglobulins having heavy chains that are derived from a plurality of rearrangements of a single human $V_H$ gene segment (or sing human $V_H$ gene family member) and one of a plurality of $D_H$ gene segments and one of a plurality of $J_H$ gene segments, is provided. In one embodiment, the human $V_H$ gene segment is a human $V_H$1-69 gene segment. In one embodiment, the human $V_H$ gene segment is a human $V_H$1-2 gene segment.

In one aspect, a method is provided for generating a population of human immunoglobulin heavy chain variable domains whose CDR1 and CDR2 are derived from the same germline $V_H$ gene segment, and whose CDR3 are derived from the germline gene segment and two or more human D segments, and two or more human J segments; the method comprising immunizing a non-human animal as described herein with an antigen of interest, and allowing the non-human animal to mount an immune response to the antigen of interest, wherein the immune response comprises expressing the human heavy chain variable domains in the context of a light chain variable domain. In one embodiment, the non-human animal is a rodent (e.g., a mouse or rat). In one embodiment, the human $V_H$ gene segment, human D segment, and human J segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a genetically modified non-human animal is provided, wherein the non-human animal is incapable of expressing a non-human $V_H$ domain, and wherein each immunoglobulin heavy chain of the heavy chain population expressed in the animal comprises a human $V_H$ domain comprising a CDR1 and a CDR2 that are identical but for one or more somatic hypermutations, and wherein the heavy chain population comprises a plurality of CDR3 sequences derived from a plurality of rearrangements with a plurality of D and J gene segments.

In one aspect, a biological system for generating variation in CDR3 identity and length is provided, comprising a genetically modified non-human animal as described herein, wherein the non-human animal comprises no more than or no more than two human $V_H$ gene segments, and two or more D gene segments and one or more J gene segments, wherein the non-human animal further comprises a humanized immunoglobulin light chain locus. In various embodiments, the non-human animal in response to immunization with an antigen of interest generates an immune response that comprises expressing an immunoglobulin heavy chain population characterized by each heavy chain having CDR1s and CDR2s that differ only by somatic hypermutation, and CDR3s that differ by rearrangement and somatic hypermutation. In one embodiment, the biological system is a mouse that is genetically modified as described herein. In one embodiment, the human $V_H$ gene segment and the human $V_L$ gene segment are at endogenous mouse heavy and light immunoglobulin loci, respectively. In one embodiment, one or more of the human $V_H$ gene segment and the human $V_L$ gene segment are on transgenes (i.e., at a locus other than an endogenous immunoglobulin locus).

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric. In the foregoing Examples, when the use of kits and/or reagents from various suppliers is indicated, all procedures were carried out according to manufacturer's specifications.

Example 1 Construction of Restricted Heavy Chain Loci

A uniquely engineered human heavy chain locus containing a single human $V_H$ gene segment located upstream of all the human $D_H$ and $J_H$ gene segments was created by a series of homologous recombination reactions in bacterial cells (BHR) using Bacterial Artificial Chromosome (BAC) DNA. Several targeting constructs for creation of a single $V_H$ containing heavy chain locus were constructed using VELOCIGENE® genetic engineering technology (see, e.g., U.S. Pat. No. 6,586,251 and Valenzuela, D. M. et al. (2003) High-throughput engineering of the mouse genome coupled with high-resolution expression analysis. *Nature Biotechnology* 21(6): 652-659).

Construction of a Human $V_H$1-69 Restricted Heavy Chain Locus. Briefly, four modifications were performed using human BAC DNA to create a targeting construct containing a human $V_H$1-69 gene segment with all the human $D_H$ and $J_H$ segments (FIG. 1). In the first modification, a modified human BAC containing multiple distal (5') human $V_H$ gene segments, including $V_H$1-69, an upstream hygromycin selection cassette and a 5' mouse homology arm was targeted with a second spectinomycin cassette, which also contained a modified recombination signal sequence (RSS; BHR 1, FIG. 1, top left). This modified recombination signal sequence (RSS) introduced two point mutations (T to A and G to A) in the 3' RSS region of the human $V_H$1-69 gene changing the RSS nonamer to the optimal consensus sequence. Thus, the first modification (BHR 1) created a human genomic fragment containing the human $V_H$1-69 gene segment with a modified 3' RSS, a unique AsiSI restriction site about 180 bp downstream of the RSS and a spectinomycin cassette (FIG. 1, middle left).

The second modification (BHR 2) included the use of a neomycin (Neo) cassette flanked by Frt sites to delete the hygromycin cassette and 5' human $V_H$ gene segments upstream of the $V_H$1-69 gene segment. This modification was targeted 5' to the human $V_H$1-69 gene segment to leave intact about 8.2 kb of the promoter region of human $V_H$1-69 and the 5' mouse homology arm (FIG. 1, bottom left).

The third modification (BHR 3) included another spectinomycin cassette flanked by uniquely engineered 5' PI- SceI and 3' AsiSI sites targeted to a human genomic fragment containing the first three functional human $V_H$ gene segments and all the human $D_H$ and $J_H$ gene segments (FIG. 1, middle right). The human genomic fragment was previously targeted with a neomycin cassette and contained 5' and 3' homology arms containing the mouse genomic sequence 5' and 3' of the endogenous heavy chain locus including the 3' intronic enhancer and the IgM gene. This modification deleted the 5' mouse genomic sequence and human $V_H$ gene segments, leaving about 3.3 kb of the $V_H$-$D_H$ intergenic region upstream of the human $D_H$1-1 gene segment, all of the human $D_H$ and $J_H$ segments, and the 3' mouse genomic fragment containing the 3' intronic enhancer and the IgM gene (FIG. 1, bottom right).

The fourth modification was achieved by employing the unique PI-SceI and AsiSI sites (described above) to ligate the two modified BACs from BHR 2 and BHR 3 (FIG. 1, bottom center), which yielded the final targeting construct. The final targeting construct for the creation of a modified heavy chain locus containing a single human $V_H$ gene segment and all the human $D_H$ and $J_H$ gene segments in ES cells contained, from 5' to 3', a 5' homology arm containing about 20 kb of mouse genomic sequence upstream of the endogenous heavy chain locus, a 5' Frt site, a neomycin cassette, a 3' Frt site, about 8.2 kb of the human $V_H$1-69 promoter, the human $V_H$1-69 gene segment with a modified 3' RSS, 27 human $D_H$ gene segments, six human $J_H$ segments, and a 3' homology arm containing about 8 kb of mouse genomic sequence downstream of the mouse $J_H$ gene segments including the 3' intronic enhancer and IgM gene (FIG. 1, bottom). The Human $V_H$1-69 Targeting Vector (SEQ ID NO: 3) was linearized and electroporated into mouse ES cells heterozygous for a deletion of the endogenous heavy chain locus.

Construction of a Human $V_H$1-2 Restricted Heavy Chain Locus.

Using the steps described above, other polymorphic $V_H$ gene segments in the context of mouse heavy chain constant regions are employed to construct a series of mice having a restricted number immunoglobulin heavy chain V segments (e.g., 1, 2, 3, 4, or 5), wherein the V segments are polymorphic variants of a V gene family member. Exemplary polymorphic $V_H$ gene segments are derived from human $V_H$ gene segments including, e.g., $V_H$1-2, $V_H$2-26, $V_H$2-70 and $V_H$3-23. Such human $V_H$ gene segments are obtained, e.g., by de novo synthesis (e.g., Blue Heron Biotechnology, Bothell, Wash.) using sequences available on published databases. Thus, DNA fragments encoding each $V_H$ gene are, in some embodiments, generated independently for incorporation into targeting vectors, as described herein. In this way, multiple modified immunoglobulin heavy chain loci comprising a restricted number of $V_H$ gene segments are engineered in the context of mouse heavy chain constant regions. An exemplary targeting strategy for creating a restricted humanized heavy chain locus containing a human $V_H$1-2 gene segment, 27 human $D_H$ gene segments, and six human $J_H$ gene segments is shown in FIG. 2.

Briefly, a modified human BAC clone containing three human $V_H$ gene segments ($V_H$6-1, $V_H$1-2, $V_H$1-3), 27 human $D_H$ gene segments, and six human $J_H$ gene segments (see U.S. Ser. No. 13/404,075; filed 24 Feb. 2012, herein incorporated by reference) is used to create a restricted humanized heavy chain locus containing a human $V_H$1-2 gene segment. This modified BAC clone functionally links the aforementioned human heavy chain gene segments with the mouse intronic enhancer and the IgM constant region. The restricted human $V_H$1-2 based heavy chain locus is achieved by two homologous recombinations using the modified human BAC clone described above.

For the first homologous recombination, 205 bp of the human $V_H$6-1 gene segment (from about 10 bp upstream (5') of the $V_H$6-1 start codon in exon 1 to about 63 bp downstream (3') of the beginning of exon 2) in the modified human BAC clone is deleted by bacterial homologous recombination using a spectinomycin (aadA) cassette flanked by unique PI-SceI restriction sites (FIG. 2, BHR 1). This allows for subsequent removal of the aadA cassette without disrupting other human gene segments within the restricted heavy chain locus.

For the second homologous recombination, the 5' end of the modified human BAC clone including the entire human $V_H$1-3 gene segment and about 60 bp downstream (3') of the gene segment is deleted by homologous recombination using a hygromycin cassette containing flanking 5' AsiSI and 3' AscI restriction sites (FIG. 2, BHR 2). As described above, the spectinomycin cassette is optionally removed after confirmation of the final targeting vector including deletion of the two human $V_H$ gene segments flanking the human $V_H$1-2 gene segment (FIG. 2, bottom). An exemplary human $V_H$1-2 targeting vector is set forth in SEQ ID NO: 70.

Employing polymorphic $V_H$ gene segments in a restricted immunoglobulin heavy chain locus represents a novel approach for generating antibodies, populations of antibodies, and populations of B cells that express antibodies having heavy chains with diverse CDRs derived from a single human $V_H$ gene segment. Exploiting the somatic hypermutation machinery of the host animal along with combinatorial association with rearranged human immunoglobulin light chain variable domains results in the engineering of unique heavy chains and unique $V_H N_L$ pairs that expand the immune repertoire of genetically modified animals and enhance their usefulness as a next generation platform for making human therapeutics, especially useful as a platform for making neutralizing antibodies specific for human pathogens.

Thus, using the strategy outlined above for incorporation of additional and/or other polymorphic $V_H$ gene segments into the mouse immunoglobulin heavy chain locus allows for the generation of novel antibody repertoires for use in neutralizing human pathogens that might otherwise effectively evade the host immune system.

Targeted ES cells described above were used as donor ES cells and introduced into an 8-cell stage mouse embryo by the VELOCIMOUSE® method (supra). Mice bearing a humanized heavy chain locus containing a single human $V_H$ gene segment, all the human $D_H$ and $J_H$ gene segments operably linked to the mouse immunoglobulin constant region genes were identified by genotyping using a modification of allele assay (Valenzuela et al., supra) that detected the presence of the neomycin cassette, the human $V_H$ gene segment and a region within the human $D_H$ and $J_H$ gene segments as well as endogenous heavy chain sequences. Table 4 sets forth the primers and probes used in this assay to confirm mice harboring a restricted heavy chain locus containing a single human $V_H$1-69 gene segment, 27 human $D_H$ gene segments and six human $J_H$ gene segments.

Mice bearing an engineered heavy chain locus that contains a single human $V_H$ gene segment can be bred to a FLPe deletor mouse strain (see, e.g., Rodriguez, C. I. et al. (2000) High-efficiency deleter mice show that FLPe is an alternative to Cre-loxP. *Nature Genetics* 25: 139-140) in order to remove any Frt'ed neomycin cassette introduced by the targeting vector that is not removed, e.g., at the ES cell stage or in the embryo. Optionally, the neomycin cassette is retained in the mice.

Pups are genotyped and a pup heterozygous for a humanized heavy chain locus containing a single human $V_H$ gene segment, all the human $D_R$ and $J_H$ segments operably linked to the endogenous mouse immunoglobulin constant genes is selected for characterizing the immunoglobulin heavy chain repertoire.

TABLE 4

| Name (Region Detected) | Sequence (5'-3') | SEQ ID NO: |
|---|---|---|
| hyg (hygromycin cassette) | Forward: TGCGGCCGAT CTTAGCC<br>Reverse: TTGACCGATT CCTTGCGG<br>Probe: ACGAGCGGGT TCGGCCCATT C | 4<br>5<br>6 |
| neo (neomycin cassette) | Forward: GGTGGAGAGG CTATTCGGC<br>Reverse: GAACACGGCG GCATCAG<br>Probe: TGGGCACAAC AGACAATCGG CTG | 7<br>8<br>9 |
| hIgH9T (human $D_H$-$J_H$ genomic sequence) | Forward: TCCTCCAACG ACAGGTCCC<br>Reverse: GATGAACTGA CGGGCACAGG<br>Probe: TCCCTGGAAC TCTGCCCCGA CACA | 10<br>11<br>12 |
| 77h3 (human $V_H$1-69 gene segment) | Forward: CTCTGTGGAA AATGGTATGG AGATT<br>Reverse: GGTAAGCATA GAAGGTGGGT ATCTTT<br>Probe: ATAGAACTGT CATTTGGTCC AGCAATCCCA | 13<br>14<br>15 |
| mIgHA7 (mouse $D_H$-$J_H$ genomic sequence) | Forward: TGGTCACCTC CAGGAGCCTC<br>Reverse: GCTGCAGGGT GTATCAGGTG C<br>Probe: AGTCTCTGCT TCCCCCTTGT GGCTATGAGC | 16<br>17<br>18 |
| 88710T (mouse 3' $V_H$ genomic sequence) | Forward: GATGGGAAGA GACTGGTAAC ATTTGTAC<br>Reverse: TTCCTCTATT TCACTCTTTG AGGCTC<br>Probe: CCTCCACTGT GTTAATGGCT GCCACAA | 19<br>20<br>21 |
| mIgHd10 (mouse 5' $V_H$ genomic sequence) | Forward: GGTGTGCGAT GTACCCTCTG AAC<br>Reverse: TGTGGCAGTT TAATCCAGCT TTATC<br>Probe: CTAAAAATGC TACACCTGGG GCAAAACACC TG | 22<br>23<br>24 |
| mIgHp2 (mouse $J_H$ genomic sequence) | Forward: GCCATGCAAG GCCAAGC<br>Reverse: AGTTCTTGAG CCTTAGGGTG CTAG<br>Probe: CCAGGAAAAT GCTGCCAGAG CCTG | 25<br>26<br>27 |

Example 2 Characterization of Mice Expressing Heavy Chains Derived from a Single Human $V_H$ Gene Segment Mice homozygous for a single human $V_H$ gene segment at the endogenous heavy chain locus as described in Example 1 were evaluated for expression and B cell development using flow cytometry.

Briefly, spleens and bone marrow was harvested from wild type (n=3 per group; six weeks old, male and female) and mice homozygous for a single human $V_H$ gene segment, all human $D_H$ and $J_H$ gene segments operably linked to mouse heavy chain constant regions. Red blood cells from spleens were lysed with ACK lysis buffer (Lonza Walkersville), followed by washing with complete RPMI medium.

Flow cytometry. Cells (1×10⁶) were incubated with anti-mouse CD16/CD32 (2.4G2, BD PHARMINGEN™) on ice for 10 minutes, followed by labeling with the following antibody panels for 30 minutes on ice. Bone marrow panel: anti-mouse FITC-CD43 (1B11, BioLegend), PE-ckit (2B8, BIOLEGEND®), PeCy7-IgM (II/41, EBIOSCIENCE®), PerCP-Cy5.5-IgD (11-26c.2a, BIOLEGEND®), APC-eFluor 780-6220 (RA3-6B2, EBIOSCIENCE®), APC-CD19 (MB19-1, EBIOSCIENCE®). Bone marrow and spleen panel: anti-mouse FITC-ID((187.1, BD Biosciences), PE-10, (RML-42, BIOLEGEND®), PeCy7-IgM (II/41, EBIOSCIENCE®), PerCP-Cy5.5-IgD (11-26c.2a, BIOLEGEND®), Pacific Blue-CD3 (17A2, BIOLEGEND®), APC-B220 (RA3-6B2, EBIOSCIENCE®), APC-H7-CD19 (ID3, BD Biosciences). Bone marrow: immature B cells (B220$^{int}$IgM$^+$), mature B cells (B220$^{hi}$IgM$^+$), pro B cells (CD19$^+$ckit$^+$CD43$^+$), pre B cells (CD19$^+$ckit$^-$CD43$^-$), immature Igκ$^+$ B cells (B220$^{int}$IgM$^+$Igκ$^+$Igλ$^-$), immature Igλ$^+$ B cells (B220$^{int}$IgM$^+$Igκ$^-$Igλ$^+$), mature Igκ$^+$ B cells (B220$^{int}$IgM$^+$Igκ$^+$), mature Igλ$^+$ B cells (B220$^{int}$IgM$^+$Igκ$^-$Igλ$^+$). Spleen: B cells (CD19$^+$), mature B cells (CD19$^+$IgD$^{hi}$IgM$^{int}$), transitional/immature B cells (CD19$^+$IgD$^{int}$IgM$^{hi}$) Bone marrow and spleen: Igκ$^+$ B cells (CD19$^+$Igκ$^+$Igλ$^-$), Igλ$^+$ B cells (CD19$^+$Igκ$^-$Igλ$^+$).

Following staining, cells were washed and fixed in 2% formaldehyde. Data acquisition was performed on a LSRII flow cytometer and analyzed with FLOWJO™ software (Tree Star, Inc.). Results for the splenic compartment are shown in FIGS. 3, 4A and 5-7. Results for the bone marrow compartment are shown in FIGS. 4B and 8-11B.

Human $V_H$ Expression. Expression of the human $V_H$1-69 gene segment was determined for mice heterozygous and homozygous for a human $V_H$1-69 gene segment, all human $D_H$ and $J_H$ gene segments operably linked to mouse heavy chain constant regions by a quantitative PCR assay using TAQMAN® probes.

Figure 12:
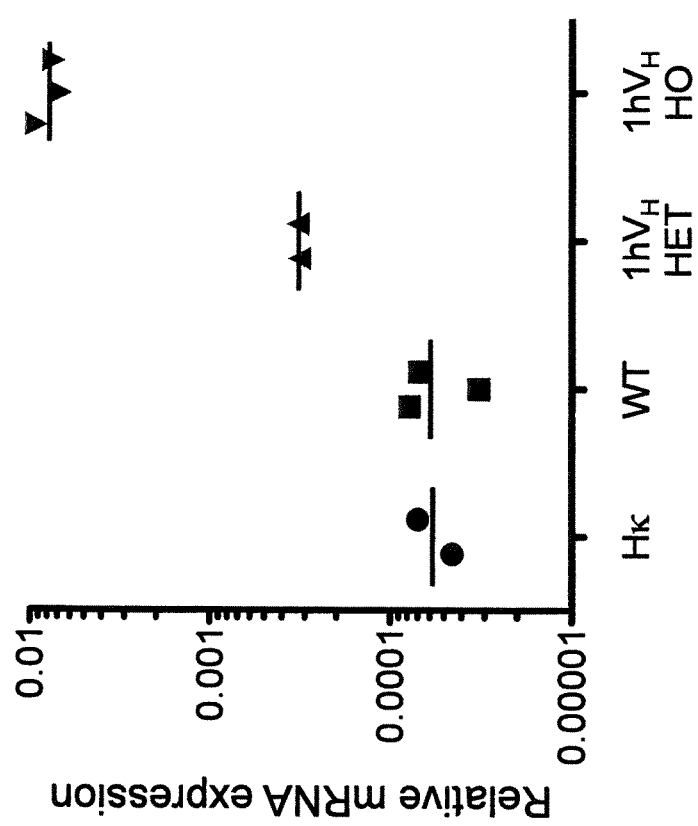
FIG. 12 shows the relative mRNA expression (y-axis) in purified splenic B cells of $V_H$1-69-derived heavy chains in a quantitative PCR assay using a probe specific for the human $V_H$1-69 gene segment in mice homozygous for a replacement of the endogenous heavy chain $V_H$, $D_H$, $J_H$, and a replacement of the endogenous light chain Vκ and Jκ gene segments with human $V_H$, $D_H$, $J_H$, Vκ and Jκ gene segments (Hκ), wild type mice (WT), mice heterozygous for a single human $V_H$ gene segment, twenty-seven human $D_H$ and six human $J_H$ gene segments at the endogenous immunoglobulin heavy chain locus (1h$V_H$ HET) and mice homozygous for a single human $V_H$ gene segment, twenty-seven human $D_H$ and six human $J_H$ gene segments at the endogenous immunoglobulin heavy chain locus (1h$V_H$ HO). Signals are normalized to expression of mouse Cκ.

Briefly, CD19$^+$ B cells were purified from the spleens of groups of mice (n=3 per group) using mouse CD19 microbeads (Miltenyi Biotec) according to manufacturer's specifications. Total RNA was purified using the RNEASY™ Mini kit (Qiagen) and genomic RNA was removed using an RNase-free DNase on-column treatment (Qiagen). About 200 ng mRNA was reverse-transcribed into cDNA using the First Stand cDNA Synthesis kit (Invitrogen), followed by amplification with the TAQMAN® Universal PCR Master Mix (Applied Biosystems) using the ABI 7900 Sequence Detection System (Applied Biosystems). Unique primer/probe combinations were employed to specifically determine expression of human $V_H$1-69-derived heavy chains (Table 5). Relative expression was normalized to the mouse κ constant region ($mC_\kappa$). The results are shown in FIG. 12.

TABLE 5

| Name | Sequence (5'-3') | SEQ ID NO: |
|---|---|---|
| hIgHV1-69 | Sense: AACTACGCAC AGAAGTTCCA GG | 28 |
|  | Anti-sense: GCTCGTGGAT TTGTCCGC | 29 |
|  | Probe: CAGAGTCACG ATTACC | 30 |
| mCK | Sense: TGAGCAGCAC CCTCACGTT | 31 |
|  | Antisense: GTGGCCTCAC AGGTATAGCT GTT | 32 |
|  | Probe: ACCAAGGACG AGTATGAA | 33 |

Example 3 Humoral Immune Response in Mice Expressing Heavy Chains Derived from a Single Human $V_H$ Gene Segment The humoral immune response was determined for mice homozygous for human heavy and κ light chain variable gene loci ($H_\kappa$) and mice homozygous for a single human $V_H$ gene segment, all human $D_H$ and $J_H$ gene segments operably linked to mouse heavy chain constant regions (1h$V_H$ HO) by comparative immunization using a human cell surface receptor (Antigen A).

Immunization.

Serum was collected from groups of mice prior to immunization with the above antigen. Antigen (2.35 µg each) was administered in an initial priming immunization mixed with 10 µg of CpG oligonucleotide (Invivogen) and 25 µg of Adju-phos (Brenntag) as adjuvants. The immunogen was administered via footpad (f.p.) in a volume of 25 µl per mouse. Subsequently, mice were boosted via f.p. with 2.3 µg of antigen along with 10 µg CpG and 25 µg Adju-Phos as adjuvants on days 3, 6, 11, 13, 17, and 20 for a total of six boosts. Mice were bled on days 15 and 22 after the fourth and sixth boosts, respectively, and antisera were assayed for antibody titers to Antigen A.

Antibody titers were determined in sera of immunized mice using an ELISA assay. Ninety six-well microtiter plates (Thermo Scientific) were coated with Antigen A (1 µg/ml) in phosphate-buffered saline (PBS, Irvine Scientific) overnight at 4° C. The following day, plates were washed with phosphate-buffered saline containing 0.05% Tween 20 (PBS-T, Sigma-Aldrich) four times using a plate washer (Molecular Devices). Plates were then blocked with 250 µl of 1% bovine serum albumin (BSA, Sigma-Aldrich) in PBS and incubated for one hour at room temperature. The plates were then washed four times with PBS-T. Sera from immunized mice and pre-immune sera were serially diluted ten-fold in 0.1% BSA PBS-T starting at 1:100 and added to the blocked plates in duplicate and incubated for one hour at room temperature. The last two wells were left blank to be used as secondary antibody control. The plates were again washed four times with PBS-T in a plate washer. A 1:5000 dilution of goat anti-mouse IgG-Fc-Horse Radish Peroxidase (HRP, Jackson Immunoresearch) conjugated secondary antibody was added to the plates and incubated for one hour at room temperature. Plates were again washed eight times with PBS-T and developed using TMB/$H_2O_2$ as substrate. The substrate was incubated for twenty minutes and the reaction stopped with 1 N $H_2SO_4$ (VWR). Plates were read on a spectrophotometer (Victor, Perkin Elmer) at 450 nm. Antibody titers were calculated using GRAPHPAD PRISM™ (GraphPad Software, Inc).

Figure 19:
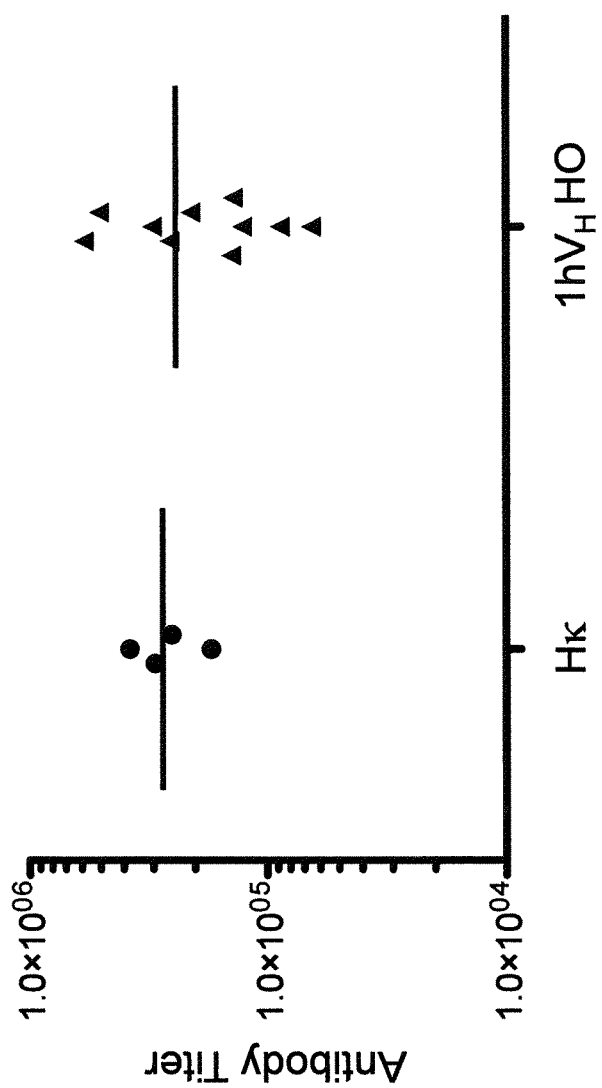
FIG. 19 shows the antibody titer from mice homozygous for human heavy and human κ light chain variable gene loci (Hκ; n=4) and mice homozygous for a single human $V_H$1-69 gene segment, twenty-seven human $D_R$ and six human $J_R$ gene segments at the endogenous immunoglobulin heavy chain locus (1h$V_H$HO; n=10) that were immunized with a human cell surface receptor (Antigen A).

Serum titer was calculated as serum dilution within experimental titration range at the signal of antigen binding equivalent to two times above background. Antibody titer for the humoral immune response against a human cell surface receptor (Antigen A) is set forth in FIG. 19.

In a similar experiment, humoral immune responses were determined for mice homozygous for human heavy and κ light chain variable gene loci ($H_\kappa$) and mice homozygous for a single human $V_H$ gene segment, all human $D_H$ and $J_H$ gene segments operably linked to mouse heavy chain constant regions (1h$V_H$ HO) by comparative immunization using influenza viral vaccines FLUVIRIN® (Novartis Vaccines) and FLUMIST® (MedImmune LLC).

Briefly, serum was collected from groups of mice prior to immunization with the above antigen (as described above). Mice (n=5) homozygous for a single human $V_H$ gene segment ($V_H$1-69), all human $D_H$ and $J_H$ gene segments operably linked to mouse heavy chain constant regions (1h$V_H$ HO) were immunized intra-nasally (i.n.) with FLUMIST® (live attenuated influenza vaccine) at ⅓ the normal dose/mouse. One normal dose of FLUMIST® contains $10^{6.5-7.5}$ FFU (fluorescent focus units) of live attenuated influenza vaccine. Therefore, each mouse was primed with 70 µl FLUMIST® on day 1 followed by i.n. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUMIST® (as described above).

In a similar manner, in immunizations with FLUVIRIN®, pre-immune serum was collected from mice prior to initiation of immunization. Mice (n=5) homozygous for a single human $V_H$ gene segment ($V_H$1-69), all human $D_H$ and $J_H$ gene segments operably linked to mouse heavy chain constant regions (1h$V_H$ HO) were immunized with FLUVIRIN® (trivalent inactivated influenza vaccine) via footpad (f.p.) with 0.75 µg each of hemagglutinin/mouse/boost. Mice were primed on day 1 followed by f.p. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUVIRIN® (as described above).

Figure 20:
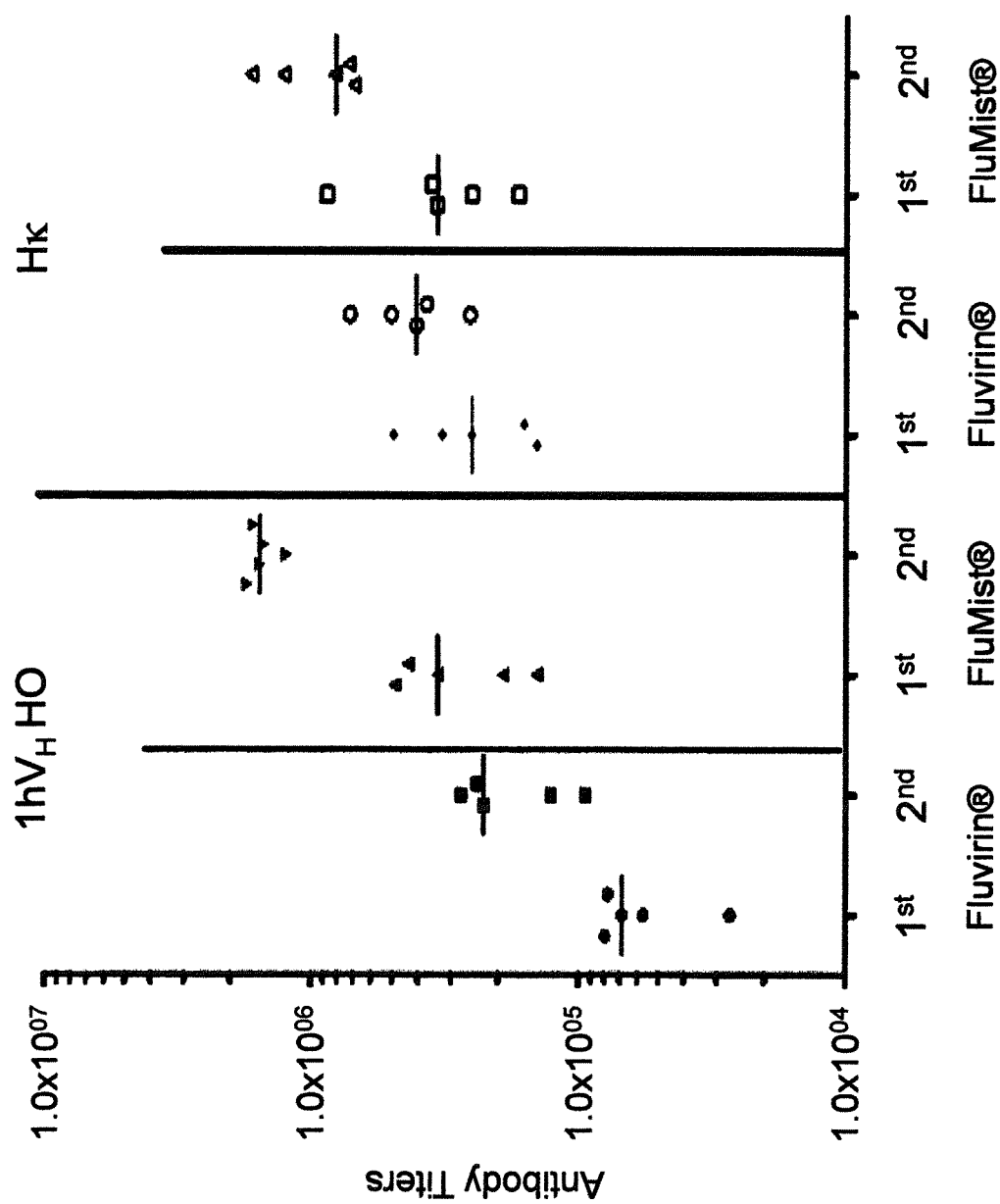
FIG. 20 shows the antibody titer from mice homozygous for human heavy and human κ light chain variable gene loci (fix; n=5) and mice homozygous for a single human $V_H$1-69 gene segment, twenty-seven human $D_R$ and six human $J_R$ gene segments at the endogenous immunoglobulin heavy chain locus (1h$V_H$HO; n=5) that were immunized with two different influenza vaccines.

Serum titer was calculated as serum dilution within experimental titration range at the signal of antigen binding equivalent to two times above background. Antibody titer for the humoral immune response against FLUMIST® and FLUVIRIN® is set forth in FIG. 20.

As shown in this Example, antibody titers generated in $1hV_H$ HO mice were comparable to those generated in mice having a plurality of human $V_H$ gene segments ($H_\kappa$) for both a human cell surface receptor and a viral antigen (e.g., influenza). Thus, mice having immunoglobulin heavy chain loci restricted to a single $V_H$ gene segment are capable of mounting a robust immune response to antigen in a manner comparable to mice having immunoglobulin heavy chain loci containing a plurality of human $V_H$ gene segments (e.g., 80 $V_H$).

Example 4 Analysis of Antibody Gene Usage and CDR3 Length in Mice Having a Restricted Immunoglobulin Heavy Chain Locus Splenocytes harvested from mice homozygous for a single human $V_H$ gene segment at the endogenous heavy chain locus and homozygous for a replacement of the endogenous κ light chain variable loci with human κ light chain variable loci immunized with a human cell surface receptor (Antigen A) were analyzed for heavy and light chain gene segment usage by reverse-transcriptase polymerase chain reaction (RT-PCR) on mRNA from splenic B cells.

Briefly, spleens were harvested and homogenized in 1×PBS (Gibco) using glass slides. Cells were pelleted in a centrifuge (500×g for 5 minutes), and red blood cells were lysed in ACK Lysis buffer (Gibco) for 3 minutes. Cells were washed with 1×PBS and filtered using a 0.7 μm cell strainer. B-cells were isolated from spleen cells using MACS magnetic positive selection for CD19 (Miltenyi Biotec). Total RNA was isolated from pelleted B-cells using the RNeasy Plus Kit (Qiagen). PolyA⁺ mRNA was isolated from total RNA using the Oligotex® Direct mRNA mini kit (Qiagen).

Double-stranded cDNA was prepared from splenic B cell mRNA by 5' RACE using the SMARTer™ Pico cDNA Synthesis Kit (Clontech) with substitution of the supplied reverse transcriptase and dNTPs with Superscript® II and dNTPs (Invitrogen). $V_H$ and Vκ antibody repertoires were amplified from the cDNA using primers specific for IgM, IgG, or Igκ constant regions and the SMARTer™ 5' RACE primer (Table 6). PCR products were purified using a QIAquick® PCR Purification Kit (Qiagen). A second round of PCR was done using the same 5' RACE primer and a nested 3' primer specific for the IgM, IgG, or Igκ constant regions (Table 7). Second round PCR products were purified using a SizeSelect™ E-Gel® system (Invitrogen). A third PCR was performed with primers that added 454 adapters and barcodes. Third round PCR products were purified using Agencourt® AMPure® XP Beads (Beckman Coulter). Purified PCR products were quantified by SYBR® qPCR using a KAPA Library Quantification Kit (KAPA Biosystems). Pooled libraries were subjected to emulsion PCR (emPCR) using a 454 GS Junior Titanium Series Lib-A emPCR Kit (Roche Diagnostics) and bidirectional sequencing using Roche 454 GS Junior instrument according to manufacturer's specifications.

Bioinformatic Analysis.

The 454 sequences were sorted based on the sample barcode perfect match and trimmed for quality. Sequences were annotated based on alignment of rearranged immunoglobulin sequences to human germline V(D)J segment database using local installation of Igblast (NCBI, v2.2.25+). A sequence was marked as ambiguous and removed from analysis when multiple best hits with identical score were detected. A set of perl scripts was developed to analyze results and store data in mysql database. CDR3 region was defined between conserved C codon and FGXG motif for light and WGXG motif for heavy chains. CDR3 length was determined using only productive antibodies. From the nucleic acid sequences and predicted amino acid sequences of the antibodies, gene usage was identified for IgM-primed (15,650), IgG-primed (18,967), and Igκ-primed (26,804) sequences. Results are shown in Table 8, Table 9, FIG. 21 and FIG. 22.

Table 8 sets forth the percentage of observed human $D_H$ and $J_H$ gene segments used among IgM-primed (15,650 sequences) and IgG-primed (18,967 sequences) $V_H$1-69 derived heavy chain variable region sequences. Human $D_H$4-4/$D_H$4-11 and human $D_H$5-5/$D_H$5-18 gene segments are presented in Table 8 together due to identical sequence identity between the respective pairs of $D_H$ gene segments. Table 9 sets forth the percentage of human Vκ and Jκ gene segments observed among light chains (26,804 sequences) cognate with $V_H$1-69 derived heavy chain variable regions. Percentages in Tables 8 and 9 represent rounded values and in some cases may not equal 100% when added together.

Figure 21:
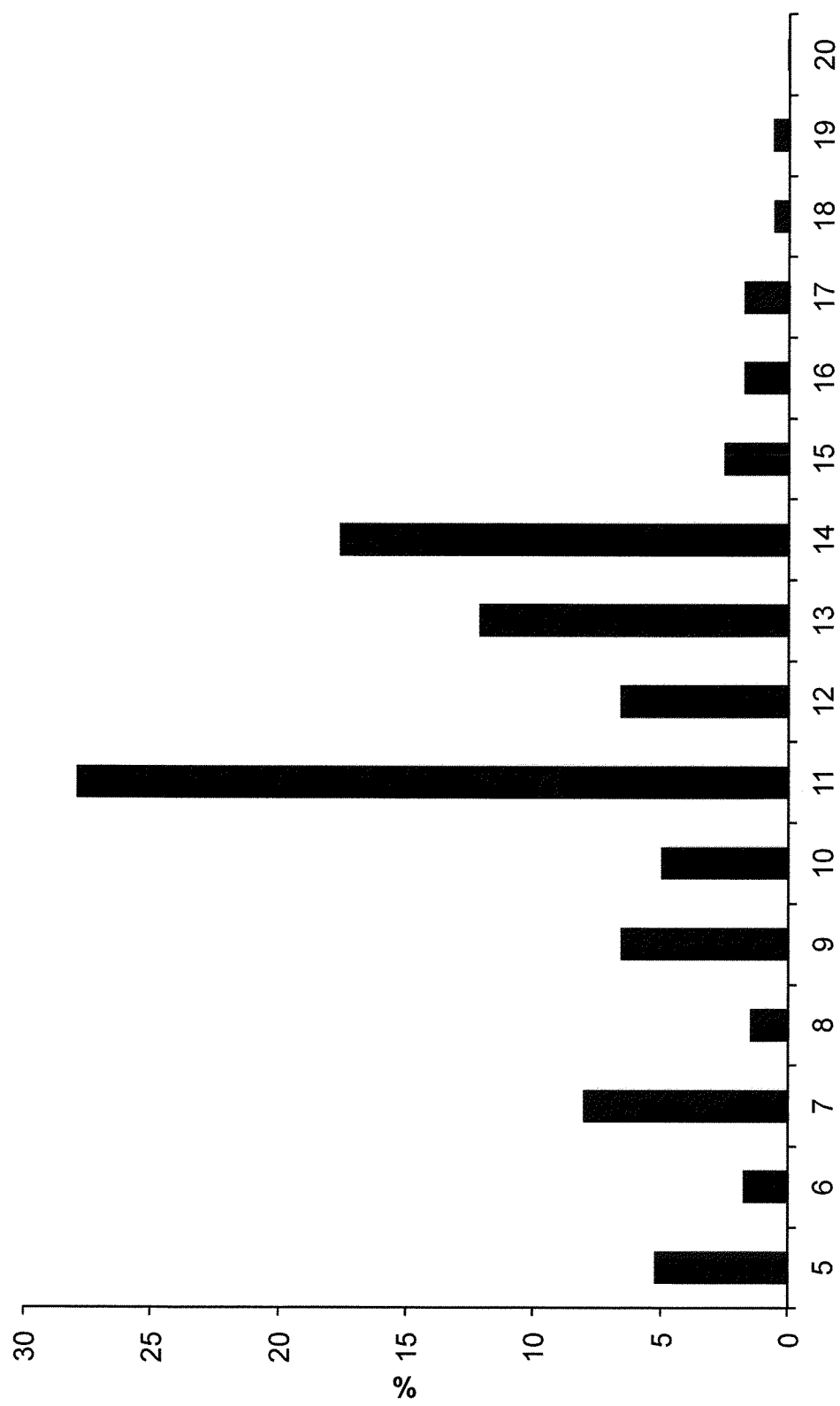
FIG. 21 shows the percentage (y-axis) of IgM-primed heavy chains having a specified amino acid length for the $V_H$ CDR3 region (x-axis) from mice homozygous for a single human $V_H$1-69 gene segment, twenty-seven human $D_R$ and six human $J_R$ gene segments at the endogenous immunoglobulin heavy chain locus and homozygous for a replacement of the endogenous κ light chain variable loci with human κ light chain variable loci that were immunized with a human cell surface receptor (Antigen A).
Figure 22:
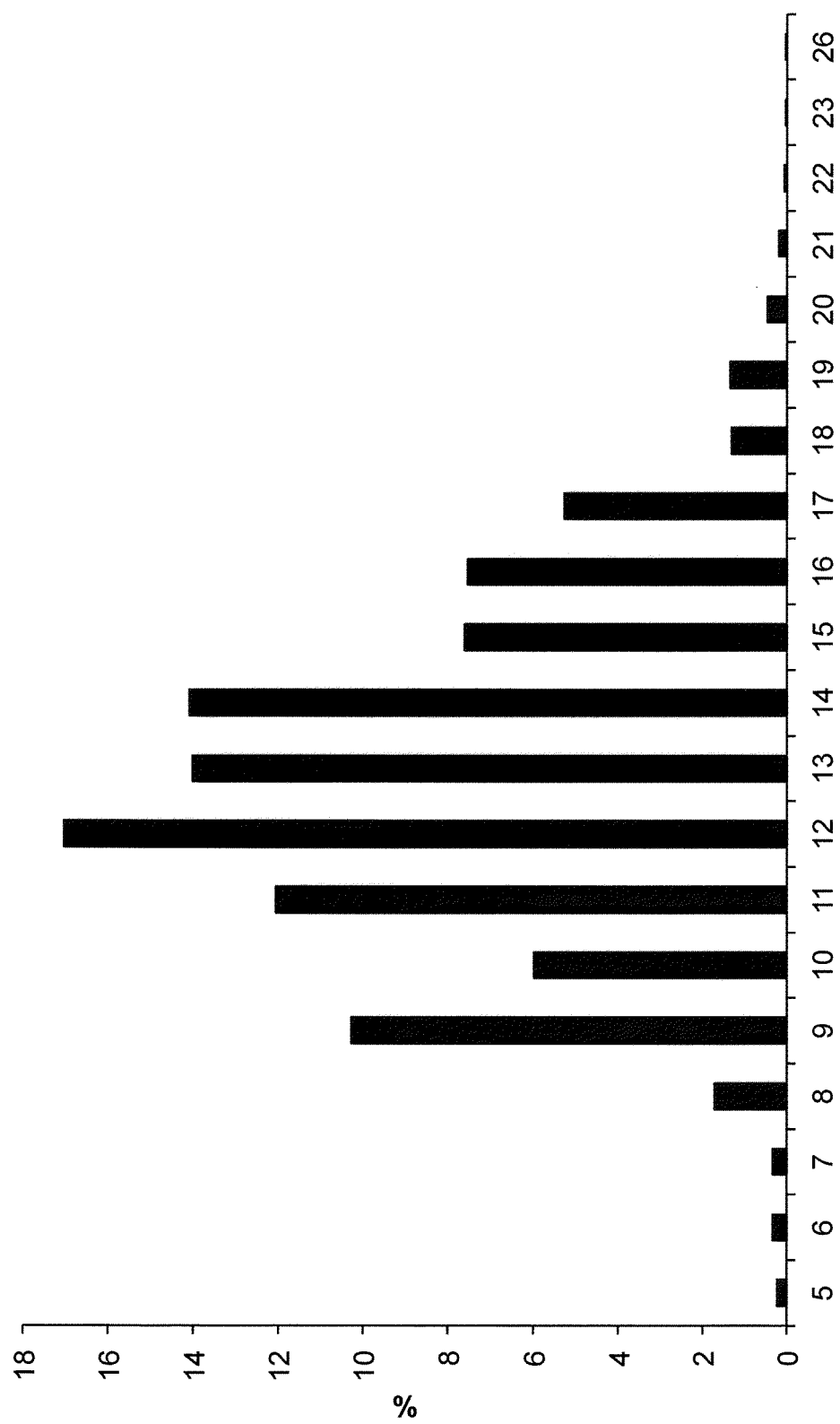
FIG. 22 shows the percentage (y-axis) of IgG-primed heavy chains having a specified amino acid length for the $V_H$ CDR3 region (x-axis) from mice homozygous for a single human $V_H$1-69 gene segment, twenty-seven human $D_R$ and six human $J_R$ gene segments at the endogenous immunoglobulin heavy chain locus and homozygous for a replacement of the endogenous κ light chain variable loci with human κ light chain variable loci that were immunized with a human cell surface receptor (Antigen A).

Amino acid length of the CDR3 region of IgM-primed $V_H$1-69-derived heavy chains is shown in FIG. 21. Amino acid length of the CDR3 region of IgG-primed $V_H$1-69-derived heavy chains is shown in FIG. 22.

As shown in Tables 8 and 9, mice according to the invention generate antigen-specific antibodies containing $V_H$1-69-derived heavy chains, which demonstrate a variety of rearrangements of a human $V_H$1-69 gene segment with a variety of human $D_H$ segments and human $J_H$ segments. Further, the antigen-specific antibodies contain cognate human light chains containing human Vκ domains resulting from a variety of rearrangements of human Vκ and Jκ gene segments.

TABLE 6

| Primer | Sequence (5'-3') |
| --- | --- |
| 3' Cg1 outer | GGAAGGTGTG CACACCGCTG GAC (SEQ ID NO: 71) |
| 3' Cg2ac outer | GGAAGGTGTG CACACCACTG GAC (SEQ ID NO: 72) |
| 3' Cg2b outer | GGAAGGTGTG CACACTGCTG GAC (SEQ ID NO: 73) |
| 3' Cg3 outer | AGACTGTGCG CACACCGCTG GAC (SEQ ID NO: 74) |
| 3' mIgM CH1 outer | TCTTATCAGA CAGGGGGCTC TC (SEQ ID NO: 75) |
| 3' mIgκC outer | AAGAAGCACA CGACTGAGGC AC (SEQ ID NO: 76) |

TABLE 7

| Primer | Sequence (5'-3') |
|---|---|
| 3' mIgG1/2b CH1 inner | AGTGGATAGA CWGATGGGGG TG (SEQ ID NO: 77) |
| 3' mIgG2a/2c CH1 inner | AGTGGATAGA CCGATGGGGC TG (SEQ ID NO: 78) |
| 3' mIgG3 CH1 inner | AAGGGATAGA CAGATGGGGC TG (SEQ ID NO: 79) |
| 3' mIgM CH1 inner | GGAAGACATT TGGGAAGGAC TG (SEQ ID NO: 80) |
| 3' mIgκC-2 inner | GGAAGATGGA TACAGTTGGT GC (SEQ ID NO: 81) |

TABLE 8

| Human $D_H$ | IgM | IgG | Human $J_H$ | IgM | IgG |
|---|---|---|---|---|---|
| 1-1 | 1.2 | 6.0 | 1 | 7.5 | 1.5 |
| 1-7 | 39.9 | 9.0 | 2 | 3.3 | 4.2 |
| 1-14 | 0.5 | 2.3 | 3 | 22.2 | 12.8 |
| 1-20 | 2.3 | 1.4 | 4 | 51.5 | 36.4 |
| 1-26 | 3.5 | 5.7 | 5 | 10.5 | 9.5 |
| 2-2 | 1.1 | 3.2 | 6 | 4.9 | 29.4 |
| 2-8 | 0.7 | 0.6 | | | |
| 2-15 | 0.3 | 1.2 | | | |
| 2-21 | 0.7 | 0.3 | | | |
| 3-3 | 6.3 | 5.2 | | | |
| 3-9 | 0.6 | 0.6 | | | |
| 3-10 | 0.9 | 10.3 | | | |
| 3-16 | 0.9 | 2.0 | | | |
| 3-22 | 5.1 | 2.7 | | | |
| 4-4/4-11 | 1.5 | 4.0 | | | |
| 4-17 | 1.5 | 4.7 | | | |
| 4-23 | 11.5 | 2.4 | | | |
| 5-12 | 1.1 | 1.8 | | | |
| 5-5/5-18 | 1.3 | 3.2 | | | |
| 5-24 | 0.3 | 3.3 | | | |
| 6-6 | 1.8 | 4.5 | | | |
| 6-13 | 6.1 | 7.4 | | | |
| 6-19 | 3.0 | 5.1 | | | |
| 6-25 | 0.1 | 0.6 | | | |
| 7-27 | 3.3 | 7.3 | | | |

TABLE 9

| Human $V_κ$ | % Observed | Human $J_κ$ | % Observed |
|---|---|---|---|
| 1-5 | 3.4 | 1 | 28.1 |
| 1-6 | 1.3 | 2 | 25.3 |
| 1-8 | 0 | 3 | 12.1 |
| 1-9 | 1.3 | 4 | 22.5 |
| 1-12 | 1.0 | 5 | 11.1 |
| 1-13 | 0 | | |
| 1-16 | 2.5 | | |
| 1-17 | 3.6 | | |
| 1-22 | 0 | | |
| 1-27 | 0.5 | | |
| 1-32 | 0 | | |
| 1-33 | 14.3 | | |
| 1-35 | 0 | | |
| 1-37 | 0 | | |
| 1-39 | 1.6 | | |
| 2-4 | 0 | | |
| 2-10 | 0 | | |
| 2-14 | 0 | | |
| 2-18 | 0 | | |
| 2-19 | 0 | | |
| 2-23 | 0 | | |
| 2-24 | 0.7 | | |
| 2-26 | 0 | | |
| 2-28 | 0 | | |
| 2-29 | 0 | | |
| 2-30 | 1.9 | | |
| 2-36 | 0 | | |
| 2-38 | 0 | | |
| 2-40 | 1.5 | | |
| 3-7 | 0 | | |
| 3-11 | 2.7 | | |
| 3-15 | 3.9 | | |
| 3-20 | 41.2 | | |
| 3-25 | 0 | | |
| 3-31 | 0 | | |
| 3-34 | 0 | | |
| 4-1 | 13.2 | | |
| 5-2 | 0.1 | | |
| 6-21 | 0 | | |
| 7-3 | 0 | | |

We claim:
1. A rat or mouse whose germline genome comprises a restricted endogenous immunoglobulin heavy chain locus characterized by the presence of
(i) only a single human $V_H$ gene segment, wherein the single human $V_H$ gene segment is a $V_H3$ segment family member,
(ii) one or more human $D_H$ gene segments,
(iii) one or more human $J_H$ gene segments, and
(iv) an endogenous immunoglobulin heavy chain constant region nucleic acid sequence comprising an endogenous IgM gene,
wherein the single human $V_H$ gene segment, the one or more human $D_H$ gene segments, and the one or more human $J_H$ gene segments are capable of rearranging to encode a diverse repertoire of human heavy chain variable domains,
wherein each human heavy chain variable domain of the diverse repertoire
(a) comprises framework (FR)1, complementarity determining region (CDR)1, FR2, CDR2, and FR3 sequences that are derived from the single human $V_H$ gene segment and CDR3 and FR4 sequences that are distinct,
(b) is operably linked to an endogenous IgM constant region encoded by the endogenous IgM gene, and
(c) is expressed in the context of a cognate light chain, and
wherein the rat or mouse expresses each human heavy chain variable domain of the diverse repertoire in the context of its cognate light chain.
2. The rat or mouse of claim 1, wherein the restricted endogenous immunoglobulin heavy chain variable region locus comprises a deletion of all or substantially all endogenous $V_H$, $D_H$, and $J_H$ gene segments.
3. The rat or mouse of claim 1, wherein the single human $V_H3$ segment family member is selected from the group consisting of a $V_H3$-7 gene segment, a $V_H3$-9 gene segment, a $V_H3$-11 gene segment, a $V_H3$-13 gene segment, a $V_H3$-15 gene segment, a $V_H3$-16 gene segment, a $V_H3$-20 gene segment, a $V_H3$-21 gene segment, a $V_H3$-23 gene segment, a $V_H3$-30 gene segment, a $V_H3$-30-3 gene segment, a $V_H3$-30-5 gene segment, a $V_H3$-33 gene segment, a $V_H3$-35 gene segment, a $V_H3$-38 gene segment, a $V_H3$-43 gene segment, a $V_H3$-48 gene segment, a $V_H3$-49 gene segment, a $V_H3$-53 gene segment, a $V_H3$-64 gene segment, a $V_H3$-66 gene segment, a $V_H3$-72 gene segment, a $V_H3$-73 gene segment, and a $V_H3$-74 gene segment.
4. The rat or mouse of claim 1, further comprising a humanized immunoglobulin light chain locus comprising, in operable linkage: one or more human $V_L$ gene segments, one or more human $J_L$ gene segments, and an immunoglobulin light chain constant region gene, wherein:
(i) the one or more human $V_L$ gene segments are one or more human Vκ gene segments, the one or more human $J_L$ gene segments are one or more human Jκ gene segments, and the immunoglobulin light chain constant region gene is an immunoglobulin light chain κ constant region gene or
(ii) the one or more human $V_L$ gene segments are one or more human Vλ gene segments, the one or more human $J_L$ gene segments are one or more human Jλ, gene segments, and the immunoglobulin light chain constant region gene is an immunoglobulin light chain λ, constant region gene, and
wherein the humanized immunoglobulin light chain locus encodes each cognate light chain for each human heavy chain variable domain of the diverse repertoire, and wherein each cognate light chain comprises a human light chain variable domain.
5. The rat or mouse of claim 4, wherein the immunoglobulin light chain constant region gene is an endogenous immunoglobulin light chain constant region gene.
6. A mouse whose germline genome comprises
(A) at an endogenous immunoglobulin heavy chain locus, a replacement of all or substantially all
(i) endogenous $V_H$ gene segments,
(ii) endogenous $D_H$ gene segments, and
(iii) endogenous $J_H$ gene segments
with
(i) only a single human $V_H$ gene segment, wherein the single human $V_H$ gene segment is a $V_H3$ segment family member,
(ii) one or more human $D_H$ gene segments, and
(iii) one or more human $J_H$ gene segments,
such that the single human $V_H$ gene segment, the one or more human D gene segments, and the one or more human $J_H$ gene segments are operably linked to an endogenous IgM constant region gene,
wherein the single human $V_H$, gene segment, the one or more human $D_H$ gene segments, and the one or more human $J_H$ gene segments are capable of rearranging to encode a diverse repertoire of human heavy chain variable domains,
wherein each human heavy chain variable domain of the diverse repertoire
(a) comprises framework (FR) 1, complementarity determining region (CDR)1, FR2, CDR2, and FR3 sequences that are derived from the single human $V_H$ gene segment and CDR3 and FR4 sequences that are distinct,
(b) is operably linked to an endogenous IgM constant region encoded by the endogenous IgM gene, and
(c) is expressed in the context of a cognate light chain, and
(B) at an endogenous immunoglobulin light chain locus, a replacement of all or substantially all
(i) endogenous $V_L$ gene segments and
(ii) endogenous $J_L$ gene segments
with
(i) a plurality of human $V_L$ gene segments and
(ii) a plurality of human $J_L$ gene segments
such that the plurality of human $V_L$ gene segments and the plurality of human $J_L$ gene segments are operably linked to an endogenous immunoglobulin light chain constant region,
wherein
(a) the plurality of human $V_L$ gene segments is a plurality of human Vκ gene segments, the plurality of human $J_L$ gene segments is a plurality of human Jκ gene segments, and the endogenous immunoglobulin light chain constant region gene is an endogenous immunoglobulin light chain κ constant region gene or
(b) the plurality of human $V_L$ gene segments is a plurality of human Vλ, gene segments, the plurality of human $J_L$ gene segments is a plurality of human Jλ, gene segments, and the endogenous immunoglobulin light chain constant region gene is an endogenous immunoglobulin light chain λ constant region gene,
wherein the endogenous immunoglobulin light chain locus encodes each cognate light chain for each human heavy chain variable domain of the diverse repertoire, and wherein each cognate light chain comprises a human light chain variable domain, and wherein mouse expresses each human heavy chain variable domain of the diverse repertoire in the context of its cognate light chain.

7. A cell or tissue derived from the rat or mouse of claim 1.

* * * * *

UNITED STATES PATENT AND TRADEMARK OFFICE
CERTIFICATE OF CORRECTION

PATENT NO. : 11,261,248 B2
APPLICATION NO. : 16/265825
DATED : March 1, 2022
INVENTOR(S) : Lynn Macdonald, John McWhirter and Andrew J. Murphy It is certified that error appears in the above-identified patent and that said Letters Patent is hereby corrected as shown below:

On the Title Page

(56) References Cited
OTHER PUBLICATIONS

Page 2, second Column, Line 57:
"Brüggeman"
Should be:
--Brüggemann--

Page 3, first Column, Line 53:
"dusters"
Should be:
--clusters--

Page 5, first Column, Line 26:
"y"
Should be:
--γ--

In the Specification

Column 6, Line 64:
"$J_R$"
Should be:
--$J_H$--

Column 6, Line 65:
"$D_R$"

Signed and Sealed this
Twenty-eighth Day of June, 2022

Katherine Kelly Vidal
*Director of the United States Patent and Trademark Office*

Should be:
--$D_H$--

Column 6, Line 65:
"$J_R$"
Should be:
--$J_H$--

Column 6, Line 67:
"$J_R$"
Should be:
--$J_H$--

Column 7, Line 3:
"$D_R$"
Should be:
--$D_H$--

Column 7, Line 4:
"$J_R$"
Should be:
--$J_H$--

Column 8, Line 44:
"$D_R$"
Should be:
--$D_H$--

Column 8, Line 45:
"$D_R$"
Should be:
--$D_H$--

Column 8, Line 46:
"$J_R$"
Should be:
--$J_H$--

Column 8, Line 47:
"$J_R$"
Should be:
--$J_H$--

Column 8, Line 55:
"$D_R$"

Should be:
--$D_H$--

Column 8, Line 56:
"$J_R$"
Should be:
--$J_H$--

Column 8, Line 65:
"$D_R$"
Should be:
--$D_H$--

Column 8, Line 66:
"$J_R$"
Should be:
--$J_H$--

Column 8, Line 67:
"$J_R$"
Should be:
--$J_H$--

Column 9, Line 8:
"$D_R$"
Should be:
--$D_H$--

Column 9, Line 9:
"$J_R$"
Should be:
--$J_H$--

Column 21, Line 19:
"x"
Should be:
--κ--

Column 23, Line 7:
"a an"
Should be:
--an--

Column 27, Line 19:
"Vλ\"

Should be:
--Vλ--

Column 28, Line 48:
"$D_R$"
Should be:
--$D_H$--

Column 28, Line 48:
"$J_R$"
Should be:
--$J_H$--

Column 28, Line 54:
"$J_R$"
Should be:
--$J_H$--

Column 28, Line 59:
"$J_R$"
Should be:
--$J_H$--

Column 28, Line 64:
"$D_R$"
Should be:
--$D_H$--

Column 28, Line 64:
"$J_R$"
Should be:
--$J_H$--

Column 29, Line 1:
"$V_R$"
Should be:
--$V_H$--

Column 29, Line 2:
"$D_R$"
Should be:
--$D_H$--

Column 29, Line 2:
"$J_R$"

CERTIFICATE OF CORRECTION (continued)
U.S. Pat. No. 11,261,248 B2

Should be:
--$J_H$--

Column 29, Line 7:
"$D_R$"
Should be:
--$D_H$--

Column 29, Line 12:
"$D_R$"
Should be:
--$D_H$--

Column 29, Line 13:
"$J_R$"
Should be:
--$J_H$--

Column 29, Line 19:
"$D_R$"
Should be:
--$D_H$--

Column 29, Line 19:
"$J_R$"
Should be:
--$J_H$--

Column 29, Line 27:
"$D_R$"
Should be:
--$D_H$--

Column 31, Line 9:
"$D_R$"
Should be:
--$D_H$--

Column 31, Line 9:
"$J_R$"
Should be:
--$J_H$--

Column 31, Line 16:
"fix"

Should be:
--Hκ--

Column 31, Line 17:
"$D_R$"
Should be:
--$D_H$--

Column 31, Line 17:
"$J_R$"
Should be:
--$J_H$--

Column 31, Line 24:
"$D_R$"
Should be:
--$D_H$--

Column 31, Line 25:
"$J_R$"
Should be:
--$J_H$--

Column 31, Line 33:
"$D_R$"
Should be:
--$D_H$--

Column 31, Line 34:
"$J_R$"
Should be:
--$J_H$--

Column 33, Line 10:
"$J_R$"
Should be:
--$J_H$--

Column 33, Line 29:
"Vκ96L"
Should be:
--W96L--

Column 33, Line 63:
"form"

Should be:
--from--

Column 39, Line 55:
"$V_HE$"
Should be:
--$V_{H\varepsilon}$--

Column 40, Line 11:
"1/1-69"
Should be:
--V1-69--

Column 40, Line 54:
"Retroviology"
Should be:
--Retrovirology--

Column 41, Line 44:
"form"
Should be:
--from--

Column 46, Column 35:
"$V_HN_L$"
Should be:
--$V_H/V_L$--

Column 47, Line 6:
"$D_R$"
Should be:
--$D_H$--

Column 48, Line 1:
"780-6220"
Should be:
--780-B220--

Column 48, Line 3:
"FITC-ID("
Should be:
--FITC-Igκ--

Column 48, Line 4:
"PE-10"

Should be:
--PE-Igλ--

Column 48, Line 47:
"B220$^{int}$IgM$^+$ Igκ$^+$Igλ"
Should be:
--B220$^{int}$IgM$^+$Igκ$^+$Igλ$^-$--

Column 48, Line 49:
"B220$^{int}$IgM$^+$ Igκ$^+$"
Should be:
--B220$^{hi}$IgM$^+$Igκ$^+$Igλ$^-$--

Column 48, Lines 49-50:
"B220$^{int}$IgM$^+$ Igκ$^-$ Igλ$^+$"
Should be:
--B220$^{hi}$IgM$^+$Igκ$^-$Igλ$^+$--

In the Claims

Claim 2, Line 2, Column 303, Line 33:
"endogenous immunoglobulin heavy chain variable region"
Should be:
--endogenous immunoglobulin heavy chain--

Claim 6, Line 14, Column 304, Line 20:
"D"
Should be:
--D$_H$--

Claim 6, Line 17, Column 304, Line 23:
"VH"
Should be:
--V$_H$--

Claim 6, Line 24, Column 304, Line 30:
"(FR) 1"
Should be:
--(FR)1--